United States Patent
Sun et al.

(10) Patent No.: US 8,551,955 B2
(45) Date of Patent: Oct. 8, 2013

(54) DIMERIC SMAC MIMETICS

(75) Inventors: Haizhou Sun, Dallas, TX (US);
Xiaoming Xu, Dallas, TX (US); Ming Zhou, Dallas, TX (US); Susan Harran, Dallas, TX (US); Gunnar James Hanson, Dallas, TX (US); Lai Wang, Dallas, TX (US)

(73) Assignee: Joyant Pharmaceuticals, Inc., Dallas, TX (US)

( * ) Notice: Subject to any disclaimer, the term of this patent is extended or adjusted under 35 U.S.C. 154(b) by 327 days.

(21) Appl. No.: 12/914,840

(22) Filed: Oct. 28, 2010

(65) Prior Publication Data

US 2011/0195043 A1 Aug. 11, 2011

Related U.S. Application Data

(60) Provisional application No. 61/255,788, filed on Oct. 28, 2009.

(51) Int. Cl.
*A61K 38/06* (2006.01)
*A61K 38/08* (2006.01)
*C07C 45/87* (2006.01)

(52) U.S. Cl.
USPC ......... 514/21.7; 514/21.9; 568/452; 530/330; 530/328

(58) Field of Classification Search
None
See application file for complete search history.

(56) References Cited

FOREIGN PATENT DOCUMENTS

WO WO 2007/021825 * 2/2007
WO WO2008128121 10/2008

OTHER PUBLICATIONS

Li, 2004, Science 305, 1471-1474.*
International Search Report and Written Opinion in counterpart PCT/US10/54546, 2011.

* cited by examiner

*Primary Examiner* — Satyanarayana R Gudibande
(74) *Attorney, Agent, or Firm* — Richard Aron Osman

(57) ABSTRACT

The invention provides small molecule mimics of the Smac peptide that are dimers or dimer-like compounds having two binding domains connected by a linker. These compounds are useful to promote apoptosis. The invention includes pharmaceutical compositions comprising such compounds and methods to use them to treat conditions including cancer and autoimmune disorders.

20 Claims, No Drawings

DIMERIC SMAC MIMETICS

This application claims priority to U.S. Ser. No. 61/255,788, filed Oct. 28, 2009 and having the same title and inventors.

TECHNICAL FIELD

The present invention relates to dimer and dimer-like small molecule promoters of apoptosis. These compounds mimic the activity of the protein known as Smac, and are thereby able to promote the initiation of apoptosis. The compounds are therefore useful in treating conditions where initiating apoptosis is desirable, such as in pathological cells or tissues. The invention also relates in part to methods for using such compounds, and pharmaceutical compositions containing these compounds.

BACKGROUND ART

Apoptosis plays a central role in the development and homeostasis of all multi-cellular organisms. Abnormal inhibition of apoptosis is a hallmark of cancer and autoimmune diseases, whereas excessive activation of cell death is implicated in neuro-degenerative disorders such as Alzheimer's disease. Pro-apoptotic chemotherapeutic drugs provide a recent approach to overcoming the clinical problem of drug resistance; see, e.g. Makin et al., Cell Tissue Res. (July 2000) 301(1):143-152 ("Apoptosis and cancer chemotherapy").

The mechanism of apoptosis is conserved across species and executed with a cascade of sequential activation of proteases called caspases. Once activated, these caspases are responsible for proteolytic cleavage of a broad spectrum of cellular targets that ultimately lead to cell death. IAPs (inhibitor-of-apoptosis proteins) are a family of proteins that regulate apoptosis by inhibiting caspases. The viral and cellular IAPs contain one to three N-terminal baculovirus IAP repeat (BIR) motifs and a C-terminal RING finger domain. Examples of human IAPs include the X-linked IAP (XIAP), cIAP2 (also referred to as HIAP1 or BIRC3) and cIAP1 (also referred to as HIAP2 or BIRC2).

A mitochondrial protein called Smac ('second mitochondria-derived activator of caspases') has been shown to bind to and inhibit a wide variety of IAPs, thereby promoting caspase activation, and is believed to be a key regulator of apoptosis in mammals. See Du, et al., Cell (2000) 102:33-43; Verhagen et al., Cell (2000) 102:43-53; and Vucic et al., Biochem. J. (2005) 385(1):11-20. N-terminal Smac-derived peptides and mimetics have been shown to similarly inhibit IAPs, and promote caspase activation. IAPs are components of TNFR (tumor necrosis factor receptor), so IAP inhibitors can divert TNFR signaling from an NfkB-mediated pro-inflammatory signal, to an anti-inflammatory apoptotic signal.

Defective apoptosis regulation can confer resistance to many current treatment protocols, leading to tumor growth. This may occur as a result of overexpression of IAPs, which inhibit the caspases that would otherwise initiate apoptosis. Alternatively, deregulation can occur as a result of underproduction of the Smac peptides that act to inhibit IAP activity. Thus, a deficiency of Smac can allow IAP to prevent apoptosis from occurring when it should. A Smac mimetic, such as the compounds of the present invention, can replace the activity of Smac and thus promote desired apoptosis.

Debatin, et al., WO 03/086470, describes Smac-peptides as therapeutic agents useful against cancer and autoimmune diseases; they are reported to act by sensitizing the cells toward TRAIL-induced or anticancer drug-induced apoptosis. (TRAIL stands for TNF related apoptosis-inducing ligand). See also Li, et al., Science (3 Sep. 2004) 305:1471-14744. Debatin provides in vivo evidence that Smac induces the eradication of certain tumors such as glioblastoma tumor models in animals when administered in combination with TRAIL. According to Debatin, aggressive cancer phenotypes, which result from deregulation of signaling pathways, commonly fail to undergo apoptosis when they otherwise would, allowing rapid and abnormal tissue growth. Bockbrader, et al., disclose efficacy of Smac mimic compounds on breast cancer cell lines when used in conjunction with TRAIL or etoposide, or when used in cells that express TRAIL at relatively high levels. Oncogene (2005) 24:7381-7388.

Similarly, according to Debatin, defects in apoptosis regulation play a key role in the pathogenesis of autoimmune disorders, including lupus erythematodes disseminatus and rheumatoid arthritis. Accordingly, compounds that mimic the activity of Smac can treat some of the effects of such conditions.

Dimeric compounds have been disclosed in U.S. Pat. No. 7,309,792 and U.S. Patent Applications US 2008/0119532, US 2008/0051389 and US 2009/0104151. The compounds have two binding domains linked by a linker that is broadly described. Dimeric Smac inhibitors have also been disclosed in U.S. Pat. Nos. 7,547,724, 7,579,320, 7,589,118, and U.S. Patent Applications US 2007/0093429, US 2007/0219140, and US 2009/0192140. Another U.S. Patent Application, US 2006/0025347, describes small molecule compounds having activity related to promotion of apoptosis. However, while the latter reference mentions that dimeric compounds can be used, none of the compounds it discloses have a dimeric structure.

Several recent patent applications, for example, US 2006/0025347, US 2005/0197403, WO 2006/069063, US 2006/0014700, WO 2005/094818, and WO 2005/097791, each of which is incorporated herein by reference in its entirety, disclose monomeric IAP inhibitors, but do not describe dimeric structures.

DISCLOSURE OF THE INVENTION

The invention provides dimer and dimer-like compounds of Formula (I) that possess two structurally similar binding domains. These binding domains are linked by a linking group, and while similar, the domains need not be identical. In certain embodiments, each binding domain is the same, so the molecule is symmetric about its linking group. In other embodiments, the two binding domains are different.

In one aspect, the invention provides a compound of Formula (I):

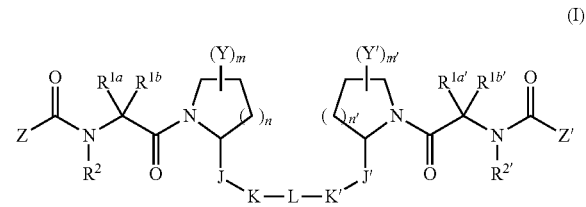

or a pharmaceutically acceptable salt or hydrate form thereof; and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, $OC(O)R$, $NRC(O)R$, $NRCOOR$, $NRC(O)NR_2$, $NRSO_2R$, $CN$, $C(O)NR_2$, $C(O)R$, $COOR$, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as a ring member;

each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or $R^{1a}$ and $R^{1b}$, or $R^{1a'}$ and $R^{1b'}$ may be taken together with the carbon atom to which they are attached to form an optionally substituted 3-7 membered ring, optionally containing a heteroatom selected from N, O and S as a ring member;

each $R^2$ and $R^{2'}$ is independently H or optionally substituted C1-C8 alkyl;

each of J and J' is independently —C(O)—, —$CH_2$— or —CHR"—, where R" is C1-C4 alkyl;

each of K and K' is independently selected from the group consisting of —NR'—$(CR^X_2)_p$—NR'—, —NR'—$(CR^X_2)_p$—O—, —O—$(CR^X_2)_p$—NR'—, —O—$(CR^X_2)_p$—O—, —NR'—$(CR^X_2)_p$—S—, —S—$(CR^X_2)_p$—NR', —O—$(CR^X_2)_p$—S—, —S—$(CR^X_2)_p$—O—, and —S—$(CR^X_2)_p$—S—, wherein each R' is independently H or $C_{1-4}$ alkyl, each $R^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or two $R^X$ substituents are taken together to form an optionally substituted saturated, unsaturated or aromatic carbocyclic or heterocyclic ring; and each p is independently 2-4;
each n and n' is independently 0-3;
each m and m' is independently 0-4;
each Z and Z' independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In another aspect, the invention provides a compound of formula (VI):

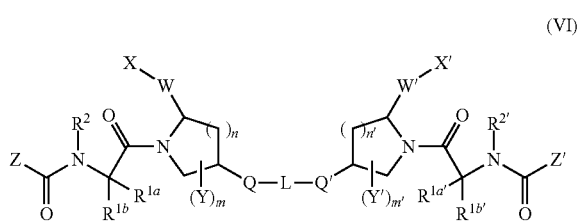

(VI)

or a pharmaceutically acceptable salt or hydrate form thereof; and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, $OC(O)R$, $NRC(O)R$, $NRCOOR$, $NRC(O)NR_2$, $NRSO_2R$, $CN$, $C(O)NR_2$, $C(O)R$, $COOR$, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as a ring member;

each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or $R^{1a}$ and $R^{1b}$, or $R^{1a'}$ and $R^{1b'}$ may be taken together with the carbon atom to which they are attached to form an optionally substituted 3-7 membered ring, optionally containing a heteroatom selected from N, O and S as a ring member;

each $R^2$ and $R^{2'}$ is independently H or optionally substituted C1-C8 alkyl;

each W and W' independently represents an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each Q and Q' independently represents —O—, —S— or —$NR^5$—, where each $R^5$ is independently H, or optionally substituted C1-C8 alkyl, or optionally substituted C1-C8 heteroalkyl; or one or both of Q and Q' may be a bond when L comprises a ring;

each n and n' is independently 0-3;
each m and m' is independently 0-4;
each Z and Z' independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In a further aspect, the invention provides a compound of formula (VIII):

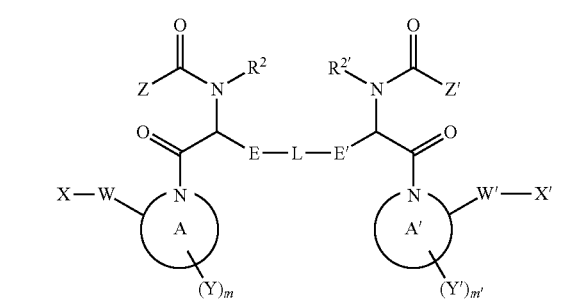

(VIII)

or a pharmaceutically acceptable salt or hydrate form thereof; and including any stereoisomeric forms thereof;

wherein each of ring A and ring A' independently represents a C3-C12 azacyclic ring, each of which may contain 0-2 additional heteroatoms selected from N, O, S as ring members;

wherein each Y and Y' independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as ring members;

each W and W' is independently an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted C$_5$-C$_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each E and E' independently represents —CH$_2$—, —CH(OR)—, —CH(R)—, —(CH$_2$)$_r$D-, CH(R)D-, —CR=CR— or —C≡C—, wherein r is 1-4, each D is independently O, NR, or S, and wherein each R is independently H, or optionally substituted C$_1$-C$_8$ alkyl or optionally substituted C$_1$-C$_8$ heteroalkyl; or one or both of E and E' can be a bond where L comprises a ring;

each R$^2$ and R$^{2'}$ is independently H or optionally substituted C1-C8 alkyl;

each m and m' is independently 0-4;

each Z and Z' is independently an optionally substituted C1-C6 aminoalkyl; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In still another aspect, the invention provides a compound of formula (X):

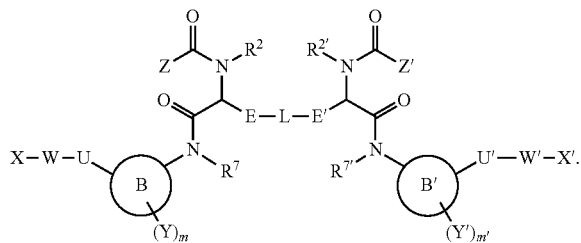

(X)

or a pharmaceutically acceptable salt or hydrate form thereof; and including any stereoisomeric forms thereof;

wherein each of ring B and ring B' is independently a C3-C12 carbocyclic ring or a C3-C12 heterocyclic ring containing 1-3 heteroatoms selected from N, O, S as ring members; and wherein each Y and Y' independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as ring members;

each U and U' independently represents —NR$^8$—, —O—, or —S(O)$_v$—, wherein each R$^8$ is independently H or C1-C4 alkyl, and v is 0-2;

each W and W' is independently an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted C$_5$-C$_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each E and E' independently represents —CH$_2$—, —CH(OR)—, —CH(R)—, —(CH$_2$)$_r$D-, CH(R)D-, or —CR=CR— or —C≡C—, wherein r is 1-4, each D is independently O, NR, or S, and wherein each R is independently H, or optionally substituted C$_1$-C$_8$ alkyl or optionally substituted C$_1$-C$_8$ heteroalkyl; or one or both of E and E' can be a bond where L comprises a ring;

each R$^2$ and R$^{2'}$ is independently H or optionally substituted C1-C8 alkyl;

each R$^7$ and R$^{7'}$ is independently H or optionally substituted C1-C4 alkyl;

each m and m' is independently 0-4;

each Z and Z' is independently an optionally substituted C1-C6 aminoalkyl; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In yet another aspect, the invention provides a compound of formula (XII):

$$\Phi^1\text{-L-}\Phi^2 \quad \quad (XII)$$

or a pharmaceutically acceptable salt or hydrate form thereof; and including any stereoisomeric forms thereof;

wherein Φ¹ and Φ² are independently selected from the group consisting of:

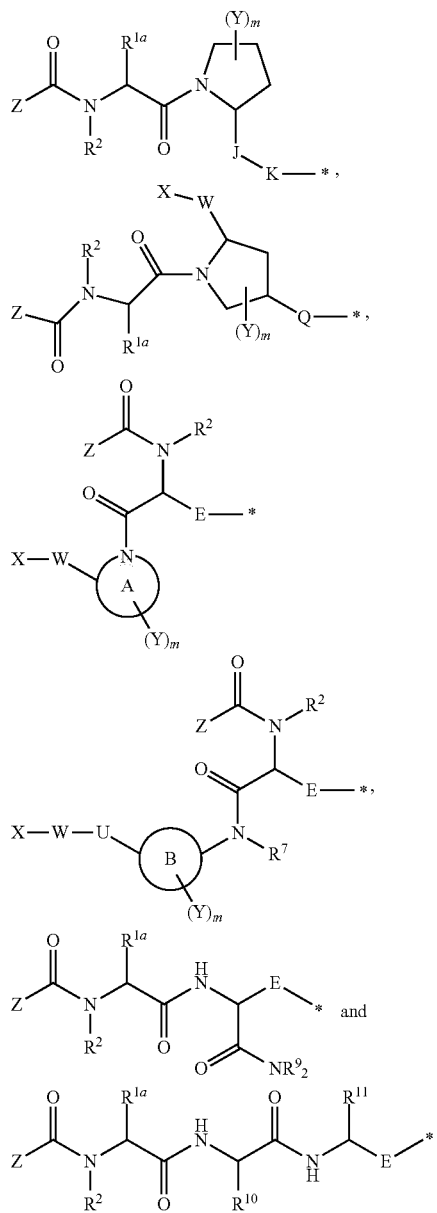

wherein * represents the point of attachment to L;

each Y independently represents an optionally substituted C1-C8 alkyl, C5-C12 aryl, C5-C20 arylalkyl, or a heteroform of one of these; or is =O, OR, SR, S(O)R, SO₂R, SO₂NR₂, NR₂, OC(O)R, NRC(O)R, NRCOOR, NRC(O)NR₂, NRSO₂R, CN, C(O)NR₂, C(O)R, COOR, NO₂ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as a ring member;

each $R^{1a}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or each $R^2$ is independently H or optionally substituted C1-C8 alkyl;

each J is independently —C(O)—, —CH₂— or —CHR''—, where R'' is C1-C4 alkyl;

each of K and K' is independently selected from the group consisting of —NR'—$(CR^X_2)_p$—NR'—, —NR'—$(CR^X_2)_p$—O—, —O—$(CR^X_2)_p$—NR'—, —O—$(CR^X_2)_p$—O—, —NR'—$(CR^X_2)_p$—S—, —S—$(CR^X_2)_p$—NR'—, —O—$(CR^X_2)_p$—S—, —S—$(CR^X_2)_p$—O—, and —S—$(CR^X_2)_p$—S—, wherein each R' is independently H or $C_{1-4}$ alkyl, each $R^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or two $R^X$ substituents are taken together to form an optionally substituted saturated, unsaturated or aromatic carbocyclic or heterocyclic ring; and each p is independently 2-4;

each Q represents —O—, —S— or —$NR^5$—, where each $R^5$ is independently H, or optionally substituted C1-C8 alkyl, or optionally substituted C1-C8 heteroalkyl; or Q may be a bond when L comprises a ring;

each E represents —CH₂—, —CH(OR)—, —CH(R)—, —(CH₂)ᵣD-, —CH(R)D-, or —CR=CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or E can be a bond where L comprises a ring;

W is an optionally substituted C1-C6 alkylene or C1-C6 heteroalkylene; or W and/or W' can be a bond where X comprises an optionally substituted C5-C6 aryl or heteroaryl ring;

X is independently an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W;

each U independently represents —$NR^8$—, —O—, or —S(O)ᵥ—, wherein each $R^8$ is independently H or C1-C4 alkyl, and v is 0-2;

wherein ring A represents a C3-C12 azacyclic ring, which may contain 0-2 additional heteroatoms selected from N, O, S as ring members;

wherein the B ring represents a C3-C12 carbocyclic ring or a C3-C12 heterocyclic ring containing 1-3 heteroatoms selected from N, O, S as ring members;

each $R^9$ is independently H or optionally substituted C1-C8 alkyl;

each $R^{10}$ is independently H or optionally substituted C1-C8 alkyl;

each $R^{11}$ is independently H or optionally substituted C1-C8 alkyl;

m is 0-4;

each Z independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

The invention also includes the pharmaceutically acceptable salts of the compounds of the formulae described herein.

The invention also provides pharmaceutical compositions comprising at least one compound of any of the formulae described herein and one or more pharmaceutically acceptable carriers or excipients. Pharmaceutical compositions comprising at least one of these compounds can be utilized in methods of treatment such as those described herein. Also provided are methods of using these compounds and compositions for the treatment of specified conditions as further described herein.

In one aspect, the invention provides a method for treating or ameliorating a cell proliferative disorder, comprising administering to a subject in need thereof an effective amount of a compound according to any of the formulae disclosed herein, thereby treating or ameliorating said cell proliferative disorder.

In another aspect, the invention provides a method for reducing cell proliferation or inducing cell death, comprising contacting a cell with an effective amount of a compound according to any of the formulae disclosed herein, thereby reducing cell proliferation or inducing cell death.

In a further aspect, the invention provides a method for inhibiting cell proliferation, comprising contacting a cell with a compound according to any of the formulae disclosed herein, in an amount effective to inhibit proliferation of the cells.

These and other embodiments of the invention are described in the description that follows.

MODES OF CARRYING OUT THE INVENTION

The present invention may be understood more readily by reference to the following detailed description of the preferred embodiments of the invention and the Examples included herein. It is to be understood that the terminology used herein is for the purpose of describing specific embodiments only and is not intended to be limiting. It is further to be understood that unless specifically defined herein, the terminology used herein is to be given its traditional meaning as known in the relevant art.

As used herein, the singular form "a", "an", and "the" include plural references unless indicated otherwise. For example, "an" excipient includes one or more excipients.

The terms "treat", "treating" or "treatment" in reference to a particular disease or disorder includes prevention of the disease or disorder, and/or lessening, improving, ameliorating or removing the symptoms and/or pathology of the disease or disorder.

The term "therapeutically effective amount" or "effective amount" is intended to mean that amount of a drug or pharmaceutical agent that will elicit the biological or medical response of a cell, tissue, system, animal or human that is being sought by a researcher, veterinarian, medical doctor or other clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder.

A compound described herein may be in a therapeutically effective amount in a pharmaceutical formulation or medicament, which is an amount that can lead to a desired biological effect, leading to ameliorating, alleviating, lessening, or removing symptoms of a disease or condition, for example. The terms also can refer to reducing or stopping a cell proliferation rate (e.g., slowing or halting tumor growth) or reducing the number of proliferating cancer cells (e.g., removing part or all of a tumor), or a decrease in the rate of advancement of a disease or disorder.

As used herein, "subject" refers to a human or animal subject. In certain preferred embodiments, the subject is human.

As used herein, "hydrocarbyl residue" refers to a residue which contains only carbon and hydrogen, unless otherwise provided. The residue may be aliphatic or aromatic, straight-chain, cyclic, branched, saturated or unsaturated, or any combination of these. The hydrocarbyl residue, when so stated, however, may contain heteroatoms in addition to or instead of the carbon and hydrogen members of the hydrocarbyl group itself. Thus, when specifically noted as containing or optionally containing heteroatoms, the hydrocarbyl group may contain one or more heteroatoms as indicated within the "backbone" of the hydrocarbyl residue, and when optionally substituted, the hydrocarbyl residue may also have one or more carbonyl groups, amino groups, hydroxyl groups and other suitable substituents as further described herein in place of one or more hydrogens of the parent hydrocarbyl residue.

As used herein, the terms "alkyl," "alkenyl" and "alkynyl" include straight-chain, branched-chain and cyclic monovalent hydrocarbyl radicals, and combinations of these, which contain only C and H when they are unsubstituted. Examples include methyl, ethyl, isobutyl, tert-butyl, cyclohexyl, cyclopentylethyl, 2-propenyl, 3-butynyl, and the like. The total number of carbon atoms in each such group is sometimes described herein, e.g., when the group can contain up to ten carbon atoms it may be described as 1-10C or as C1-C10 or as $C_{1-10}$. When heteroatoms (typically N, O and S) are allowed to replace carbon atoms of an alkyl, alkenyl or alkynyl group, as in heteroalkyl groups, for example, the numbers describing the group, though still written as e.g. C1-C6, represent the sum of the number of carbon atoms in the group plus the number of such heteroatoms that are included as replacements for carbon atoms in the ring or chain being described.

Typically, the alkyl, alkenyl and alkynyl substituents of the invention contain 1-10C (alkyl) or 2-10C (alkenyl or alkynyl). Preferably they contain 1-8C (alkyl) or 2-8C (alkenyl or alkynyl). Sometimes they contain 1-4C (alkyl) or 2-4C (alkenyl or alkynyl). A single group can include more than one type of multiple bond, or more than one multiple bond; such groups are included within the definition of the term "alkenyl" when they contain at least one carbon-carbon double bond, and they are included within the term "alkynyl" when they contain at least one carbon-carbon triple bond.

Alkyl, alkenyl and alkynyl groups are often substituted to the extent that such substitution makes sense chemically. Typical substituents include, but are not limited to, halo, =O, =N—CN, =N—OR, =NR, OR, $NR_2$, SR, $SO_2R$, $SO_2NR_2$, $NRSO_2R$, $NRCONR_2$, NRCOOR, NRCOR, CN, COOR, $CONR_2$, OOCR, COR, and $NO_2$, wherein each R is independently H, C1-C8 alkyl, C2-C8 heteroalkyl, C1-C8 acyl, C2-C8 heteroacyl, C2-C8 alkenyl, C2-C8 heteroalkenyl, C2-C8 alkynyl, C2-C8 heteroalkynyl, C5-C12 aryl, or C5-C12 heteroaryl, and each R is optionally substituted with one or more groups selected from halo, =O, =N—CN, =N—OR', =NR'OR', $NR'_2$, SR', $SO_2R'$, $SO_2NR'_2$, $NR'SO_2R'$, $NR'CONR'_2$, $NR'COOR'$, NR'COR', CN, COOR', $CONR'_2$, OOCR', COR' and $NO_2$, wherein each R' is independently H, C1-C8 alkyl, C2-C8 heteroalkyl, C1-C8 acyl, C2-C8 heteroacyl, C5-C12 aryl or C5-C12 heteroaryl. Alkyl, alkenyl and alkynyl groups can also be substituted by C1-C8 acyl, C2-C8 heteroacyl, C5-C12 aryl or C5-C12 heteroaryl, each of which can be substituted by the substituents that are appropriate for the particular group.

"Heteroalkyl", "heteroalkenyl", and "heteroalkynyl" and the like are defined similarly to the corresponding hydrocarbyl (alkyl, alkenyl and alkynyl) groups, but the 'hetero' terms refer to groups that contain one or more heteroatoms selected from O, S and N and combinations thereof, within the backbone residue; thus at least one carbon atom of a corresponding alkyl, alkenyl, or alkynyl group is replaced by one of the specified heteroatoms to form a heteroalkyl, heteroalkenyl, or heteroalkynyl group. Preferably, each heteroalkyl, heteroalkenyl and heteroalkynyl group contains only 1-2 heteroatoms as part of the skeleton of backbone of the heteroalkyl group, i.e., not including substituents that may be present.

The typical and preferred sizes for heteroforms of alkyl, alkenyl and alkynyl groups are generally the same as for the corresponding hydrocarbyl groups, and the substituents that may be present on the heteroforms are the same as those described above for the hydrocarbyl groups. Where such groups contain N, the nitrogen atom may be present as NH or it may be optionally substituted if the heteroalkyl or similar group is described as optionally substituted. Where such groups contain S, the sulfur atom may optionally be oxidized to SO or $SO_2$ unless otherwise indicated. For reasons of chemical stability, it is also understood that, unless otherwise specified, such groups do not include more than two contiguous heteroatoms as part of the heteroalkyl chain, although an oxo group may be present on N or S as in a nitro or sulfonyl group. Thus —C(O)NH$_2$ can be a C2 heteroalkyl group substituted with =O; and —SO$_2$NH— can be a C2 heteroalkylene, where S replaces one carbon, N replaces one carbon, and S is substituted with two =O groups.

While "alkyl" as used herein includes cycloalkyl and cycloalkylalkyl groups, the term "cycloalkyl" may be used herein to specifically describe a carbocyclic non-aromatic group that is connected via a ring carbon atom, and "cycloalkylalkyl" may be used to describe a carbocyclic non-aromatic group that is connected to the base molecule through an alkyl linker. Similarly, "heterocyclyl" may be used to describe a non-aromatic cyclic group that contains at least one heteroatom as a ring member, typically selected from N, O and S, and that is connected to the molecule via a ring atom of the cyclic group, which may be C or N; and "heterocyclylalkyl" may be used to describe such a group that is connected to another molecule through an alkyl linker. The sizes and substituents that are suitable for the cycloalkyl, cycloalkylalkyl, heterocyclyl, and heterocyclylalkyl groups are the same as those described above for alkyl groups. The size of a cycloalkylalkyl or heterocyclylalkyl group describes the total number of carbon atoms or of carbon atoms plus heteroatoms that replace carbon atoms of an alkyl, alkenyl, alkynyl, cycloalkyl, or alkylenyl portion. In frequent embodiments, cycloalkyl and heterocyclyl rings are C3-C12, C3-C10 or C3-C8 rings, and may comprise monocyclic, bicyclic or polycyclic ring systems. As used herein, these terms also include rings that contain a double bond or two, as long as the ring is not aromatic. As used herein, cycloalkyl may also include bridged carbocyclic ring systems, such as the adamantyl ring system.

As used herein, "acyl" encompasses groups comprising an alkyl, alkenyl, alkynyl, aryl or arylalkyl radical attached at one of the two available valence positions of a carbonyl carbon atom, e.g., —C(=O)R where R is an alkyl, alkenyl, alkynyl, aryl, or arylalkyl group, and heteroacyl refers to the corresponding groups wherein at least one carbon other than the carbonyl carbon has been replaced by a heteroatom chosen from N, O and S. Thus heteroacyl includes, for example, —C(=O)OR and —C(=O)NR$_2$ as well as —C(=O)-heteroaryl.

Acyl and heteroacyl groups are bonded to any group or molecule to which they are attached through the open valence of the carbonyl carbon atom. Typically, they are C1-C8 acyl groups, which include formyl, acetyl, pivaloyl, and benzoyl, and C2-C8 heteroacyl groups, which include methoxyacetyl, ethoxycarbonyl, and 4-pyridinoyl. The hydrocarbyl groups, aryl groups, and heteroforms of such groups that comprise an acyl or heteroacyl group can be substituted with the substituents described herein as generally suitable substituents for each of the corresponding component of the acyl or heteroacyl group.

"Aromatic" moiety or "aryl" moiety refers to a monocyclic or fused bicyclic moiety having the well-known characteristics of aromaticity; examples include phenyl and naphthyl. Similarly, "heteroaromatic" and "heteroaryl" refer to such monocyclic or fused bicyclic ring systems which contain as ring members one or more heteroatoms selected from O, S and N. The inclusion of a heteroatom permits aromaticity in 5-membered rings as well as 6-membered rings.

Typical heteroaromatic systems include monocyclic C5-C6 aromatic groups such as pyridyl, pyrimidyl, pyrazinyl, pyridazinyl, triazinyl, thienyl, furanyl, pyrrolyl, pyrazolyl, thiazolyl, isothiazolyl, oxazolyl, isoxazolyl, imidazolyl, triazolyl, thiadiazolyl, oxadiazolyl, and tetrazolyl rings, and the fused bicyclic moieties formed by fusing one of these monocyclic groups with a phenyl ring or with any of the heteroaromatic monocyclic groups to form a C8-C12 bicyclic group such as indolyl, benzimidazolyl, indazolyl, benzotriazolyl, isoquinolinyl, quinolinyl, benzothiazolyl, benzofuranyl, benzothienyl, benzisoxazolyl, pyrazolopyridyl, quinazolinyl, quinoxalinyl, cinnolinyl, and the like. Any monocyclic or fused ring bicyclic system which has the characteristics of aromaticity in terms of electron distribution throughout the ring system is included in this definition. It also includes bicyclic groups where at least the ring which is directly attached to the remainder of the molecule has the characteristics of aromaticity, even though it may be fused to a non-aromatic ring, such as tetrahydronaphthyl, indanyl, fluorenyl, and the like. Typically, the ring systems contain 5-12 ring member atoms. Preferably the monocyclic heteroaryl groups contain 5-6 ring members, and the bicyclic heteroaryls contain 8-12 ring members.

Aryl and heteroaryl moieties may be optionally substituted with a variety of substituents including C1-C8 alkyl, C2-C8 alkenyl, C2-C8 alkynyl, C5-C12 aryl, C1-C8 acyl, and heteroforms of these, each of which can itself be further substituted; other substituents for aryl and heteroaryl moieties include halo, OR, NR$_2$, SR, SO$_2$R, SO$_2$NR$_2$, NRSO$_2$R, NRCONR$_2$, NRCOOR, NRCOR, CN, COOR, CONR$_2$, OOCR, —C(O)R, and NO$_2$, wherein each R is independently H, C1-C8 alkyl, C2-C8 heteroalkyl, C2-C8 alkenyl, C2-C8 heteroalkenyl, C2-C8 alkynyl, C2-C8 heteroalkynyl, C5-C12 aryl, C5-C12 heteroaryl, C5-C21 arylalkyl, or C5-C21 heteroarylalkyl, and each R is optionally substituted as described above for alkyl groups.

Preferred optional substituents when present on an aryl or heteroaryl ring include optionally halogenated alkyl (C1-C4), optionally halogenated alkoxy (C1-C4), halo, —NH$_2$, —OH, —CN, —NO$_2$, and NR$_2$, where each R is independently H or C1-4 alkyl.

The substituent groups on an aryl or heteroaryl group may of course be further substituted with the groups described herein as suitable for each type of group that comprises the substituent. Thus, for example, an arylalkyl substituent may be optionally substituted on the aryl portion with substituents described herein as typical for aryl groups, and it may be further substituted on the alkyl portion with substituents described herein as typical or suitable for alkyl groups.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is C1-C8 alkyl or a hetero form thereof. These linkers may also include a carbonyl group, thus making them able to provide substituents as an acyl or heteroacyl moiety.

An aryl or heteroaryl ring in an arylalkyl or heteroarylalkyl group may be optionally substituted with the same substituents described above for aryl groups. Preferably, an arylalkyl group includes a phenyl ring optionally substituted with the groups defined above for aryl groups and a C1-C8 alkylene that is unsubstituted or is substituted with one or two C1-C4 alkyl groups or heteroalkyl groups, where the alkyl or heteroalkyl groups can optionally cyclize to form a ring such as cyclopropane, dioxolane, or oxacyclopentane.

Similarly, a heteroarylalkyl group preferably includes a C5-C6 monocyclic heteroaryl group that is optionally substituted with the groups described above as substituents typical on aryl groups and a C1-C8 alkylene that is unsubstituted or is substituted with one or two C1-C4 alkyl groups or heteroalkyl groups, or it includes an optionally substituted phenyl ring or C5-C6 monocyclic heteroaryl and a C1-C8 heteroalkylene that is unsubstituted or is substituted with one or two C1-C4 alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —(CH$_2$)$_m$— where m is 1-14 and preferably m is 1-8, though where specified, an alkylene can also be substituted by other groups, and can be of other lengths, and the open valences need not be at opposite ends of a chain. Thus —CH(Me)- and —C(Me)$_2$- may also be referred to as alkylenes, as can a cyclic group such as cyclopropan-1,1-diyl. However, for clarity, a three-atom linker that is an alkylene group, for example, refers to a divalent group in which the available valences for attachment to other groups are separated by three atoms such as —(CH$_2$)$_3$—, i.e., the specified length represents the number of atoms linking the attachment points rather than the total number of atoms in the hydrocarbyl group: —C(Me)$_2$- would thus be a one-atom linker, since the available valences are separated by only one atom. Where an alkylene group is substituted, the substituents include those typically present on alkyl groups as described herein. Thus, —C(=O)— is an example of a one-carbon substituted alkylene. Where it is described as unsaturated, the alkylene group may contain one or more double or triple bonds, and may be referred to as alkenylene group if it contains at least one carbon-carbon double bond, or as an alkynylene group if it contains at least one carbon-carbon triple bond.

"Heteroalkylene" as used herein is defined similarly to the corresponding alkylene groups, but the 'hetero' terms refer to groups that contain one or more heteroatoms selected from O, S and N and combinations thereof, within the backbone residue; thus at least one carbon atom of a corresponding alkylene group is replaced by one of the specified heteroatoms to form a heteroalkylene group. Thus, —C(=O)NH— is an example of a two-carbon substituted heteroalkylene, where N replaces one carbon, and C is substituted with a =O group.

"Arylene" as used herein refers to divalent or trivalent aromatic or heteroaromatic ring systems that are bonded to their attachment points through a bond, for example, a phenylene moiety.

"Arylalkylene" as used herein refers to divalent or trivalent aromatic and heteroaromatic ring systems (sometimes referred to as "heterarylalkylene") which are bonded to their attachment points through alkylene linking groups, including substituted or unsubstituted, saturated or unsaturated, cyclic and acyclic linking groups. In some embodiments, the alkylene linking group is unsaturated, and may be referred to as arylalkenylene group if it contains at least one carbon-carbon double bond, or as an arylalkynylene group if it contains at least one carbon-carbon triple bond. Typically the alkylene linker is a C1-C8 alkylene or a heteroform thereof. Frequently, the aromatic or heteroaromatic group is attached to two C1-C8 alkylene linkers, each of which acts as a point of attachment to the remainder of the molecule, for example, a group of the formula and —CH$_2$—Ar—CH$_2$— or —(CH$_2$)$_q$—Ar—(CH$_2$)$_q$, where q is 1-8 and Ar represents an aromatic or heteroaromatic ring. These linkers may also include a carbonyl group, thus making them able to provide substituents such as an acyl or heteroacyl moiety. For example, —(CH$_2$)$_2$C(O)—Ar—C(O)(CH$_2$)$_2$— —C(O)—Ar—C(O)—, and —C(O)—Ar—CH$_2$— are examples of arylalkylene groups substituted with a carbonyl group.

"Heteroarylalkylene" as used herein is defined similarly to the corresponding arylalkylene group, but contains one or more heteroatoms, selected from O, S and N and combinations thereof, within the alkylene residue or the aromatic ring; thus at least one carbon atom of a corresponding alkylene group or one carbon atom of the aromatic ring is replaced by one of the specified heteroatoms to form a heteroarylalkylene group. For example, —(CH$_2$)$_2$NHC(O)—Ar—C(O)NH ((CH$_2$)$_2$— and —CH$_2$-pyridyl-CH$_2$— are examples of heteroarylalkylene groups.

In general, any alkyl, alkenyl, alkynyl, acyl, or aryl or arylalkyl group or any heteroform of one of these groups that is contained in a substituent may itself be optionally substituted by additional substituents. The nature of these substituents is similar to those recited with regard to the primary substituents themselves if the substituents are not otherwise described. Thus, where an embodiment of, for example, R'" is alkyl, this alkyl may optionally be substituted by the remaining substituents listed as embodiments for R'" where this makes chemical sense, and where this does not undermine the size limit provided for the alkyl per se; e.g., alkyl substituted by alkyl or by alkenyl would simply extend the upper limit of carbon atoms for these embodiments, and is not intended to be included. However, alkyl substituted by halo, aryl, heteroaryl, amino, hydroxy, alkoxy (C1-C4 alkyl), =O, =S, and the like would be included within the scope of the invention, and the atoms of these substituent groups are not counted in the number used to describe the alkyl, alkenyl, etc. group that is being described.

Where no number of substituents is specified, each such alkyl, alkenyl, alkynyl, acyl, or aryl group may be optionally substituted with a number of substituents according to its available valences and in accord with known principles of chemical stability; in particular, any of these groups may be optionally substituted with fluorine atoms at any or all of the available valences on carbon atoms, for example.

"Heteroform" as used herein refers to a derivative of a group such as an alkyl, aryl, or acyl, wherein at least one carbon atom of the designated carbocyclic group has been replaced by a heteroatom selected from N, O and S. Thus the heteroforms of alkyl, alkenyl, alkynyl, acyl, aryl, and arylalkyl are heteroalkyl, heteroalkenyl, heteroalkynyl, heteroacyl, heteroaryl, and heteroarylalkyl, respectively. It is understood that, unless otherwise specified, no more than two N, O or S atoms are ordinarily connected sequentially, except where an oxo group is attached to N or S to form a nitro or sulfonyl group.

"Optionally substituted" as used herein indicates that the particular group or groups being described may have no non-hydrogen substituents, or the group or groups may have one or more non-hydrogen substituents. If not otherwise specified, the total number of such substituents that may be present is equal to the number of H atoms present on the unsubstituted form of the group being described. Where an optional substituent is attached via a double bond, such as a carbonyl oxygen (=O), the group takes up two available valences, so the total number of substituents that may be included is reduced according to the number of available valences. Optionally substituted compounds may also be referred to herein as "substituted or unsubstituted compounds."

"Halo," as used herein includes fluoro, chloro, bromo and iodo. Fluoro and chloro are often preferred.

"Amino" as used herein refers to $NH_2$, but where an amino is described as "substituted" or "optionally substituted", the term includes NR'R" wherein each R' and R" is independently H, or is an alkyl, alkenyl, alkynyl, acyl, aryl, or arylalkyl group or a heteroform of one of these groups, and each of the alkyl, alkenyl, alkynyl, acyl, aryl, or arylalkyl groups or heteroforms of one of these groups is optionally substituted with the substituents described herein as suitable for the corresponding type of group. The term also includes forms wherein R' and R" are linked together to form a 3-8 membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the terms "carbocycle" or "carbocyclic" refer to a cyclic compound containing only carbon atoms in the ring, whereas the terms "heterocycle" or "heterocyclic" refer to a cyclic compound comprising at least one heteroatom. The carbocyclic and heterocyclic structures encompass compounds having monocyclic, bicyclic or multiple ring systems, and unless otherwise indicated, may be saturated, partially unsaturated or aromatic, and may be optionally substituted with one or more substituent groups suitable for the nature of the ring structure. Typically, carbocyclic and heterocyclic rings contain 3-12 atoms as ring members. Monocyclic carbocyclic and heterocyclic rings typically contain 3-7 atoms as ring members, and bicyclic carbocyclic and heterocyclic rings typically contain 8-12 atoms as ring members.

As used herein, the term "heteroatom" refers to any atom that is not carbon or hydrogen, such as nitrogen, oxygen or sulfur.

As used herein, an 'azacyclic' ring refers to a heterocyclic ring containing at least one nitrogen as a ring member, wherein the azacyclic group is attached to the base molecule through a nitrogen atom of the azacyclic ring. The azacyclic ring may contain 0-2 additional heteroatoms selected from N, O and S as ring members. The azacyclic rings described herein may be saturated or unsaturated, and may be optionally substituted. Preferred substituents when present on an azacyclic ring include, e.g., oxo (C=O), halo, C1-4 alkyl, C1-4 alkoxy. Typically these azacyclic groups are optionally substituted C3-C12 membered rings. In frequent embodiments, the azacyclic ring comprises a 3-8 membered monocyclic or an 8-12 membered fused bicyclic ring systems, which may comprise an aromatic or heteroaromatic ring fused to the nitrogen containing ring.

The term "solvate," as used herein, refers to a complex of variable stoichiometry formed by a solute (by way of example, a compound of Formula (I)-(XII), or a salt thereof, as described herein) and a solvent. Non-limiting examples of a solvent are water (i.e., a hydrate), acetone, methanol, ethanol and acetic acid.

The term "pharmaceutically acceptable," as used herein, refers a material, such as a carrier or diluent, which does not abrogate the biological activity or properties of the compounds described herein. Such materials are administered to an individual without causing undesirable biological effects or interacting in a deleterious manner with any of the components of the composition in which it is contained.

The term "pharmaceutically acceptable salt," as used herein, refers to a formulation of a compound that does not cause significant irritation to an organism to which it is administered and does not abrogate the biological activity and properties of the compounds described herein.

The invention provides dimer and dimer-like compounds that possess two structurally similar binding domains. These binding domains are linked by a linking group, and while similar, the domains need not be identical. In certain embodiments, each binding domain is the same, so the molecule is symmetric about its linking group. In other embodiments, the two binding domains are different. As further described herein for specific embodiments, this linkage can comprise numerous alternatives that can include an optionally substituted alkylene or heteroalkylene chain that may be saturated or unsaturated, an optionally substituted carbocyclic or heterocyclic ring which may be saturated, unsaturated or aromatic, and may also include a combination of cyclic and acyclic features.

The apoptosis-promoting compounds provided herein are sometimes referred to as 'dimers'. These 'dimers' include both symmetrical dimers containing two identical monomeric binding domains, as well as unsymmetrical dimers. Unsymmetrical dimers may contain the same core group which is differentially substituted, or may contain two different core groups attached to the linking group, L, which links the monomeric moieties together. Symmetrical dimers contain two identical monomeric units attached to the linking group, L.

In one aspect, the invention provides a compound of Formula (I):

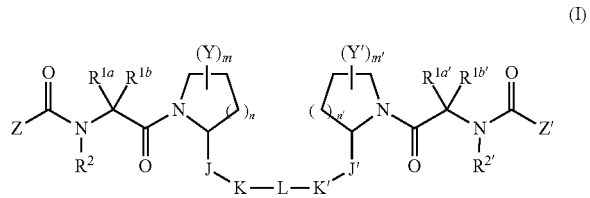

(I)

or a pharmaceutically acceptable salt or hydrate form thereof; and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as a ring member;

each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or $R^{1a}$ and $R^{1b}$, or $R^{1a'}$ and $R^{1b'}$ may be taken together with the carbon atom to which they are attached to form an optionally substituted 3-7 membered ring, optionally containing a heteroatom selected from N, O and S as a ring member;

each $R^2$ and $R^{2'}$ is independently H or optionally substituted C1-C8 alkyl;

each of J and J' is independently —C(O)—, —$CH_2$— or —CHR"—, where R" is C1-C4 alkyl;

each of K and K' is independently selected from the group consisting of —NR'—$(CR^X_2)_p$—NR'—, —NR'—$(CR^X_2)_p$—O—, —O—$(CR^X_2)_p$—NR'—, —O—$(CR^X_2)_p$—O—, —NR'—$(CR^X_2)_p$—S—, —S—$(CR^X_2)_p$—NR', —O—$(CR^X_2)_p$—S—, —S—$(CR^X_2)_p$—O—, and —S—$(CR^X_2)_p$—S—, wherein each R' is independently H or $C_{1-4}$ alkyl, each $R^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8cycloalkyl, or C3-C8heterocyclyl; or two $R^X$ substituents are taken together to form an optionally substituted saturated, unsaturated or aromatic carbocyclic or heterocyclic ring; and each p is independently 2-4;

each n and n' is independently 0-3;

each m and m' is independently 0-4;

each Z and Z' independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In another aspect, the invention provides a compound of Formula (II):

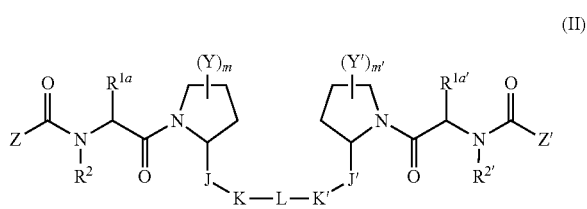

(II)

or a pharmaceutically acceptable salt or hydrate form thereof; and including any stereoisomeric forms thereof;

wherein J, J', L, K, K', $R^{1a}$, $R^{1a'}$, $R^2$, $R^{2'}$, Y, Y', Z, Z', m and m' are defined as for Formula (I).

Compounds of Formula (I) and (II) comprise two binding domains that can be the same or different, and are linked via the moiety represented as —K-L-K'—, where K, K' and L are define as provided herein, where K and K' may be the same or different. In frequent embodiments, K and K' are the same. In other embodiments, they are different.

In some embodiments of Formula (I), each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted.

In certain preferred embodiments, $R^{1b}$ and $R^{1b'}$ are both H. In other preferred embodiments, each of $R^{1a}$ and $R^{1a'}$ is C1-C8 alkyl, preferably C1-C4 alkyl. In frequent embodiments, $R^{1a}$ and/or $R^{1a'}$ are methyl, ethyl, propyl, isopropyl, n-butyl, sec-butyl, isobutyl or tert-butyl.

In other embodiments of Formula (I), $R^{1a}$ and $R^{1b}$ or $R^{1a'}$ and $R^{1b'}$ may be taken together with the carbon atom to which they are attached to form an optionally substituted 3-7 membered ring, optionally containing a heteroatom selected from N, O and S as a ring member.

In compounds of Formula (I), each n and n' is independently 0-3, such that the nitrogen-containing ring which forms the core of the binding domain is a substituted azetidine, pyrrolidine, piperidine or homopiperidine ring.

In some embodiments of Formula (I) and (II), the core ring of the binding domain is optionally substituted by up to four groups designated as $(Y)_m$ or $(Y')_{m'}$, where m and m' are independently 0-4. When present, each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group. In frequent embodiments, m and m' are independently 0 or 1. In certain preferred embodiments, both m and m' are 0. In other preferred embodiments, both m and m' are 1.

In other embodiments of Formula (I) and (II), two Y or Y' groups on the same or adjacent atoms can cyclize to form an optionally substituted 3-7 membered ring that can be saturated, unsaturated or aromatic, and which ring may include one or more heteroatoms selected from O, S and N as a ring member. In some such embodiments, two Y groups or Y' groups on adjacent atoms can cyclize to form an optionally substituted phenyl ring fused to the core nitrogen-containing ring, so that one or both of the binding domains comprises a fused ring system, such as an optionally substituted indoline, isoindoline, tetrahydroquinoline or tetrahydroisoquinoline ring, for example.

In compounds of Formula (I) and (II), each $R^2$ and $R^{2'}$ is independently H or optionally substituted C1-C4 alkyl. In frequent embodiments, each of $R^2$ and $R^{2'}$ is H or methyl; preferably, each of $R^2$ and $R^{2'}$ is H.

In compounds of Formula (I) and (II), each of J and J' is independently —C(O)—, —CH$_2$— or —CHR"—, where R" is C1-C4 alkyl. In certain preferred embodiments, each of J and J' is —C(O)—. In other preferred embodiments, each of J and J' is —CH$_2$—.

In compounds of the formula (I)-(V), each of K and K' (where present) independently comprises a diamine, aminoalcohol, diol, aminothiol, dithiol, or mercaptoalcohol moiety, wherein the N, O and S atoms of the amino, alcohol, and/or thiol groups, respectively, form the point(s) of attachment to the binding domain via the group J or J' on the one hand, and the linker, L, on the other hand. For example, when K comprises a diamino moiety, one of the amino groups is attached to J and the other is attached to L. Suitable diamine, aminoalcohol, diol, aminothiol, dithiol, or mercaptoalcohol moieties include 1,2-diamines, 1,2-aminoalcohols, 1,2-diols, 1,2-aminothiols, 1,2-dithiols, or 1,2-mercaptoalcohols, 1,3-diamines, 1,3-aminoalcohols, 1,3-diols, 1,3-aminothiols, 1,3-dithiols, or 1,3-mercaptoalcohols, and 1,4-diamines, 1,4-aminoalcohols, 1,4-diols, 1,4-aminothiols, 1,4-dithiols, or 1,4-mercaptoalcohols. These moieties may be cyclic or acyclic and may be optionally substituted.

In compounds of formula (I) and (II), each of K and K' can be independently selected from the group consisting of —NR'—(CR$^X$$_2$)$_p$—NR'—, —NR'—(CR$^X$$_2$)$_p$—O—, —O—(CR$^X$$_2$)$_p$—NR'—, —O—(CR$^X$$_2$)$_p$—O—, —NR'—(CR$^X$$_2$)$_p$—S—, —S—(CR$^X$$_2$)$_p$—NR'—, —O—(CR$^X$$_2$)$_p$—S—, —S—(CR$^X$$_2$)$_p$—O—, and —S—(CR$^X$$_2$)$_p$—S—, wherein each R' is independently H or C$_{1-4}$ alkyl; each R$^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or wherein two R$^X$ substituents are taken together to form an optionally substituted saturated, unsaturated or aromatic carbocyclic or heterocyclic ring; and each p is independently 2-4.

In compounds of Formula (I) and (II), each Z and Z' independently represents an optionally substituted C1-C6 aminoalkyl group. In some embodiments, Z and/or Z' can be a 1-aminoalkyl group. For example, Z and/or Z' can be a 1-aminoalkyl group such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. In a typical embodiment, each of Z and Z' is 1-aminopropyl, or 1-aminoethyl, or aminomethyl, or 1-methylaminopropyl, or 1-methylaminoethyl, or methylaminomethyl. Alternatively, Z or Z' can be 1-ethylaminomethyl or 1-ethylaminoethyl. In certain embodiments, Z and Z' are the same. Where Z or Z' has a chiral center adjacent to the carbonyl to which it is connected, the chiral center may have either the (R) or the (S) configuration. For specific embodiments, it is sometimes preferably in the (S) absolute configuration.

In certain embodiments, Z and/or Z' represent a group of the formula —CH(R$^3$)NR$^4$$_2$, where R$^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and each R$^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group. In specific preferred embodiments, each of R$^3$ and R$^4$ is independently selected from H and C1-C4 alkyl. In certain preferred embodiments, R$^3$ is C1-C4 alkyl, one R$^4$ is H and the other R$^4$ is C1-C4 alkyl. In other preferred embodiments, R$^3$ is C1-4 alkyl substituted by hydroxyl; for example, in some embodiments, R$^3$ is —CH$_2$OH. In some such embodiments, each R$^4$ is independently selected from H and C1-C4 alkyl.

In compounds of Formulae (I)-(V), L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

It will be apparent to one of skill in the art that the linking group, L, as described for any of the formulae presented herein, may itself be symmetrical or unsymmetrical. By way of example only, unsymmetrical linking groups, L, include, e.g., -Phenyl-CH$_2$— and —C(O)—CH$_2$—; examples of symmetrical linking groups, L, include, e.g., —C(O)—(CH$_2$)$_4$—C(O)—, —C(O)-phenyl-C(O)—, —(CH$_2$)$_6$— and —CH$_2$—C≡C—C≡C—CH$_2$—.

In another aspect, the invention provides a compound of Formula (III):

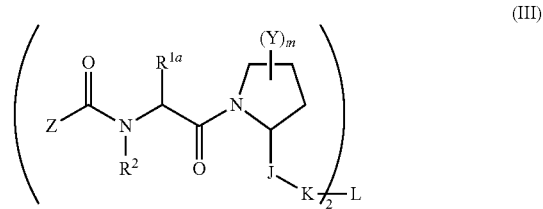

(III)

or a pharmaceutically acceptable salt or hydrate form thereof; and including any stereoisomeric forms thereof;

wherein J, L, K, $R^{1a}$, $R^2$, Y, Z, and m are defined as for Formula (I).

In a further aspect, the invention provides a compound of formula (IV):

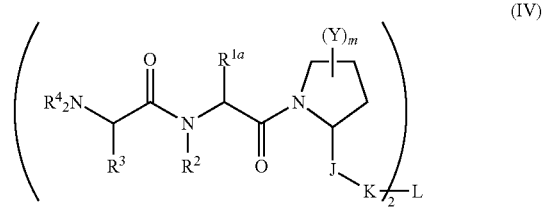

(IV)

or a pharmaceutically acceptable salt or hydrate form thereof; and including any stereoisomeric forms thereof;

wherein each Y represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as a ring member;

R$^{1a}$ is H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted;

R$^2$ is H or optionally substituted C1-C8 alkyl;

J is —C(O)—, —CH$_2$— or —CHR''—, where R'' is C1-C4 alkyl;

K is selected from the group consisting of —NR'—(CR$^X_2$)$_p$—NR'—, —NR'—(CR$^X_2$)$_p$—O—, —O—(CR$^X_2$)$_p$—NR'—, —O—(CR$^X_2$)$_p$—O—, —NR'—(CR$^X_2$)$_p$—S—, —S—(CR$^X_2$)$_p$—NR', —O—(CR$^X_2$)$_p$—S—, —S—(CR$^X_2$)$_p$—O—, and —S—(CR$^X_2$)$_p$—S—, wherein each R' is independently H or C$_{1-4}$ alkyl;

each R$^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or two R$^X$ substituents are taken together to form an optionally substituted saturated, unsaturated or aromatic carbocyclic or heterocyclic ring; and each p is independently 2-4;

m is 0-4;

R$^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group;

each R$^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of Formula (IV), the compound has the structure of Formula (IV-A) or (IV-B):

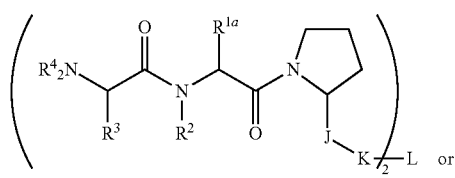

(IV-A)

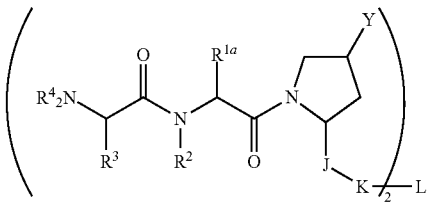

(IV-B)

or a pharmaceutically acceptable salt or hydrate form thereof; and including any stereoisomeric forms thereof;

wherein J, K, L, R$^{1a}$, R$^2$, R$^3$, R$^4$ and Y are defined as for Formula (IV).

In a further aspect, the invention provides a compound of formula (V):

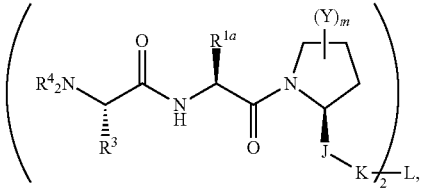

(V)

or a pharmaceutically acceptable salt or hydrate form thereof; and including any stereoisomeric forms thereof;

wherein each Y represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as a ring member;

R$^{1a}$ is H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted;

J is —C(O)—, —CH$_2$— or —CHR''—, where R'' is C1-C4 alkyl;

K is selected from the group consisting of —NR'—(CR$^X_2$)$_p$—NR'—, —NR'—(CR$^X_2$)$_p$—O—, —O—(CR$^X_2$)$_p$—NR'—, —O—(CR$^X_2$)$_p$—O—, —NR'—(CR$^X_2$)$_p$—S—, —S—(CR$^X_2$)$_p$—NR', —O—(CR$^X_2$)$_p$—S—, —S—(CR$^X_2$)$_p$—O—, and —S—(CR$^X_2$)$_p$—S—, wherein each R' is independently H or C$_{1-4}$ alkyl;

each R$^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or two R$^X$ substituents are taken together to form an optionally substituted saturated, unsaturated or aromatic carbocyclic or heterocyclic ring; and each p is independently 2-4;

m is 0-4;

$R^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group;

each $R^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of Formula (V), the compound has the structure of Formula (V-A) of (V-B):

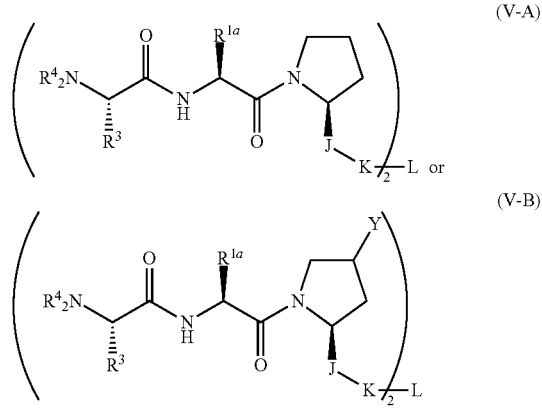

or a pharmaceutically acceptable salt or hydrate form thereof;

wherein J, K, L, $R^{1a}$, $R^3$, $R^4$ and Y are defined as for Formula (V).

In compounds of Formula (III), Z represents an optionally substituted C1-C6 aminoalkyl group. In frequent embodiments, Z is a 1-aminoalkyl group. For example, Z can be a 1-aminoalkyl group such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. In a typical embodiment, Z is 1-aminopropyl, or 1-aminoethyl, or aminomethyl, or 1-methylaminopropyl, or 1-methylaminoethyl, or methylaminomethyl. Alternatively, Z can be 1-ethylaminomethyl or 1-ethylaminoethyl. Where Z has a chiral center adjacent to the carbonyl to which it is connected, the chiral center may have either the (R)- or the (S)-configuration. For specific embodiments, it is sometimes preferably in the (S)-configuration.

In certain embodiments of Formula (III), Z represents a group of the formula $CH(R^3)NR^4_2$, where $R^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and each $R^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group. In specific preferred embodiments, each of $R^3$ and $R^4$ is independently selected from H and C1-C4 alkyl. In certain preferred embodiments, $R^3$ is C1-C4 alkyl, one $R^4$ is H and the other $R^4$ is C1-C4 alkyl. In other preferred embodiments, $R^3$ is C1-4 alkyl substituted by hydroxyl; for example, in some embodiments, $R^3$ is —$CH_2OH$. In some such embodiments, each $R^4$ is independently selected from H and C1-C4 alkyl.

In compounds of Formula (III) and (IV), $R^2$ is H or optionally substituted C1-C4 alkyl. In frequent embodiments, $R^2$ is H or methyl; preferably, each of $R^2$ is H.

In compounds of Formulae (III)-(V), $R^{1a}$ is H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted. In certain embodiments, $R^{1a}$ is C1-C8 alkyl, preferably C1-C4 alkyl. In frequent embodiments, $R^{1a}$ is methyl, ethyl, propyl, isopropyl, n-butyl, sec-butyl, isobutyl or tert-butyl.

In some embodiments of Formulae (III)-(V), the pyrrolidine ring of the binding domain may be substituted by up to four groups designated as $(Y)_m$, where m is 0-4. When present, each Y represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, $NRC(O)NR_2$, $NRSO_2R$, CN, $C(O)NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group. In frequent embodiments, m is 0 or 1. In certain preferred embodiments, m is 0. In other preferred embodiments, m is 1.

In other embodiments of Formulae (III)-(V), two Y groups on the same or adjacent atoms can cyclize to form an optionally substituted 3-7 membered ring that can be saturated, unsaturated or aromatic, and which ring may include one or more heteroatoms selected from O, S and N as a ring member. In some such embodiments, two Y groups on adjacent atoms can cyclize to form an optionally substituted phenyl ring fused to the core nitrogen-containing ring, so that one or both of the binding domains comprises a fused ring system, such as an optionally substituted indoline, isoindoline, tetrahydroquinoline or tetrahydroisoquinoline ring, for example.

In compounds of Formulae (III)-(V), J is —C(O)—, —$CH_2$— or —CHR"—, where R" is C1-C4 alkyl. In certain preferred embodiments, J is —C(O)—. In other preferred embodiments, J is —$CH_2$—.

In compounds of Formulae (III)-(V), K is selected from the group consisting of —NR'—$(CR^X_2)_p$—NR'—, —NR'—$(CR^X_2)_p$—O—, —O—$(CR^X_2)_p$—NR'—, —O—$(CR^X_2)_p$—O—, —NR'—$(CR^X_2)_p$—S—, —S—$(CR^X_2)_p$—NR', —O—$(CR^X_2)_p$—S—, —S—$(CR^X_2)_p$—O—, and —S—$(CR^X_2)_p$—S—, wherein each R' is independently H or $C_{1-4}$ alkyl; each $R^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or wherein two $R^X$ substituents are taken together to form an optionally substituted saturated, unsaturated or aromatic carbocyclic or heterocyclic ring; and each p is independently 2-4.

In compounds of Formula (IV) and (V), the group referred to as Z in formulae (I)-(III) is replaced by a group of the formula —$CH(R^3)NR^4_2$, where $R^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and each $R^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group. In specific preferred embodiments, each of $R^3$ and $R^4$ is independently selected from H and C1-C4 alkyl. In certain preferred embodiments, $R^3$ is C1-C4 alkyl, one $R^4$ is H and the other $R^4$ is C1-C4 alkyl. In a particularly preferred embodiment, $R^3$ is methyl, one $R^4$ is H and the other $R^4$ is methyl. In other preferred embodiments, $R^3$ is C1-4 alkyl substituted by hydroxyl; for example, in some embodiments, $R^3$ is —CH₂OH. In some such embodiments, each $R^4$ is independently selected from H and C1-C4 alkyl.

In some embodiments, the group represented as —CH($R^3$)$NR^4_2$ is a 1-aminopropyl, 1-aminoethyl, aminomethyl, 1-methylaminopropyl, 1-methylaminoethyl, methylaminomethyl, 1-ethylaminomethyl or 1-ethylaminoethyl. The carbon atom bearing the substituent $R^3$ has a chiral center when $R^3$ is not H. The chiral center may have either the (R)- or the (S)-configuration, and it is sometimes preferably in the (S)-configuration.

It will be understood that compounds of formula (I) include compounds of formulae (II), (III), (IV) and (V); that compounds of formula (IV) include compounds of formulae (IV-A) and (IV-B); and that compounds of formula (V) include compounds of formulae (V-A) and (V-B).

In some embodiments of Formulae (I)-(V) disclosed herein, each of K and K' (where present) represents a 1,2-aminoalcohol or 1,2-diamino moiety having the structure:

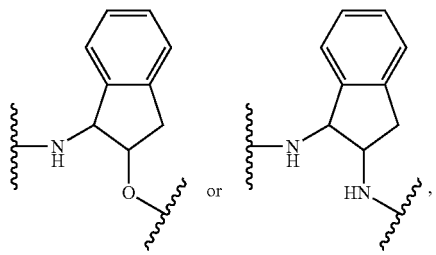 [SMILES: *NC1c2ccccc2CC1O* ; "or" ; *NC1Cc2ccccc2C1N* ; ","]

and including any stereoisomeric forms thereof.

In some such embodiments, each of K and K' (where present) is selected from the group consisting of:

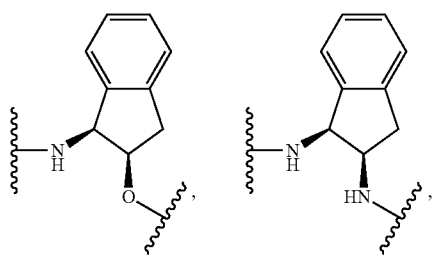

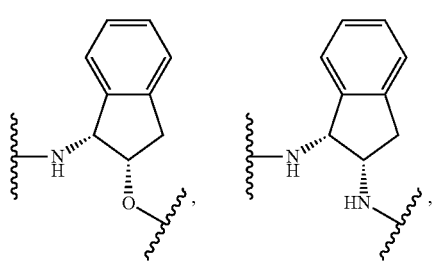

-continued

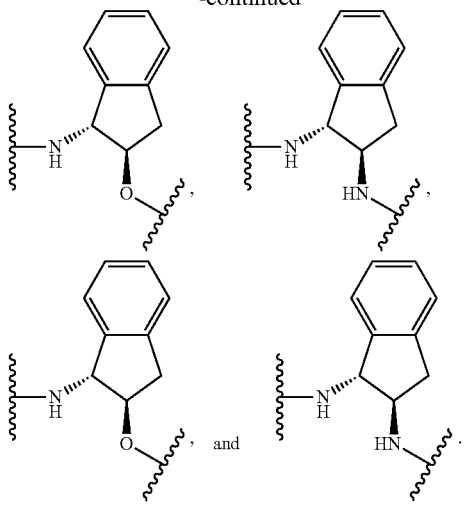

In certain embodiments of Formulae (I)-(V), K and K' (where present) exclude the following groups:

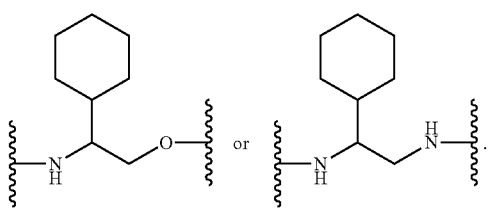 [SMILES: *NC(CO*)C1CCCCC1 ; *NCC(N*)C1CCCCC1]

In compounds of Formulae (I)-(V), L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of Formulae (I)-(V), L is an optionally substituted and/or unsaturated C1-C14 alkylene or C1-C14 heteroalkylene. For example, L may represent a C1-C14 alkylene, C1-C14 alkenylene, C1-C14 alkynylene linker, or a heteroform of one of these, each of which may be optionally substituted. In some such embodiments, L comprises a saturated, partially unsaturated or aromatic carbocyclic or heterocyclic ring that forms part of the path between two K and/or K' groups. In frequent embodiments, L is substituted with one or more carbonyl substituents (=O), to form a linker comprising one or more acyl groups.

In certain embodiments described for any of the formulae herein, L is symmetric about its central atom (if the chain connecting the two available valences is an odd number of atoms in length) or its central bond (if the chain connecting the two available valences is an even number of atoms in length). In some embodiments of Formulae I-V, L is 2-8 atoms in length, counting along the shortest path between two K groups or between K and K'. In certain embodiments, L can also include one or more heteroatoms selected from N, O and S, but does not include a disulfide linkage.

Where L comprises a ring, the ring(s) may be cycloalkyl, heterocyclyl, aryl, or heteroaryl, and may be further substituted. In some embodiments of Formulae I-V, such rings may be directly attached to K and/or K' or may be attached to K and/or K' through a C1-C8 alkylene or heteroalkylene group. Frequently, the ring which is part of L is substituted by carboxy groups which form the point of attachment to K and/or K', such that an ester or amide linkage is formed by the bond between K/K' and L.

In certain embodiments, L comprises an optionally substituted 5- or 6-membered aromatic or heteroaromatic ring. In specific embodiments, L comprises at least one optionally substituted phenyl, pyridyl, pyrazole or triazole ring. Such rings may be 1,2-disubstituted, or 1,3-disubstituted, or 1,4-disubstituted, by the groups K and K', which may be directly attached to the ring or may be separated from the ring by one or more atoms that are included in L, for example by a C1-C8 alkylene or heteroalkylene group.

Rings which comprise part of the linker, L, may be optionally substituted to the extent such substitution makes chemical sense. Preferred optional substituents when present on a ring which comprises part of L include alkyl (C1-C4), alkoxy (C1-C4), —CF3, —OCF3, halo, —OH, —NO2, —CN, or NRY2, where each RY is independently H or C1-C4 alkyl.

In certain embodiments, L comprises an optionally substituted arylene or arylalkylene group, or a heteroform of one of these, to which K and K' are directly or indirectly attached. For example, L can be —CH2-Ar—CH2-, —C(O)—Ar—C(O)—, —SO2-Ar—SO2-, —C(O)—Ar— or —Ar—, where Ar represents an optionally substituted 5- or 6-membered aromatic or heteroaromatic ring. In some embodiments, L comprises a phenyl ring that may be 1,2-disubstituted, or 1,3-disubstituted, or 1,4-disubstituted by the groups K and/or K', which may be directly or indirectly attached to the ring. In other embodiments, L comprises an optionally substituted 5- or 6-membered heteroaryl ring, which may contain from 1-4 heteroatoms selected from N, O and S as a ring member. In further embodiments, L comprises an optionally substituted C3-C10 cycloalkylene ring.

Embodiments of L described herein for compounds of formula I-V are also suitable for compounds of formulae VI-XII.

In another aspect, the invention provides a compound of formula (VI):

(VI)

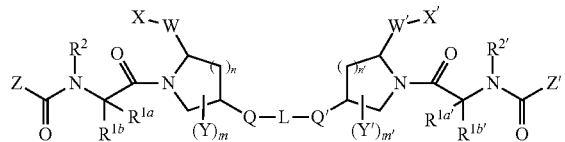

or a pharmaceutically acceptable salt or hydrate form thereof; and including any stereoisomeric forms thereof;

wherein each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as a ring member;

each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or $R^{1a}$ and $R^{1b}$, or $R^{1a'}$ and $R^{1b'}$ may be taken together with the carbon atom to which they are attached to form an optionally substituted 3-7 membered ring, optionally containing a heteroatom selected from N, O and S as a ring member;

each $R^2$ and $R^{2'}$ is independently H or optionally substituted C1-C8 alkyl;

each W and W' is independently an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each Q and Q' independently represents —O—, —S— or —$NR^5$—, where each $R^5$ is independently H, or optionally substituted C1-C8 alkyl, or optionally substituted C1-C8 heteroalkyl; or one or both of Q and Q' may be a bond when L comprises a ring;

each n and n' is independently 0-3;

each m and m' is independently 0-4;

each Z and Z' independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In another aspect, the invention provides a compound of formula (VII):

(VII)

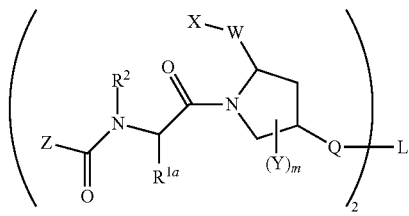

or a pharmaceutically acceptable salt or hydrate form thereof; and including any stereoisomeric forms thereof;

wherein each Y independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as a ring member;

$R^{1a}$ is H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted;

$R^2$ is H or optionally substituted C1-C8 alkyl;

W is an optionally substituted C1-C6 alkylene or C1-C6 heteroalkylene; or W can be a bond where X comprises an optionally substituted C5-C6 aryl or heteroaryl ring;

each X is an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W;

Q represents —O—, —S— or —$NR^5$—, where each $R^5$ is independently H, or optionally substituted C1-C8 alkyl, or optionally substituted C1-C8 heteroalkyl; or Q may be a bond when L comprises a ring;

m is 0-4;

Z represents an optionally substituted C1-C6 aminoalkyl group; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In compounds of formula (VI), each Q and Q' independently represents —O—, —S— or —$NR^5$—, where each $R^5$ is independently H, or a C1-C4 alkyl. In some embodiments of formula (VI), Q and Q' are the same. In specific embodiments of formula (VI), each of Q and Q' is —NH—. In other embodiments, each Q and Q' may independently represent a bond when L comprises a ring. In specific embodiments, each Q and Q' independently represents a bond when L comprises at least one phenyl, pyridine, pyrazole or triazole ring.

In compounds of formula (VII), Q represents —O—, —S— or —$NR^5$—, where each $R^5$ is independently H, or a C1-C4 alkyl. In specific embodiments of formula (VII), each Q is —NH—. In other embodiments, each Q represents a bond when L comprises a ring. In specific embodiments, each Q represents a bond when L comprises at least one phenyl, pyridine, pyrazole or triazole ring.

In compounds of formula (VI), n and n' can independently be 0-3, and in some embodiments n and n' are the same. In certain embodiments, n and n' are each selected from 1 and 2 and can be the same or different; in specific embodiments, n and n' are both 1.

In compounds of formula (VI) and (VII), each of $(Y)_m$ and $(Y')_{m'}$, where present, represents one or more substituents optionally present on the nitrogen-containing ring, and each of m and m' is 0-4. In compounds of formula (VI), each of the nitrogen-containing core rings may be differently substituted. In some such embodiments, each Y and/or Y' is independently selected from the substituents described herein as suitable for alkyl groups. For example, each Y and/or Y' may independently represent C1-C8 alkyl, =O, OR, $NR_2$, OC(O)R, NRC(O)R, $NRSO_2R$ or COOR, wherein each R is independently H, C1-C8 alkyl or C1-C8 heteroalkyl. In certain embodiments, two Y or Y" groups on a single nitrogen-containing core ring groups may cyclize to form a saturated, unsaturated or aromatic ring having 3-6 ring members and optionally containing one or more heteroatoms (N, O or S) as a ring member, and such ring embodiments may be optionally substituted with suitable substituents as described herein.

In certain embodiments of formula (VI), m and m' are the same. In many embodiments of formula (VI), each of m and m' is either 0 or 1. Specific embodiments include m=m'=1 and m=m'=0. In some embodiments where m and m' are 1, each of Y and Y' are the same. In certain embodiments of formula (VII), m is 0 or 1. In some embodiments, m is 0. In other embodiments, m is 1.

In some embodiments of formula (VI), each of $R^{1a}$, $R^{1b}$, $R^{1a'}$ and $R^{1b'}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted. In some such embodiments, one of and $R^{1b}$ is H, and the other is C1-C4 alkyl, C2-C4 alkenyl, C2-C4 alkynyl and one of $R^{1a'}$ and $R^{1b'}$ is H, and the other is C1-C4 alkyl, C2-C4 alkenyl, or C2-C4 alkynyl.

In some embodiments of formula (VI), $R^{1a}$ and $R^{1b}$, or $R^{1a'}$ and $R^{1b'}$ may be taken together with the carbon atom to which they are attached to form an optionally substituted 3-7 membered ring, optionally containing a heteroatom selected from N, O and S as a ring member.

In some embodiments of formula (VII), each of is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted. In some such embodiments, is C1-C4 alkyl, C2-C4 alkenyl, C2-C4 alkynyl. In certain embodiments, is selected from methyl, ethyl, allyl, n-propyl, isopropyl, cyclopropyl, n-butyl, isobutyl, sec-butyl, tert-butyl, propyn-3-yl, cyclohexyl, or phenyl.

For compounds of formula (VI), each $R^2$ and $R^{2'}$ is independently H or optionally substituted C1-C8 alkyl; in preferred embodiments, $R^2$ and $R^{2'}$ are H. For compounds of formula (VII), $R^2$ is H or optionally substituted C1-C8 alkyl; in preferred embodiments, $R^2$ is H.

Each of Z and/or Z' in compounds of formula (VI) or (VII) is independently an optionally substituted C1-C6 aminoalkyl group. This can be a C1-C6 alkyl group that is substituted with at least one amine group and is optionally substituted with one or more other groups suitable as substituents for an alkyl group.

In some embodiments of formula (VI) and (VII), Z represents a group of the formula —$CH(R^3)NR^4_2$, where $R^3$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group; and each $R^4$ is H, or an optionally substituted C1-C8 alkyl, C1-C8 heteroalkyl, C2-C8 alkenyl, C2-C8 heteroalkenyl, C2-C8 alkynyl or C2-C8 heteroalkynyl group. In specific preferred embodiments, each of $R^3$ and $R^4$ is independently selected from H and C1-C4 alkyl. In certain preferred embodiments, $R^3$ is C1-C4 alkyl, one $R^4$ is H and the other $R^4$ is C1-C4 alkyl. In some such embodiments, $R^3$ is H or a C1-C4 alkyl group such as methyl, ethyl, allyl, or propyl. In certain preferred embodiments, each $R^4$ is independently H or a C1-C4 alkyl group, such as methyl, ethyl or propyl. In some preferred embodiments, $R^3$ is a C1-C4 alkyl group, one $R^4$ group is H and the other is C1-C4 alkyl. In other preferred embodiments, $R^3$ is C1-4 alkyl substituted by hydroxyl; for example, in some embodiments, $R^3$ is —$CH_2OH$. In some such embodiments, each $R^4$ is independently selected from H and C1-C4 alkyl. Sometimes, each Z and/or Z' represents a group of the formula —CH(Me)NHMe or —CH($CH_2OH$)NHMe.

In some embodiments of Formula (VI) and (VII), Z and/or Z' can be a 1-aminoalkyl group such as a 1-aminomethyl or 1-aminoethyl or 1-aminopropyl, where the amine group is substituted with one or two optionally substituted C1-C8 alkyl groups, and may also be substituted with a C1-C8 acyl or heteroacyl group. In a typical embodiment, each of Z and/or Z' is 1-aminopropyl, or 1-aminoethyl, or aminomethyl, or 1-methylaminopropyl, or 1-methylaminoethyl, or methylaminomethyl. Alternatively, Z and/or Z' can be 1-ethylaminomethyl or 1-ethylaminoethyl. In certain embodiments of Formula (VI), Z and Z' are the same.

Where Z or Z' has a chiral center adjacent to the carbonyl to which it is connected, the chiral center may have either the (R) or the (S) configuration. For specific embodiments, it is sometimes preferably in the (S) absolute configuration. In specific embodiments, Z and/or Z' is a group of the formula —CH($R^3$)$NR^4_2$, as further described herein.

In some embodiments of formula (VI), each W and W' is independently an optionally substituted C1-C6 alkylene or C1-C6 heteroalkylene linker to which X or X' is attached. In other embodiments of formula (VI), each W and W' independently represents a bond where X and/or X' comprises an optionally substituted C5-C6 aryl or heteroaryl ring.

Each of W and W' in formula (VI) is independently selected, so they can be the same or different. In some embodiments, W and W' are the same; in many embodiments, each of W and W' is substituted with =O.

In some embodiments of formula (VI), each of W and W' may be represented as —C(O)$NR^Z$($CHR^Z$)$_p$—, where each p is 0-2, and each $R^Z$ is independently H, or C1-C4 alkyl or C1-C4 heteroalkyl.

In some embodiments of formula (VI), each of X and X' is an optionally substituted C1-C8 alkyl, C1-C8 heteroalkyl, C3-C10 cycloalkyl, C3-C10 heterocyclyl. In other embodiments, each of X and X' is a C5-C20 ring system comprising at least one aryl or heteroaryl group and up to four heteroatoms selected from N, O and S as a ring member, and can be a single 5-15 membered cyclic group or it can be two 5-10 membered cyclic groups that are both attached to a single atom of W or W'. Each of these cyclic groups can be a single ring, a fused ring system, or linked rings such as a biaryl group. Optionally, each X and X' can be substituted and can include up to four heteroatoms selected from O, N and S. Thus, by way of example, each X and X' can comprise an aryl or heteroaryl ring, which can be monocyclic or bicyclic, provided at least one ring of a bicyclic group is aromatic, or it can represent two 5-10 membered cyclic group provided that at least one of them comprises an aryl or heteroaryl ring.

In some embodiments of formula (VII), W is an optionally substituted C1-C6 alkylene or C1-C6 heteroalkylene linker to which X is attached. In other embodiments of formula (VII), W is a bond where X comprises an optionally substituted C5-C6 aryl or heteroaryl ring.

In many embodiments of formula (VII), W is substituted with =O. In certain embodiments, each of W may be represented as —C(O)$NR^Z$($CHR^Z$)$_p$—, where each p is 0-2, and each $R^Z$ is independently H, or C1-C4 alkyl or C1-C4 heteroalkyl.

In some embodiments of formula (VII), X is an optionally substituted C1-C8 alkyl, C1-C8 heteroalkyl, C3-C10 cycloalkyl, C3-C10 heterocyclyl. In frequent embodiments, each X in compounds of formula (VII) is an optionally substituted C5-C20 ring system comprising at least one aryl or heteroaryl group and up to four heteroatoms selected from N, O and S as a ring member, and can be a single 5-15 membered cyclic group or it can be two 5-10 membered cyclic groups that are both attached to a single atom of W. Each of these cyclic groups can be a single ring, a fused ring system, or linked rings such as a biaryl group. Optionally, each X can be substituted and can include up to four heteroatoms selected from O, N and S. Thus, by way of example, each X can comprise an aryl or heteroaryl ring, which can be monocyclic or bicyclic, provided at least one ring of a bicyclic group is aromatic, or it can represent two 5-10 membered cyclic group, provided that at least one of them comprises an aryl or heteroaryl ring.

In specific embodiments of formula (VI), each X and X' independently comprises an optionally substituted phenyl ring; or two phenyl rings on one atom of W or W', which can be substituted on one or both phenyl rings; or each X and X' can independently comprise a fused ring system having two aromatic rings or having a saturated 5-6 membered ring fused to a 5-6 membered aryl ring, each of which can be substituted on either or both rings. X and X' are independently selected, and may be the same or different. In specific embodiments, X and X' are sometimes the same.

In specific embodiments of formula (VII), X comprises an optionally substituted phenyl ring; or two phenyl rings on one atom of W, which can be substituted on one or both phenyl rings; or each X can comprise a fused ring system having two aromatic rings or having a saturated 5-6 membered ring fused to a 5-6 membered aryl ring, each of which can be substituted on either or both rings.

In compounds of formula (VI) and (VII), when X and/or X' comprises a 5 or 6 membered saturated ring fused to a 5 or 6 membered aryl ring, in some embodiments, X is attached to W (or X' is attached to W') through an atom in the saturated ring. In specific embodiments, each X and/or X' is independently a tetrahydronaphthyl, indanyl or fluorenyl ring system linked to nitrogen of W and/or W' through an open valence on the saturated ring of the tetrahydronaphthyl, indanyl or fluorenyl ring system. In some embodiments of formula (VI) and (VII), X comprises one or two aryl rings, preferably one or two phenyl rings; and each aryl ring is attached to W through a terminal carbon atom of W. For example, in some such embodiments, —W—X comprises an arylalkyl group, such as benzyl, 1-phenylethyl, or diphenylmethyl. In some embodiments of formula (VI), X' comprises one or two aryl rings, preferably one or two phenyl rings; and each aryl ring is attached to W' through a terminal carbon atom of W'. For example, in some embodiments, —W'—X' comprises an arylalkyl group, such as benzyl, 1-phenylethyl, or diphenylmethyl.

The aryl or heteroaryl ring in any of these embodiments may be optionally substituted. Preferred substituents when present on an aryl or heteroaryl ring that is part of X or X' include C1-C4 alkyl, C1-4 heteroalkyl, C1-C4 alkenyl, C1-4 heteroalkenyl, C1-C4 alkynyl, C1-4 heteroalkynyl, OR, $NR_2$, SR, S(O)R, $SO_2R$, C(O)R, C5-12 aryl, C5-12 heteroaryl, C5-12 arylalkyl, C5-12 heteroarylalkyl, and halo, where each R is independently H, or C1-C4 alkyl, C1-C4 heteroalkyl, C5-C12 aryl, C5-C12 heteroaryl, C5-C12 arylalkyl, or C5-C12 heteroarylalkyl, each of which may be further substituted with groups suitable for its structure; and wherein any alkyl or arylalkyl substituent may be optionally fluorinated on the alkyl portion. More preferred substituents when present on an aryl or heteroaryl ring that is part of X include C1-4 alkyl, C1-4 alkoxy, $CF_3$, $OCF_3$, halo, $NO_2$, CN, and $NR_2$, where each R is independently H or C1-4 alkyl.

In particular embodiments of formula (VI), —W—X and W'—X' represent a group of the form —C(O)NR$^Z$(CHR$^Z$)$_p$X or —C(O)NR$^Z$(CHR$^Z$)$_p$X', where each p is 0-2, and each R$^Z$ is independently H or a C1-C8 alkyl group. In certain embodiments, p is 0 or 1, and each R$^Z$ may be H or methyl. In some embodiments of Formula (VI), —W—X and W'—X' are the same, though they can be different. In specific embodiments of Formula (VI), each X and X' independently comprises one or two phenyl groups, or a tetrahydronaphthyl, indanyl or fluorenyl ring system linked to nitrogen of W through an open valence on the saturated ring of the tetrahydronaphthyl, indanyl or fluorenyl ring system.

In particular embodiments of formula (VII), —W—X represents a group of the form C(O)NH(CHR$^Z$)Ph', where R$^Z$ is H or Me, and Ph' is optionally substituted phenyl. In other embodiments, —W—X represents a group of the form —C(O)NHCH(Ph')$_2$, where Ph' is optionally substituted phenyl. In further preferred embodiments of Formula (VII), each X comprises one or two phenyl groups, or a tetrahydronaphthyl, indanyl or fluorenyl ring system linked to nitrogen of W through an open valence on the saturated ring of the tetrahydronaphthyl, indanyl or fluorenyl ring system.

In some embodiments of formula (VI) and (VII), —W—X and/or —W'—X' represents a group of the form —C(O)NH—Ar', where Ar' represents an indanyl, tetrahydronaphthyl or fluorenyl ring system, preferably bonded to the amide nitrogen through one of the atoms in the saturated ring.

In compounds of formula (VI) and (VII), L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of formula (VI) and (VII), L is an optionally substituted and/or unsaturated C1-C14 alkylene or C1-C14 heteroalkylene. For example, L may represent a C1-C14 alkylene, C1-C14 alkenylene, C1-C14 alkynylene linker, or a heteroform of one of these, each of which may be optionally substituted. In some such embodiments, L comprises a saturated, partially unsaturated or aromatic carbocyclic or heterocyclic ring that forms part of the path between two Q and/or Q' groups. In frequent embodiments, L is substituted with one or more carbonyl substituents (=O), to form a linker comprising one or more acyl groups.

In certain embodiments, L is symmetric about its central atom (if the chain connecting the two available valences is an odd number of atoms in length) or its central bond (if the chain connecting the two available valences is an even number of atoms in length). In some embodiments, L is 2-8 atoms in length, counting along the shortest path between two Q groups or between Q and Q'. In certain embodiments, L can also include one or more heteroatoms selected from N, O and S, but does not include a disulfide linkage.

Where L comprises a ring, the ring(s) may be cycloalkyl, heterocyclyl, aryl, or heteroaryl, and may be further substituted. Such rings may be directly attached to Q and/or Q' or may be attached to Q and/or Q' through a C1-C8 alkylene or heteroalkylene group. Frequently, the ring which is part of L is substituted by carboxy groups which form the point of attachment to Q and/or Q', such that an ester or amide linkage is formed by the bond between Q/Q' and L.

In certain embodiments, L comprises an optionally substituted 5- or 6-membered aromatic or heteroaromatic ring. In specific embodiments, L comprises at least one optionally substituted phenyl, pyridyl, pyrazole or triazole ring. Such rings may be 1,2-disubstituted, or 1,3-disubstituted, or 1,4-disubstituted, by the groups Q and Q', which may be directly attached to the ring or may be separated from the ring by one or more atoms that are included in L, for example by a C1-C8 alkylene or heteroalkylene group.

Rings which comprise part of the linker, L, may be optionally substituted to the extent such substitution makes chemical sense. Preferred optional substituents when present on a ring which comprises part of L include alkyl (C1-C4), alkoxy (C1-C4), —CF$_3$, —OCF$_3$, halo, —OH, —NO$_2$, —CN, or NR$^Y_2$, where each R$^Y$ is independently H or C1-C4 alkyl.

In certain embodiments, L comprises an optionally substituted arylene or arylalkylene group, or a heteroform of one of these, to which K and K' are directly or indirectly attached. For example, L can be —CH$_2$—Ar—CH$_2$—, —C(O)—Ar—C(O)—, —SO$_2$—Ar—SO$_2$—, —C(O)—Ar— or —Ar—, where Ar represents an optionally substituted 5- or 6-membered aromatic or heteroaromatic ring. In some embodiments, L comprises a phenyl ring that may be 1,2-disubstituted, or 1,3-disubstituted, or 1,4-disubstituted by the groups Q and/or Q', which may be directly or indirectly attached to the ring. In other embodiments, L comprises an optionally substituted 5- or 6-membered heteroaryl ring, which may contain from 1-4 heteroatoms selected from N, O and S as a ring member. In further embodiments, L comprises an optionally substituted C3-C10 cycloalkylene ring.

In another aspect, the invention provides a compound of formula (VIII):

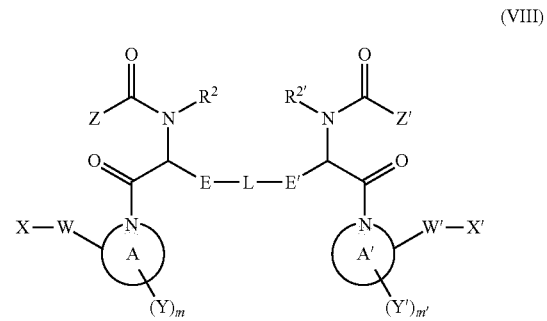

(VIII)

or a pharmaceutically acceptable salt or hydrate form thereof; and including any stereoisomeric forms thereof;

wherein each of ring A and ring A' independently represents a C3-C12 azacyclic ring, each of which may contain 0-2 additional heteroatoms selected from N, O, S as ring members;

wherein each Y and Y' independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as ring members;

each W and W' is independently an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each E and E' independently represents —$CH_2$—, —CH(OR)—, —CH(R)—, —$(CH_2)_r$D-, CH(R)D-, —CR═CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or one or both of E and E' can be a bond where L comprises a ring;

each $R^2$ and $R^{2'}$ is independently H or optionally substituted C1-C8 alkyl;

each m and m' is independently 0-4;

each Z and Z' is independently an optionally substituted C1-C6 aminoalkyl; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In a further aspect, the invention provides a compound of formula (IX):

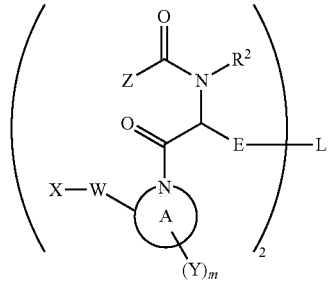

(IX)

or a pharmaceutically acceptable salt or hydrate form thereof; and including any stereoisomeric forms thereof;

wherein ring A represents a C3-C12 azacyclic ring, each of which may contain 0-2 additional heteroatoms selected from N, O, S as ring members;

wherein each Y independently represents an optionally substituted C1-C8 alkyl, C5-C12 aryl, C5-C20 arylalkyl, or a heteroform of one of these; or is ═O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as ring members;

W is an optionally substituted C1-C6 alkylene or C1-C6 heteroalkylene; or W can be a bond where X comprises an optionally substituted C5-C6 aryl or heteroaryl ring;

X is an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W;

each E represents —$CH_2$—, —CH(OR)—, —CH(R)—, —$(CH_2)_r$D-, —CH(R)D-, —CR═CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or one or both of E and E' can be a bond where L comprises a ring;

each $R^2$ is H or optionally substituted C1-C4 alkyl;

m is 0-4;

each Z is an optionally substituted C1-C6 aminoalkyl; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of Formula (VIII) and (IX), each of Ring A and Ring A' is independently selected from the group consisting of

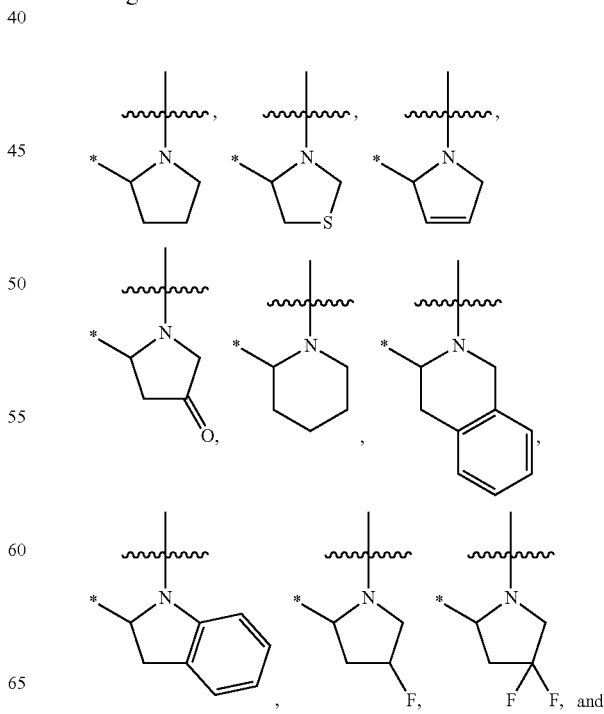

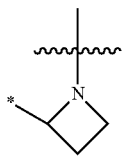

wherein * represents to the point of attachment to W or W' in ring A or Ring A', respectively.

In preferred embodiments of Formula (VIII) and (IX), ring A and ring A' are not both a pyrrolidine of the formula:

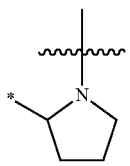 [SMILES: *C1CCCN1*]

In another aspect, the invention provides a compound of formula (X):

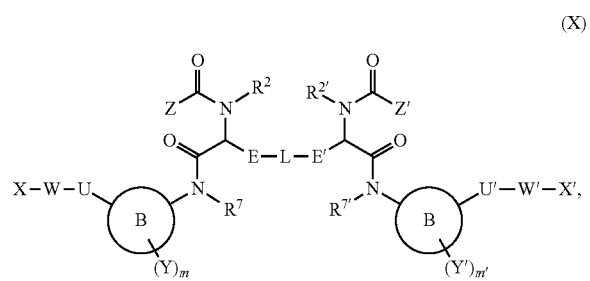

or a pharmaceutically acceptable salt or hydrate form thereof; and including any stereoisomeric forms thereof;

wherein each of ring B and ring B' is independently a C3-C12 carbocyclic ring or a C3-C12 heterocyclic ring containing 1-3 heteroatoms selected from N, O, S as ring members; and wherein each Y and Y' independently represents an optionally substituted C1-C8 alkyl, C5-C12 aryl, C5-C20 arylalkyl, or a heteroform of one of these; or is =O, OR, SR, S(O)R, $SO_2R$, $SO_2NR_2$, $NR_2$, OC(O)R, NRC(O)R, NRCOOR, NRC(O)$NR_2$, $NRSO_2R$, CN, C(O)$NR_2$, C(O)R, COOR, $NO_2$ or halo, wherein each R is independently H, $C_1$-$C_8$ alkyl, C5-C12 aryl or C5-C20 arylalkyl, or a heteroform of one of these each of which may be optionally substituted; or is any other substituent suitable for an alkyl group;

and wherein two Y or Y' groups on the same or adjacent atoms can cyclize to form an optionally substituted 3-7 membered ring that can be saturated, unsaturated or aromatic, and which ring may include one or more heteroatoms selected from O, S and N as ring members;

each U and U' independently represents —$NR^8$—, —O—, or —S(O)$_v$—, wherein each $R^8$ is independently H or C1-C4 alkyl, and v is 0-2;

each W and W' is independently an optionally substituted C1-C6 alkylene or C1-C6 heteroalkylene; or W and/or W' can be a bond where X and/or X' comprises an optionally substituted C5-C6 aryl or heteroaryl ring;

each X and X' is independently an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W';

each E and E' independently represents —$CH_2$—, —CH(OR)—, —CH(R)—, —($CH_2$)$_r$D-, CH(R)D-, or —CR=CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or one or both of E and E' can be a bond where L comprises a ring;

each $R^2$ and $R^{2'}$ is independently H or optionally substituted C1-C8 alkyl;

each $R^7$ and $R^{7'}$ is independently H or optionally substituted C1-C4 alkyl;

each m and m' is independently 0-4;

each Z and Z' is independently an optionally substituted C1-C6 aminoalkyl; and

L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In a further aspect, the invention provides a compound of formula (XI):

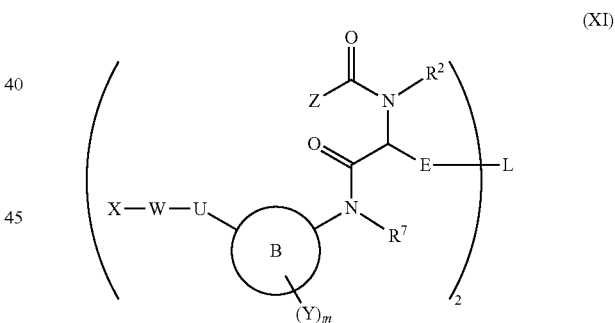

or a pharmaceutically acceptable salt or hydrate form thereof; and including any stereoisomeric forms thereof;

wherein Ring B, E, L, U, W, X, Y, Z, $R^2$, $R^7$ and m are defined as for formula (X).

In compounds of formula (X) and (XI), the B ring and/or the B' ring may a monocyclic or fused bicyclic C3-C12 carbocyclic or heterocyclic ring system, which may be saturated, unsaturated or aromatic, and may be further substituted. In compounds of formula (X), the B-ring and the B'-ring are independently selected.

In some embodiments of formula (X) and (XI), each of Ring B and Ring B' independently represents an optionally substituted indane or a tetrahydronaphthalene ring system. In some such embodiments, each of Ring B and Ring B' is independently:

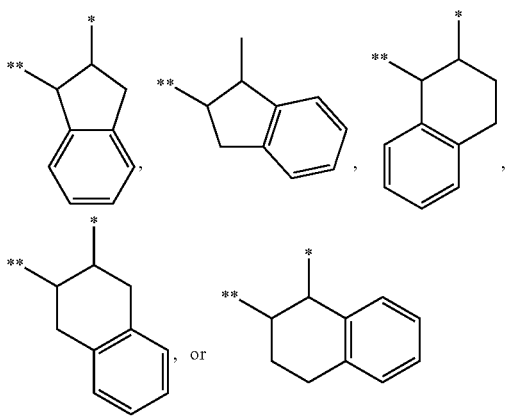

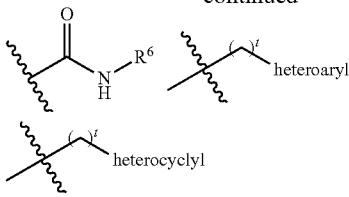

wherein ** represents to the point of attachment to U or U', and * represents the point of attachment to NR⁷ or NR⁷'.

In compounds of formulae (VI)-(XI), each W and W', where present, independently represents an optionally substituted C1-C6 alkylene or C1-C6 heteroalkylene; or W and/or W' can be a bond where X and/or X' comprises an optionally substituted C5-C6 aryl or heteroaryl ring.

In frequent embodiment of the compounds of formulae (VI)-(XI), each X and X' independently represents an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W or W', provided that each X and X' comprises at least one aryl or heteroaryl ring. In other embodiments, each X and X' is independently an optionally substituted C1-C8 alkyl, C1-C8 heteroalkyl, C3-C10 cycloalkyl, C3-C10 heterocyclyl.

In some such embodiments of formulae (VI)-(XI), W—X and/or W'—X' independently represent:

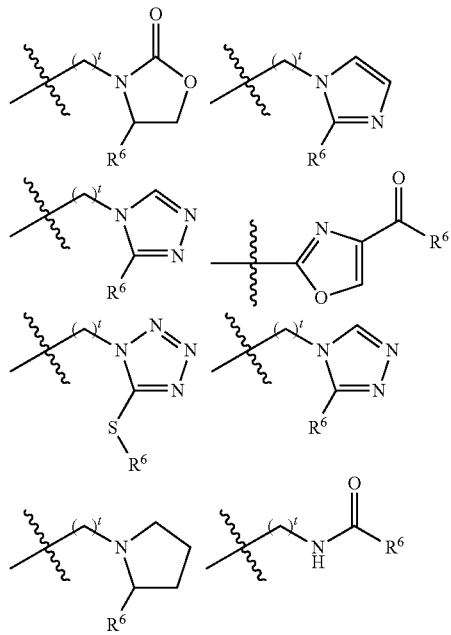

wherein each t is 1-4; and

R⁶ is aryl, heteroaryl, arylalkyl, or heteroarylalkyl, and wherein each aryl, heteroaryl, arylalkyl, heteroarylalkyl, and heterocyclyl is optionally substituted.

In compounds of formulae (VI)-(XI), L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of formulae (VI)-(XI), L is an optionally substituted and/or unsaturated C1-C14 alkylene or C1-C14 heteroalkylene. For example, L may represent a C1-C14 alkylene, C1-C14 alkenylene, C1-C14 alkynylene linker, or a heteroform of one of these, each of which may be optionally substituted. In some such embodiments, L comprises a saturated, partially unsaturated or aromatic carbocyclic or heterocyclic ring that forms part of the path between two Q and/or Q' groups in formulae (VI) and (VII), or between two E and/or E' groups in formulae (VIII)-(XI). In frequent embodiments, L is substituted with one or more carbonyl substituents (═O), to form a linker comprising one or more acyl groups.

In certain embodiments, L is symmetric about its central atom (if the chain connecting the two available valences is an odd number of atoms in length) or its central bond (if the chain connecting the two available valences is an even number of atoms in length). In some embodiments, L is 2-8 atoms in length, counting along the shortest path between two Q groups, between Q and Q', between two E groups or between E and E'. In certain embodiments, L can also include one or more heteroatoms selected from N, O and S, but does not include a disulfide linkage.

In some embodiments of formulae (VI)-(XI), where L comprises a ring, the ring(s) may be cycloalkyl, heterocyclyl, aryl, or heteroaryl, and may be further substituted. In formulae (VI) and (VII), such rings may be directly attached to Q and/or Q' or may be attached to Q and/or Q' through a C1-C8 alkylene or heteroalkylene group. Frequently, the ring which is part of L is substituted by carboxy groups which form the point of attachment to Q and/or Q', such that an ester or amide linkage is formed by the bond between Q/Q' and L. In formulae (VIII)-(XI), such rings may be directly attached to E and/or E' or may be attached to E and/or E' through a C1-C8 alkylene or heteroalkylene group. Frequently, the ring which is part of L is substituted by carboxy groups which form the point of attachment to E and/or E', such that an ester or amide linkage is formed by the bond between E/E' and L.

In certain embodiments, L comprises an optionally substituted 5- or 6-membered aromatic or heteroaromatic ring. In specific embodiments, L comprises at least one optionally substituted phenyl, pyridyl, pyrazole or triazole ring. Such rings may be 1,2-disubstituted, or 1,3-disubstituted, or 1,4- disubstituted, by the groups Q and Q' or E and E', which may be directly attached to the ring or may be separated from the ring by one or more atoms that are included in L, for example by a C1-C8 alkylene or heteroalkylene group.

Rings which comprise part of the linker, L, may be optionally substituted to the extent such substitution makes chemical sense. Preferred optional substituents when present on a ring which comprises part of L include alkyl (C1-C4), alkoxy (C1-C4), —CF$_3$, —OCF$_3$, halo, —OH, —NO$_2$, —CN, or NR$^Y$$_2$, where each R$^Y$ is independently H or C1-C4 alkyl.

In certain embodiments, L comprises an optionally substituted arylene or arylalkylene group, or a heteroform of one of these, to which Q and Q' or E and E' are directly or indirectly attached. For example, L can be —CH$_2$—Ar—CH$_2$—, —C(O)—Ar—C(O)—, —SO$_2$—Ar—SO$_2$—, —C(O)—Ar— or —Ar—, where Ar represents an optionally substituted 5- or 6-membered aromatic or heteroaromatic ring. In some embodiments, L comprises a phenyl ring that may be 1,2-disubstituted, or 1,3-disubstituted, or 1,4-disubstituted by the groups Q and/or Q', or E and/or E', which may be directly or indirectly attached to the ring. In other embodiments, L comprises an optionally substituted 5- or 6-membered heteroaryl ring, which may contain from 1-4 heteroatoms selected from N, O and S as a ring member. In further embodiments, L comprises an optionally substituted C3-C10 cycloalkylene ring.

In a further aspect, the invention provides a compound of the formula XII:

$$\Phi^1\text{-L-}\Phi^2 \qquad (XII)$$

or a pharmaceutically acceptable salt or hydrate form thereof; and including any stereoisomeric forms thereof;

wherein $\Phi^1$ and $\Phi^2$ are independently selected from the group consisting of:

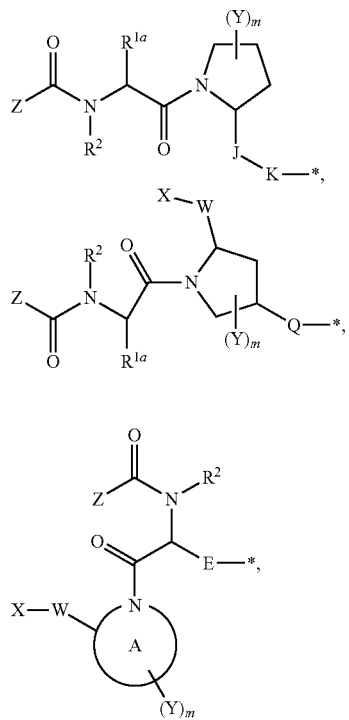

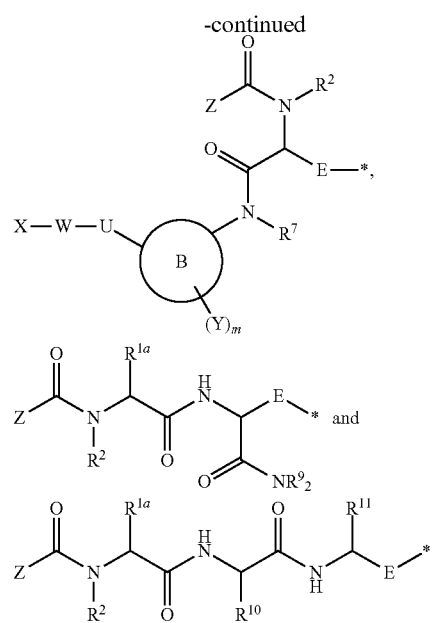

wherein * represents the point of attachment to L;

each Y independently represents an optionally substituted C1-C8 alkyl, C5-C12 aryl, C5-C20 arylalkyl, or a heteroform of one of these; or is =O, OR, SR, S(O)R, SO$_2$R, SO$_2$NR$_2$, NR$_2$, OC(O)R, NRC(O)R, NRCOOR, NRC(O)NR$_2$, NRSO$_2$R, CN, C(O)NR$_2$, C(O)R, COOR, NO$_2$ or halo, wherein each R is independently H, C$_1$-C$_8$ alkyl, C5-C12 aryl or C5-C20 arylalkyl, or a heteroform of one of these each of which may be optionally substituted; or is any other substituent suitable for an alkyl group;

and wherein two Y groups on the same or adjacent atoms can cyclize to form an optionally substituted 3-7 membered ring that can be saturated, unsaturated or aromatic, and which ring may include one or more heteroatoms selected from O, S and N as a ring member;

each R$^{1a}$ is independently H, or C1-C8 alkyl, C3-C8 cycloalkyl, C2-C8 alkenyl, C2-C8 alkynyl, C5-C12 aryl, C5-C20 arylalkyl, or a heteroform of one of these, each of which may be optionally substituted; or each R$^2$ is independently H or optionally substituted C1-C8 alkyl;

each J is independently —C(O)—, —CH$_2$— or —CHR"—, where R" is C1-C4 alkyl;

each of K and K' is independently selected from the group consisting of —NR'—(CR$^X$$_2$)$_p$—NR'—, —NR'—(CR$^X$$_2$)$_p$—O—, —O—(CR$^X$$_2$)$_p$—NR'—, —O—(CR$^X$$_2$)$_p$—O—, —NR'—(CR$^X$$_2$)$_p$—S—, —S—(CR$^X$$_2$)$_p$—NR'—, —O—(CR$^X$$_2$)$_p$—S—, —S—(CR$^X$$_2$)$_p$—O—, and —S—(CR$^X$$_2$)$_p$—S—, wherein each R' is independently H or C$_{1-4}$ alkyl, each R$^X$ is independently H, or optionally substituted C1-C8 alkyl, C2-C8 alkenyl, C2-C8 alkynyl, C1-C8 heteroalkyl, C2-C8 heteroalkenyl, C2-C8 heteroalkynyl, C5-C12 aryl, C5-C12 heteroaryl, C5-C20 arylalkyl, C5-C20 heteroarylalkyl, C3-C8 cycloalkyl, or C3-C8 heterocyclyl; or two R$^X$ substituents are taken together to form an optionally substituted saturated, unsaturated or aromatic carbocyclic or heterocyclic ring; and each p is independently 2-4;

each Q represents —O—, —S— or —NR$^5$—, where each R$^5$ is independently H, or optionally substituted C1-C8 alkyl, or optionally substituted C1-C8 heteroalkyl; or Q may be a bond when L comprises a ring;

each E represents —$CH_2$—, —CH(OR)—, —CH(R)—, —($CH_2$)$_r$D-, —CH(R)D-, —CR=CR— or —C≡C—, wherein r is 1-4, each D is independently O, NR, or S, and wherein each R is independently H, or optionally substituted $C_1$-$C_8$ alkyl or optionally substituted $C_1$-$C_8$ heteroalkyl; or E can be a bond where L comprises a ring;

W is an optionally substituted C1-C6 alkylene or C1-C6 heteroalkylene; or W and/or W' can be a bond where X comprises an optionally substituted C5-C6 aryl or heteroaryl ring;

X is an optionally substituted C1-C8 alkyl, C1-C8 heteroalkyl, C3-C10 cycloalkyl, C3-C10 heterocyclyl, or an optionally substituted $C_5$-$C_{20}$ ring system comprising at least one aromatic ring and up to four heteroatoms selected from N, O and S as a ring member, and can represent either a single 5-15 membered cyclic group or two 5-10 membered cyclic groups that are both attached to the same atom of W;

each U independently represents —$NR^8$—, —O—, or —S(O)$_v$—, wherein each $R^8$ is independently H or C1-C4 alkyl, and v is 0-2;

wherein ring A represents a C3-C12 azacyclic ring, which may contain 0-2 additional heteroatoms selected from N, O, S as ring members;

wherein the B ring represents a C3-C12 carbocyclic ring or a C3-C12 heterocyclic ring containing 1-3 heteroatoms selected from N, O, S as ring members;

each $R^9$ is independently H or optionally substituted C1-C8 alkyl;

each $R^{10}$ is independently H or optionally substituted C1-C8 alkyl;

each $R^{11}$ is independently H or optionally substituted C1-C8 alkyl;

m is 0-4;

each Z independently represents an optionally substituted C1-C6 aminoalkyl group; and L represents a C1-C14 alkylene, C1-C14 alkenylene, C1-C14 alkynylene, C3-C8 cycloalkylene, C5-C21 cycloalkylalkylene, C5-C12 arylene, C5-C21 arylalkylene, C5-C21 arylalkenylene, C5-C21 arylalkynylene, C1-C14 heteroalkylene, C1-C14 heteroalkenylene, C1-C14 heteroalkynylene, C3-C8 heterocyclyl, C5-C21 heterocyclylalkylene, C5-C12 heteroarylene, C5-C21 heteroarylalkylene, C5-C21 heteroarylalkenylene, or C5-C21 heteroarylalkynylene linker, each of which may be optionally substituted.

In some embodiments of formula (XII), each of wherein $Φ^1$ and $Φ^2$ comprise the same core group but are differentially substituted, so that the compound of formula (XII) is unsymmetrical. In other embodiments, each of wherein $Φ^1$ and $Φ^2$ comprise different core groups, so that the compound of formula (XII) is a heterodimer. In other embodiments, each of wherein $Φ^1$ and $Φ^2$ comprise identical core groups, and the compound of formula (XII) is a symmetrical homodimer.

In compounds of formula (XII), the groups $R^{1a}$, $R^2$, Y, m, J, K, W, X, Q, E, Ring A, Ring B, U, and $R^7$ are the same as for compounds of formula (I)-(XI) containing the corresponding core structures. Accordingly, embodiments of formula (I)-(XI) described herein for groups $R^{1a}$, $R^2$, Y, m, J, K, W, X, Q, E, Ring A, Ring B, U, and $R^7$ are also suitable for compounds of formula (XII). In compounds of formula (XII), each of $R^9$, $R^{10}$ and $R^{11}$ is independently an optionally substituted C1-C8 alkyl.

In some embodiments of any of the formulae provided herein, L comprises an optionally substituted C1-C14 alkylene or C1-C14 heteroalkylene which may be saturated or unsaturated. For example, L can be —($CH_2$)$_q$ where q is 1-8, and may be optionally substituted with groups suitable for an alkyl group. In certain embodiments, the alkylene chain is substituted with one or two carbonyl oxygens (=O).

When L is unsaturated, it is sometimes a C2-C14 alkenylene or C2-C14 alkynylene linker. For example, it is sometimes a C2-C14 alkenylene or C2-C14 alkynylene linker. For example, in certain embodiments, L represents an optionally substituted C2-C8 alkenylene or C2-C8 alkynylene linker. For example, L can be an optionally substituted bis-acetylenic linker, such as —($CH_2$)$_q$—C≡C—C≡C—($CH_2$)$_q$— or —C≡C—C≡C—($CH_2$)$_q$C(O)— where q is 0-5; an arylalkynyl linker, such as -Ph-C≡C—($CH_2$)$_q$— where q is 0-5; a 1,4-but-2-enylene (—$CH_2$—CH=CH—$CH_2$—); 1,10-deca-4,6-diynylene (—($CH_2$)$_3$C≡C—C≡C($CH_2$)$_3$—; 1,7-hepta-1,3-diynylene (—C≡C—C≡C($CH_2$)$_3$—; or an optionally substituted version of one of these. L can also include one or more heteroatoms, for example, it can be —$CH_2$—O—$CH_2$— or —($CH_2$)$_2$NHC(O)ArC(O)NH($CH_2$)$_2$— or a substituted version of one of these.

In some embodiments of any of the formulae provided herein, L is selected from the group consisting of:

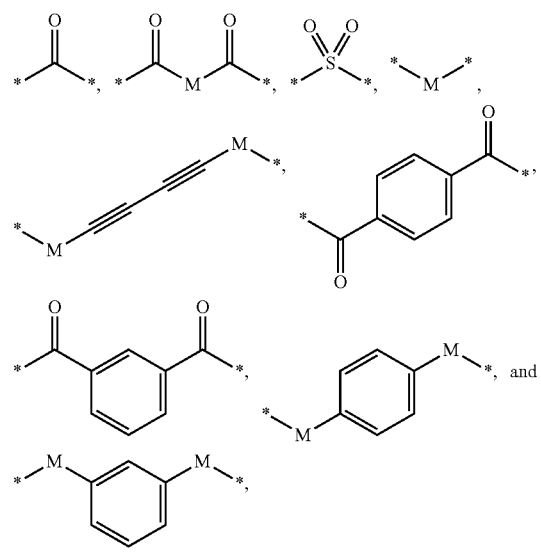

where each M is independently a bond, or a saturated or unsaturated C1-C8 alkylene or C1-C8 heteroalkylene group each of which may be optionally substituted.

In some embodiments, L represents a structure selected from the following group:

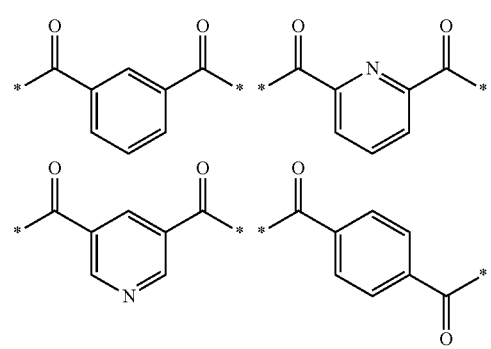

-continued

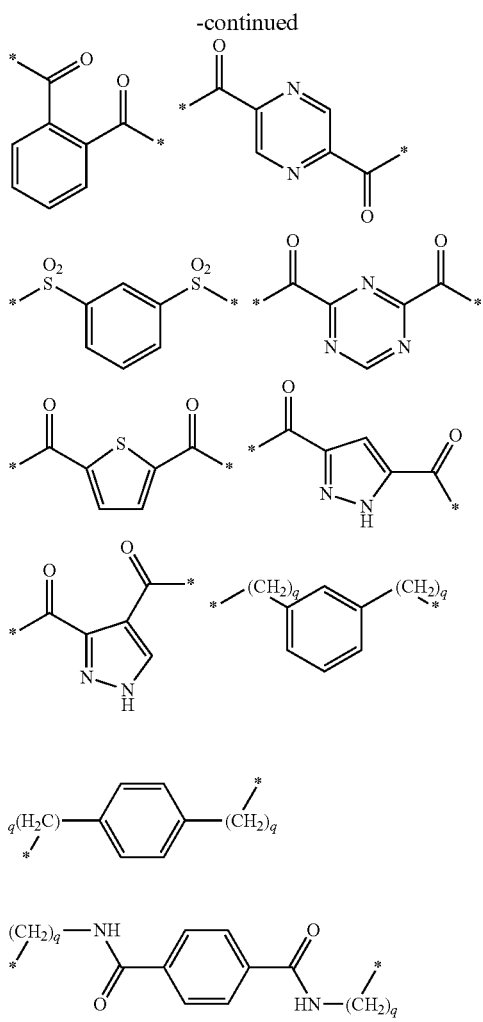

wherein * represents the point of attachment from the linker L to the adjacent group K and/or K' in formulae (I)-(V), Q and/or Q' in formulae (VI)-(VII), and E and/or E' in formulae (VIII)-(XI), or the appropriate group K, Q and E in compounds of formula (XII). Each q in such compounds is independently 0-8, and each aromatic, heteroaromatic or heterocyclic ring is optionally substituted. In certain embodiments, the ring that comprises part of L is substituted with one or more substituents selected from the group consisting of —OH, C1-C4 alkyl, C1-C4 alkoxy, halo, $NO_2$ or $NH_2$.

In particular embodiments, L represents a structure

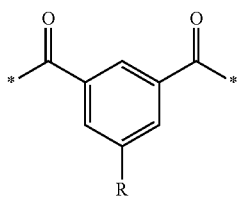

wherein * represents the point of attachment from the linker to the group K, K', Q, Q', E or E', and R is —OH, —OMe, Me, halo, $NO_2$ or $NH_2$. In certain embodiments, R is OH, OMe, Me or $NH_2$ In other preferred embodiments, L represents a structure:

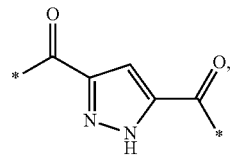 [SMILES: *C(=O)c1cc(C(*)=O)[nH]n1]

wherein * represents the point of attachment from the linker to the group K, K', Q, Q', E or E'.

In other embodiments, L represents a structure selected from the following group:

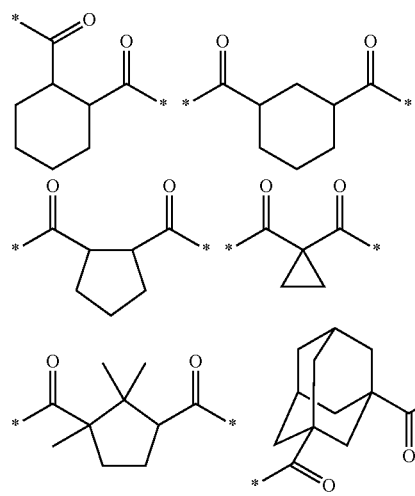

wherein * represents the point of attachment from the linker to the group K, K', Q, Q', E or E'.

In some embodiments of the formulae provided herein, L represents a structure selected from the following group:

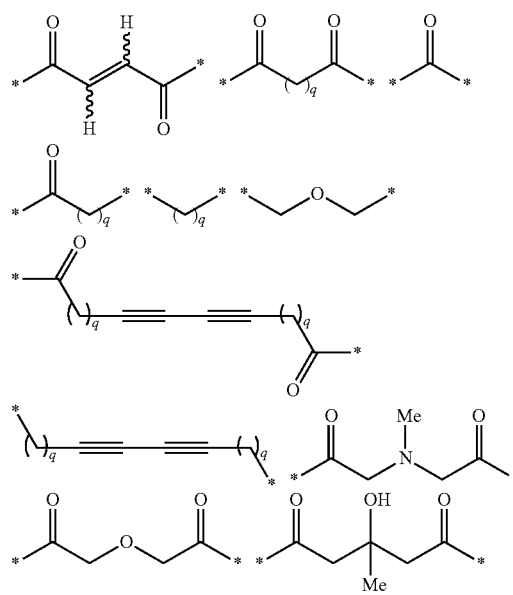

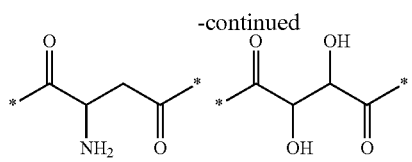

wherein * represents the point of attachment from the linker to the group K, K', Q, Q', E or E', and each q is independently 0-8, and each alkylene group may be optionally substituted.

The compounds of the invention may contain one or more chiral centers. The invention includes each of the isolated stereoisomeric forms as well as mixtures of stereoisomers in varying degrees of chiral purity, including racemic mixtures. It also encompasses the various diastereomers and tautomers that can be formed. The compounds of the invention may also exist in more than one tautomeric form; the depiction herein of one tautomer is for convenience only, and is also understood to encompass other tautomers of the form shown.

The compounds of the invention may be isolated as salts where an ionizable group such as a basic amine or a carboxylic acid is present. The invention includes the salts of these compounds that have pharmaceutically acceptable counterions. Such salts are well known in the art, and include, for example, salts of acidic groups formed by reaction with organic or inorganic bases, and salts of basic groups formed by reaction with organic or inorganic acids, as long as the counterions introduced by the reaction are acceptable for pharmaceutical uses. Methods for preparation of the appropriate salts or the exchange of one salt for another are well-established in the art. In some cases, the compounds may contain both an acidic and a basic functional group, in which case they may have two ionized groups and yet have no net charge.

Examples of inorganic bases with alkali metal hydroxides (e.g., sodium hydroxide, potassium hydroxide, etc.), alkaline earth metal hydroxides (e.g., of calcium, magnesium, etc.), and hydroxides of aluminum, ammonium, etc. Examples of organic bases that could be used include trimethylamine, triethylamine, pyridine, picoline, ethanolamine, diethanolamine, triethanolamine, dicyclohexylamine, N,N'-dibenzylethylenediamine, caffeine, and various other amines.

Examples of inorganic acids that could be used include hydrochloric acid, hydrobromic acid, nitric acid, sulfuric acid, phosphoric acid, etc. Examples of organic acids include formic acid, oxalic acid, acetic acid, tartaric acid, methanesulfonic acid, benzenesulfonic acid, malic acid, citric acid, lactic acid, glycolic acid, methanesulfonic acid, benzenesulfonic acid, p-toluenesulfonic acid, etc. Also included are salts with basic amino acids such as arginine, lysine, ornithine, etc., and salts with acidic amino acids such as aspartic acid, glutamic acid, etc.

In some embodiments, the compounds of the invention exist in the form of a solvate or a solvate of a salt. In particular embodiments, the compounds are provided as a hydrate or a hydrate of a salt.

The compounds of the invention can be used to prepare pharmaceutical compositions containing at least one compound of any of the formulae disclosed herein and at least one pharmaceutically acceptable excipient. The compositions comprise a compound of the invention admixed with at least one pharmaceutically acceptable excipient, and preferably with at least one such excipient other than water or a solvent such as DMSO. Such compositions can be optimized for various conditions and routes of administration using guidance that is widely relied on for such purposes including Remington's *Pharmaceutical Sciences*, latest edition, Mack Publishing Co., Easton, Pa., which is incorporated herein by reference.

Provided herein are methods for treating or ameliorating a cell proliferative disorder, comprising administering to a subject in need thereof an effective amount of a compound according to any of the formulae disclosed herein, thereby treating or ameliorating the cell-proliferative disorder. In some embodiments, cell proliferation is reduced or cell death or apoptosis is induced.

In frequent embodiments, the cell proliferative disorder is cancer. In certain embodiments the cell proliferative condition is a tumor-associated cancer. The cancer sometimes is cancer of the breast, prostate, pancreas, lung, colon, rectum, skin, ovary, testes, brain or liver. In some embodiments, the cell proliferative condition is a non-tumor cancer, such as a hematopoietic cancer, including, e.g., leukemia (e.g, acute or chronic, lymphocytic or myelogenous leukemias), lymphoma (Hodkins or non-Hodgkins lymphoma), or myeloma.

The compounds of the invention are suitable to treat a wide variety of cancers. In particular, they are suitable to treat breast cancer, prostate cancer, pancreatic cancer, lung cancer (SCLC and NSCLC), hematopoietic cancer (e.g., leukemia, lymphoma, myeloma), colon cancer, rectal cancer, skin cancer (e.g., melanoma), ovarian cancer, testicular cancer, brain cancer (e.g., neuroblastoma or glioblastoma), or liver cancer.

Also provided herein are methods for inhibiting cell proliferation, comprising contacting cells with a compound described herein in an amount effective to inhibit proliferation of the cells. The contacting may be in vitro, ex vivo or in vivo. The cells sometimes are in a cell line, such as a cancer cell line, for example a cell line derived from breast cancer, prostate cancer, pancreatic cancer, lung cancer (SCLC and NSCLC), hematopoietic cancer (e.g., leukemia, lymphoma, myeloma), colon cancer, rectal cancer, skin cancer (e.g., melanoma), ovarian cancer, testicular cancer, brain cancer (e.g., neuroblastoma or glioblastoma), or liver cancer. The cells sometimes are in a tissue, can be in a subject, at times are in a tumor, and sometimes are in a tumor in a subject. In certain embodiments, the method further comprises inducing cell apoptosis.

The compounds of the invention are also suitable to treat various autoimmune disorders, particularly rheumatoid arthritis, lupus, vasculitis, glomerulonephritis, type-I diabetes, pernicious anemia, myasthenia gravis, Guillain-Barre syndrome, and infections with autoimmune effects such as AIDS, malaria, Chagas disease, and Lyme disease.

Therapeutic Combinations

The compounds of the invention are not on their own very cytotoxic: they depend for their activity on potentiation of the effects of other effectors, which may be natural, endogenous substances, or they may be additional therapeutic substances. For example, Smac mimics have been shown to strongly potentiate the activity of TRAIL or etoposide when co-administered. Accordingly, the compounds of the invention may be used in conjunction with or in combination with an additional therapeutic having anticancer effects. Such additional therapeutic can be a drug, or it can be a radiation treatment. Similarly, the methods of the invention include methods wherein a subject diagnosed as in need of treatment for inflammation and/or cancer is treated with at least one compound of the invention, and is simultaneously, concurrently or sequentially treated with one or more of the additional therapeutic agents.

Where an additional drug is administered, it is typically one known to have cytostatic, cytotoxic or antineoplastic activity. These agents include, for example and without limitation: antimetabolites such as cytarabine, fludaragine, 5-fluoro-2'-deoxyuridine, gemcitabine, hydroxyurea, methotrexate; DNA active agents such as bleomycin, chlorambucil, cisplatin, cyclophosphamide; intercalating agents such as doxorubicin, adriamycin and mitoxantrone; protein synthesis inhibitors such as L-asparaginase, cycloheximide, puromycin; topoisomerase I inhibitors such as camptothecin or topotecan; topoisomerase II inhibitors such as etoposide and teniposide; microtubule inhibitors such as colcemid, colchicines, paclitaxel, docetaxel, vinblastine and vincristine; and kinase inhibitors such as flavopiridol, staurosporin, and hydroxystaurosporine. These agents may also include hormonal therapies and molecular targeted agents, such as receptor tyrosine kinase (RTK) inhibitors (e.g., PDGF-R, VEGF-R, and EGFR inhibitors), and monoclonal antibodies, among others.

Preferred additional drugs for co-administration with the compounds of the invention include those that affect Hsp90 (heat-shock protein 90). Suitable Hsp90 inhibitors include ansamycin derivatives such as geldanomycin and geldanomycin derivatives including 17-(allylamino)-17-desmethoxygeldanamycin (17-AAG), its dihydro derivative, 17-AAGH$_2$, and 17-amino derivatives of geldanamycin such as 17-dimethylaminoethylamino-17-demethoxy-geldanamycin (17-DMAG), 11-oxogeldanamycin, and 5,6-dihydrogeldanamycin, which are disclosed in U.S. Pat. Nos. 4,261,989; 5,387,584; and 5,932,566, each of which is incorporated herein by reference. Other suitable Hsp90 inhibitors include radicicol and oximes and other analogs thereof, disclosed in Soga, et al., *Curr. Cancer Drug Targets* (2003) 3:359-369, and in Yamamoto, et al., *Angew. Chem.* (2003) 42:1280-1284; and in Moulin, et al., *J. Amer. Chem. Soc.* (2005) 127:6999-7004; purine derivatives such as PU3, PU24FCl and PUH64 (see Chiosis et al., *ACS Chem. Biol.* (2006) 1(5):279-284 and those disclosed in PCT Application No. WO 2002/0236075; related heterocyclic derivatives disclosed in PCT Application No. WO 2005/028434; and 3,4-diarylpyrazole compounds disclosed in Cheung, et al., *Bioorg. Med. Chem. Lett.* (2005) 15:3338-3343. Antibodies or antibody fragments that selectively bind to Hsp90 may also be administered as drugs to cause inhibition of Hsp90, and can be used in combination with the compounds of the invention.

Natural effectors such as TRAIL, a TRAIL receptor antibody, TNF-α and TNF-β can also be administered for this purpose, and are also preferred, as are active fragments of these peptides and antibodies.

Where a compound of the invention is utilized to potentiate the effects of another therapeutic, the two agents may be co-administered, or they may be administered separately where their administration is timed so the two agents act concurrently or sequentially. For example, the two agents may be administered as a single pharmaceutical dosage formulation that contains both a compound of the invention and an additional anticancer agent, or they may be simultaneously administered as separate dosage formulations. Alternatively, the compound and the anticancer agent may be administered at essentially the same time, for example, concurrently, or at separately staggered times, for example, sequentially. In certain examples, the individual components of the combination may be administered separately, at different times during the course of therapy, or concurrently, in divided or single combination forms. Thus, the present invention encompasses simultaneous, staggered, or alternating treatment with a compound of one of the formulae disclosed herein and a second agent. The compound of the invention may be administered before the anticancer agent, or the anticancer agent may be administered before the compound of the invention, for example, with a time difference of seconds, minutes, hours, days, or weeks. In examples of a staggered treatment, a course of therapy with the compound of the invention may be administered, followed by a course of therapy with the anticancer agent, or the reverse order of treatment may be used, more than one series of treatments with each component may be used.

Formulation and Administration

Formulations of the compounds and compositions of the invention may be prepared in a manner suitable for systemic administration or topical or local administration. Systemic formulations include those designed for injection (e.g., intramuscular, intravenous or subcutaneous injection) and those prepared for transdermal, transmucosal, or oral administration. The formulation will generally include a diluent as well as, in some cases, adjuvants, buffers, preservatives and the like. The compounds can be administered also in liposomal compositions or as microemulsions.

Injection methods are sometimes appropriate routes for administration of the compounds for systemic treatments and sometimes also for localized treatments. These include methods for intravenous, intramuscular, subcutaneous, and other methods for internal delivery that bypass the mucosal and dermal barriers to deliver the composition directly into the subject's living tissues.

For injection, formulations can be prepared in conventional forms as liquid solutions or suspensions or as solid forms suitable for solution or suspension in liquid prior to injection or as emulsions. Suitable excipients include, for example, water, saline, dextrose, glycerol and the like. Such compositions may also contain amounts of nontoxic auxiliary substances such as wetting or emulsifying agents, pH buffering agents and the like, such as, for example, sodium acetate, sorbitan monolaurate, and so forth.

Various sustained release systems for drugs have also been devised and can be utilized with the compounds of the invention. See, for example, U.S. Pat. No. 5,624,677. The present compositions can be utilized in such controlled-release delivery systems where appropriate.

Systemic administration may also include relatively non-invasive methods such as the use of suppositories, transdermal patches, transmucosal delivery and intranasal administration. Oral administration is also suitable for compounds of the invention, which are more robust than the Smac peptide itself and are thus advantageously more orally bioavailable. Suitable forms include syrups, capsules, tablets, and the like as in understood in the art.

Selection of a particular route of administration for a given subject and indication is well within the ordinary level of skill in the art. For example, rectal delivery as a suppository is often appropriate where the subject experiences nausea and vomiting that precludes effective oral delivery. Transdermal patches are commonly capable of delivering a controlled-release dosage over several days or to a specific locus, and are thus suitable for subjects where these effects are desired.

Transmucosal delivery is also appropriate for some of the compositions and methods of the invention. Thus the compositions of the invention may be administered transmucosally using technology and formulation methods that are known in the art.

For administration to animal or human subjects, the dosage of a compound of the invention is typically 1-2400 mg per administration, sometimes between 10-1000 mg per administration or 10-250 mg per administration.

However, dosage levels are highly dependent on the nature of the condition, the condition of the patient, the judgment of the practitioner, and the frequency and mode of administration. Selection of a dosage of such compounds is within the skill of an ordinary artisan, and may be accomplished by starting at a relatively low dosage and increasing the dosage until an acceptable effect is achieved.

Frequency of administration of the compounds of the invention can also be readily determined by one skilled in the art using well known techniques. For example, the patient may be administered a low dosage of a compound or composition of the invention at a low frequency such as once per day or less often; and the dosage and/or frequency of administration may be systematically increased until a desired effect is achieved in the patient.

The following examples are offered to illustrate but not to limit the invention.

EXAMPLE 1

Representative Compounds of the Invention

Representative compounds of the present invention are provided in Tables 1-5 and 11-14.

TABLE 1

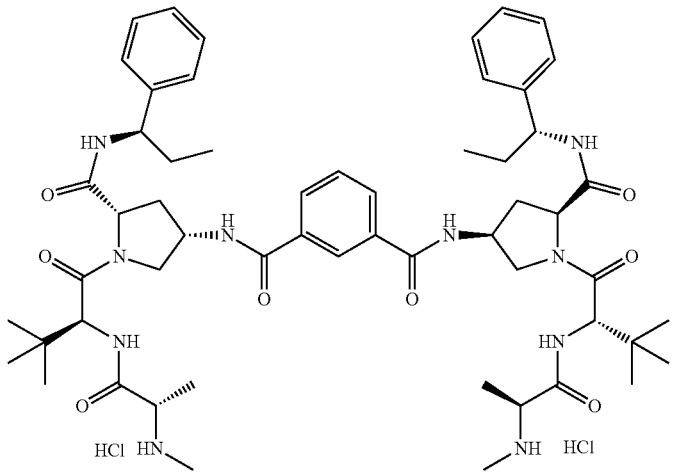 [SMILES: CC[C@@H](NC(=O)[C@@H]1C[C@H](NC(=O)c2cccc(C(=O)N[C@H]3C[C@@H](C(=O)N[C@H](CC)c4ccccc4)N(C(=O)[C@@H](NC(=O)[C@H](C)NC)C(C)(C)C)C3)c2)CN1C(=O)[C@@H](NC(=O)[C@H](C)NC)C(C)(C)C)c1ccccc1 ; Cl ; Cl]

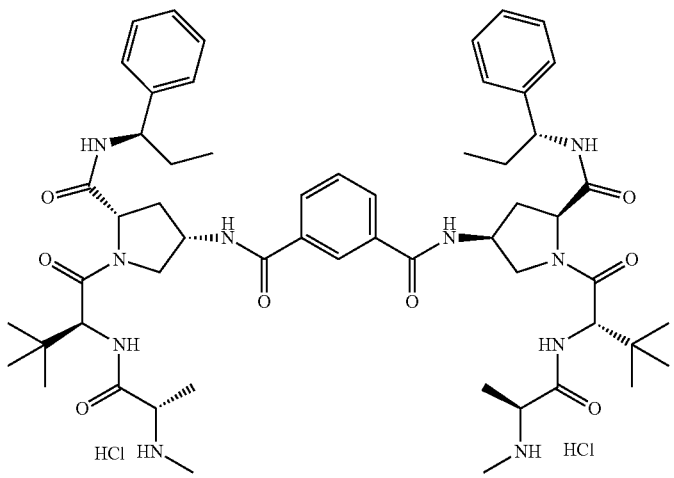 [SMILES: CC[C@@H](NC(=O)[C@@H]1C[C@H](NC(=O)c2cccc(C(=O)N[C@H]3C[C@@H](C(=O)N[C@H](CC)c4ccccc4)N(C(=O)[C@@H](NC(=O)[C@H](C)NC)C(C)(C)C)C3)c2)CN1C(=O)[C@@H](NC(=O)[C@H](C)NC)C(C)(C)C)c1ccccc1 ; Cl ; Cl]

TABLE 1-continued
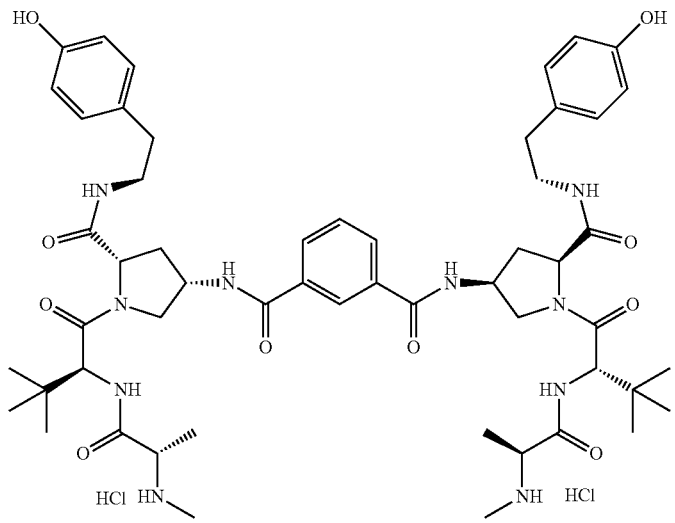
3
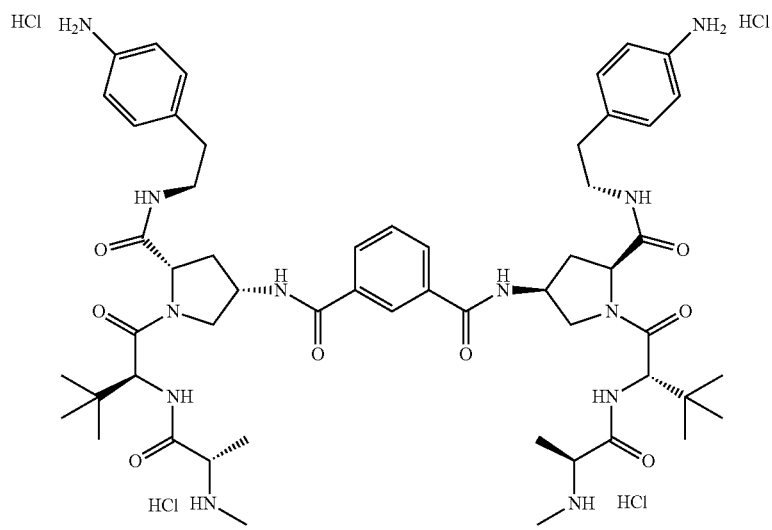
4
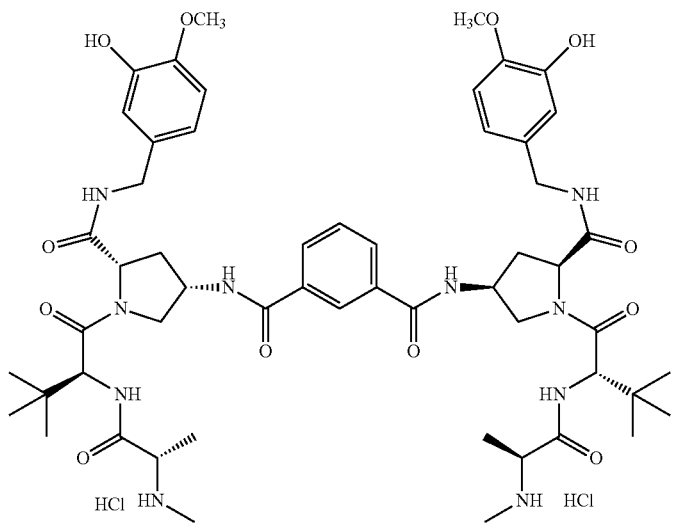 [SMILES: CN[C@@H](C)C(=O)N[C@H](C(=O)N1C[C@@H](NC(=O)c2cccc(C(=O)N[C@H]3C[C@@H](C(=O)NCc4ccc(OC)c(O)c4)N(C(=O)[C@@H](NC(=O)[C@H](C)NC)C(C)(C)C)C3)c2)C[C@H]1C(=O)NCc1ccc(OC)c(O)c1)C(C)(C)C ; Cl ; Cl]
5

TABLE 1-continued
| | |
|---|---|
| 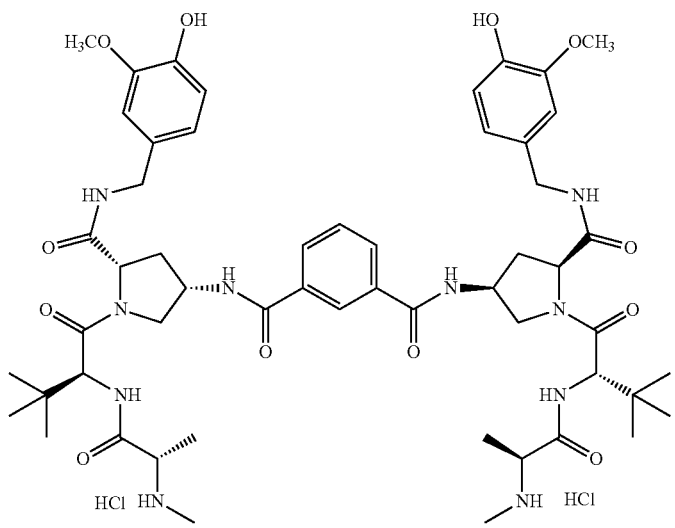 [SMILES: CN[C@@H](C)C(=O)N[C@H](C(=O)N1C[C@@H](NC(=O)c2cccc(C(=O)N[C@H]3C[C@@H](C(=O)NCc4ccc(O)c(OC)c4)N(C(=O)[C@@H](NC(=O)[C@H](C)NC)C(C)(C)C)C3)c2)C[C@H]1C(=O)NCc1ccc(O)c(OC)c1)C(C)(C)C ; Cl ; Cl] | 6 |
| 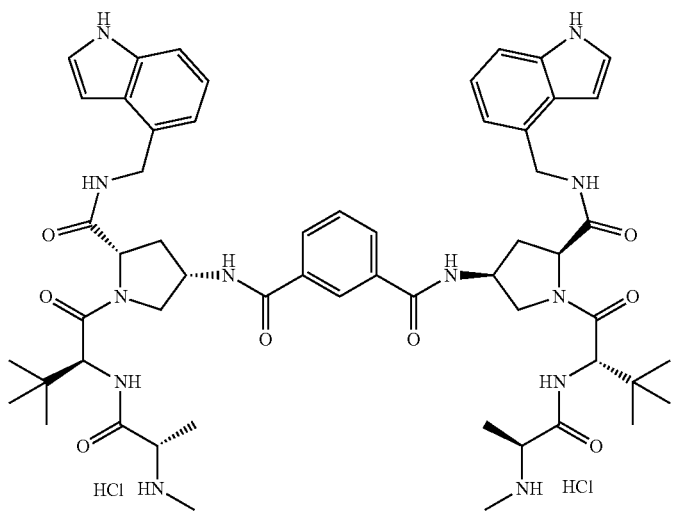 [SMILES: CN[C@@H](C)C(=O)N[C@H](C(=O)N1C[C@@H](NC(=O)c2cccc(C(=O)N[C@H]3C[C@@H](C(=O)NCc4cccc5[nH]ccc45)N(C(=O)[C@@H](NC(=O)[C@H](C)NC)C(C)(C)C)C3)c2)C[C@H]1C(=O)NCc1cccc2[nH]ccc12)C(C)(C)C ; Cl ; Cl] | 7 |
| 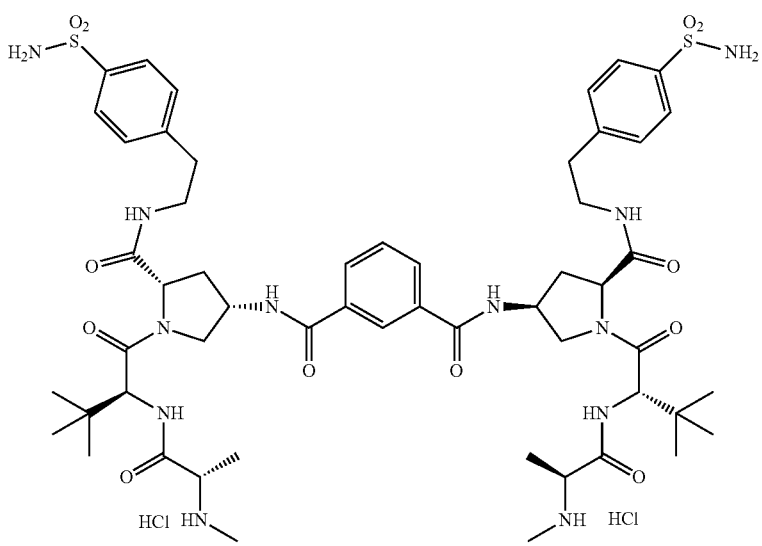 [SMILES: CN[C@@H](C)C(=O)N[C@H](C(=O)N1C[C@@H](NC(=O)c2cccc(C(=O)N[C@H]3C[C@@H](C(=O)NCCc4ccc(S(N)(=O)=O)cc4)N(C(=O)[C@@H](NC(=O)[C@H](C)NC)C(C)(C)C)C3)c2)C[C@H]1C(=O)NCCc1ccc(S(N)(=O)=O)cc1)C(C)(C)C ; Cl ; Cl] | 8 |

TABLE 1-continued
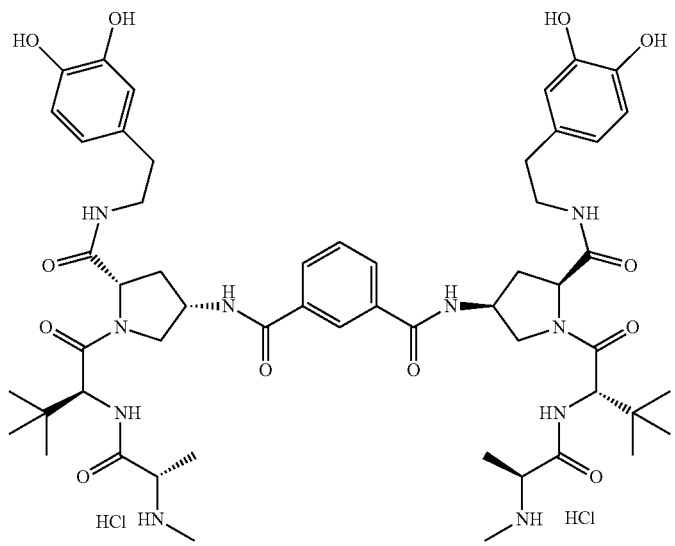 [SMILES: CN[C@@H](C)C(=O)N[C@H](C(=O)N1C[C@@H](NC(=O)c2cccc(C(=O)N[C@H]3C[C@@H](C(=O)NCCc4ccc(O)c(O)c4)N(C(=O)[C@@H](NC(=O)[C@H](C)NC)C(C)(C)C)C3)c2)C[C@H]1C(=O)NCCc1ccc(O)c(O)c1)C(C)(C)C ; Cl ; Cl]
9
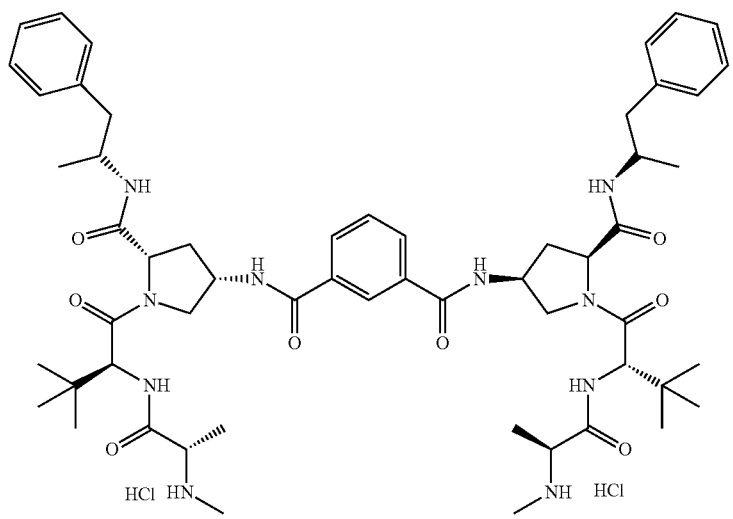
10
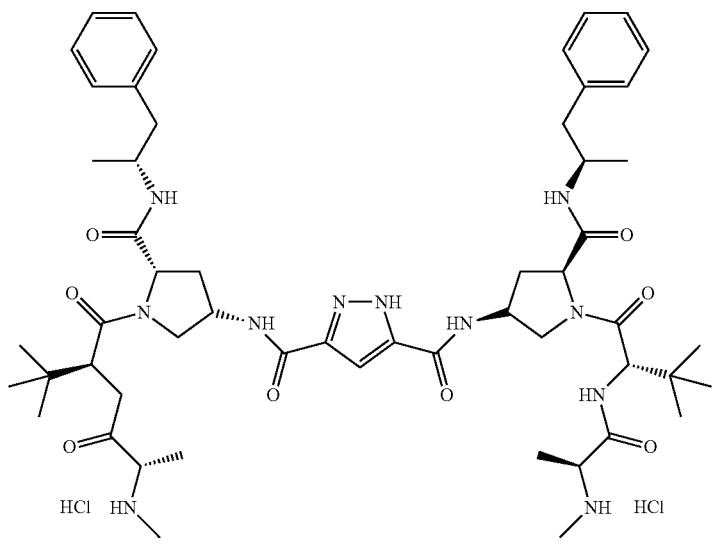
11

TABLE 1-continued
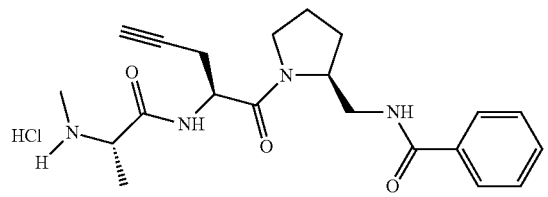 [SMILES: Cl ; C#CC[C@H](NC(=O)[C@H](C)NC)C(=O)N1CCC[C@H]1CNC(=O)c1ccccc1]
12
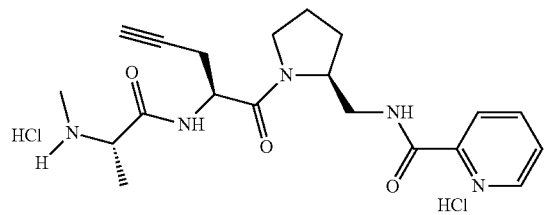 [SMILES: Cl ; C#CC[C@H](NC(=O)[C@H](C)NC)C(=O)N1CCC[C@H]1CNC(=O)c1ccccn1 ; Cl]
13
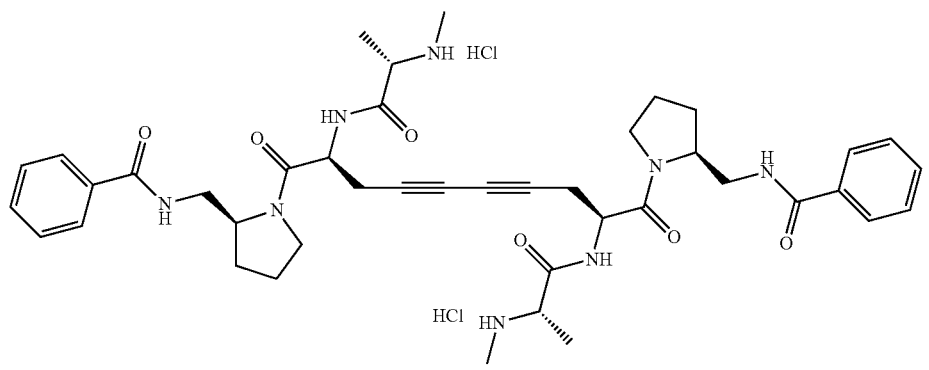 [SMILES: CN[C@@H](C)C(=O)N[C@@H](CC#CC#CC[C@H](NC(=O)[C@H](C)NC)C(=O)N1CCC[C@H]1CNC(=O)c1ccccc1)C(=O)N1CCC[C@H]1CNC(=O)c1ccccc1 ; Cl ; Cl]
14
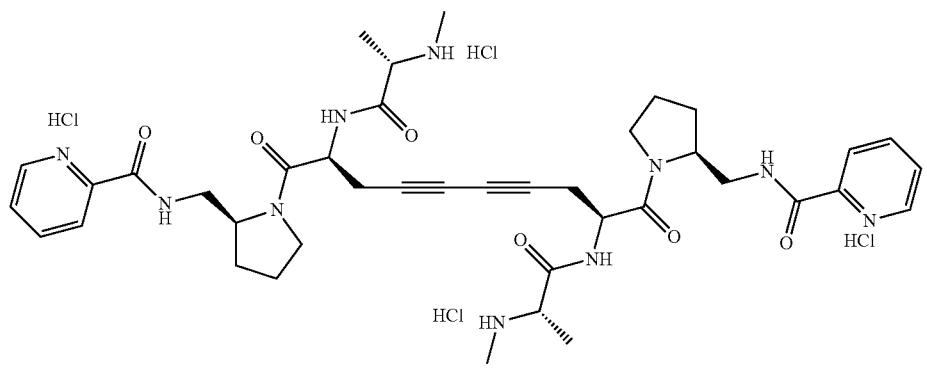 [SMILES: CN[C@@H](C)C(=O)N[C@@H](CC#CC#CC[C@H](NC(=O)[C@H](C)NC)C(=O)N1CCC[C@H]1CNC(=O)c1ccccn1)C(=O)N1CCC[C@H]1CNC(=O)c1ccccn1 ; Cl ; Cl ; Cl ; Cl]
15
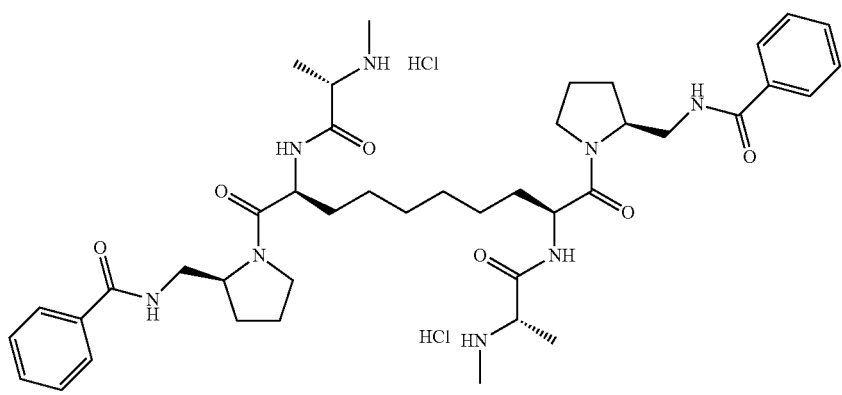 [SMILES: CN[C@@H](C)C(=O)N[C@@H](CCCCCC[C@H](NC(=O)[C@H](C)NC)C(=O)N1CCC[C@H]1CNC(=O)c1ccccc1)C(=O)N1CCC[C@H]1CNC(=O)c1ccccc1 ; Cl ; Cl]
16

TABLE 1-continued
17
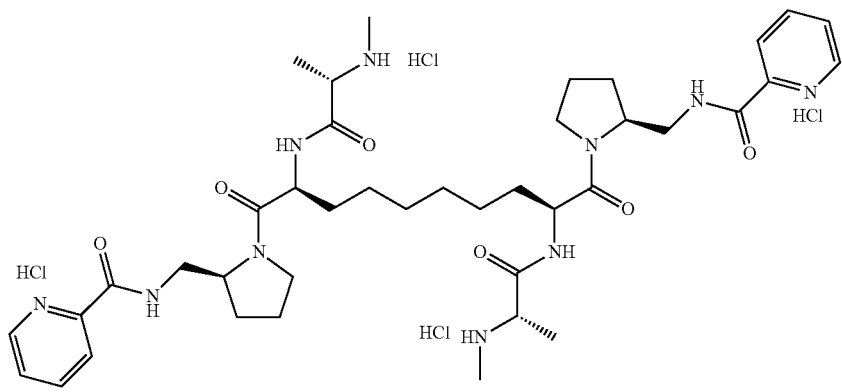 [SMILES: CN[C@@H](C)C(=O)N[C@@H](CCCCCC[C@H](NC(=O)[C@H](C)NC)C(=O)N1CCC[C@H]1CNC(=O)c1ccccn1)C(=O)N1CCC[C@H]1CNC(=O)c1ccccn1 ; Cl ; Cl ; Cl ; Cl]
18
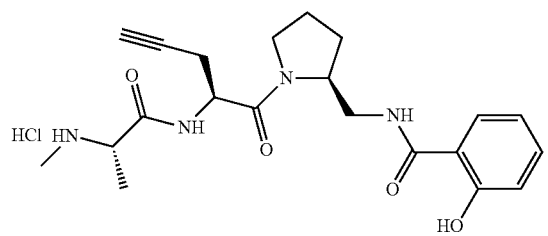 [SMILES: Cl ; C#CC[C@H](NC(=O)[C@H](C)NC)C(=O)N1CCC[C@H]1CNC(=O)c1ccccc1O]
19
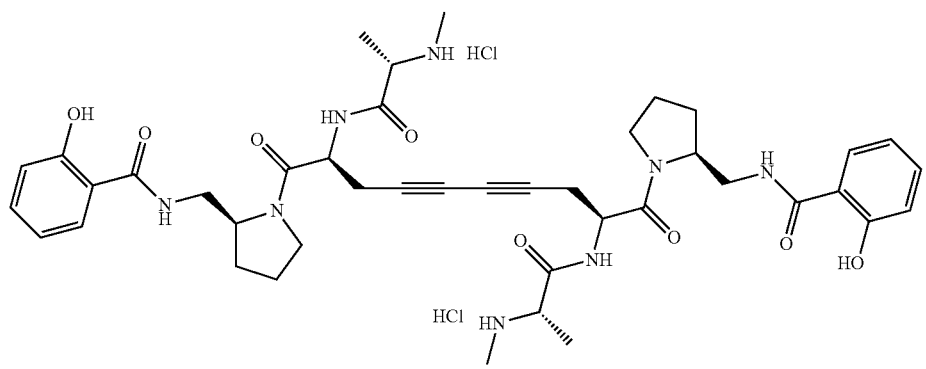 [SMILES: CN[C@@H](C)C(=O)N[C@@H](CC#CC#CC[C@H](NC(=O)[C@H](C)NC)C(=O)N1CCC[C@H]1CNC(=O)c1ccccc1O)C(=O)N1CCC[C@H]1CNC(=O)c1ccccc1O ; Cl ; Cl]
20
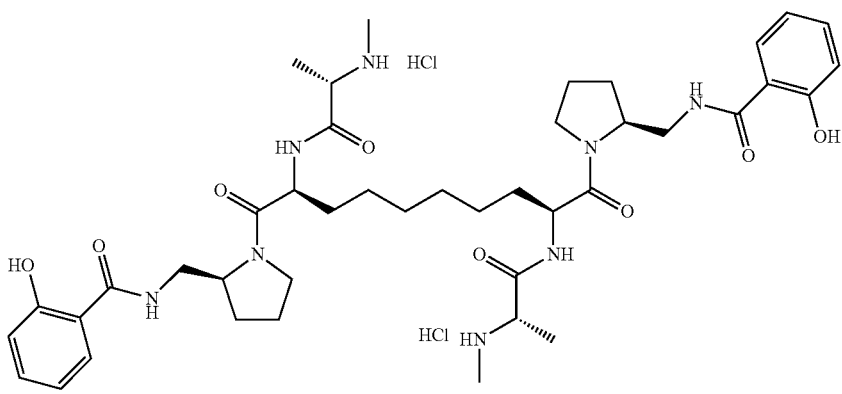 [SMILES: CN[C@@H](C)C(=O)N[C@@H](CCCCCC[C@H](NC(=O)[C@H](C)NC)C(=O)N1CCC[C@H]1CNC(=O)c1ccccc1O)C(=O)N1CCC[C@H]1CNC(=O)c1ccccc1O ; Cl ; Cl]

TABLE 1-continued
21
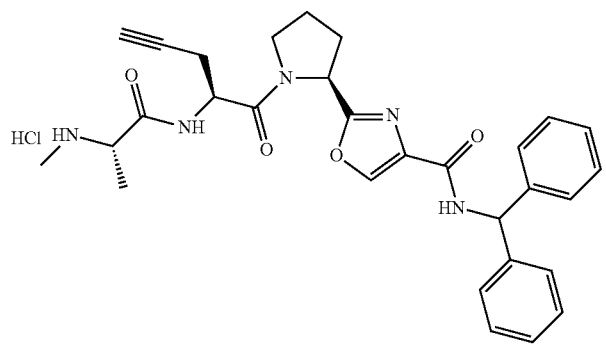 [SMILES: Cl ; C#CC[C@H](NC(=O)[C@H](C)NC)C(=O)N1CCC[C@H]1c1nc(C(=O)NC(c2ccccc2)c2ccccc2)co1]
22
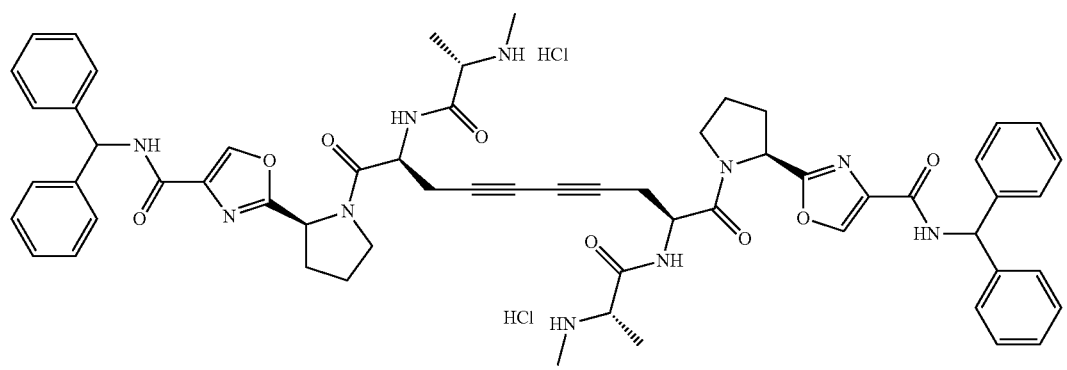 [SMILES: CN[C@@H](C)C(=O)N[C@@H](CC#CC#CC[C@H](NC(=O)[C@H](C)NC)C(=O)N1CCC[C@H]1c1nc(C(=O)NC(c2ccccc2)c2ccccc2)co1)C(=O)N1CCC[C@H]1c1nc(C(=O)NC(c2ccccc2)c2ccccc2)co1 ; Cl ; Cl]
23
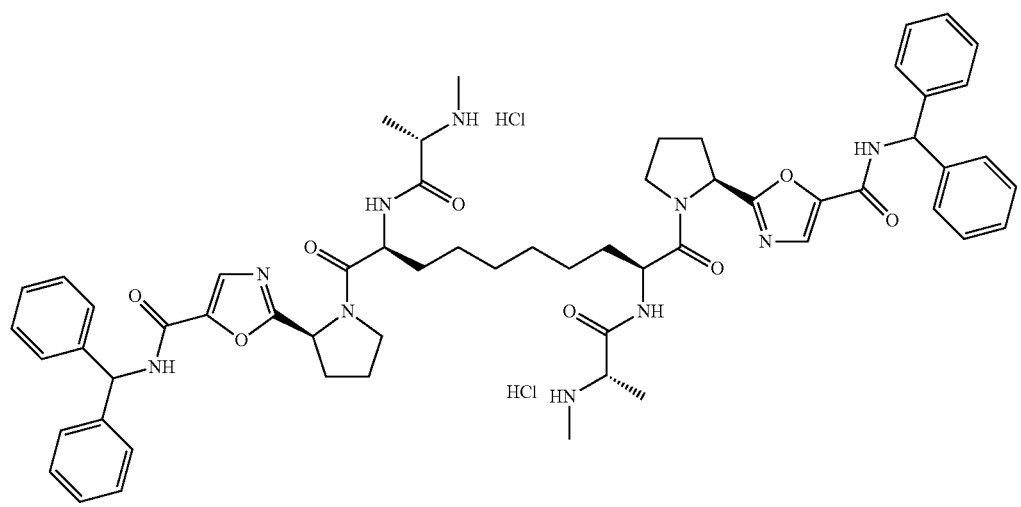 [SMILES: CN[C@@H](C)C(=O)N[C@@H](CCCCCC[C@H](NC(=O)[C@H](C)NC)C(=O)N1CCC[C@H]1c1ncc(C(=O)NC(c2ccccc2)c2ccccc2)o1)C(=O)N1CCC[C@H]1c1ncc(C(=O)NC(c2ccccc2)c2ccccc2)o1 ; Cl ; Cl]
24
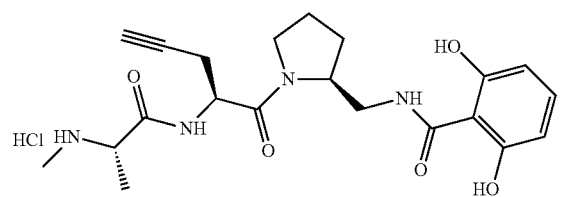 [SMILES: Cl ; C#CC[C@H](NC(=O)[C@H](C)NC)C(=O)N1CCC[C@H]1CNC(=O)c1c(O)cccc1O]

TABLE 1-continued
| | |
|---|---|
| 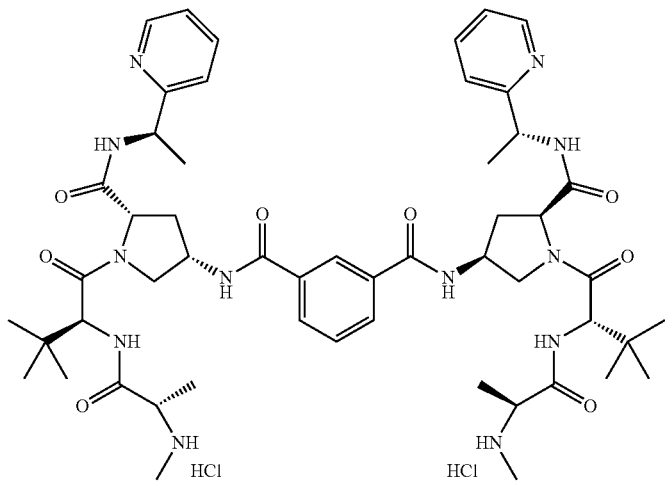 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccn4)N(C(=O)[C@@H](NC(=O)[C@H](C)NC)C(C)(C)C)C3)c2)C[C@H]1C(=O)N[C@H](C)c1ccccn1)C(C)(C)C ; Cl ; Cl] | 25 |
| 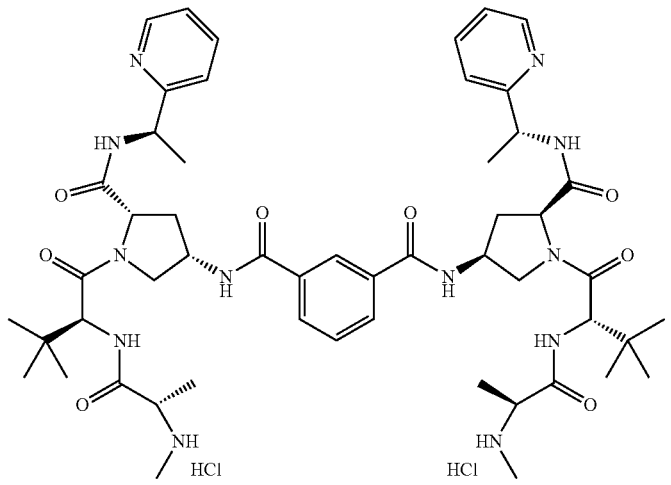 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccn4)N(C(=O)[C@@H](NC(=O)[C@H](C)NC)C(C)(C)C)C3)c2)C[C@H]1C(=O)N[C@H](C)c1ccccn1)C(C)(C)C ; Cl ; Cl] | 26 |
| 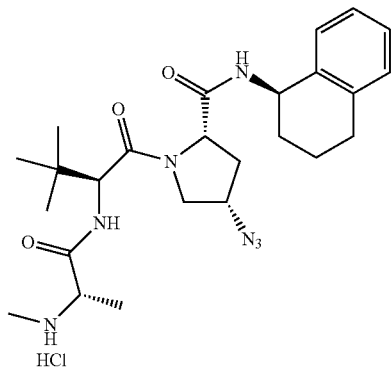 [SMILES: CN[C@@H](C)C(=O)N[C@H](C(=O)N1C[C@@H](N=[N+]=[N-])C[C@H]1C(=O)N[C@@H]1CCCc2ccccc21)C(C)(C)C ; Cl] | 27 |
| 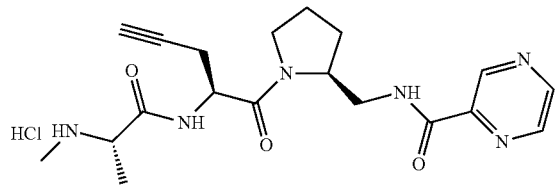 [SMILES: Cl ; C#CC[C@H](NC(=O)[C@H](C)NC)C(=O)N1CCC[C@H]1CNC(=O)c1cnccn1] | 28 |

TABLE 1-continued
| | |
|---|---|
| 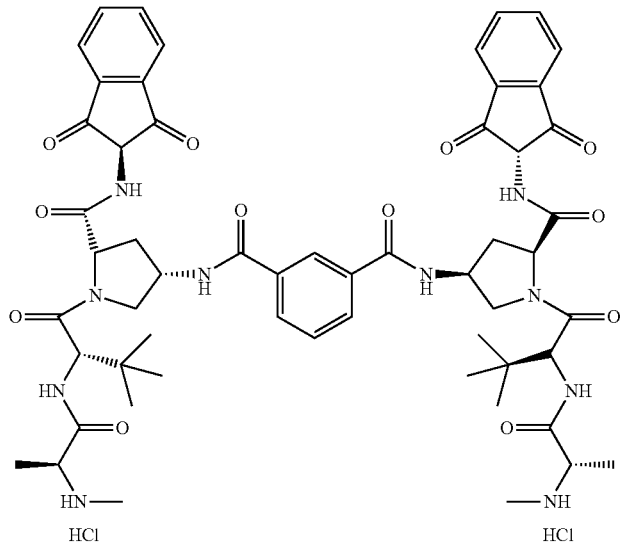 | 29 |
| 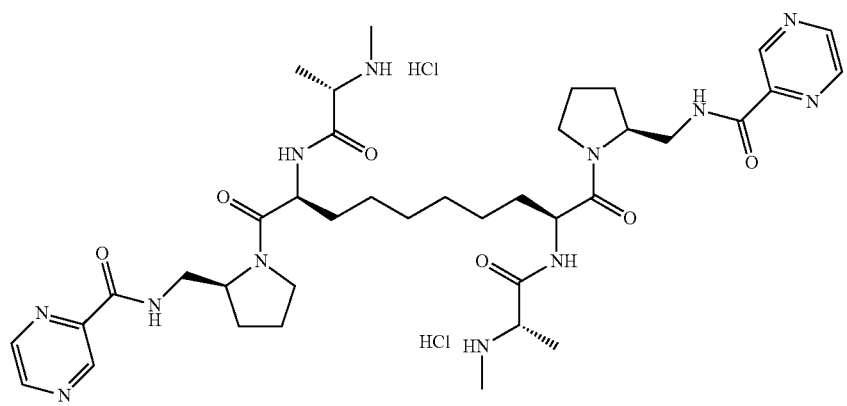 [SMILES: CN[C@@H](C)C(=O)N[C@@H](CCCCCC[C@H](NC(=O)[C@H](C)NC)C(=O)N1CCC[C@H]1CNC(=O)c1cnccn1)C(=O)N1CCC[C@H]1CNC(=O)c1cnccn1 ; Cl ; Cl] | 30 |
| 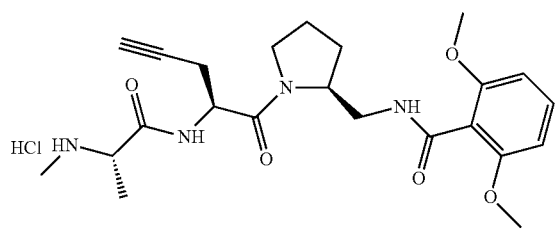 [SMILES: Cl ; C#CC[C@H](NC(=O)[C@H](C)NC)C(=O)N1CCC[C@H]1CNC(=O)c1c(OC)cccc1OC] | 31 |
| 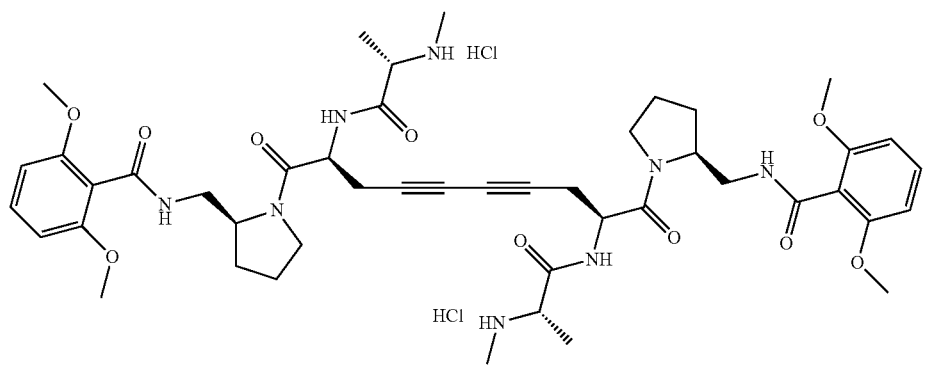 [SMILES: CN[C@@H](C)C(=O)N[C@@H](CC#CC#CC[C@H](NC(=O)[C@H](C)NC)C(=O)N1CCC[C@H]1CNC(=O)c1c(OC)cccc1OC)C(=O)N1CCC[C@H]1CNC(=O)c1c(OC)cccc1OC ; Cl ; Cl] | 32 |

TABLE 1-continued
33
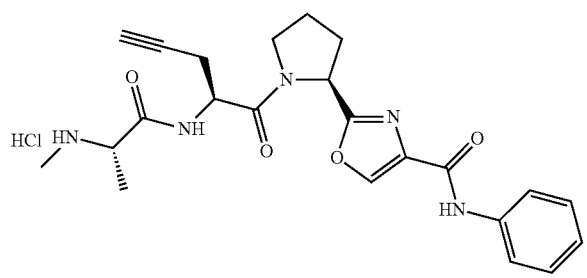 [SMILES: Cl ; C#CC[C@H](NC(=O)[C@H](C)NC)C(=O)N1CCC[C@H]1c1nc(C(=O)Nc2ccccc2)co1]
34
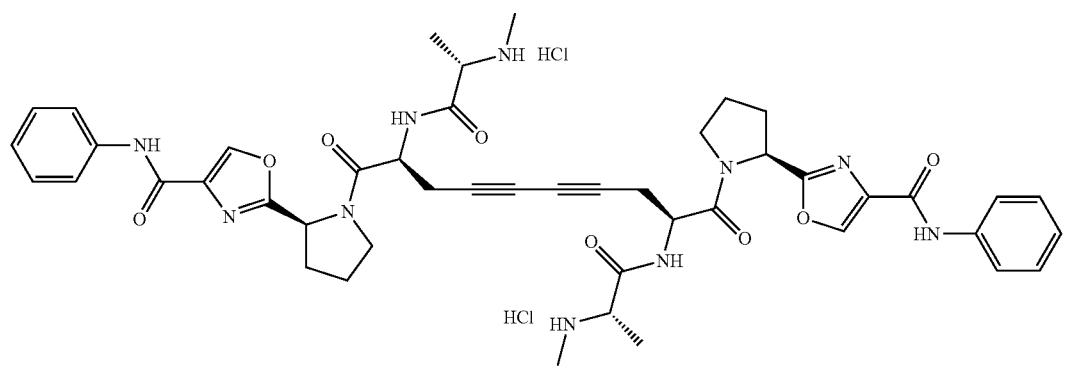 [SMILES: CN[C@@H](C)C(=O)N[C@@H](CC#CC#CC[C@H](NC(=O)[C@H](C)NC)C(=O)N1CCC[C@H]1c1nc(C(=O)Nc2ccccc2)co1)C(=O)N1CCC[C@H]1c1nc(C(=O)Nc2ccccc2)co1 ; Cl ; Cl]
35
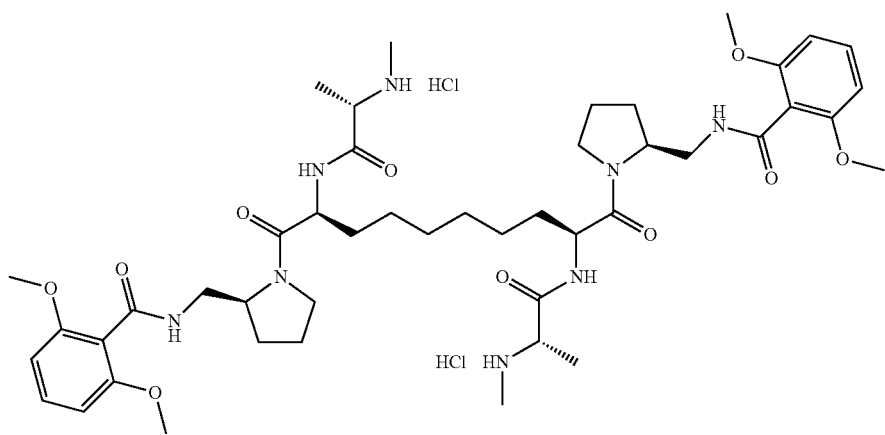
36
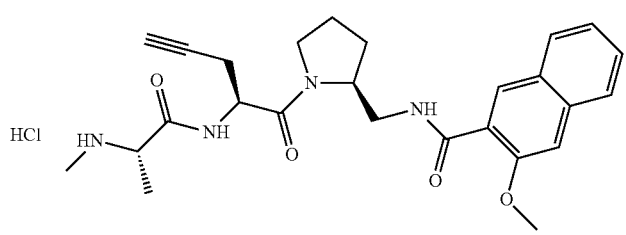 [SMILES: Cl ; C#CC[C@H](NC(=O)[C@H](C)NC)C(=O)N1CCC[C@H]1CNC(=O)c1cc2ccccc2cc1OC]

TABLE 1-continued
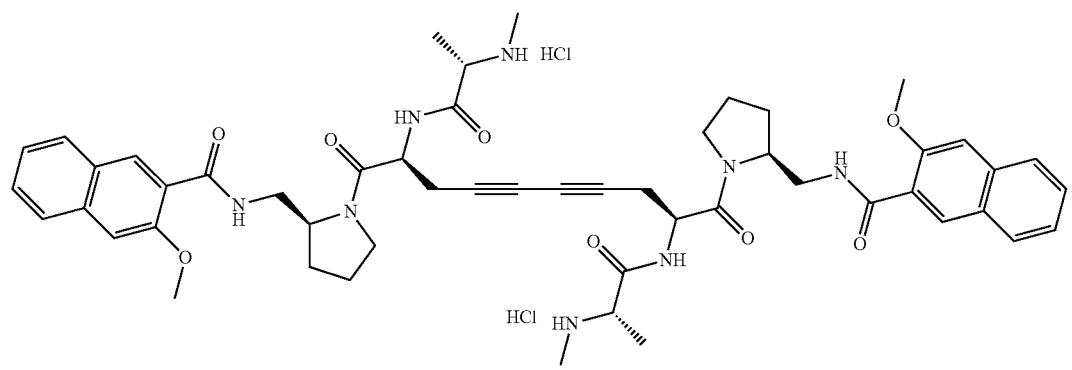 [SMILES: CN[C@@H](C)C(=O)N[C@@H](CC#CC#CC[C@H](NC(=O)[C@H](C)NC)C(=O)N1CCC[C@H]1CNC(=O)c1cc2ccccc2cc1OC)C(=O)N1CCC[C@H]1CNC(=O)c1cc2ccccc2cc1OC ; Cl ; Cl]
37
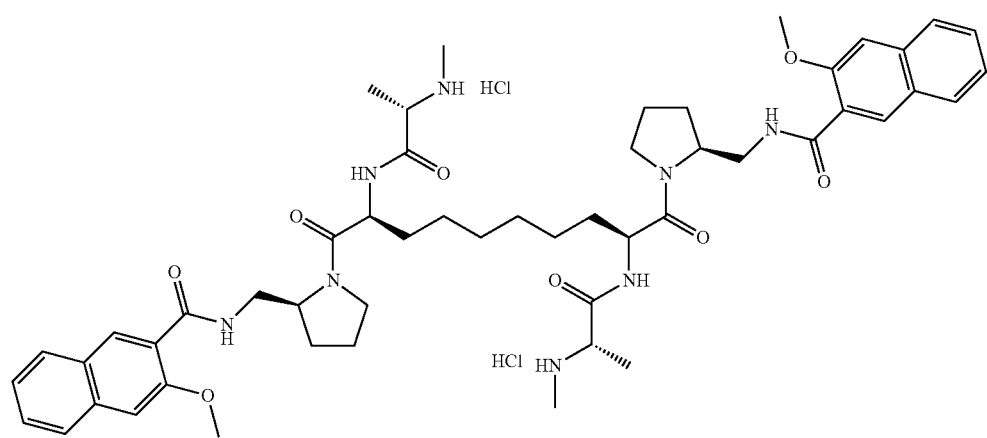 [SMILES: CN[C@@H](C)C(=O)N[C@@H](CCCCCC[C@H](NC(=O)[C@H](C)NC)C(=O)N1CCC[C@H]1CNC(=O)c1cc2ccccc2cc1OC)C(=O)N1CCC[C@H]1CNC(=O)c1cc2ccccc2cc1OC ; Cl ; Cl]
38
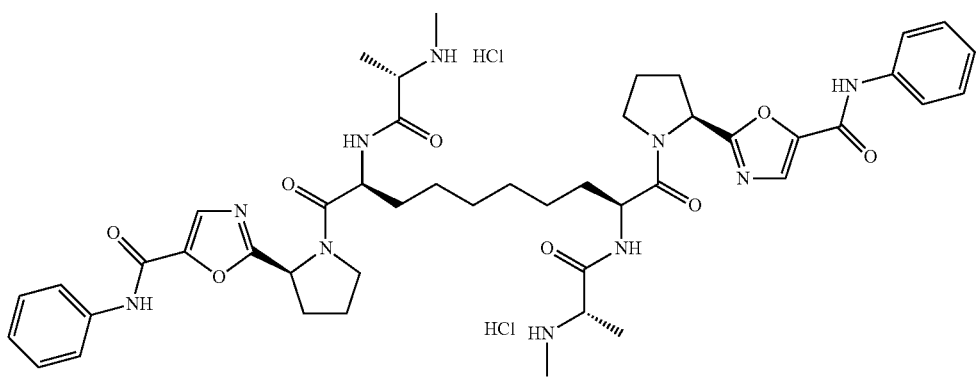 [SMILES: CN[C@@H](C)C(=O)N[C@@H](CCCCCC[C@H](NC(=O)[C@H](C)NC)C(=O)N1CCC[C@H]1c1ncc(C(=O)Nc2ccccc2)o1)C(=O)N1CCC[C@H]1c1ncc(C(=O)Nc2ccccc2)o1 ; Cl ; Cl]
39

TABLE 1-continued
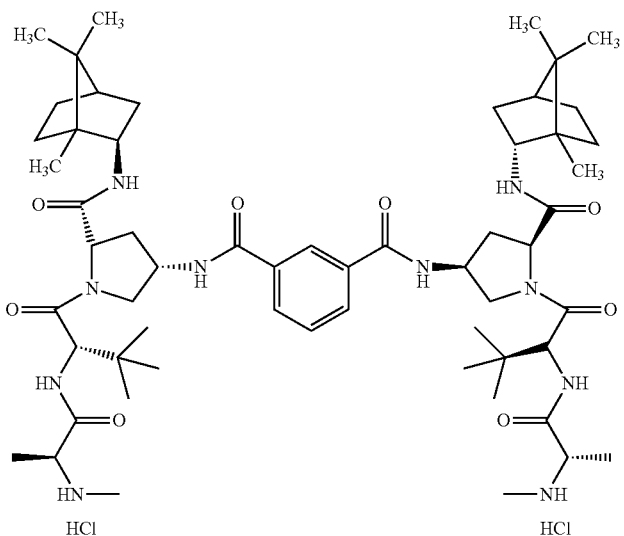
40
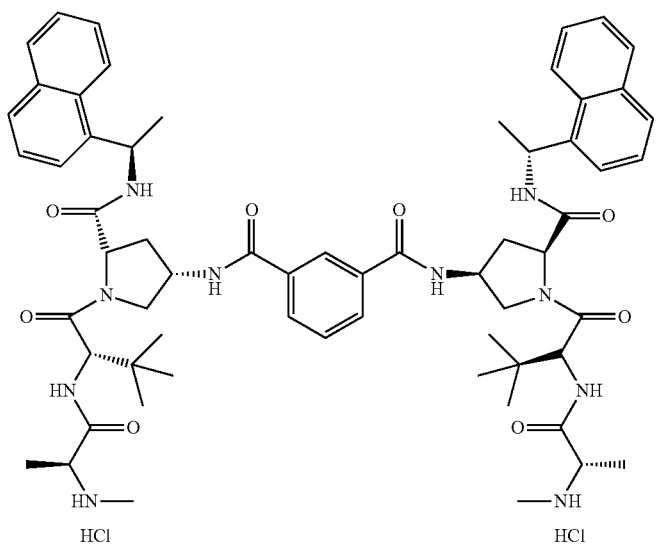
41
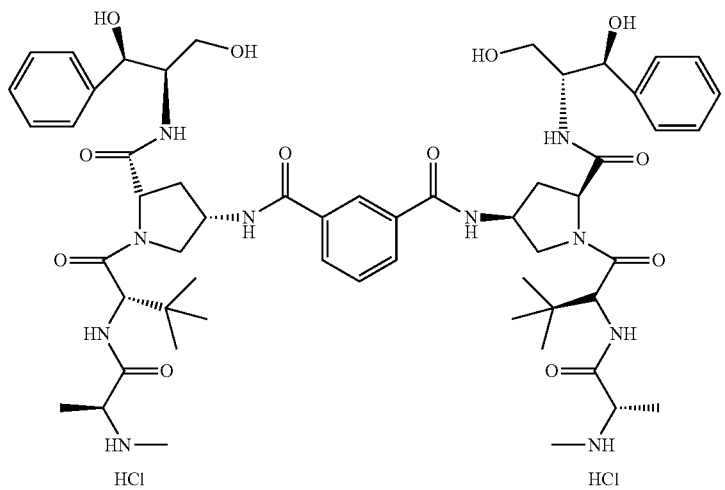
42

TABLE 1-continued
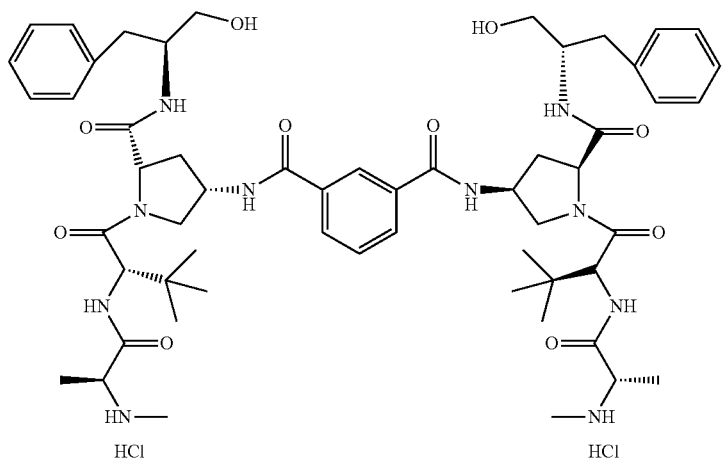
43
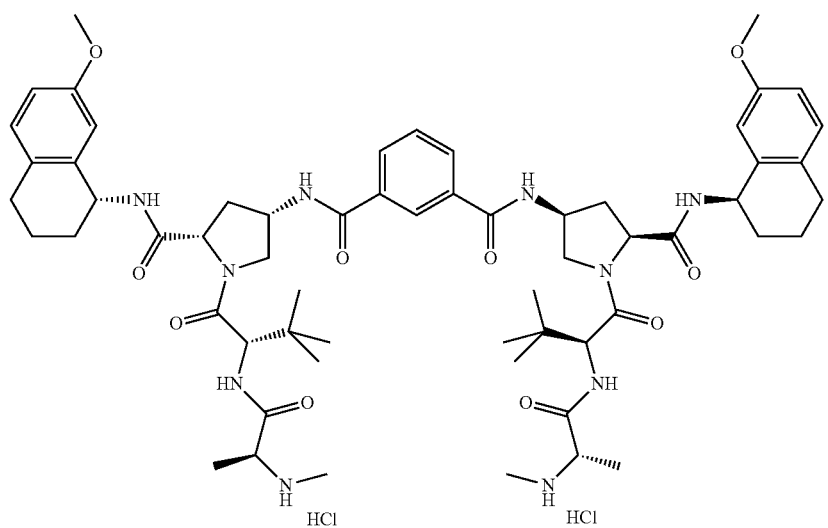 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccc(OC)cc54)N(C(=O)[C@@H](NC(=O)[C@H](C)NC)C(C)(C)C)C3)c2)C[C@H]1C(=O)N[C@@H]1CCCc2ccc(OC)cc21)C(C)(C)C ; Cl ; Cl]
44
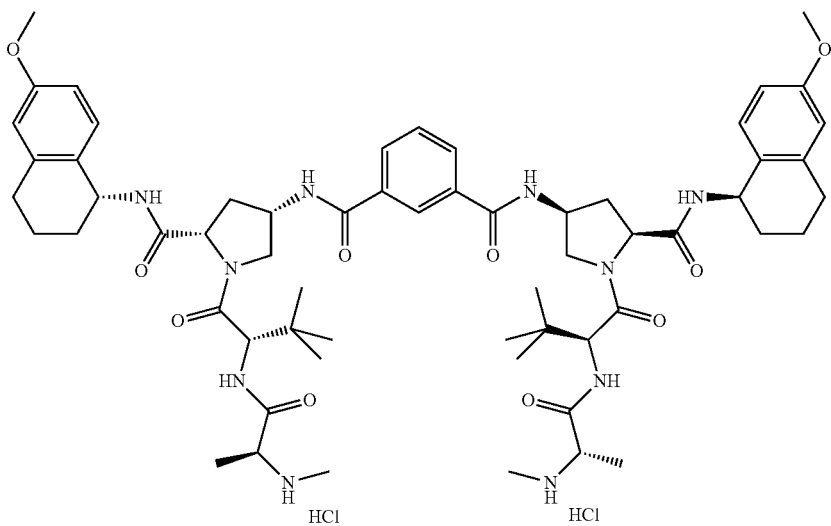 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5cc(OC)ccc54)N(C(=O)[C@@H](NC(=O)[C@H](C)NC)C(C)(C)C)C3)c2)C[C@H]1C(=O)N[C@@H]1CCCc2cc(OC)ccc21)C(C)(C)C ; Cl ; Cl]
45

TABLE 1-continued
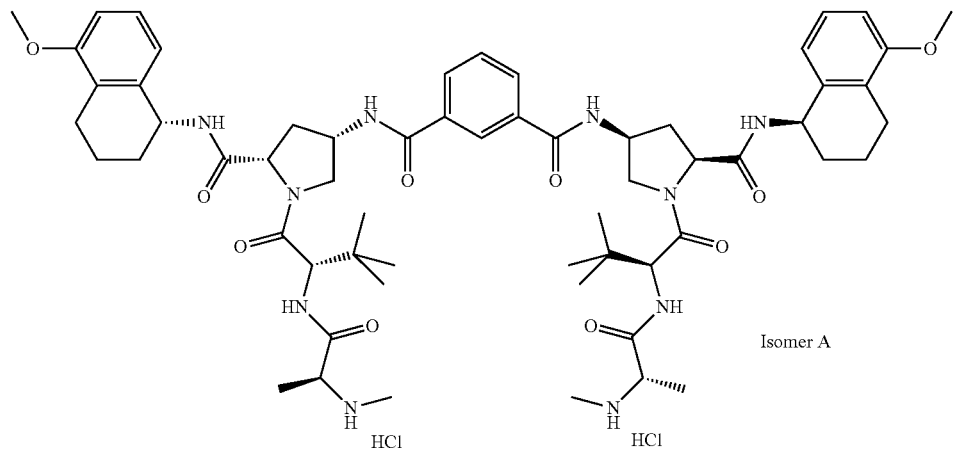
46
Isomer A
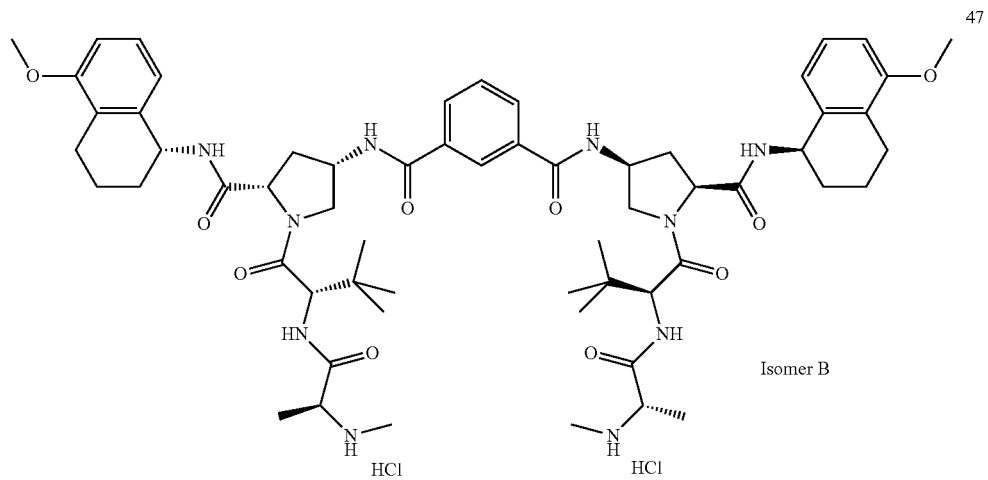
47
Isomer B
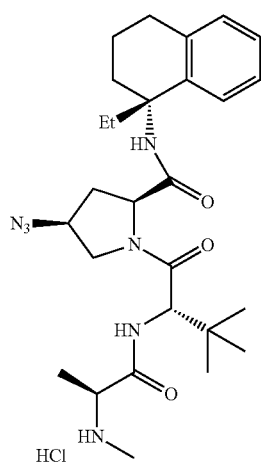 [SMILES: CC[C@@]1(NC(=O)[C@@H]2C[C@H](N=[N+]=[N-])CN2C(=O)[C@@H](NC(=O)[C@H](C)NC)C(C)(C)C)CCCc2ccccc21 ; Cl]
48
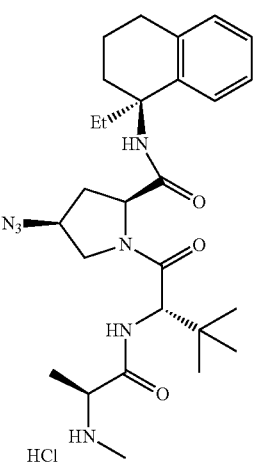 [SMILES: CC[C@]1(NC(=O)[C@@H]2C[C@H](N=[N+]=[N-])CN2C(=O)[C@@H](NC(=O)[C@H](C)NC)C(C)(C)C)CCCc2ccccc21 ; Cl]
49

TABLE 1-continued
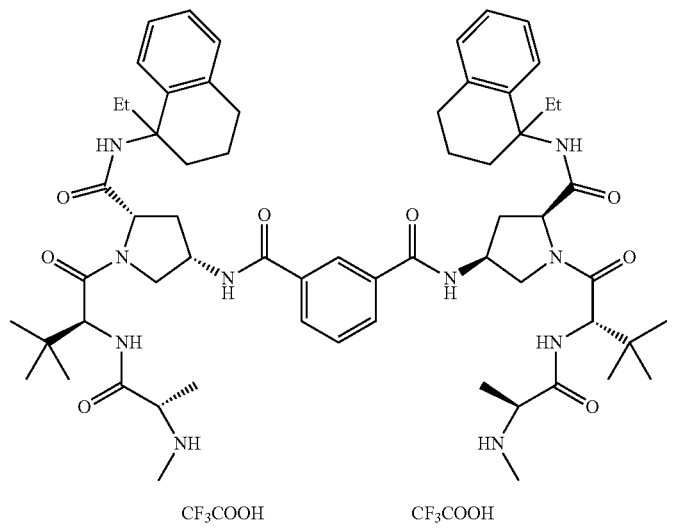 [SMILES: CCC1(NC(=O)[C@@H]2C[C@H](NC(=O)c3cccc(C(=O)N[C@H]4C[C@@H](C(=O)NC5(CC)CCCc6ccccc65)N(C(=O)[C@@H](NC(=O)[C@H](C)NC)C(C)(C)C)C4)c3)CN2C(=O)[C@@H](NC(=O)[C@H](C)NC)C(C)(C)C)CCCc2ccccc21 ; "CF3COOH" ; "CF3COOH"]
50
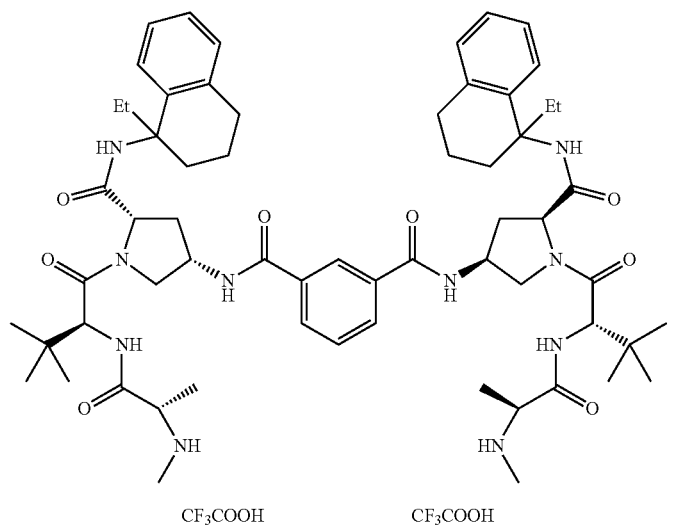 [SMILES: CCC1(NC(=O)[C@@H]2C[C@H](NC(=O)c3cccc(C(=O)N[C@H]4C[C@@H](C(=O)NC5(CC)CCCc6ccccc65)N(C(=O)[C@@H](NC(=O)[C@H](C)NC)C(C)(C)C)C4)c3)CN2C(=O)[C@@H](NC(=O)[C@H](C)NC)C(C)(C)C)CCCc2ccccc21 ; "CF3COOH" ; "CF3COOH"]
51

52

TABLE 1-continued
53
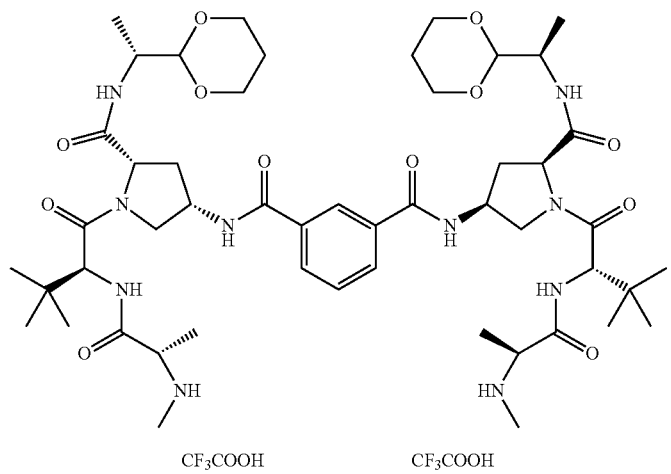 [SMILES: CN[C@@H](C)C(=O)N[C@H](C(=O)N1C[C@@H](NC(=O)c2cccc(C(=O)N[C@H]3C[C@@H](C(=O)N[C@H](C)C4OCCCO4)N(C(=O)[C@@H](NC(=O)[C@H](C)NC)C(C)(C)C)C3)c2)C[C@H]1C(=O)N[C@H](C)C1OCCCO1)C(C)(C)C ; "CF3COOH" ; "CF3COOH"]
54
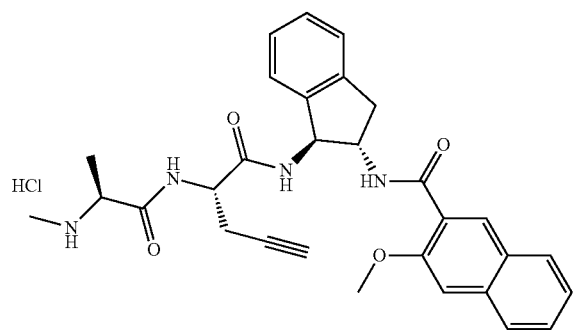 [SMILES: Cl ; C#CC[C@H](NC(=O)[C@H](C)NC)C(=O)N[C@H]1c2ccccc2C[C@@H]1NC(=O)c1cc2ccccc2cc1OC]
55
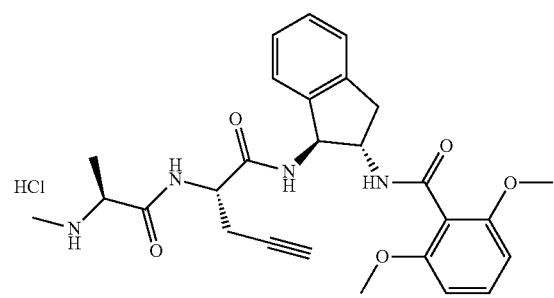

TABLE 1-continued
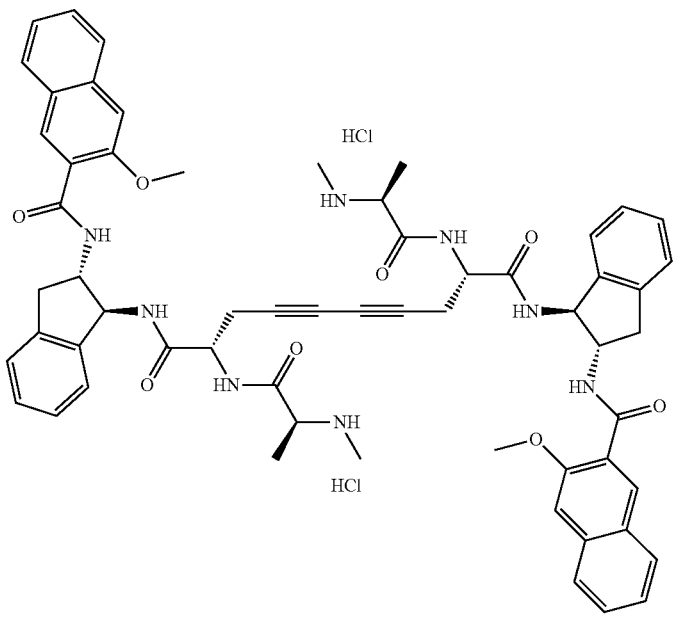 [SMILES: CN[C@@H](C)C(=O)N[C@@H](CC#CC#CC[C@H](NC(=O)[C@H](C)NC)C(=O)N[C@H]1c2ccccc2C[C@@H]1NC(=O)c1cc2ccccc2cc1OC)C(=O)N[C@H]1c2ccccc2C[C@@H]1NC(=O)c1cc2ccccc2cc1OC ; Cl ; Cl]
56
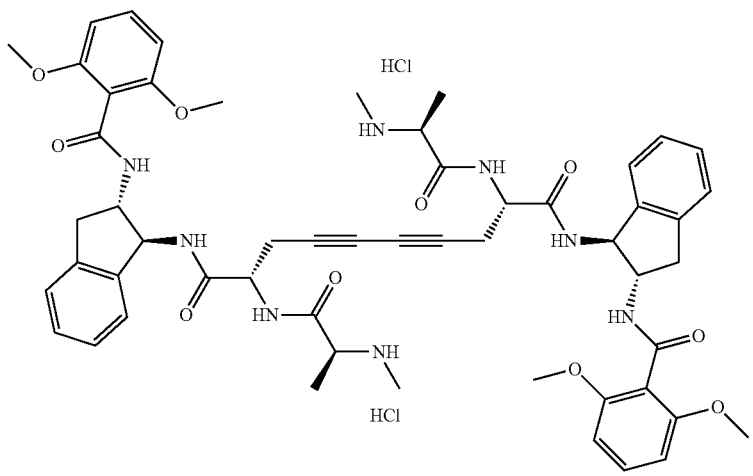
57

TABLE 1-continued
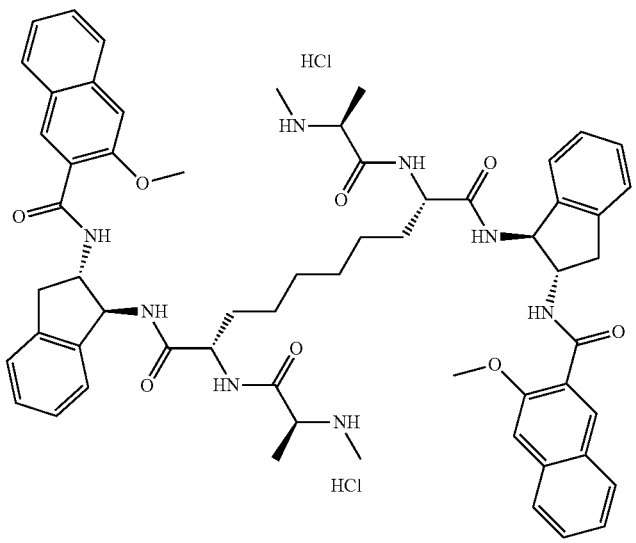 [SMILES: CN[C@@H](C)C(=O)N[C@@H](CCCCCC[C@H](NC(=O)[C@H](C)NC)C(=O)N[C@H]1c2ccccc2C[C@@H]1NC(=O)c1cc2ccccc2cc1OC)C(=O)N[C@H]1c2ccccc2C[C@@H]1NC(=O)c1cc2ccccc2cc1OC ; Cl ; Cl]
58
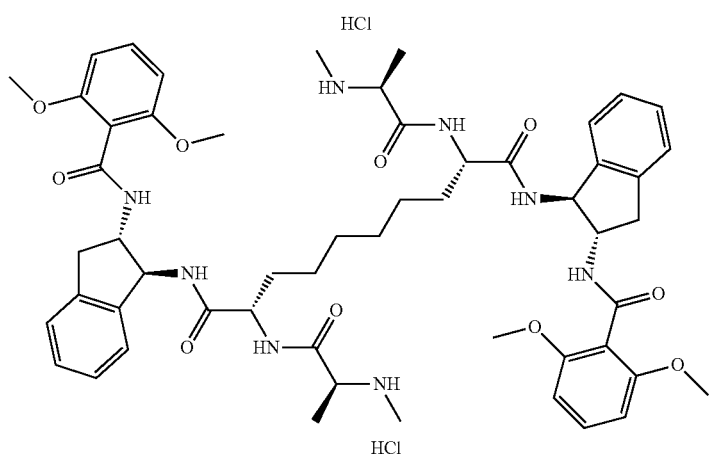
59
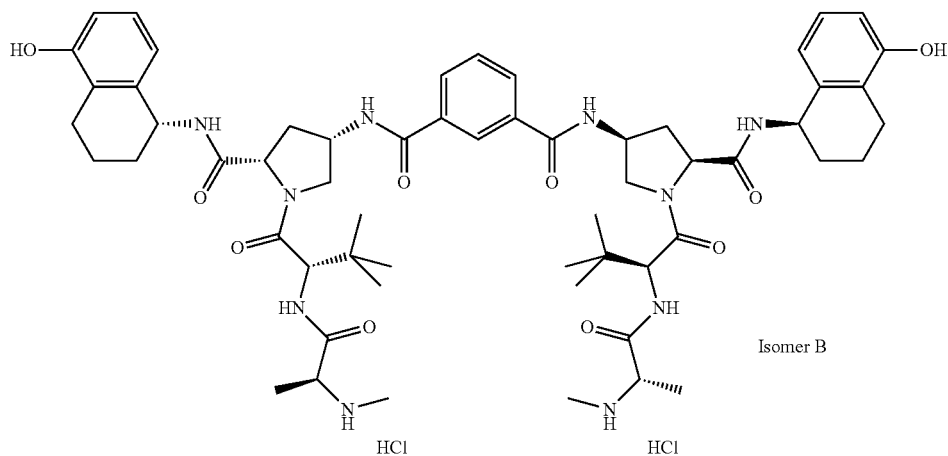 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5c(O)cccc54)N(C(=O)[C@@H](NC(=O)[C@H](C)NC)C(C)(C)C)C3)c2)C[C@H]1C(=O)N[C@@H]1CCCc2c(O)cccc21)C(C)(C)C ; Cl ; Cl]
60
Isomer B

TABLE 1-continued
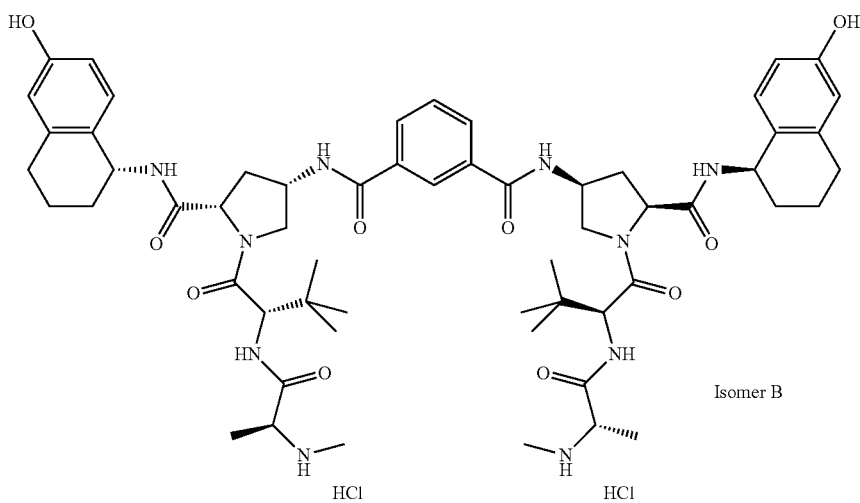 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5cc(O)ccc54)N(C(=O)[C@@H](NC(=O)[C@H](C)NC)C(C)(C)C)C3)c2)C[C@H]1C(=O)N[C@@H]1CCCc2cc(O)ccc21)C(C)(C)C ; Cl ; Cl]
61 Isomer B
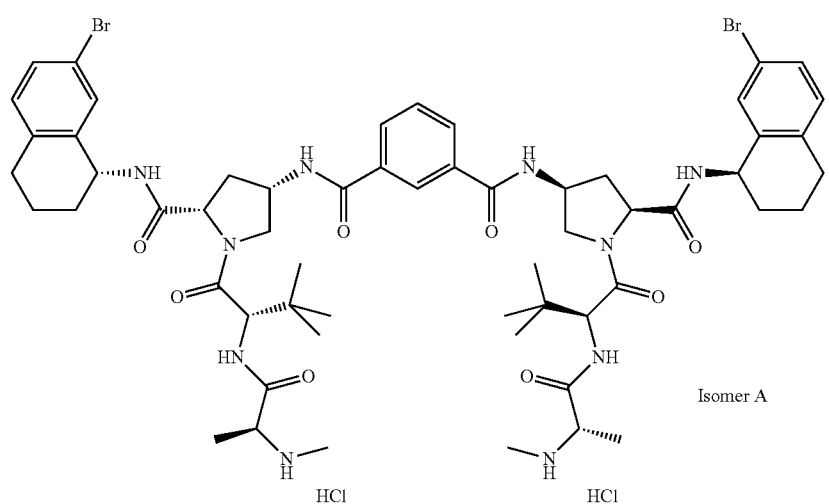 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccc(Br)cc54)N(C(=O)[C@@H](NC(=O)[C@H](C)NC)C(C)(C)C)C3)c2)C[C@H]1C(=O)N[C@@H]1CCCc2ccc(Br)cc21)C(C)(C)C ; Cl ; Cl]
62 Isomer A
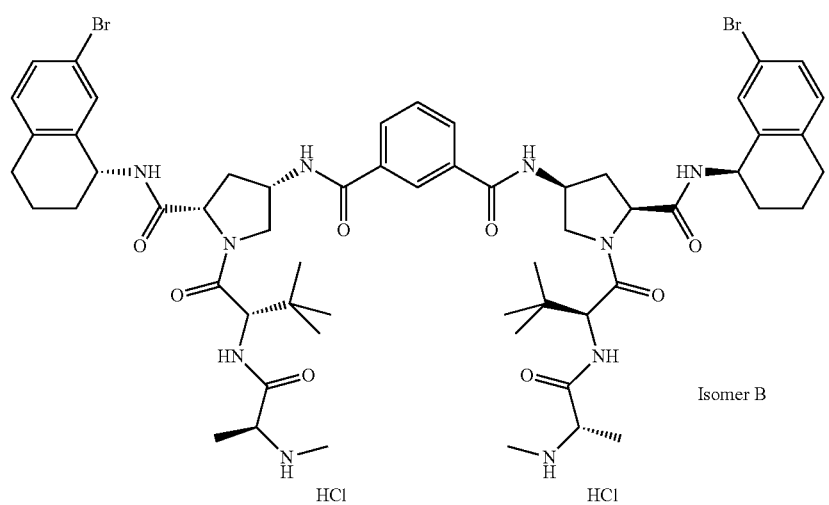 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccc(Br)cc54)N(C(=O)[C@@H](NC(=O)[C@H](C)NC)C(C)(C)C)C3)c2)C[C@H]1C(=O)N[C@@H]1CCCc2ccc(Br)cc21)C(C)(C)C ; Cl ; Cl]
63 Isomer B TABLE 1-continued
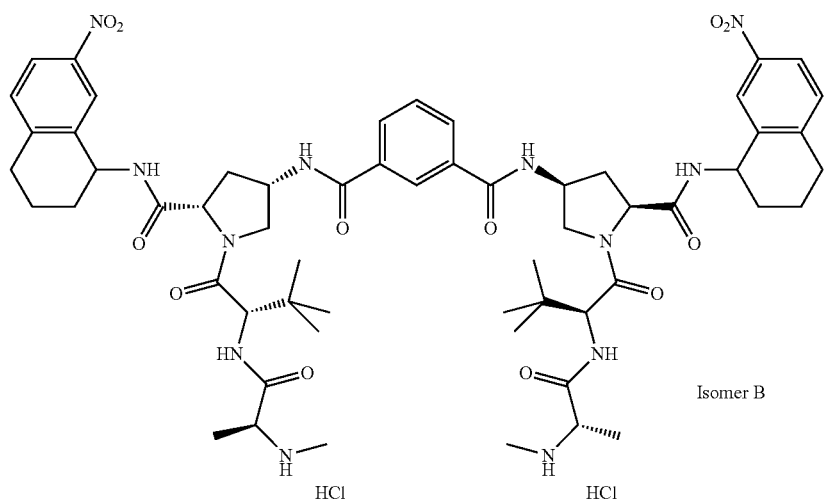 [SMILES: CN[C@@H](C)C(=O)N[C@H](C(=O)N1C[C@@H](NC(=O)c2cccc(C(=O)N[C@H]3C[C@@H](C(=O)NC4CCCc5ccc([N+](=O)[O-])cc54)N(C(=O)[C@@H](NC(=O)[C@H](C)NC)C(C)(C)C)C3)c2)C[C@H]1C(=O)NC1CCCc2ccc([N+](=O)[O-])cc21)C(C)(C)C ; Cl ; Cl]
64
Isomer B
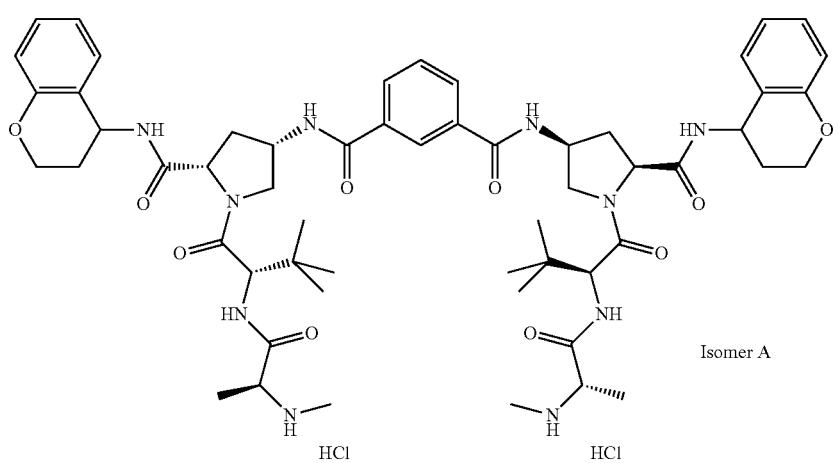 [SMILES: CN[C@@H](C)C(=O)N[C@H](C(=O)N1C[C@@H](NC(=O)c2cccc(C(=O)N[C@H]3C[C@@H](C(=O)NC4CCOc5ccccc54)N(C(=O)[C@@H](NC(=O)[C@H](C)NC)C(C)(C)C)C3)c2)C[C@H]1C(=O)NC1CCOc2ccccc21)C(C)(C)C ; Cl ; Cl]
65
Isomer A
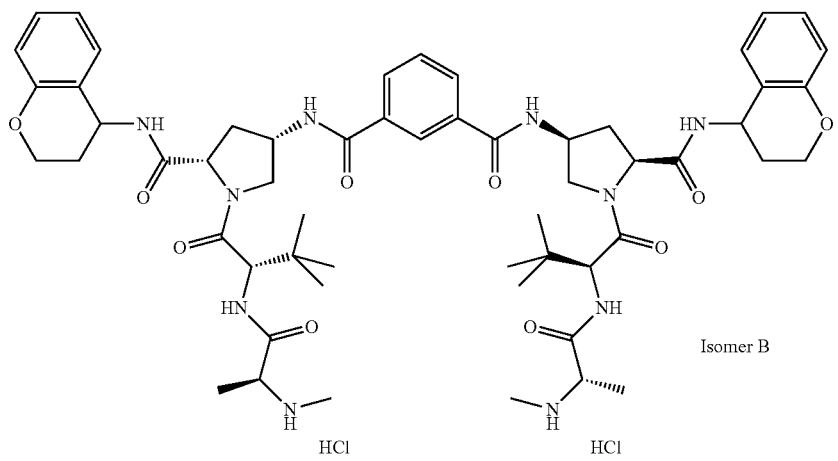 [SMILES: CN[C@@H](C)C(=O)N[C@H](C(=O)N1C[C@@H](NC(=O)c2cccc(C(=O)N[C@H]3C[C@@H](C(=O)NC4CCOc5ccccc54)N(C(=O)[C@@H](NC(=O)[C@H](C)NC)C(C)(C)C)C3)c2)C[C@H]1C(=O)NC1CCOc2ccccc21)C(C)(C)C ; Cl ; Cl]
66
Isomer B TABLE 1-continued
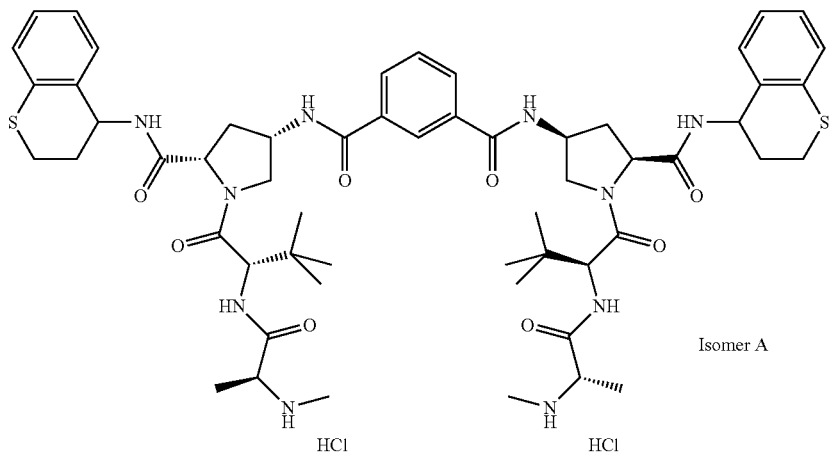 [SMILES: CN[C@@H](C)C(=O)N[C@H](C(=O)N1C[C@@H](NC(=O)c2cccc(C(=O)N[C@H]3C[C@@H](C(=O)NC4CCSc5ccccc54)N(C(=O)[C@@H](NC(=O)[C@H](C)NC)C(C)(C)C)C3)c2)C[C@H]1C(=O)NC1CCSc2ccccc21)C(C)(C)C ; Cl ; Cl]
67
Isomer A
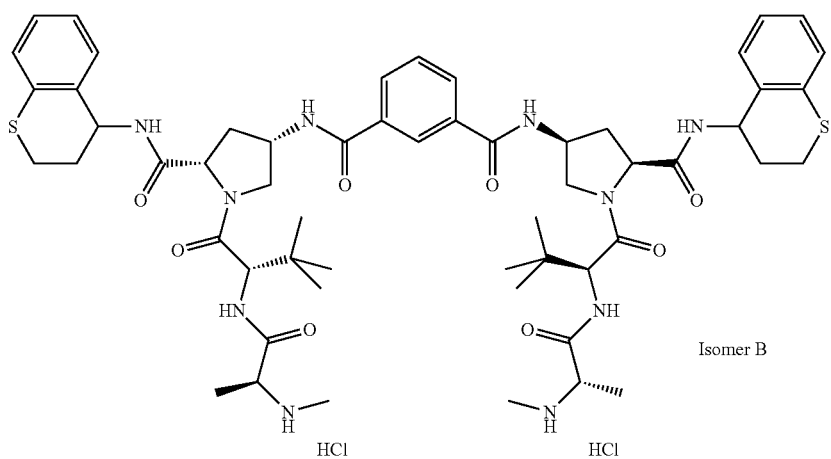 [SMILES: CN[C@@H](C)C(=O)N[C@H](C(=O)N1C[C@@H](NC(=O)c2cccc(C(=O)N[C@H]3C[C@@H](C(=O)NC4CCSc5ccccc54)N(C(=O)[C@@H](NC(=O)[C@H](C)NC)C(C)(C)C)C3)c2)C[C@H]1C(=O)NC1CCSc2ccccc21)C(C)(C)C ; Cl ; Cl]
68
Isomer B
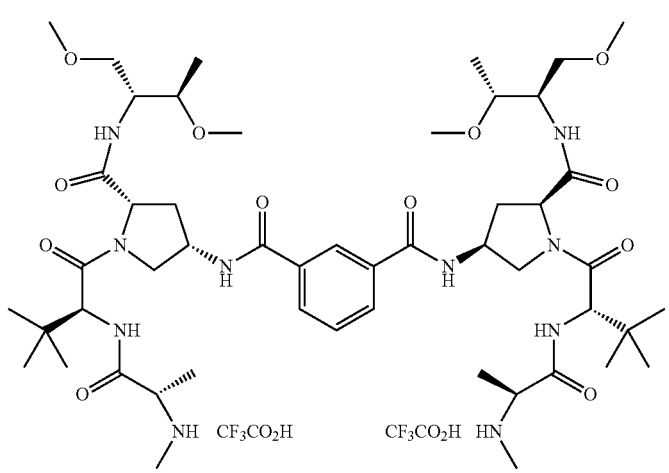 [SMILES: CN[C@@H](C)C(=O)N[C@H](C(=O)N1C[C@@H](NC(=O)c2cccc(C(=O)N[C@H]3C[C@@H](C(=O)N[C@H](COC)[C@@H](C)OC)N(C(=O)[C@@H](NC(=O)[C@H](C)NC)C(C)(C)C)C3)c2)C[C@H]1C(=O)N[C@H](COC)[C@@H](C)OC)C(C)(C)C ; "CF3CO2H" ; "CF3CO2H"]
69

TABLE 1-continued
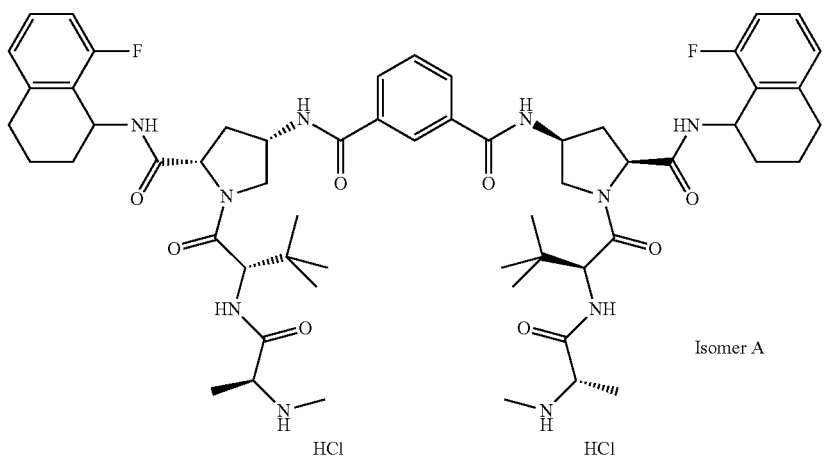 [SMILES: CN[C@@H](C)C(=O)N[C@H](C(=O)N1C[C@@H](NC(=O)c2cccc(C(=O)N[C@H]3C[C@@H](C(=O)NC4CCCc5cccc(F)c54)N(C(=O)[C@@H](NC(=O)[C@H](C)NC)C(C)(C)C)C3)c2)C[C@H]1C(=O)NC1CCCc2cccc(F)c21)C(C)(C)C ; Cl ; Cl]
70
Isomer A
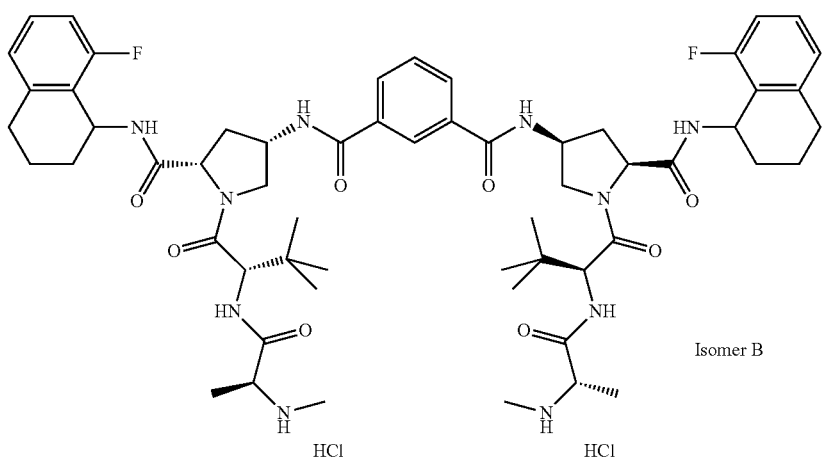 [SMILES: CN[C@@H](C)C(=O)N[C@H](C(=O)N1C[C@@H](NC(=O)c2cccc(C(=O)N[C@H]3C[C@@H](C(=O)NC4CCCc5cccc(F)c54)N(C(=O)[C@@H](NC(=O)[C@H](C)NC)C(C)(C)C)C3)c2)C[C@H]1C(=O)NC1CCCc2cccc(F)c21)C(C)(C)C ; Cl ; Cl]
71
Isomer B
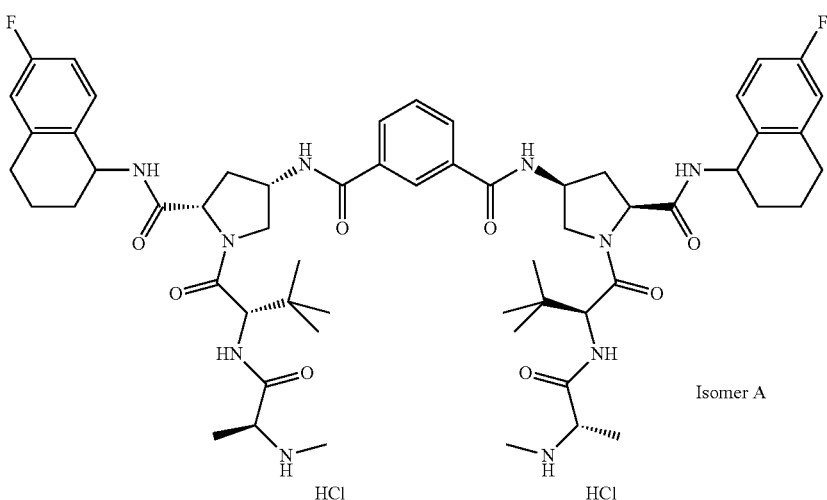 [SMILES: CN[C@@H](C)C(=O)N[C@H](C(=O)N1C[C@@H](NC(=O)c2cccc(C(=O)N[C@H]3C[C@@H](C(=O)NC4CCCc5cc(F)ccc54)N(C(=O)[C@@H](NC(=O)[C@H](C)NC)C(C)(C)C)C3)c2)C[C@H]1C(=O)NC1CCCc2cc(F)ccc21)C(C)(C)C ; Cl ; Cl]
72
Isomer A TABLE 1-continued
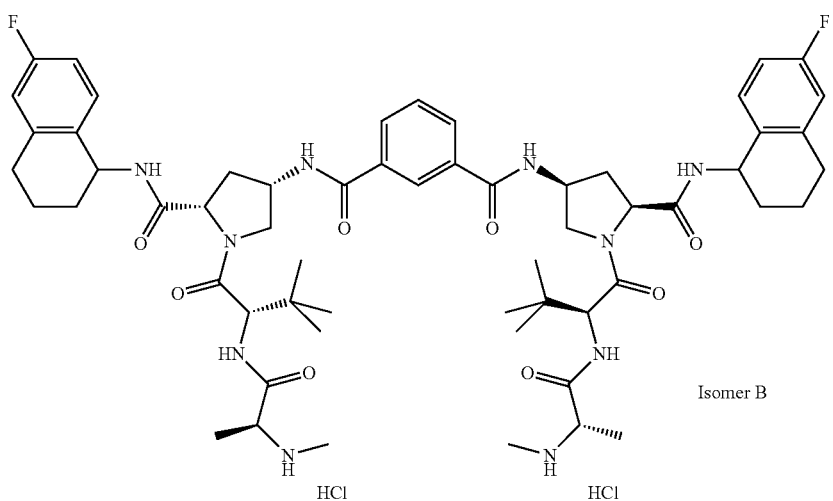 [SMILES: CN[C@@H](C)C(=O)N[C@H](C(=O)N1C[C@@H](NC(=O)c2cccc(C(=O)N[C@H]3C[C@@H](C(=O)NC4CCCc5cc(F)ccc54)N(C(=O)[C@@H](NC(=O)[C@H](C)NC)C(C)(C)C)C3)c2)C[C@H]1C(=O)NC1CCCc2cc(F)ccc21)C(C)(C)C ; Cl ; Cl]
73
Isomer B
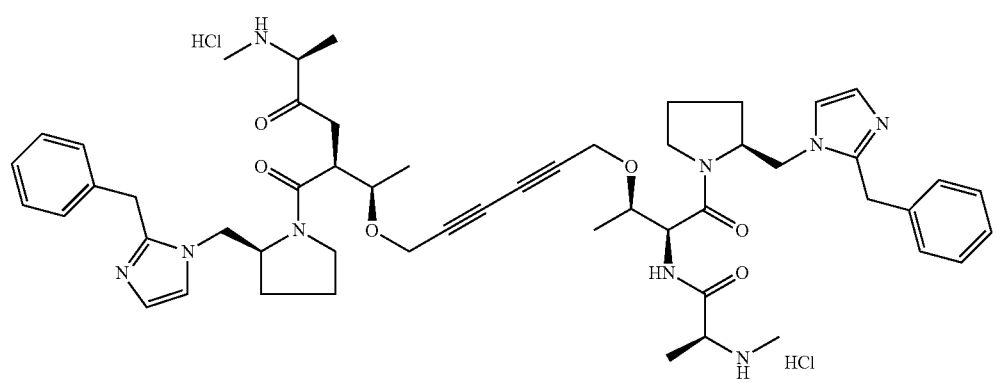 [SMILES: CN[C@@H](C)C(=O)C[C@H](C(=O)N1CCC[C@H]1Cn1ccnc1Cc1ccccc1)[C@@H](C)OCC#CC#CCO[C@H](C)[C@H](NC(=O)[C@H](C)NC)C(=O)N1CCC[C@H]1Cn1ccnc1Cc1ccccc1 ; Cl ; Cl]
74
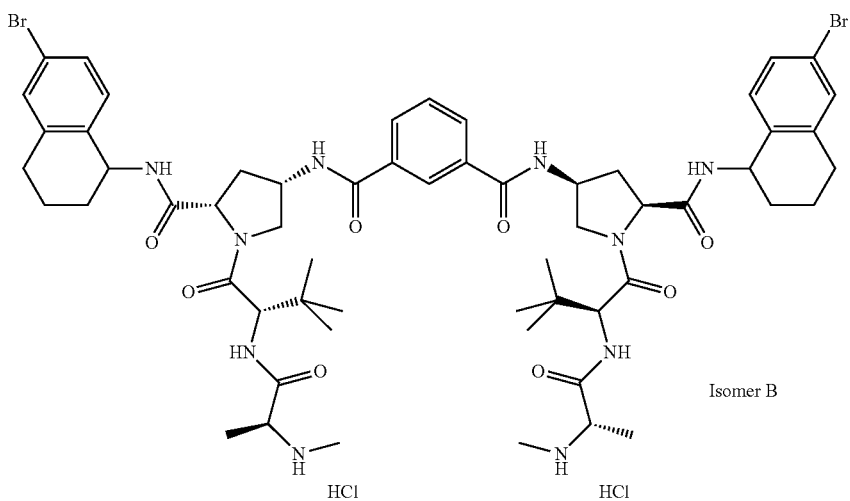 [SMILES: CN[C@@H](C)C(=O)N[C@H](C(=O)N1C[C@@H](NC(=O)c2cccc(C(=O)N[C@H]3C[C@@H](C(=O)NC4CCCc5cc(Br)ccc54)N(C(=O)[C@@H](NC(=O)[C@H](C)NC)C(C)(C)C)C3)c2)C[C@H]1C(=O)NC1CCCc2cc(Br)ccc21)C(C)(C)C ; Cl ; Cl]
75
Isomer B TABLE 1-continued
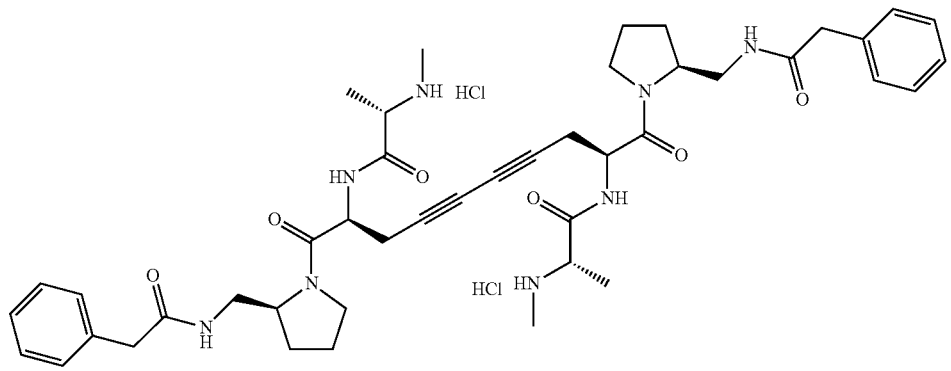 [SMILES: CN[C@@H](C)C(=O)N[C@@H](CC#CC#CC[C@H](NC(=O)[C@H](C)NC)C(=O)N1CCC[C@H]1CNC(=O)Cc1ccccc1)C(=O)N1CCC[C@H]1CNC(=O)Cc1ccccc1 ; Cl ; Cl]
76
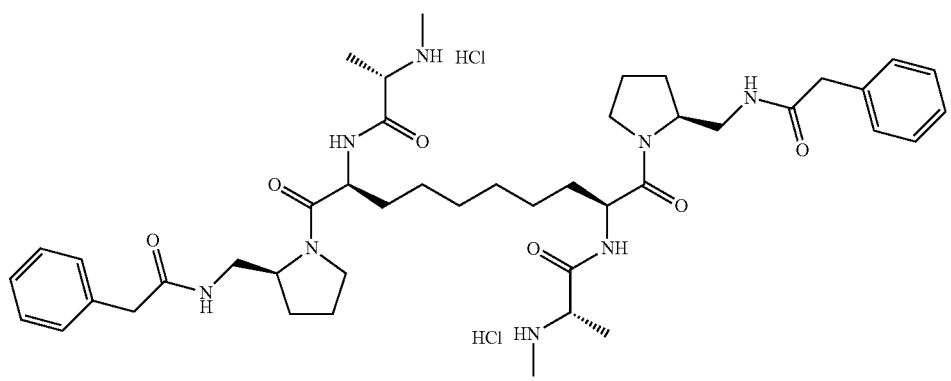 [SMILES: CN[C@@H](C)C(=O)N[C@@H](CCCCCC[C@H](NC(=O)[C@H](C)NC)C(=O)N1CCC[C@H]1CNC(=O)Cc1ccccc1)C(=O)N1CCC[C@H]1CNC(=O)Cc1ccccc1 ; Cl ; Cl]
77
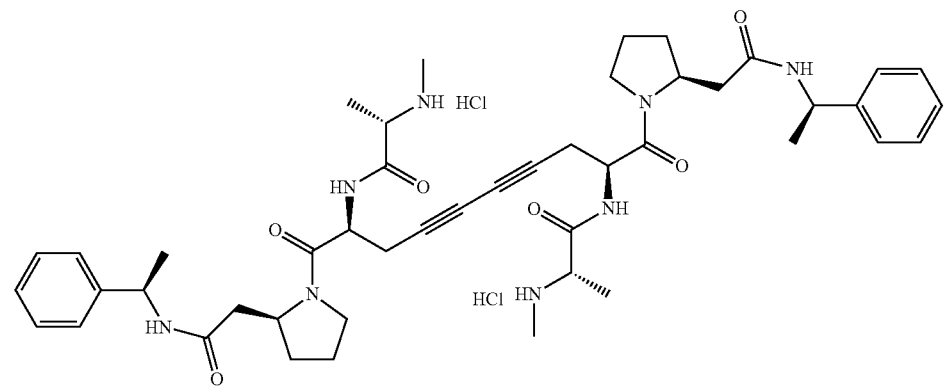 [SMILES: CN[C@@H](C)C(=O)N[C@@H](CC#CC#CC[C@H](NC(=O)[C@H](C)NC)C(=O)N1CCC[C@H]1CC(=O)N[C@H](C)c1ccccc1)C(=O)N1CCC[C@H]1CC(=O)N[C@H](C)c1ccccc1 ; Cl ; Cl]
78
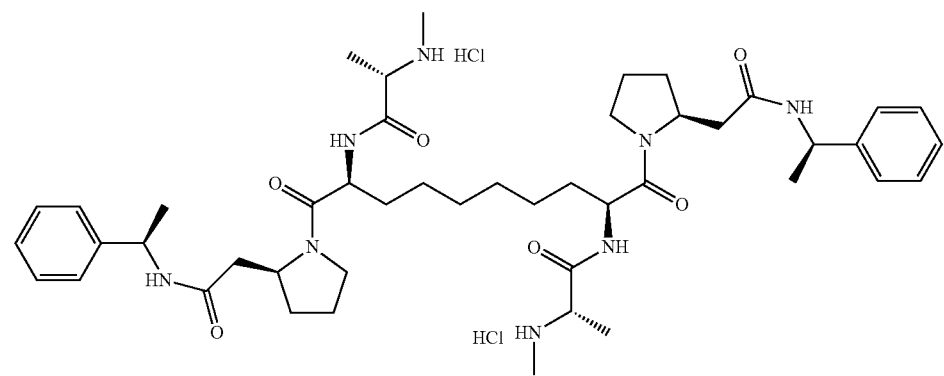 [SMILES: CN[C@@H](C)C(=O)N[C@@H](CCCCCC[C@H](NC(=O)[C@H](C)NC)C(=O)N1CCC[C@H]1CC(=O)N[C@H](C)c1ccccc1)C(=O)N1CCC[C@H]1CC(=O)N[C@H](C)c1ccccc1 ; Cl ; Cl]
79

TABLE 1-continued
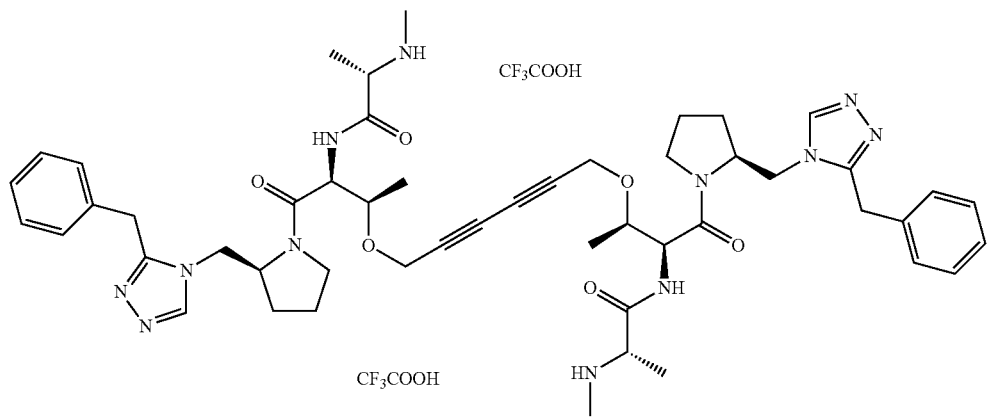 [SMILES: CN[C@@H](C)C(=O)N[C@H](C(=O)N1CCC[C@H]1Cn1cnnc1Cc1ccccc1)[C@@H](C)OCC#CC#CCO[C@H](C)[C@H](NC(=O)[C@H](C)NC)C(=O)N1CCC[C@H]1Cn1cnnc1Cc1ccccc1 ; "CF3COOH" ; "CF3COOH"]
80
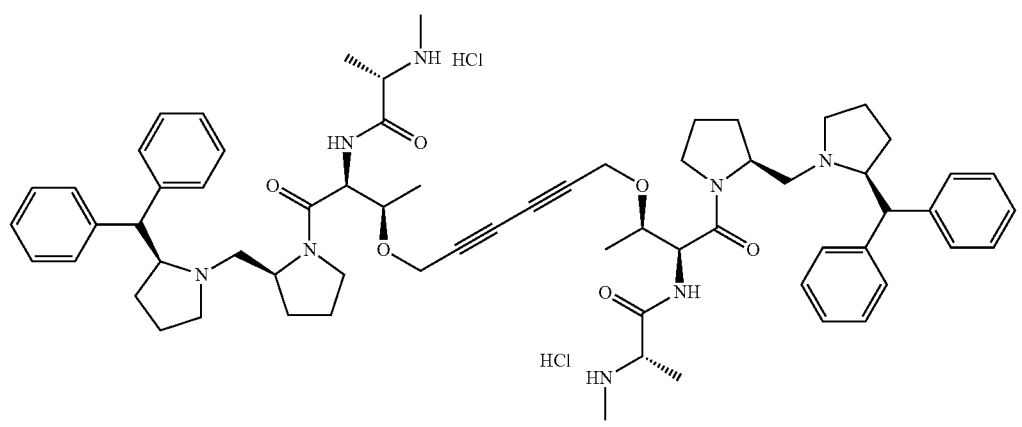 [SMILES: CN[C@@H](C)C(=O)N[C@H](C(=O)N1CCC[C@H]1CN1CCC[C@H]1C(c1ccccc1)c1ccccc1)[C@@H](C)OCC#CC#CCO[C@H](C)[C@H](NC(=O)[C@H](C)NC)C(=O)N1CCC[C@H]1CN1CCC[C@H]1C(c1ccccc1)c1ccccc1 ; Cl ; Cl]
81
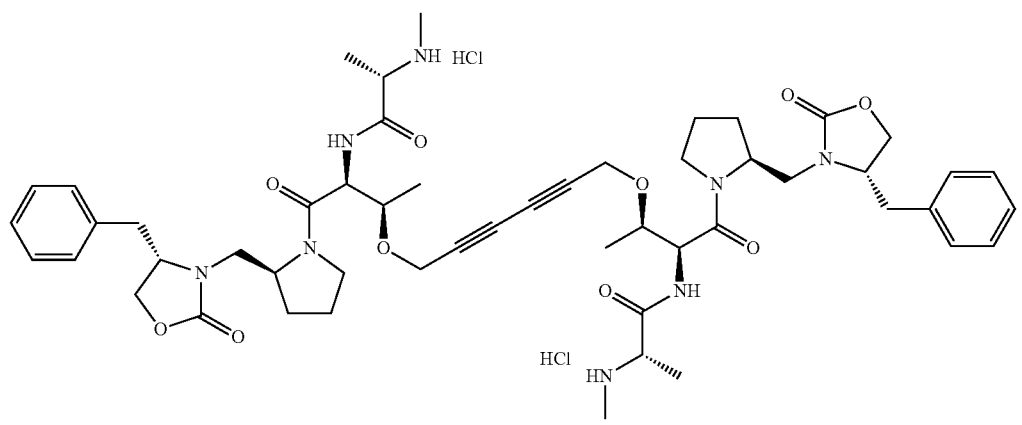 [SMILES: CN[C@@H](C)C(=O)N[C@H](C(=O)N1CCC[C@H]1CN1C(=O)OC[C@@H]1Cc1ccccc1)[C@@H](C)OCC#CC#CCO[C@H](C)[C@H](NC(=O)[C@H](C)NC)C(=O)N1CCC[C@H]1CN1C(=O)OC[C@@H]1Cc1ccccc1 ; Cl ; Cl]
82

TABLE 1-continued
83
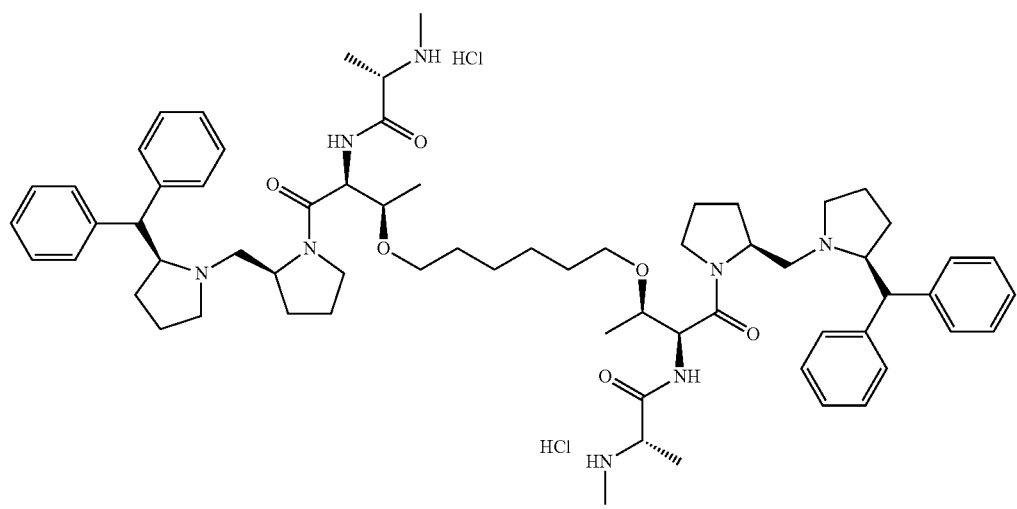 [SMILES: CN[C@@H](C)C(=O)N[C@H](C(=O)N1CCC[C@H]1CN1CCC[C@H]1C(c1ccccc1)c1ccccc1)[C@@H](C)OCCCCCCO[C@H](C)[C@H](NC(=O)[C@H](C)NC)C(=O)N1CCC[C@H]1CN1CCC[C@H]1C(c1ccccc1)c1ccccc1 ; Cl ; Cl]
84
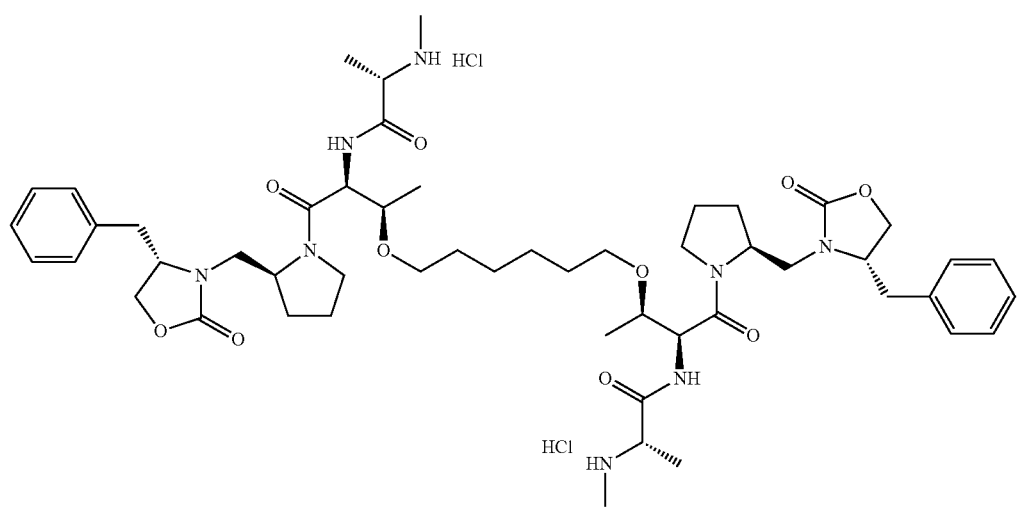 [SMILES: CN[C@@H](C)C(=O)N[C@H](C(=O)N1CCC[C@H]1CN1C(=O)OC[C@@H]1Cc1ccccc1)[C@@H](C)OCCCCCCO[C@H](C)[C@H](NC(=O)[C@H](C)NC)C(=O)N1CCC[C@H]1CN1C(=O)OC[C@@H]1Cc1ccccc1 ; Cl ; Cl]
85
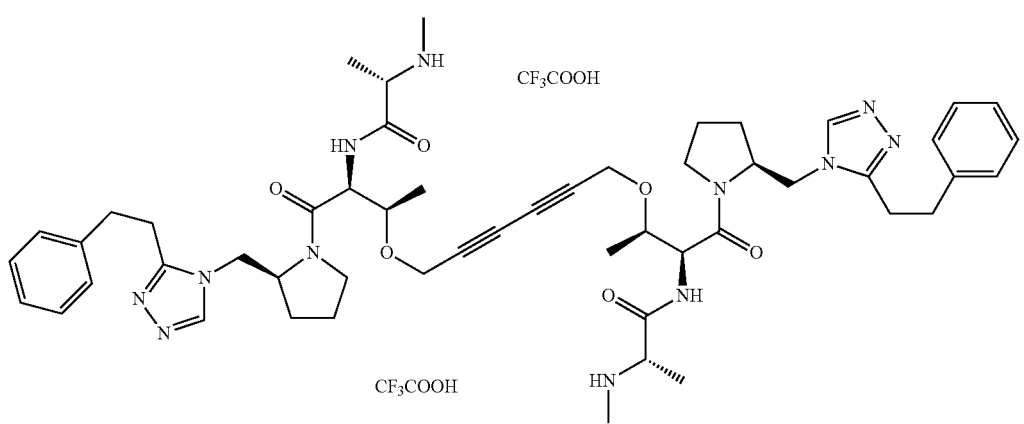 [SMILES: CN[C@@H](C)C(=O)N[C@H](C(=O)N1CCC[C@H]1Cn1cnnc1CCc1ccccc1)[C@@H](C)OCC#CC#CCO[C@H](C)[C@H](NC(=O)[C@H](C)NC)C(=O)N1CCC[C@H]1Cn1cnnc1CCc1ccccc1 ; "CF3COOH" ; "CF3COOH"]

TABLE 1-continued
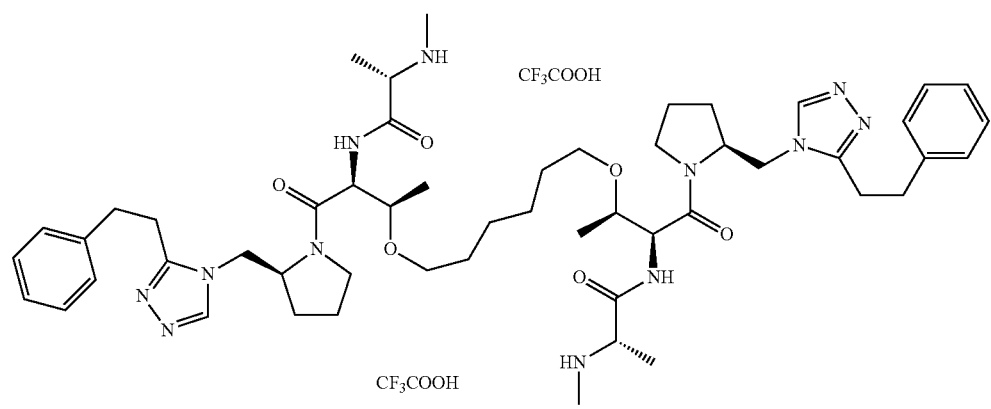 [SMILES: CN[C@@H](C)C(=O)N[C@H](C(=O)N1CCC[C@H]1Cn1cnnc1CCc1ccccc1)[C@@H](C)OCCCCCCO[C@H](C)[C@H](NC(=O)[C@H](C)NC)C(=O)N1CCC[C@H]1Cn1cnnc1CCc1ccccc1 ; "CF3COOH" ; "CF3COOH"]
86
TABLE 2
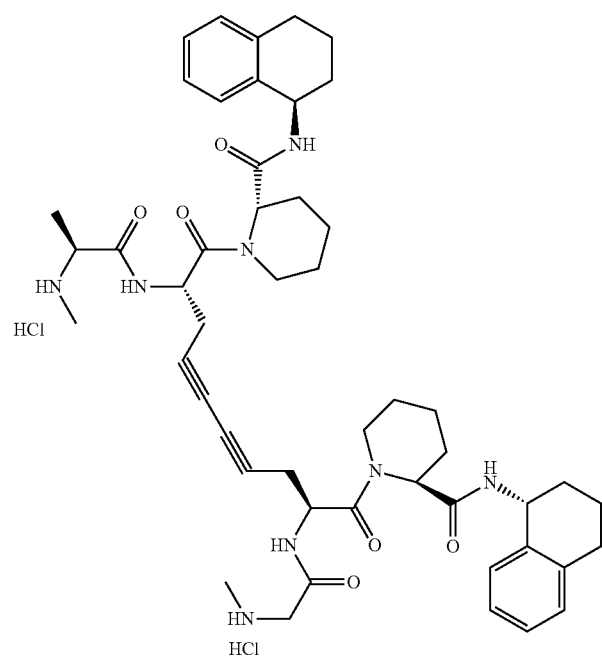 [SMILES: Cl ; CNCC(=O)N[C@@H](CC#CC#CC[C@H](NC(=O)[C@H](C)NC)C(=O)N1CCCC[C@H]1C(=O)N[C@@H]1CCCc2ccccc21)C(=O)N1CCCC[C@H]1C(=O)N[C@@H]1CCCc2ccccc21 ; Cl]
87

TABLE 2-continued
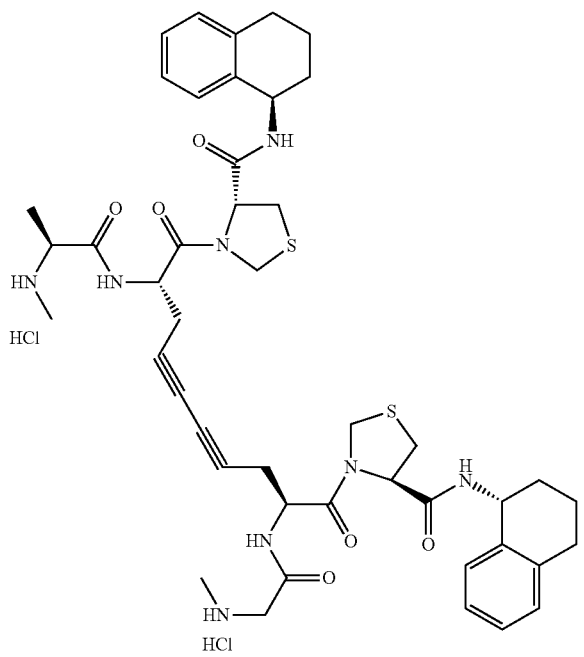 [SMILES: Cl ; CNCC(=O)N[C@@H](CC#CC#CC[C@H](NC(=O)[C@H](C)NC)C(=O)N1CSC[C@H]1C(=O)N[C@@H]1CCCc2ccccc21)C(=O)N1CSC[C@H]1C(=O)N[C@@H]1CCCc2ccccc21 ; Cl]
88

89

TABLE 2-continued
90
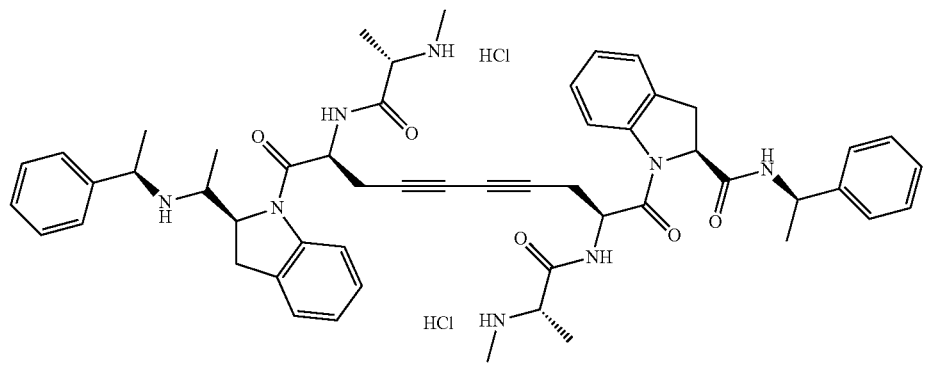 [SMILES: CN[C@@H](C)C(=O)N[C@@H](CC#CC#CC[C@H](NC(=O)[C@H](C)NC)C(=O)N1c2ccccc2C[C@H]1C(C)N[C@H](C)c1ccccc1)C(=O)N1c2ccccc2C[C@H]1C(=O)N[C@H](C)c1ccccc1 ; Cl ; Cl]
91
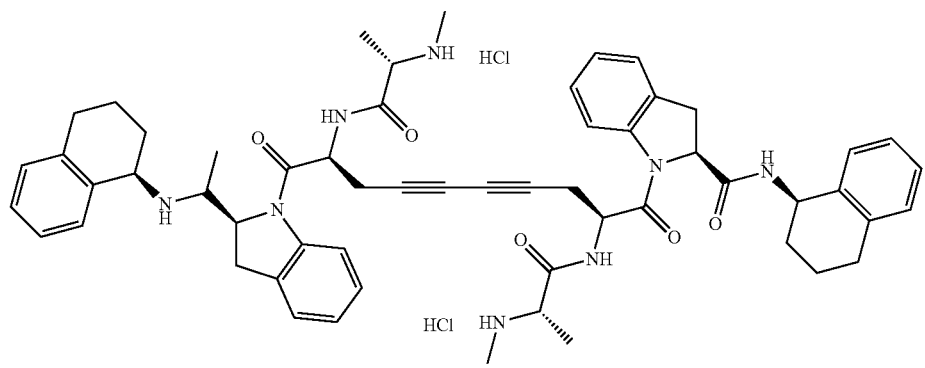 [SMILES: CN[C@@H](C)C(=O)N[C@@H](CC#CC#CC[C@H](NC(=O)[C@H](C)NC)C(=O)N1c2ccccc2C[C@H]1C(C)N[C@@H]1CCCc2ccccc21)C(=O)N1c2ccccc2C[C@H]1C(=O)N[C@@H]1CCCc2ccccc21 ; Cl ; Cl]
92
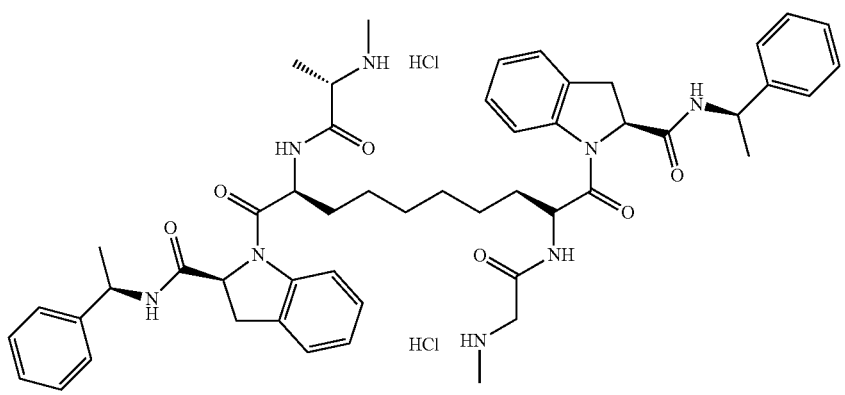
93
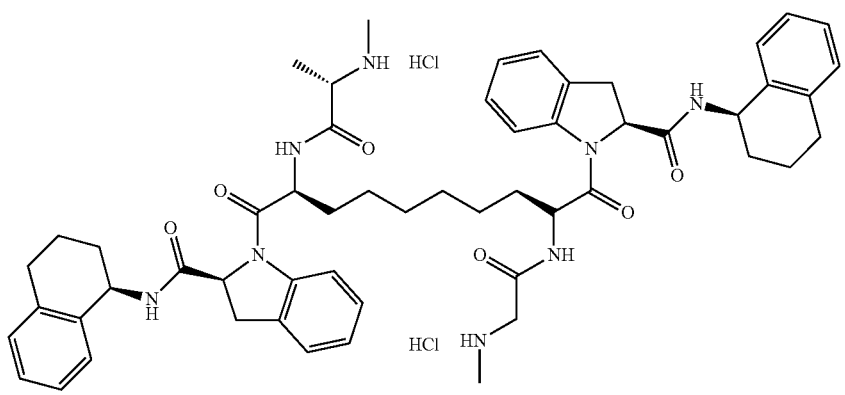

TABLE 2-continued
94
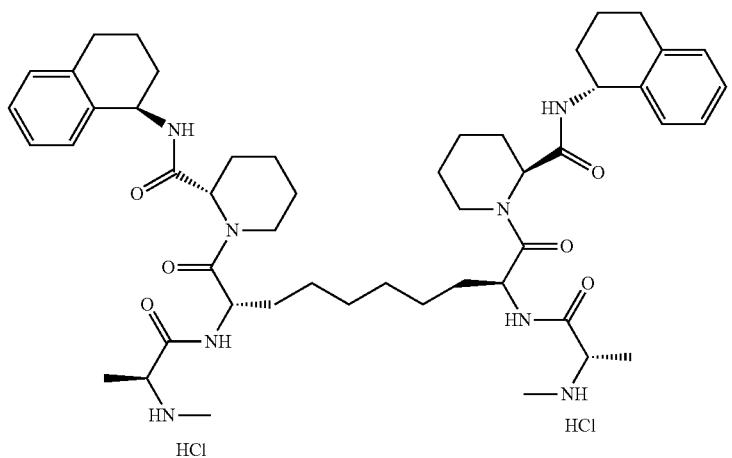 [SMILES: CN[C@@H](C)C(=O)N[C@@H](CCCCCC[C@H](NC(=O)[C@H](C)NC)C(=O)N1CCCC[C@H]1C(=O)N[C@@H]1CCCc2ccccc21)C(=O)N1CCCC[C@H]1C(=O)N[C@@H]1CCCc2ccccc21 ; Cl ; Cl]
95
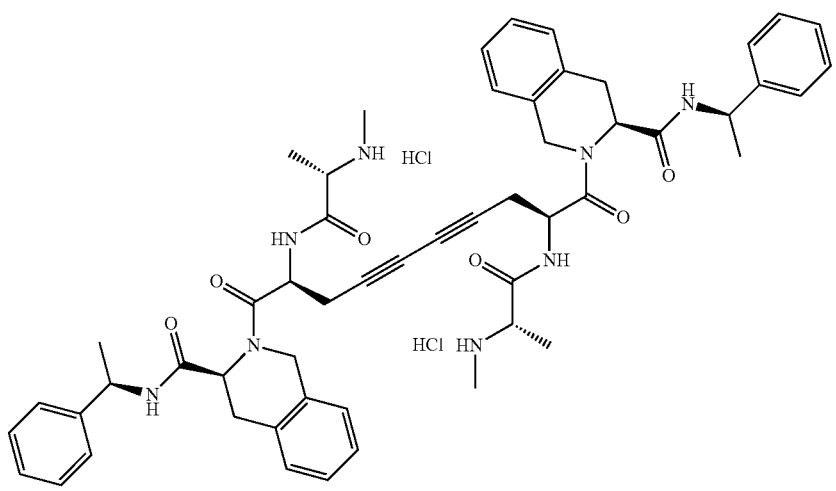 [SMILES: CN[C@@H](C)C(=O)N[C@@H](CC#CC#CC[C@H](NC(=O)[C@H](C)NC)C(=O)N1Cc2ccccc2C[C@H]1C(=O)N[C@H](C)c1ccccc1)C(=O)N1Cc2ccccc2C[C@H]1C(=O)N[C@H](C)c1ccccc1 ; Cl ; Cl]
96
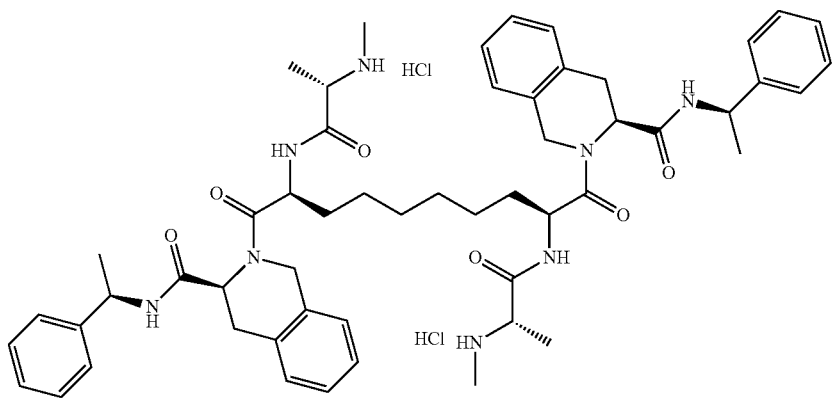 [SMILES: CN[C@@H](C)C(=O)N[C@@H](CCCCCC[C@H](NC(=O)[C@H](C)NC)C(=O)N1Cc2ccccc2C[C@H]1C(=O)N[C@H](C)c1ccccc1)C(=O)N1Cc2ccccc2C[C@H]1C(=O)N[C@H](C)c1ccccc1 ; Cl ; Cl]

TABLE 2-continued
97
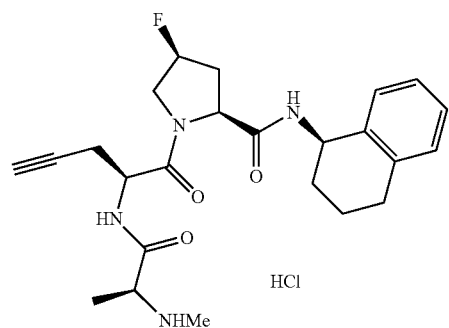 [SMILES: C#CC[C@H](NC(=O)[C@H](C)NC)C(=O)N1C[C@@H](F)C[C@H]1C(=O)N[C@@H]1CCCc2ccccc21 ; Cl]
HCl
98
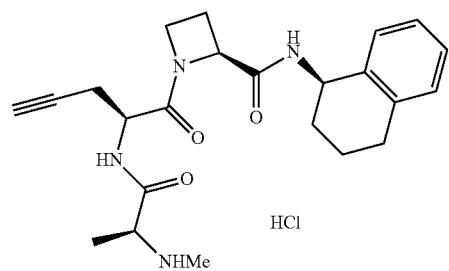 [SMILES: C#CC[C@H](NC(=O)[C@H](C)NC)C(=O)N1CC[C@H]1C(=O)N[C@@H]1CCCc2ccccc21 ; Cl]
HCl
99
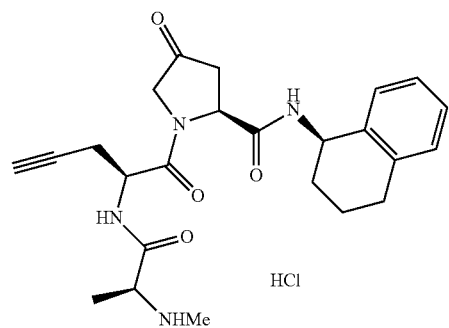 [SMILES: C#CC[C@H](NC(=O)[C@H](C)NC)C(=O)N1CC(=O)C[C@H]1C(=O)N[C@@H]1CCCc2ccccc21 ; Cl]
HCl
100
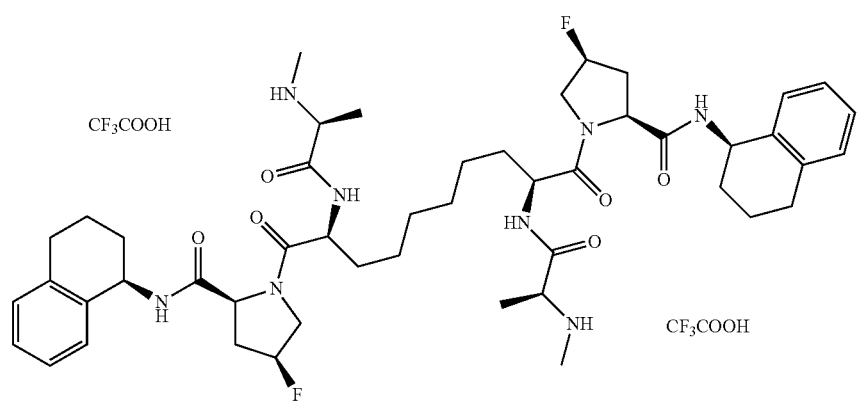 [SMILES: CN[C@@H](C)C(=O)N[C@@H](CCCCCC[C@H](NC(=O)[C@H](C)NC)C(=O)N1C[C@@H](F)C[C@H]1C(=O)N[C@@H]1CCCc2ccccc21)C(=O)N1C[C@@H](F)C[C@H]1C(=O)N[C@@H]1CCCc2ccccc21 ; "CF3COOH" ; "CF3COOH"]

TABLE 2-continued
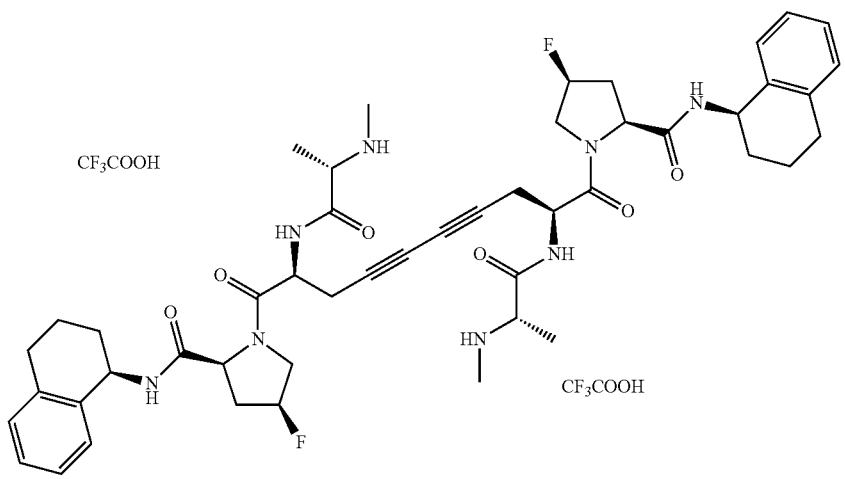 [SMILES: CN[C@@H](C)C(=O)N[C@@H](CC#CC#CC[C@H](NC(=O)[C@H](C)NC)C(=O)N1C[C@@H](F)C[C@H]1C(=O)N[C@@H]1CCCc2ccccc21)C(=O)N1C[C@@H](F)C[C@H]1C(=O)N[C@@H]1CCCc2ccccc21 ; "CF3COOH" ; "CF3COOH"]
101
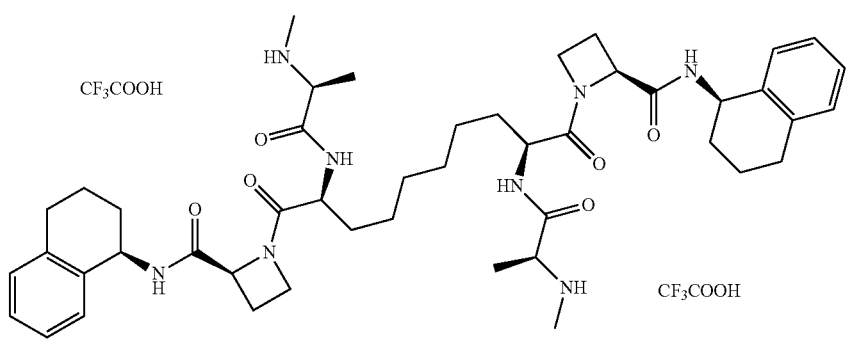 [SMILES: CN[C@@H](C)C(=O)N[C@@H](CCCCCC[C@H](NC(=O)[C@H](C)NC)C(=O)N1CC[C@H]1C(=O)N[C@@H]1CCCc2ccccc21)C(=O)N1CC[C@H]1C(=O)N[C@@H]1CCCc2ccccc21 ; "CF3COOH" ; "CF3COOH"]
102
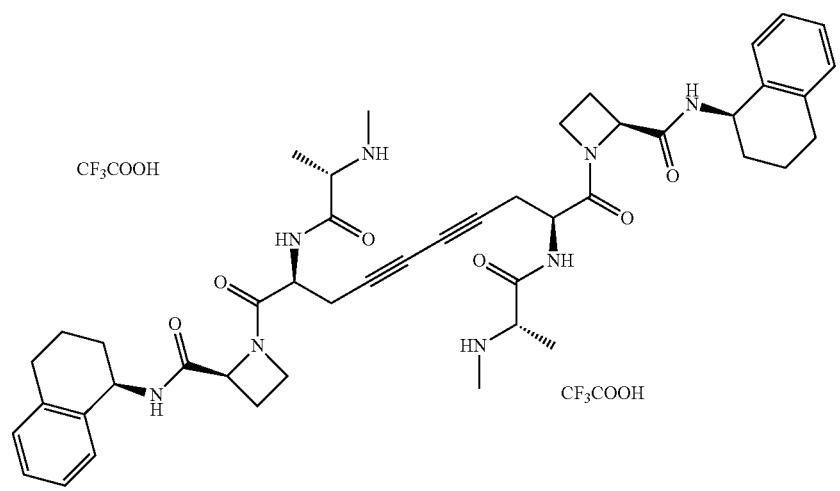 [SMILES: CN[C@@H](C)C(=O)N[C@@H](CC#CC#CC[C@H](NC(=O)[C@H](C)NC)C(=O)N1CC[C@H]1C(=O)N[C@@H]1CCCc2ccccc21)C(=O)N1CC[C@H]1C(=O)N[C@@H]1CCCc2ccccc21 ; "CF3COOH" ; "CF3COOH"]
103

TABLE 2-continued
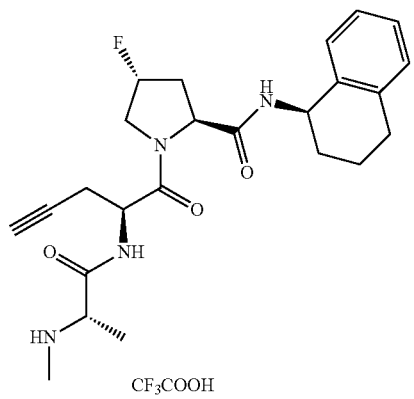 [SMILES: C#CC[C@H](NC(=O)[C@H](C)NC)C(=O)N1C[C@H](F)C[C@H]1C(=O)N[C@@H]1CCCc2ccccc21 ; "CF3COOH"]
104
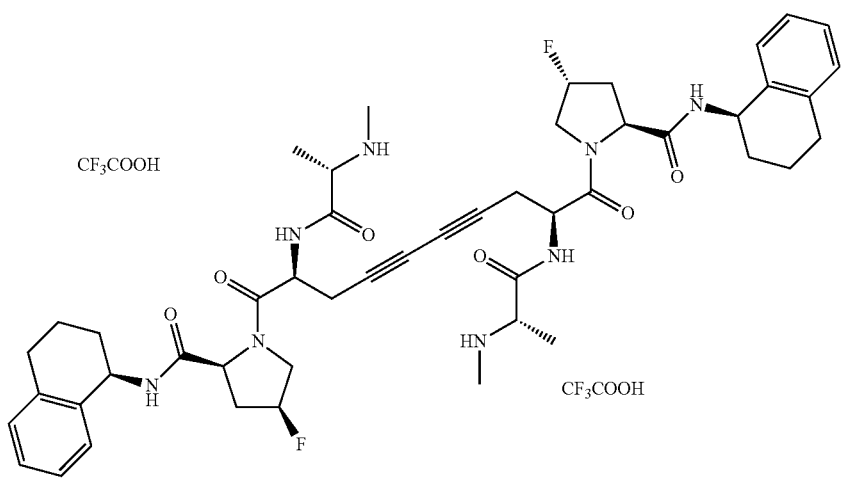 [SMILES: CN[C@@H](C)C(=O)N[C@@H](CC#CC#CC[C@H](NC(=O)[C@H](C)NC)C(=O)N1C[C@@H](F)C[C@H]1C(=O)N[C@@H]1CCCc2ccccc21)C(=O)N1C[C@H](F)C[C@H]1C(=O)N[C@@H]1CCCc2ccccc21 ; "CF3COOH" ; "CF3COOH"]
105
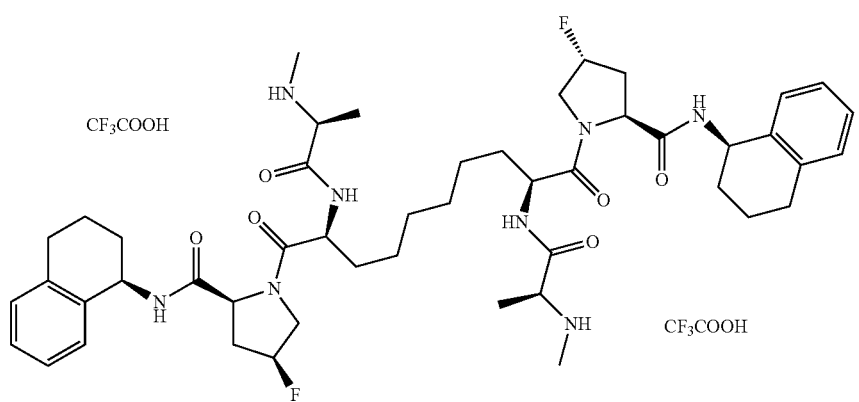 [SMILES: CN[C@@H](C)C(=O)N[C@@H](CCCCCC[C@H](NC(=O)[C@H](C)NC)C(=O)N1C[C@@H](F)C[C@H]1C(=O)N[C@@H]1CCCc2ccccc21)C(=O)N1C[C@H](F)C[C@H]1C(=O)N[C@@H]1CCCc2ccccc21 ; "CF3COOH" ; "CF3COOH"]
106

TABLE 2-continued
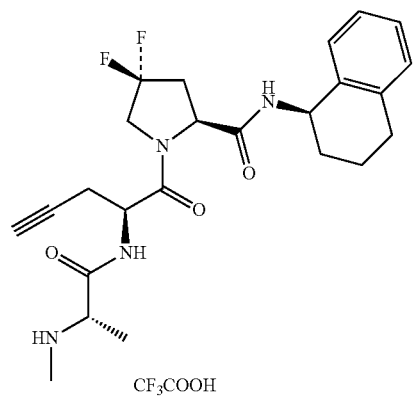
107
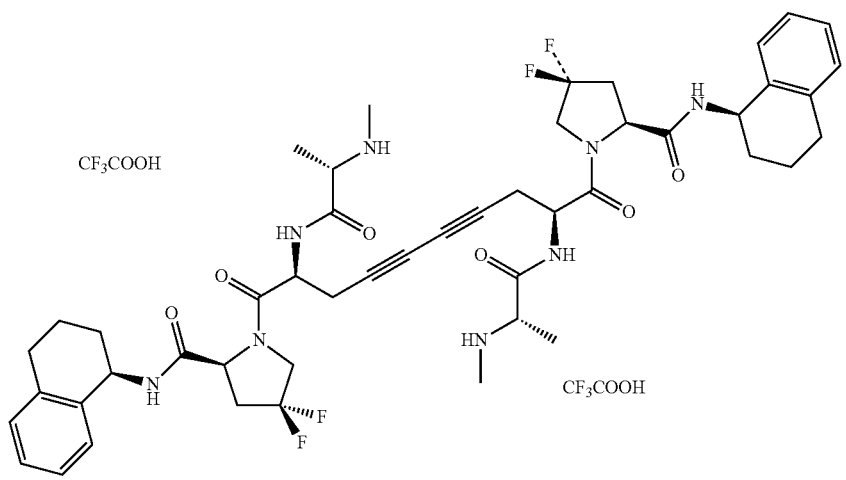
108
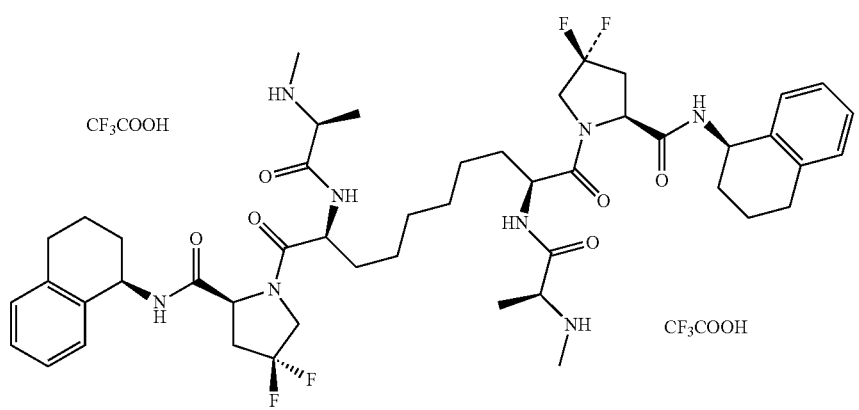
109

TABLE 3
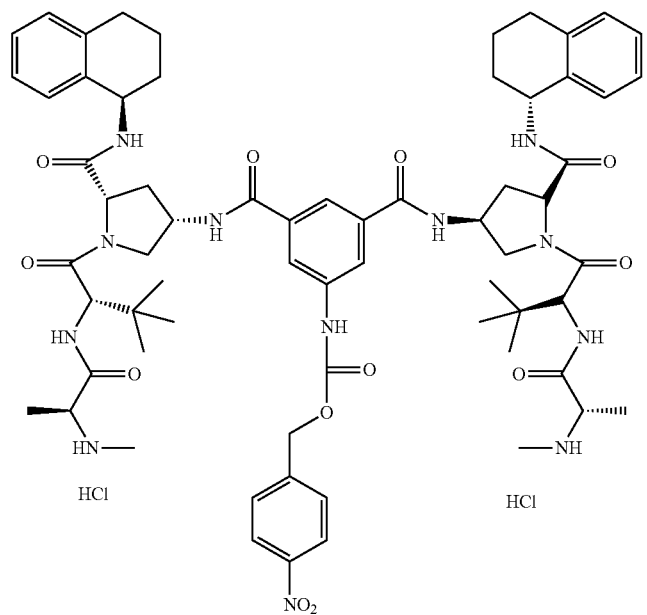
110
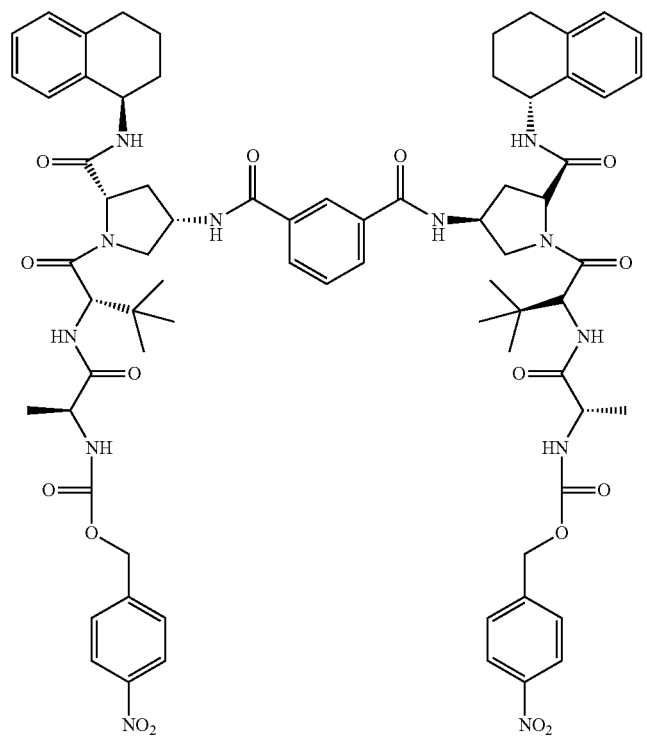
111

TABLE 3-continued
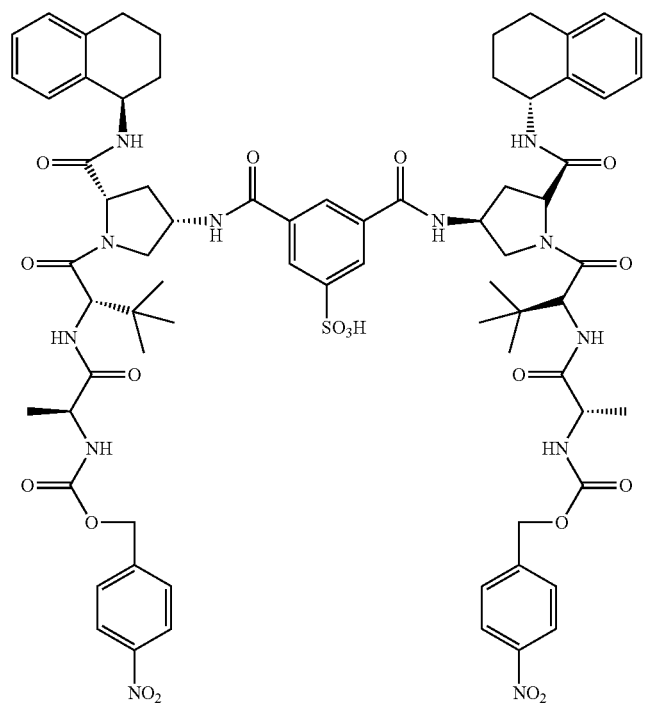
112
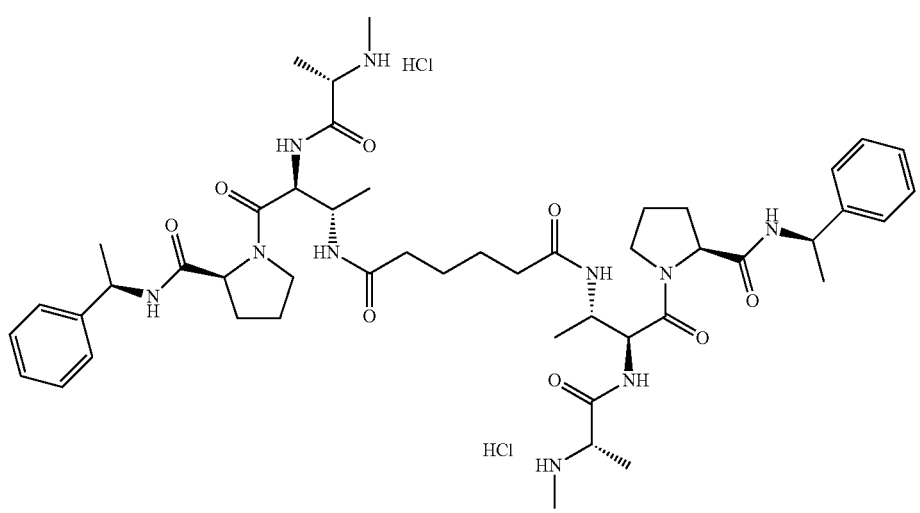 [SMILES: CN[C@@H](C)C(=O)N[C@H](C(=O)N1CCC[C@H]1C(=O)N[C@H](C)c1ccccc1)[C@H](C)NC(=O)CCCCC(=O)N[C@@H](C)[C@H](NC(=O)[C@H](C)NC)C(=O)N1CCC[C@H]1C(=O)N[C@H](C)c1ccccc1 ; Cl ; Cl]
113

TABLE 3-continued
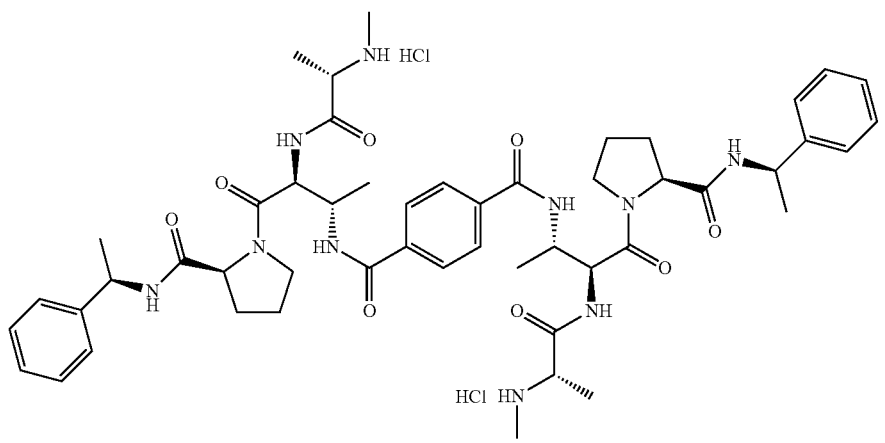 [SMILES: CN[C@@H](C)C(=O)N[C@H](C(=O)N1CCC[C@H]1C(=O)N[C@H](C)c1ccccc1)[C@H](C)NC(=O)c1ccc(C(=O)N[C@@H](C)[C@H](NC(=O)[C@H](C)NC)C(=O)N2CCC[C@H]2C(=O)N[C@H](C)c2ccccc2)cc1 ; Cl ; Cl]
114
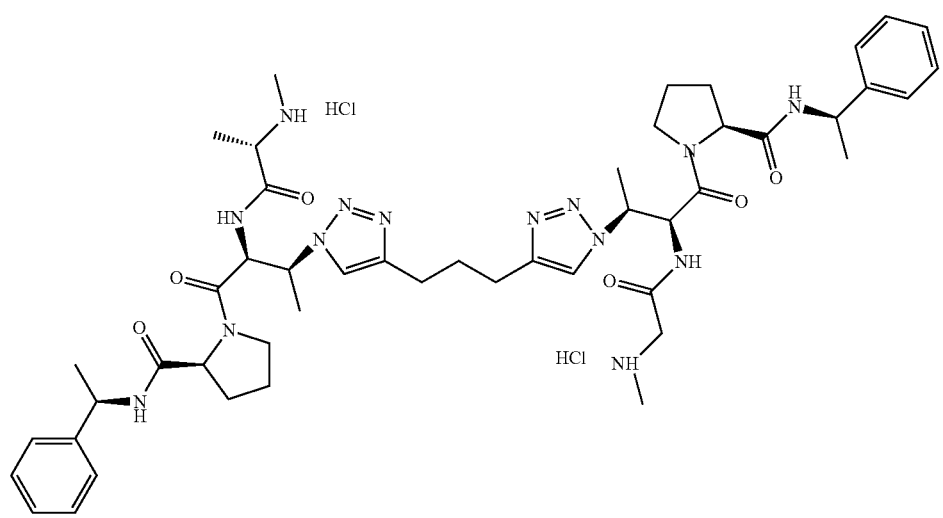
115
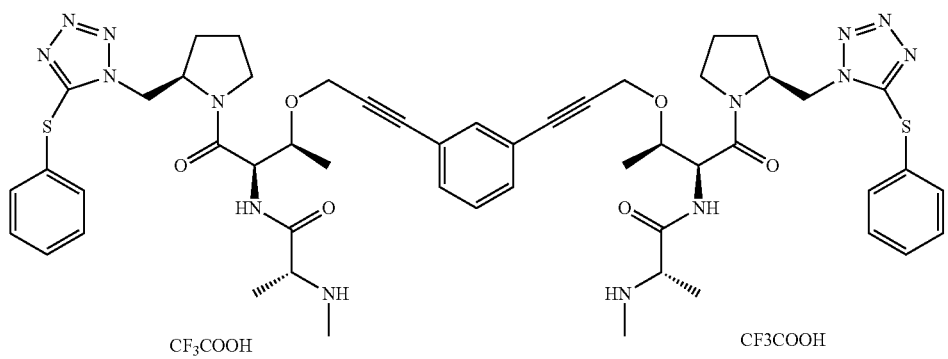 [SMILES: CN[C@@H](C)C(=O)N[C@H](C(=O)N1CCC[C@H]1Cn1nnnc1Sc1ccccc1)[C@@H](C)OCC#Cc1cccc(C#CCO[C@@H](C)[C@@H](NC(=O)[C@@H](C)NC)C(=O)N2CCC[C@@H]2Cn2nnnc2Sc2ccccc2)c1 ; "CF3COOH" ; "CF3COOH"]
116

TABLE 3-continued
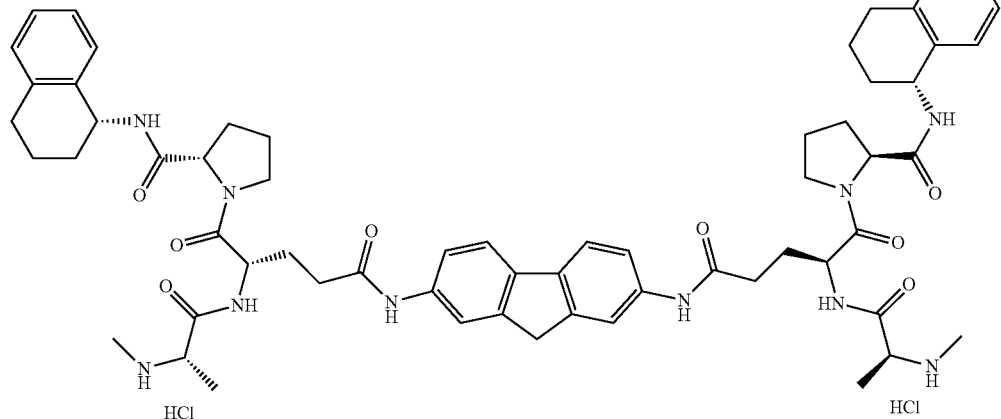
117
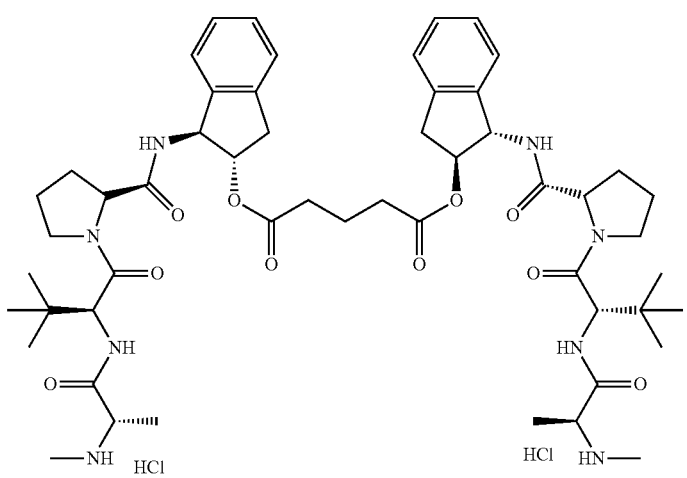
118
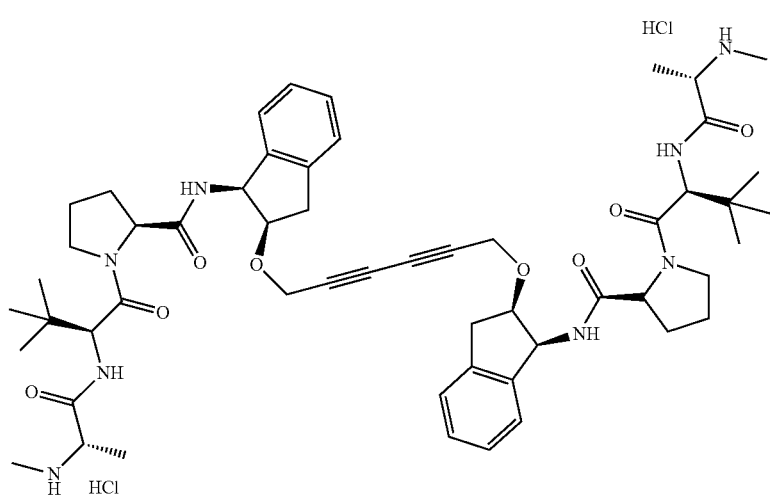
119

TABLE 3-continued
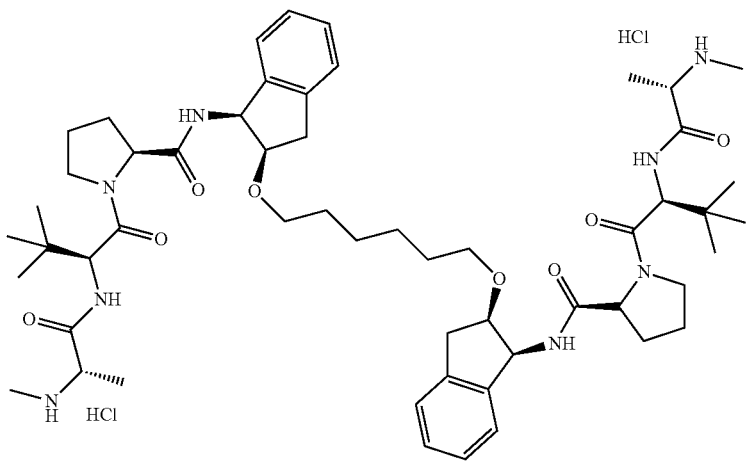
120
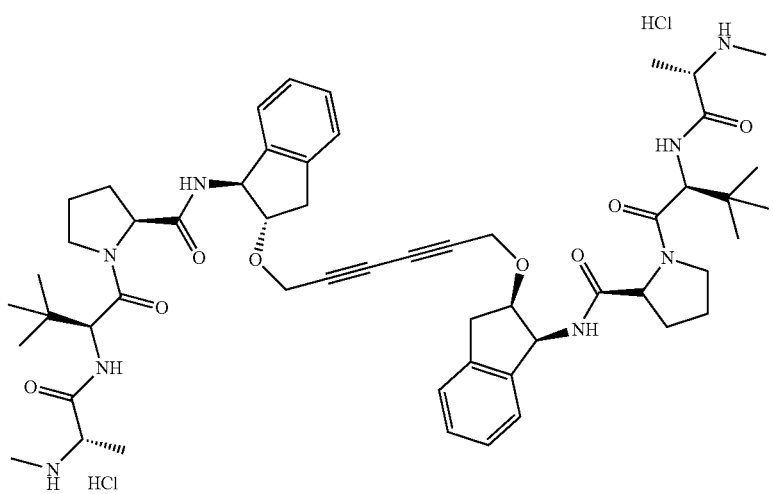
121
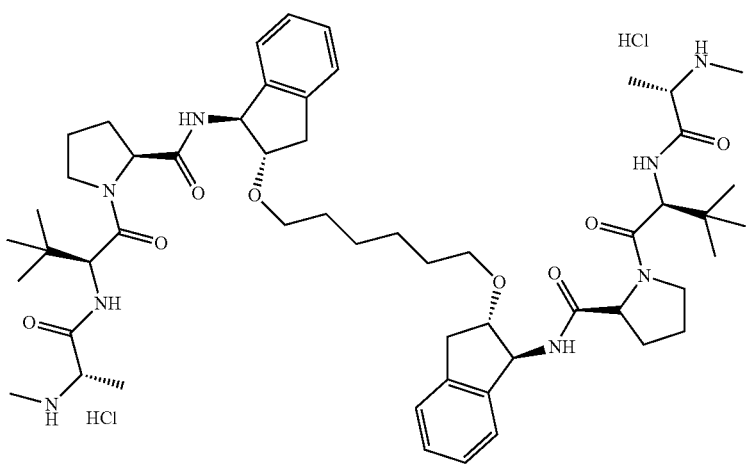
122

TABLE 3-continued
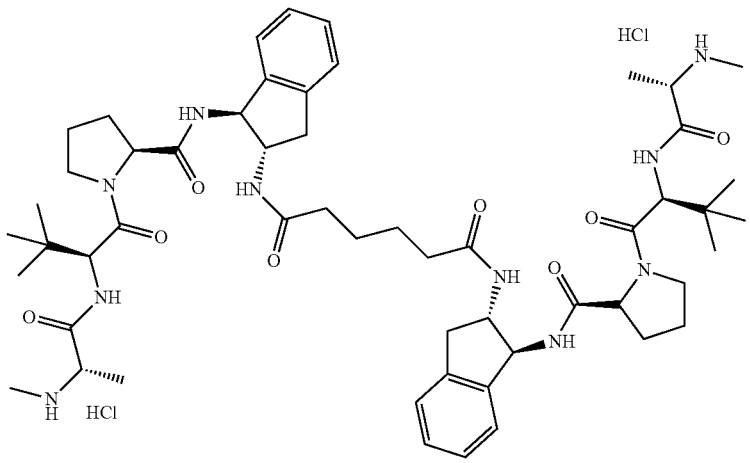
123
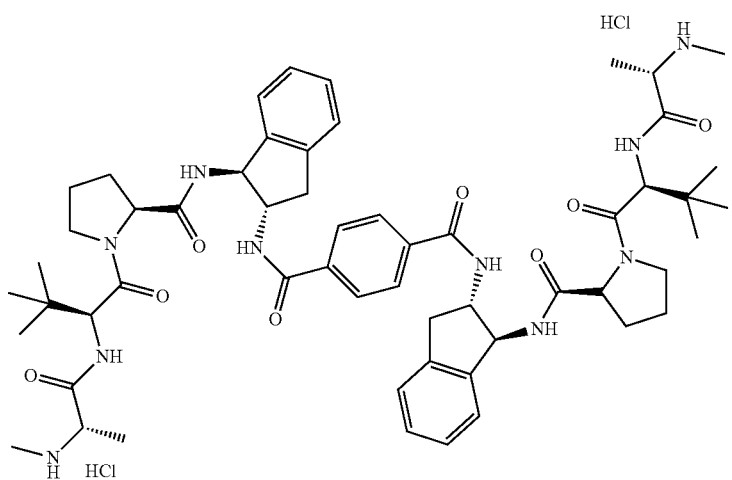
124
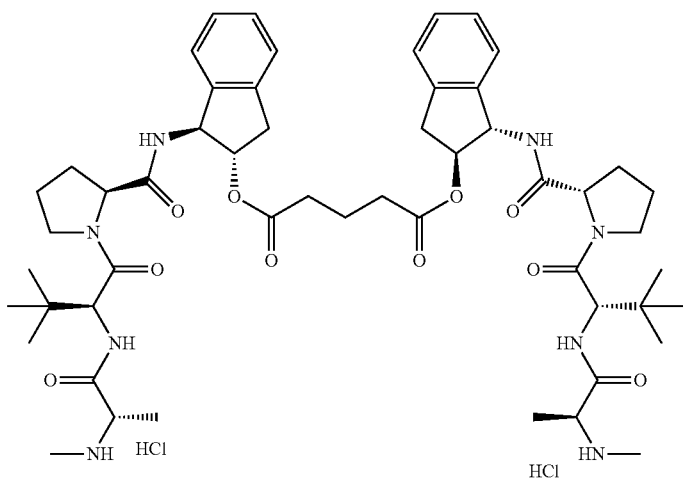 [SMILES: CN[C@@H](C)C(=O)N[C@H](C(=O)N1CCC[C@H]1C(=O)N[C@H]1c2ccccc2C[C@@H]1OC(=O)CCCC(=O)O[C@H]1Cc2ccccc2[C@@H]1NC(=O)[C@@H]1CCCN1C(=O)[C@@H](NC(=O)[C@H](C)NC)C(C)(C)C)C(C)(C)C ; Cl ; Cl]
125

TABLE 3-continued
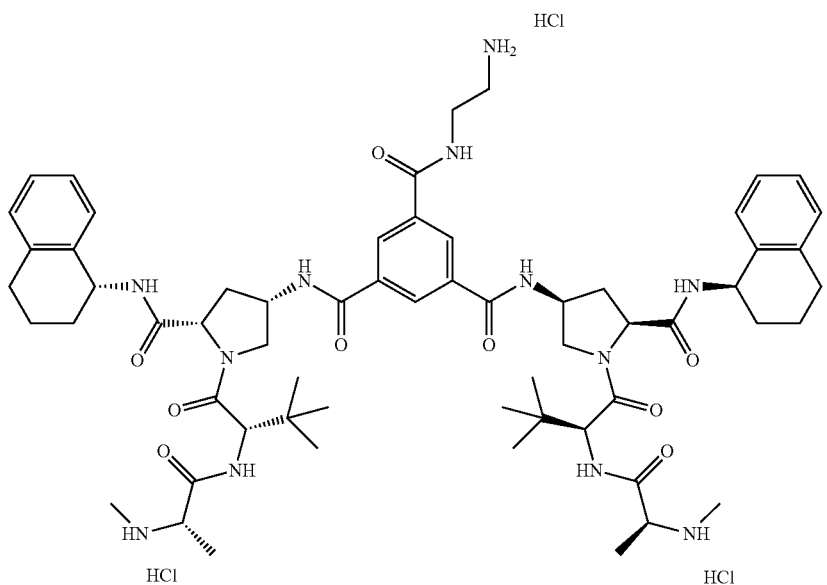 [SMILES: Cl ; CN[C@@H](C)C(=O)N[C@H](C(=O)N1C[C@@H](NC(=O)c2cc(C(=O)NCCN)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl]
126
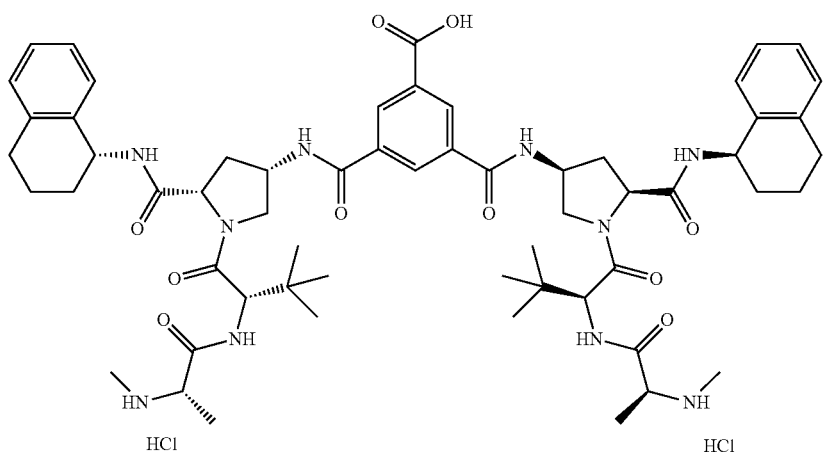 [SMILES: CN[C@@H](C)C(=O)N[C@H](C(=O)N1C[C@@H](NC(=O)c2cc(C(=O)O)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl]
127
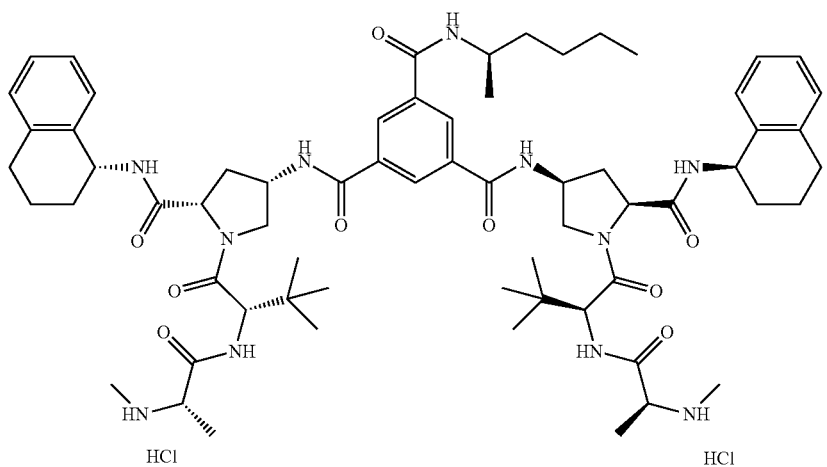 [SMILES: CCCC[C@@H](C)NC(=O)c1cc(C(=O)N[C@H]2C[C@@H](C(=O)N[C@@H]3CCCc4ccccc43)N(C(=O)[C@@H](NC(=O)[C@H](C)NC)C(C)(C)C)C2)cc(C(=O)N[C@H]2C[C@@H](C(=O)N[C@@H]3CCCc4ccccc43)N(C(=O)[C@@H](NC(=O)[C@H](C)NC)C(C)(C)C)C2)c1 ; Cl ; Cl]
128

TABLE 3-continued
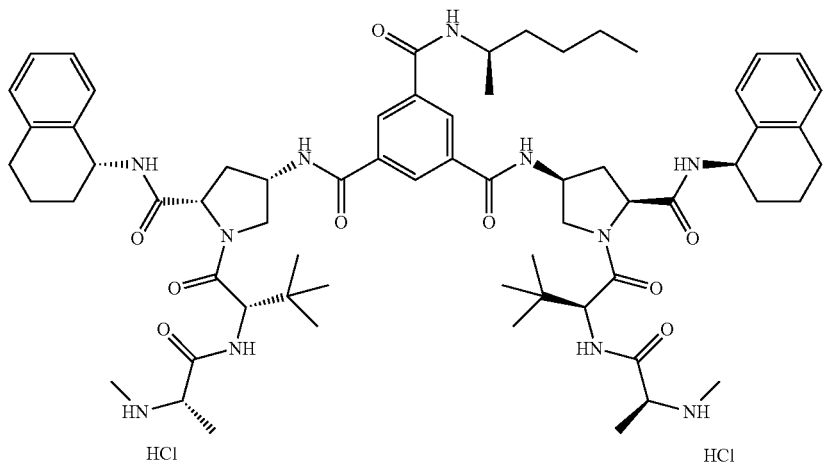 [SMILES: CCCC[C@@H](C)NC(=O)c1cc(C(=O)N[C@H]2C[C@@H](C(=O)N[C@@H]3CCCc4ccccc43)N(C(=O)[C@@H](NC(=O)[C@H](C)NC)C(C)(C)C)C2)cc(C(=O)N[C@H]2C[C@@H](C(=O)N[C@@H]3CCCc4ccccc43)N(C(=O)[C@@H](NC(=O)[C@H](C)NC)C(C)(C)C)C2)c1 ; Cl ; Cl]
129
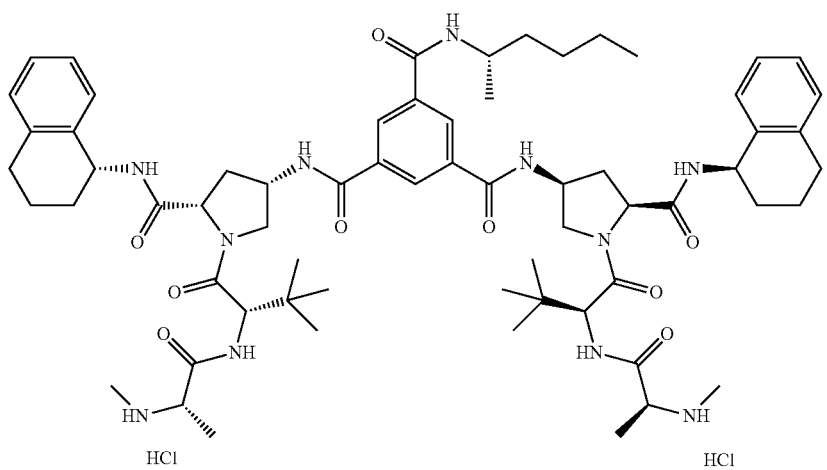 [SMILES: CCCC[C@H](C)NC(=O)c1cc(C(=O)N[C@H]2C[C@@H](C(=O)N[C@@H]3CCCc4ccccc43)N(C(=O)[C@@H](NC(=O)[C@H](C)NC)C(C)(C)C)C2)cc(C(=O)N[C@H]2C[C@@H](C(=O)N[C@@H]3CCCc4ccccc43)N(C(=O)[C@@H](NC(=O)[C@H](C)NC)C(C)(C)C)C2)c1 ; Cl ; Cl]
130
TABLE 4
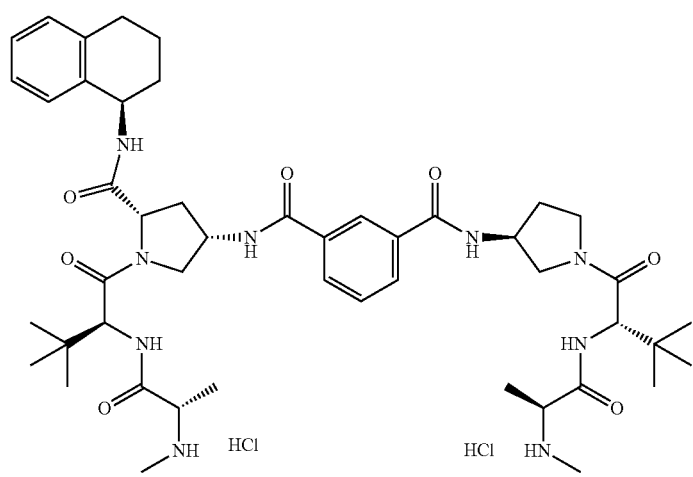 [SMILES: CN[C@@H](C)C(=O)N[C@H](C(=O)N1CC[C@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C1)C(C)(C)C ; Cl ; Cl]
131

TABLE 4-continued
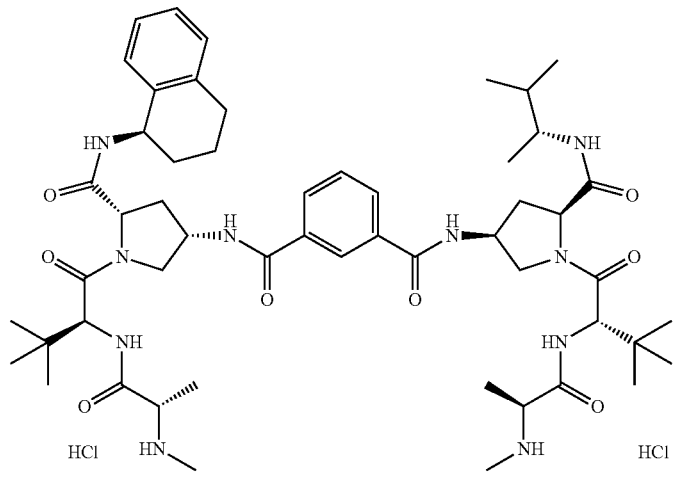 [SMILES: CN[C@@H](C)C(=O)N[C@H](C(=O)N1C[C@@H](NC(=O)c2cccc(C(=O)N[C@H]3C[C@@H](C(=O)N[C@H](C)C(C)C)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl]
132
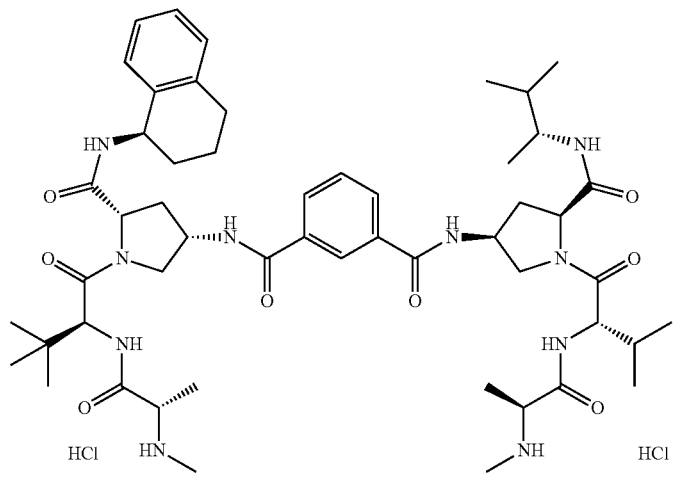 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@H](C)C(C)C)C(C)C ; Cl ; Cl]
133
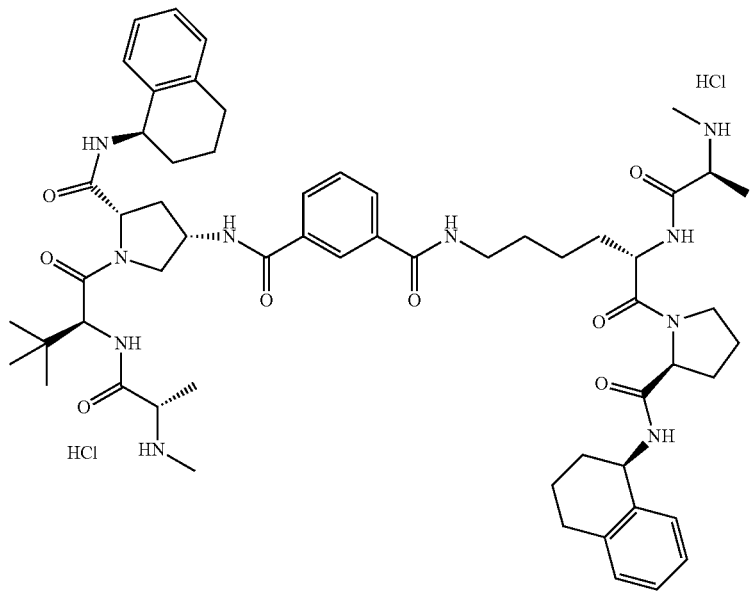 [SMILES: CN[C@@H](C)C(=O)N[C@@H](CCCCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N1CCC[C@H]1C(=O)N[C@@H]1CCCc2ccccc21 ; Cl ; Cl]
134

TABLE 4-continued
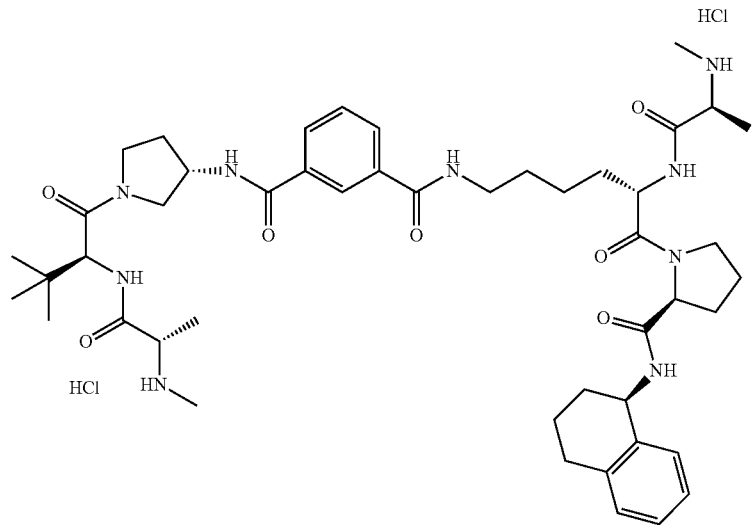 [SMILES: Cl ; CN[C@@H](C)C(=O)N[C@@H](CCCCNC(=O)c1cccc(C(=O)N[C@H]2CCN(C(=O)[C@@H](NC(=O)[C@H](C)NC)C(C)(C)C)C2)c1)C(=O)N1CCC[C@H]1C(=O)N[C@@H]1CCCc2ccccc21 ; Cl]
135
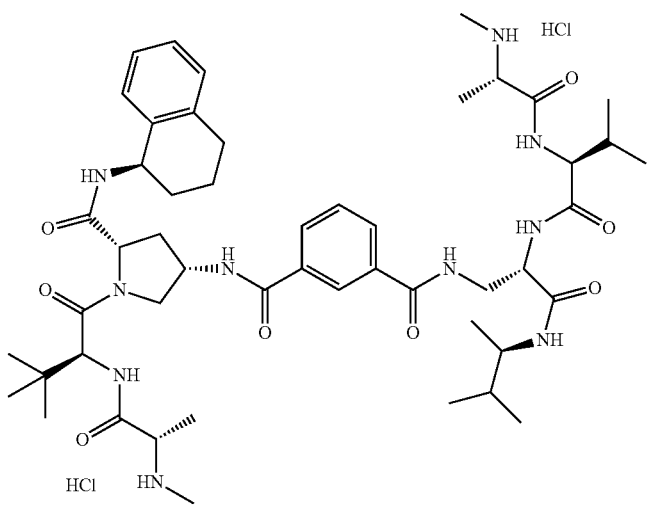 [SMILES: CN[C@@H](C)C(=O)N[C@H](C(=O)N[C@@H](CNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)C(C)C)C(C)C ; Cl ; Cl]
136
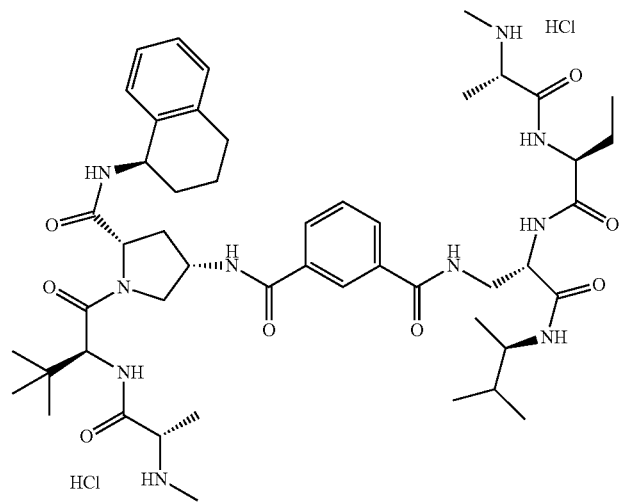 [SMILES: CC[C@H](NC(=O)[C@H](C)NC)C(=O)N[C@@H](CNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)C(C)C ; Cl ; Cl]
137

TABLE 4-continued
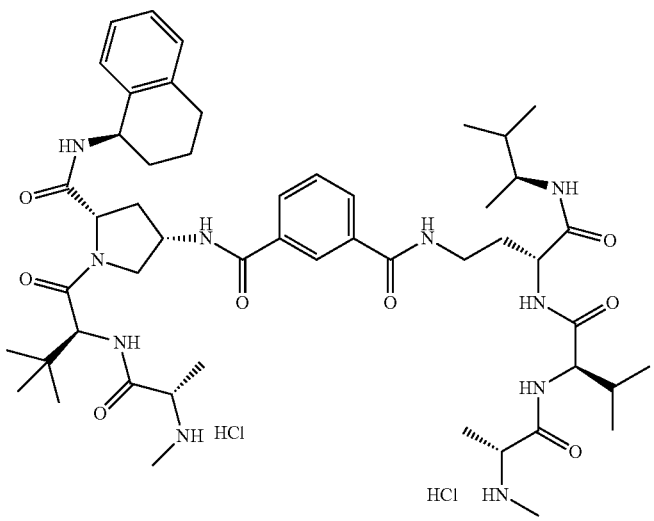 [SMILES: CN[C@@H](C)C(=O)N[C@H](C(=O)N1C[C@@H](NC(=O)c2cccc(C(=O)NCC[C@@H](NC(=O)[C@H](NC(=O)[C@@H](C)NC)C(C)C)C(=O)N[C@@H](C)C(C)C)c2)C[C@H]1C(=O)N[C@@H]1CCCc2ccccc21)C(C)(C)C ; Cl ; Cl]
138
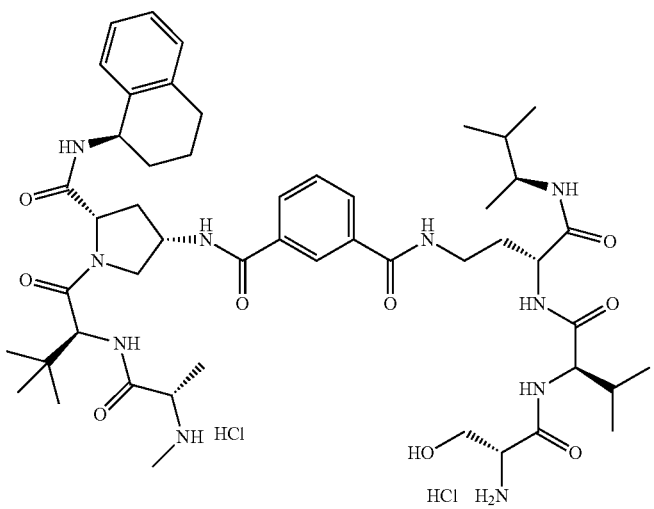 [SMILES: CN[C@@H](C)C(=O)N[C@H](C(=O)N1C[C@@H](NC(=O)c2cccc(C(=O)NCC[C@@H](NC(=O)[C@H](NC(=O)[C@H](N)CO)C(C)C)C(=O)N[C@@H](C)C(C)C)c2)C[C@H]1C(=O)N[C@@H]1CCCc2ccccc21)C(C)(C)C ; Cl ; Cl]
139
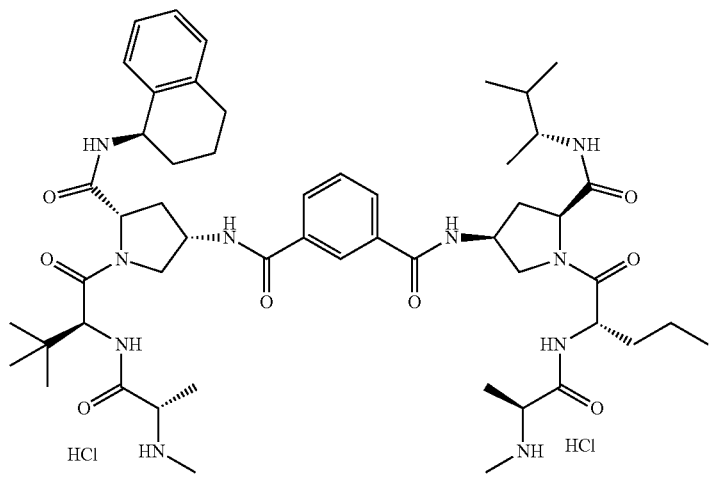 [SMILES: CCC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@H](C)C(C)C ; Cl ; Cl]
140

TABLE 4-continued
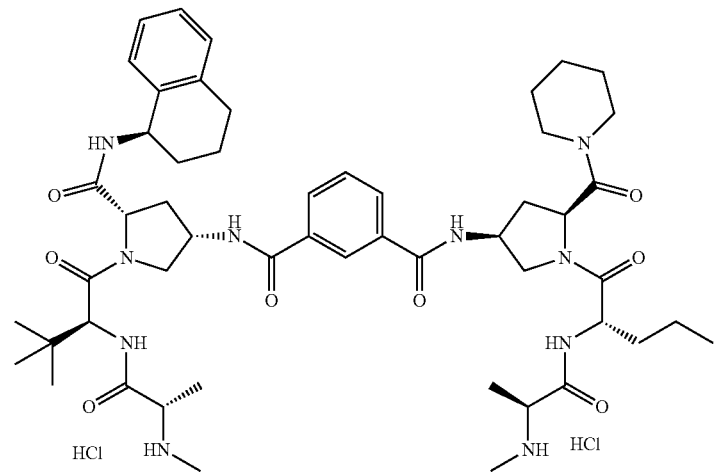 [SMILES: CCC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N1CCCCC1 ; Cl ; Cl]
141
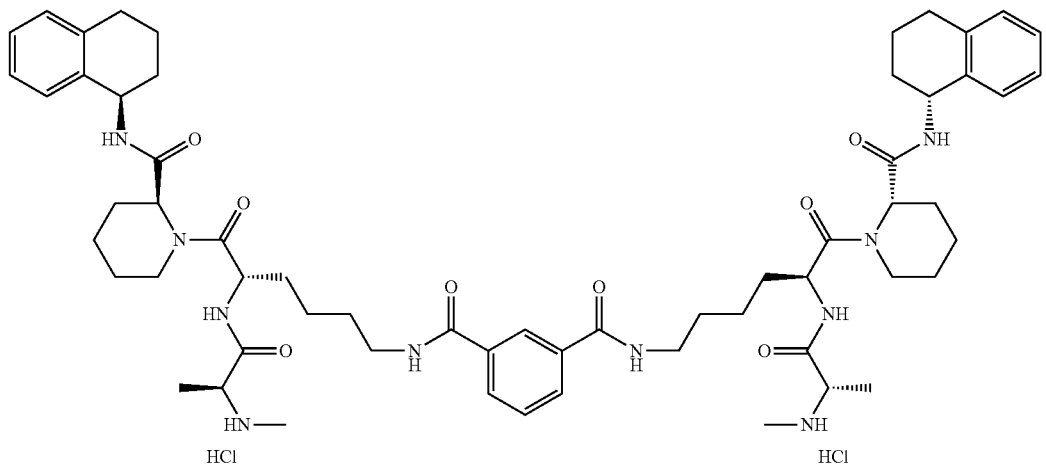 [SMILES: CN[C@@H](C)C(=O)N[C@@H](CCCCNC(=O)c1cccc(C(=O)NCCCC[C@H](NC(=O)[C@H](C)NC)C(=O)N2CCCC[C@H]2C(=O)N[C@@H]2CCCc3ccccc32)c1)C(=O)N1CCCC[C@H]1C(=O)N[C@@H]1CCCc2ccccc21 ; Cl ; Cl]
142
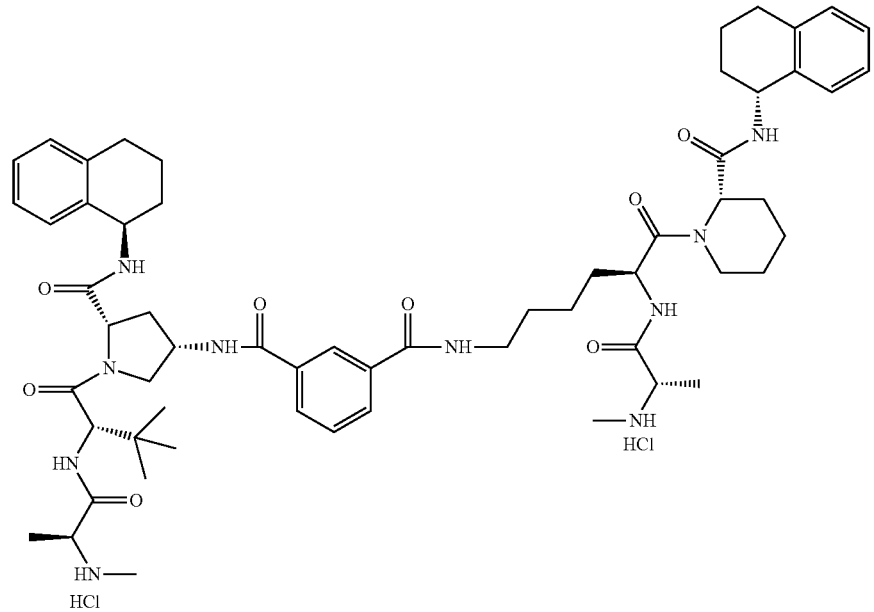 [SMILES: CN[C@@H](C)C(=O)N[C@@H](CCCCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N1CCCC[C@H]1C(=O)N[C@@H]1CCCc2ccccc21 ; Cl ; Cl]
143

TABLE 4-continued
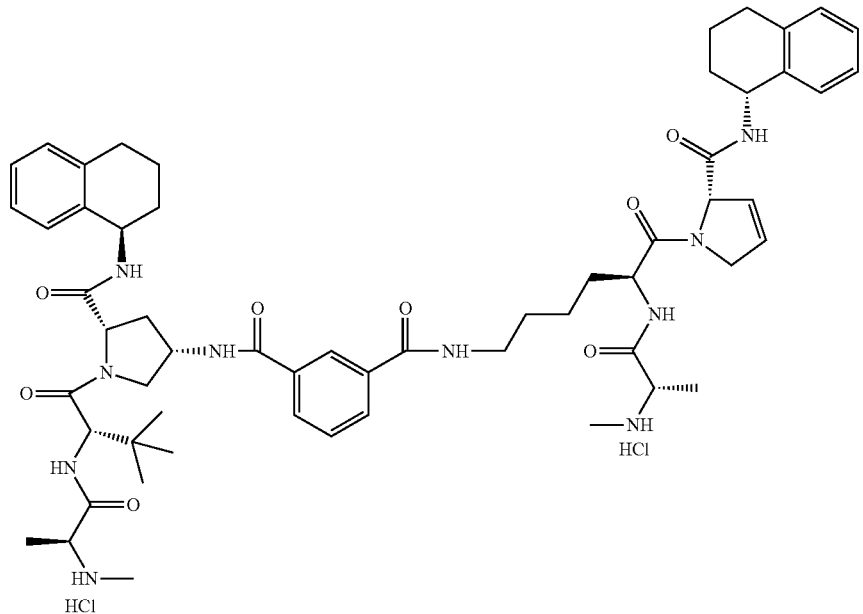 [SMILES: CN[C@@H](C)C(=O)N[C@@H](CCCCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N1CC=C[C@H]1C(=O)N[C@@H]1CCCc2ccccc21 ; Cl ; Cl]
144
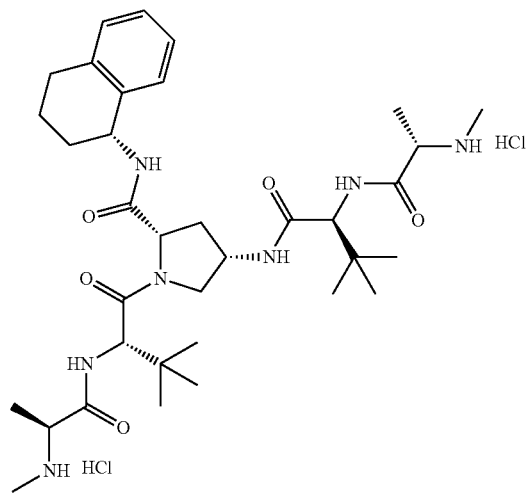
145
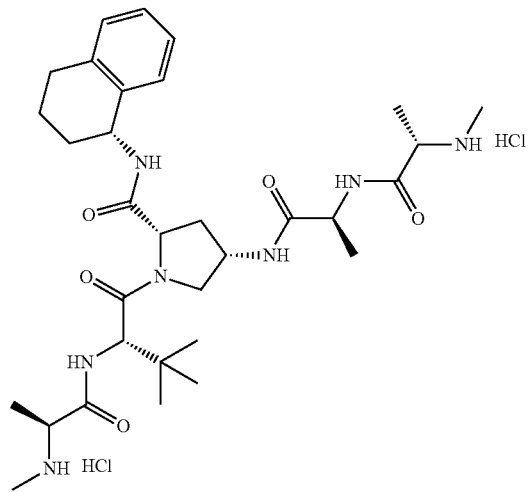
146

TABLE 4-continued
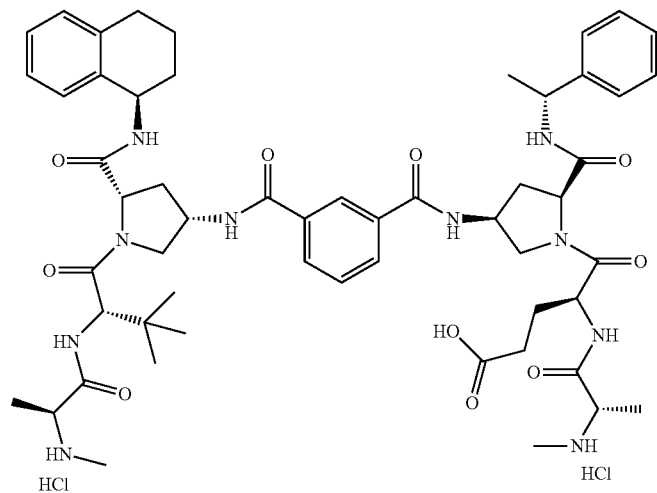 [SMILES: CN[C@@H](C)C(=O)N[C@@H](CCC(=O)O)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@H](C)c1ccccc1 ; Cl ; Cl]
147
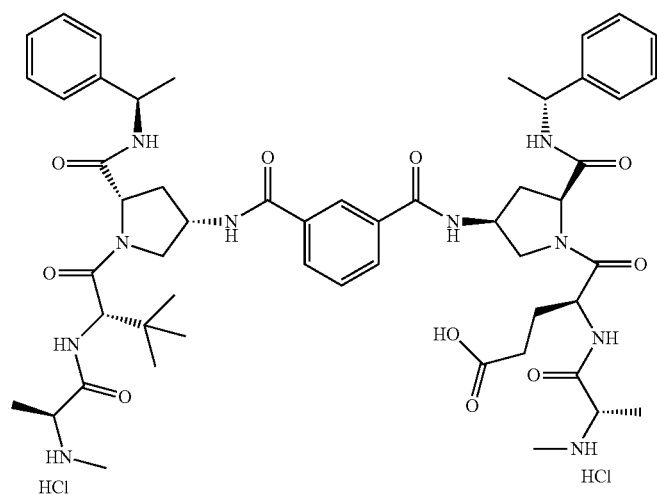 [SMILES: CN[C@@H](C)C(=O)N[C@@H](CCC(=O)O)C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1 ; Cl ; Cl]
148
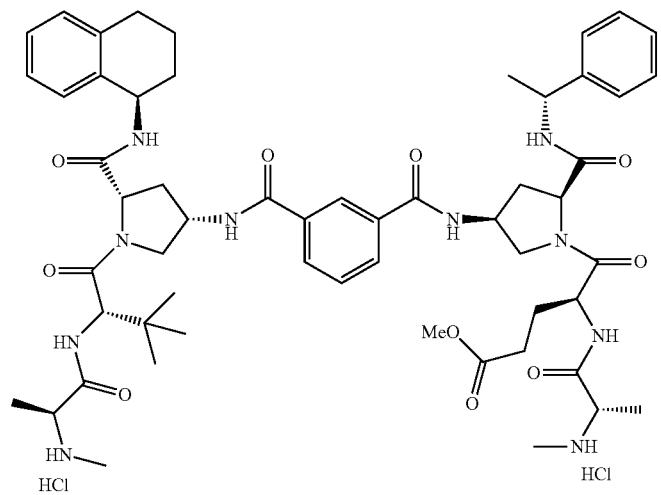 [SMILES: CN[C@@H](C)C(=O)N[C@@H](CCC(=O)OC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@H](C)c1ccccc1 ; Cl ; Cl]
149

TABLE 4-continued
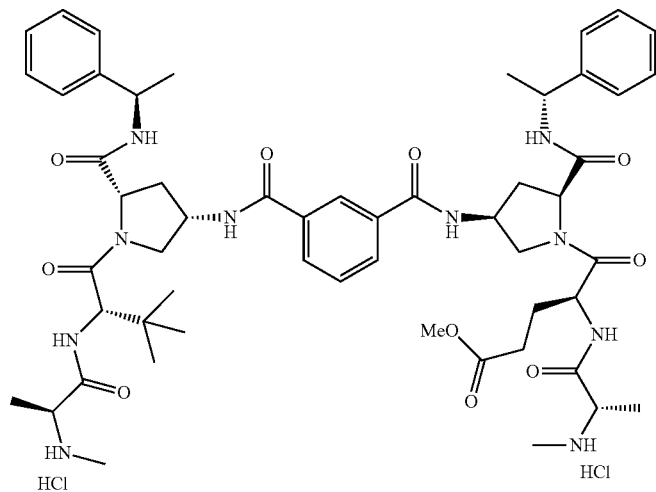 [SMILES: CN[C@@H](C)C(=O)N[C@@H](CCC(=O)OC)C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1 ; Cl ; Cl]
150
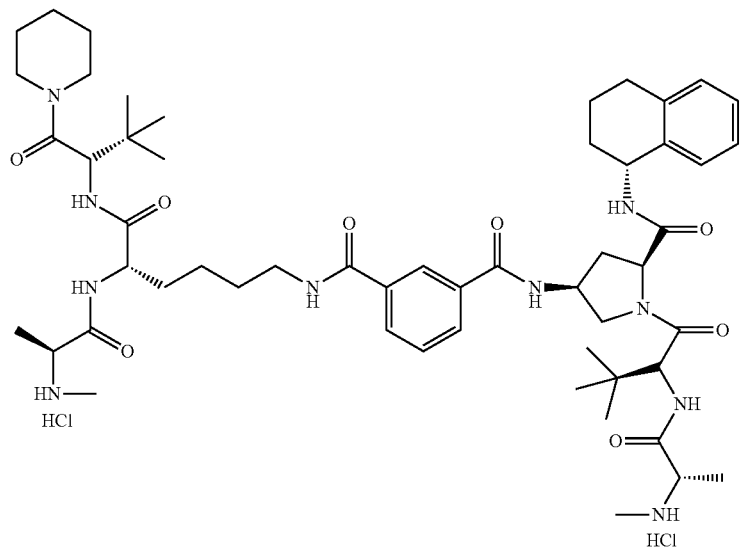
151
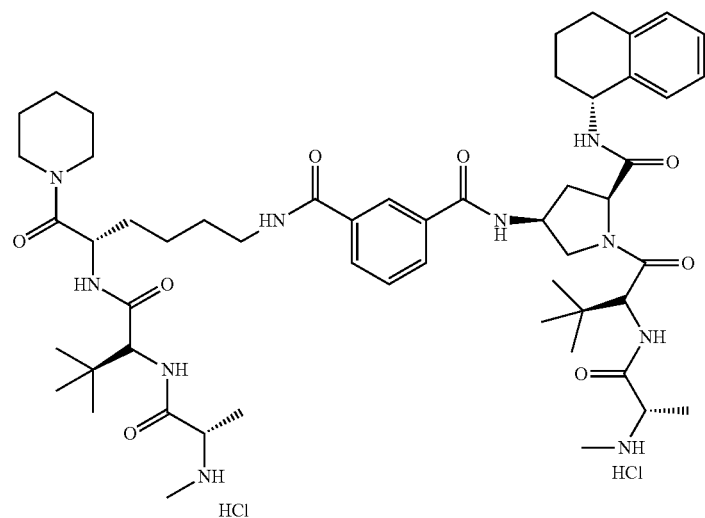
152

TABLE 4-continued
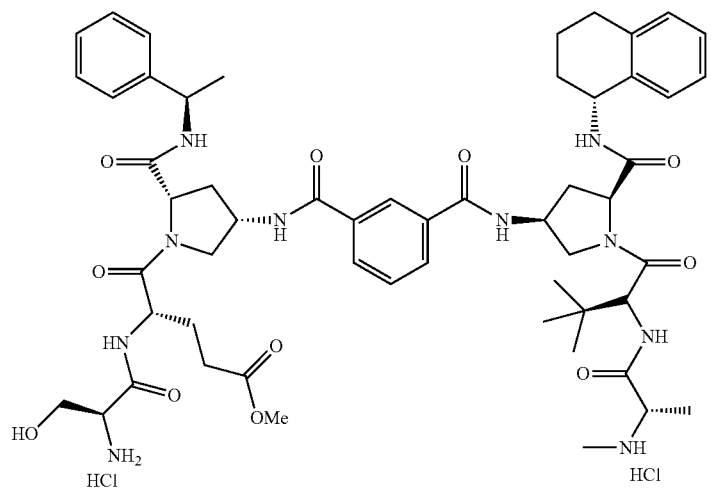
153
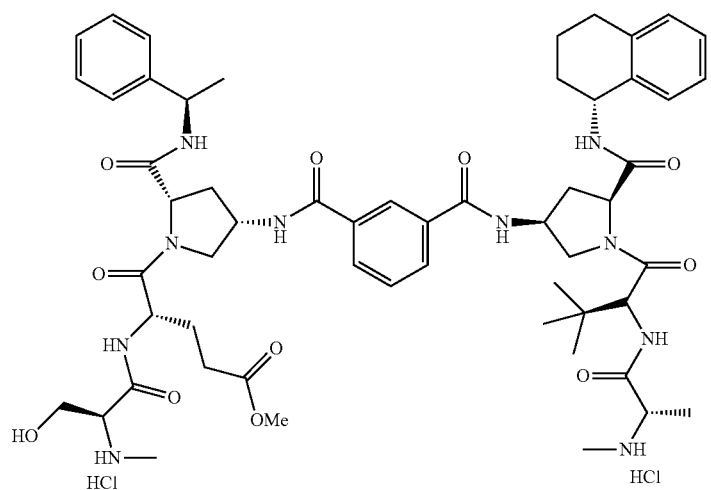
154
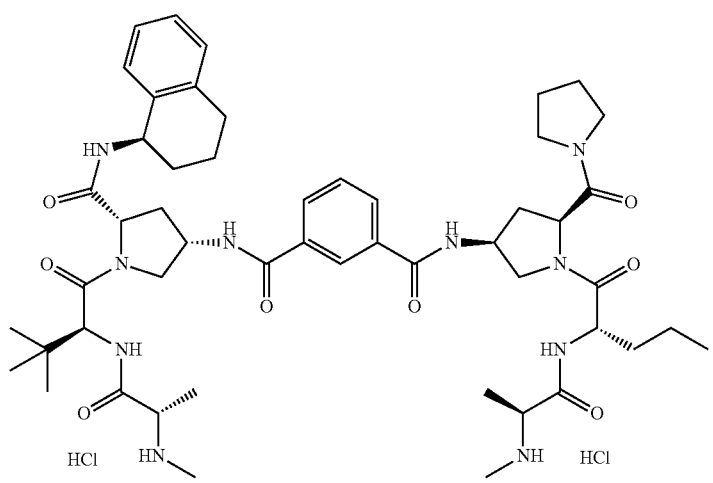 [SMILES: CCC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N1CCCC1 ; Cl ; Cl]
155

TABLE 4-continued
156
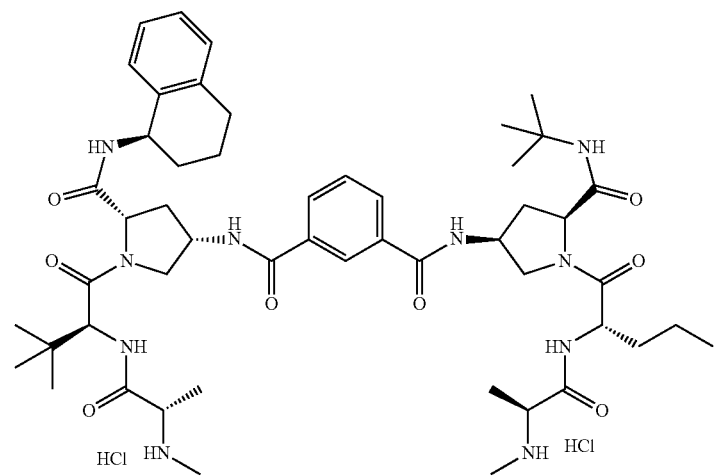 [SMILES: CCC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)NC(C)(C)C ; Cl ; Cl]
157
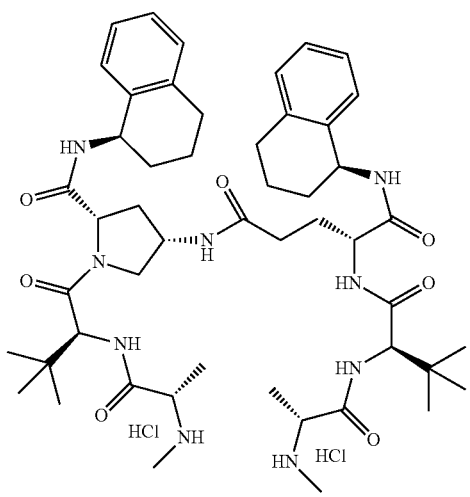 [SMILES: CN[C@@H](C)C(=O)N[C@H](C(=O)N1C[C@@H](NC(=O)CC[C@@H](NC(=O)[C@H](NC(=O)[C@@H](C)NC)C(C)(C)C)C(=O)N[C@H]2CCCc3ccccc32)C[C@H]1C(=O)N[C@@H]1CCCc2ccccc21)C(C)(C)C ; Cl ; Cl]
158
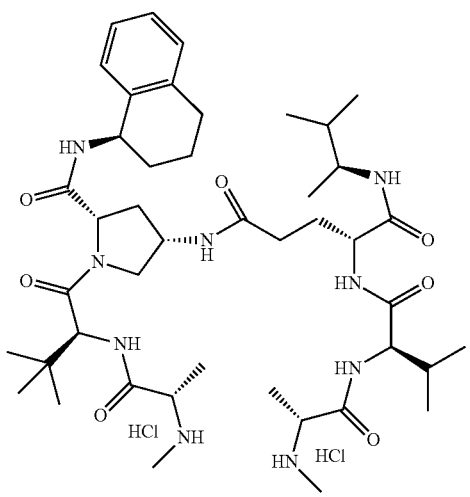 [SMILES: CN[C@@H](C)C(=O)N[C@H](C(=O)N1C[C@@H](NC(=O)CC[C@@H](NC(=O)[C@H](NC(=O)[C@@H](C)NC)C(C)C)C(=O)N[C@@H](C)C(C)C)C[C@H]1C(=O)N[C@@H]1CCCc2ccccc21)C(C)(C)C ; Cl ; Cl]
159
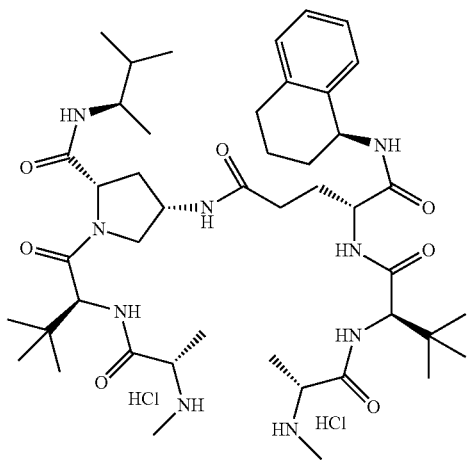 [SMILES: CN[C@@H](C)C(=O)N[C@H](C(=O)N1C[C@@H](NC(=O)CC[C@@H](NC(=O)[C@H](NC(=O)[C@@H](C)NC)C(C)(C)C)C(=O)N[C@H]2CCCc3ccccc32)C[C@H]1C(=O)N[C@H](C)C(C)C)C(C)(C)C ; Cl ; Cl]
160
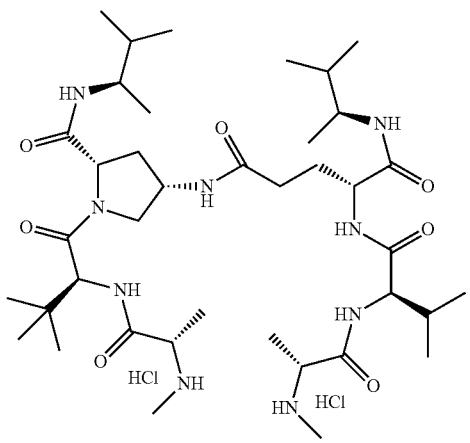 [SMILES: CN[C@@H](C)C(=O)N[C@H](C(=O)N1C[C@@H](NC(=O)CC[C@@H](NC(=O)[C@H](NC(=O)[C@@H](C)NC)C(C)C)C(=O)N[C@@H](C)C(C)C)C[C@H]1C(=O)N[C@H](C)C(C)C)C(C)(C)C ; Cl ; Cl]

TABLE 4-continued
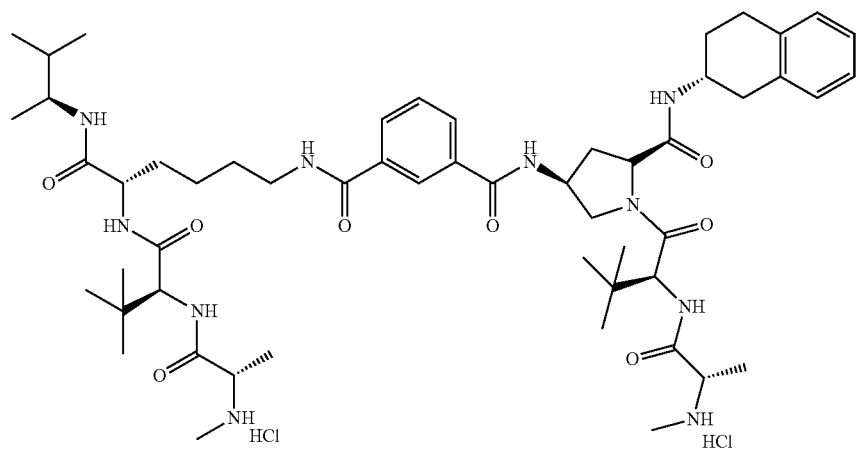
161
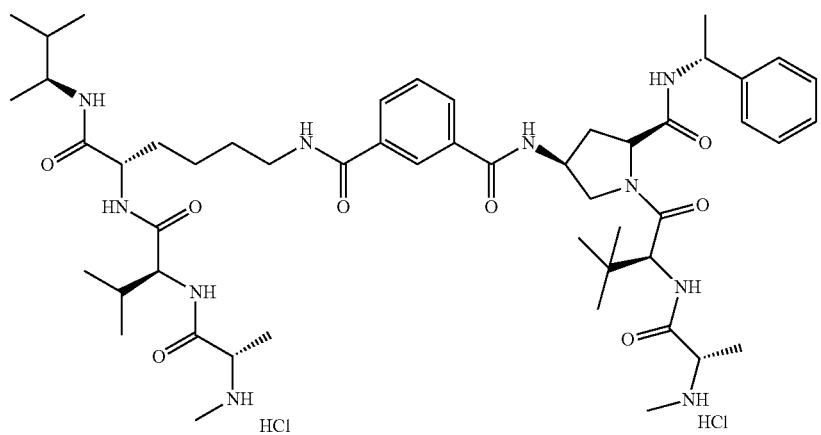
162
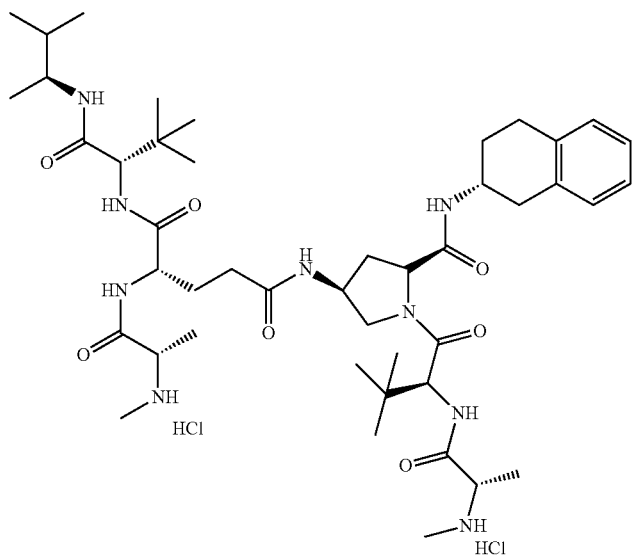
163

TABLE 4-continued
164
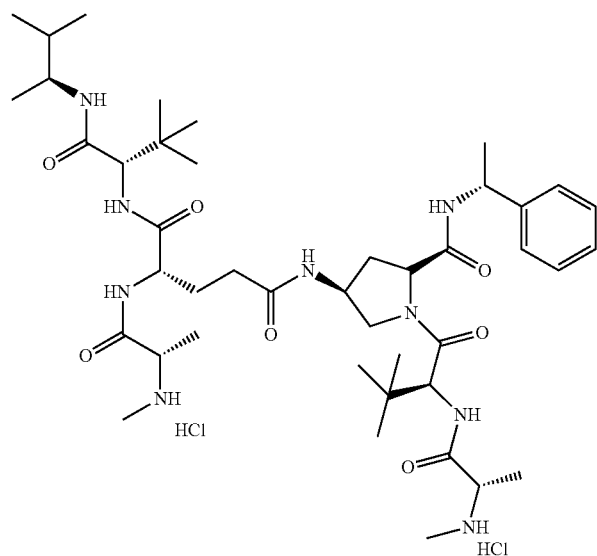
165
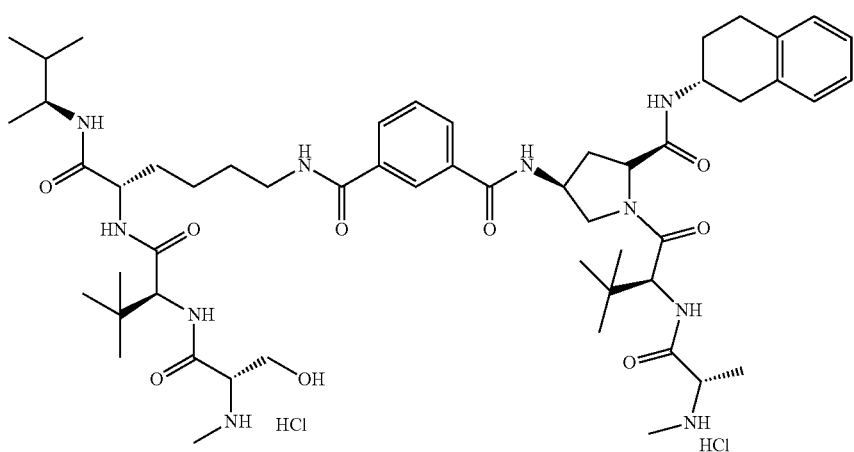
166
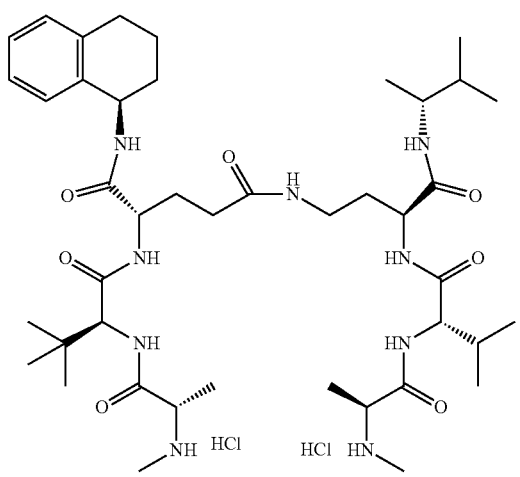 [SMILES: CN[C@@H](C)C(=O)N[C@H](C(=O)N[C@@H](CCNC(=O)CC[C@H](NC(=O)[C@@H](NC(=O)[C@H](C)NC)C(C)(C)C)C(=O)N[C@@H]1CCCc2ccccc21)C(=O)N[C@H](C)C(C)C)C(C)C ; Cl ; Cl]
167
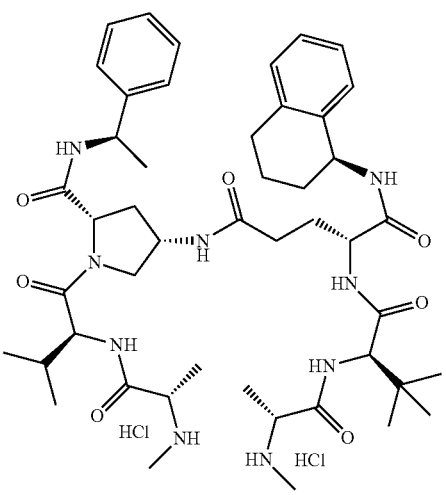 [SMILES: CN[C@@H](C)C(=O)N[C@H](C(=O)N1C[C@@H](NC(=O)CC[C@@H](NC(=O)[C@H](NC(=O)[C@@H](C)NC)C(C)(C)C)C(=O)N[C@H]2CCCc3ccccc32)C[C@H]1C(=O)N[C@H](C)c1ccccc1)C(C)C ; Cl ; Cl]

TABLE 4-continued
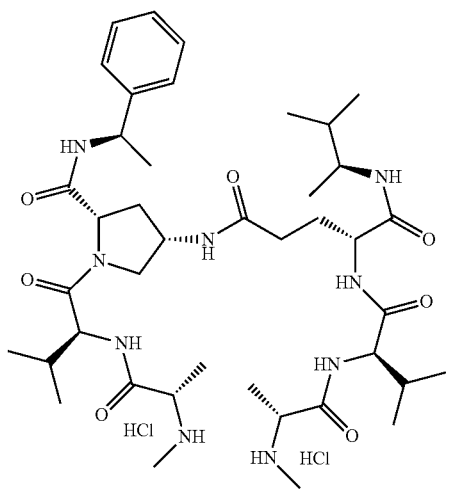 [SMILES: CN[C@@H](C)C(=O)N[C@H](C(=O)N1C[C@@H](NC(=O)CC[C@@H](NC(=O)[C@H](NC(=O)[C@@H](C)NC)C(C)C)C(=O)N[C@@H](C)C(C)C)C[C@H]1C(=O)N[C@H](C)c1ccccc1)C(C)C ; Cl ; Cl]
168
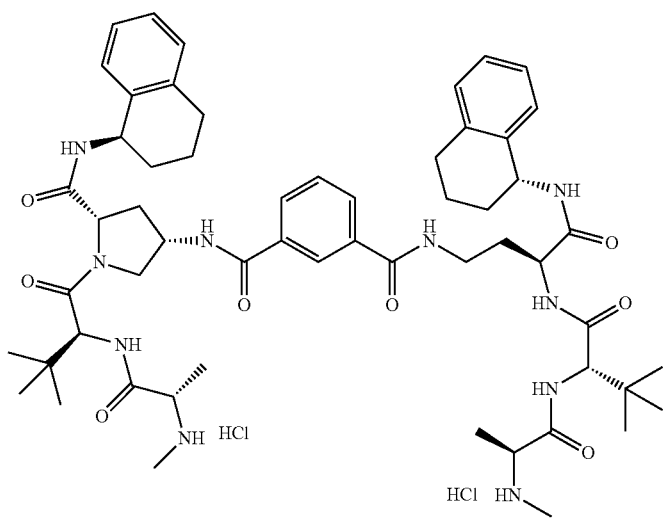 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@@H]1CCCc2ccccc21)C(C)(C)C ; Cl ; Cl]
169
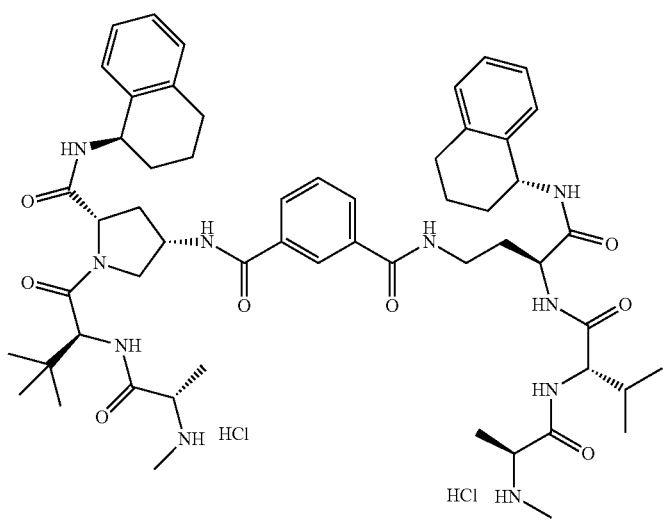 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@@H]1CCCc2ccccc21)C(C)C ; Cl ; Cl]
170

TABLE 4-continued
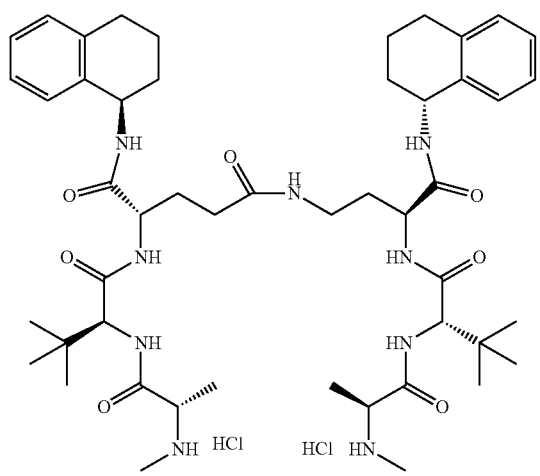 [SMILES: CN[C@@H](C)C(=O)N[C@H](C(=O)N[C@@H](CCNC(=O)CC[C@H](NC(=O)[C@@H](NC(=O)[C@H](C)NC)C(C)(C)C)C(=O)N[C@@H]1CCCc2ccccc21)C(=O)N[C@@H]1CCCc2ccccc21)C(C)(C)C ; Cl ; Cl]
171
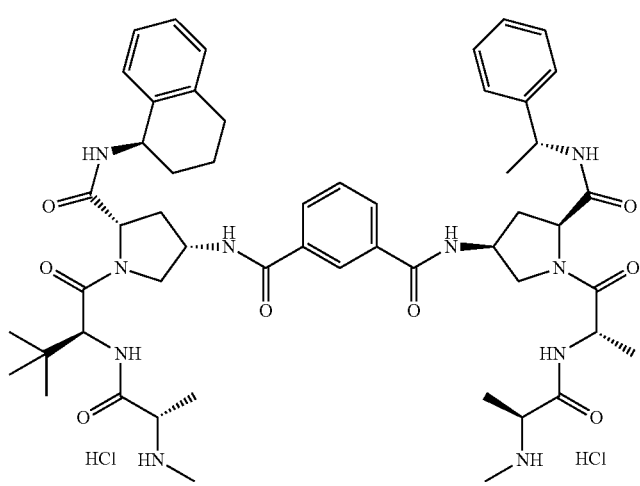 [SMILES: CN[C@@H](C)C(=O)N[C@@H](C)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@H](C)c1ccccc1 ; Cl ; Cl]
172
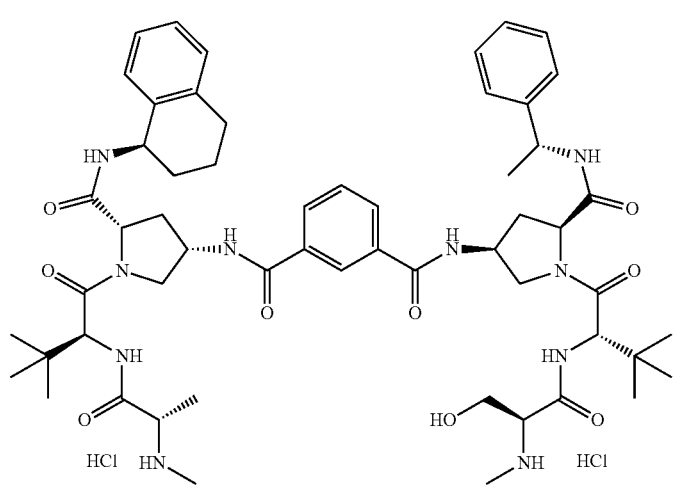 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](CO)NC)C(C)(C)C)C3)c2)C[C@H]1C(=O)N[C@@H]1CCCc2ccccc21)C(C)(C)C ; Cl ; Cl]
173

TABLE 4-continued
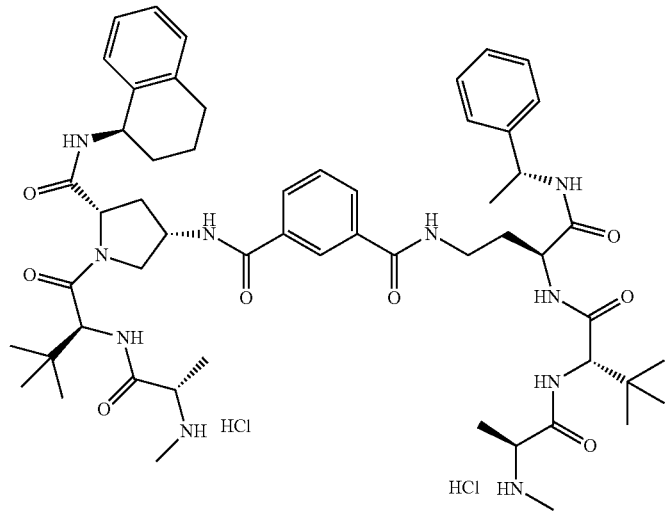 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)c1ccccc1)C(C)(C)C ; Cl ; Cl]
174
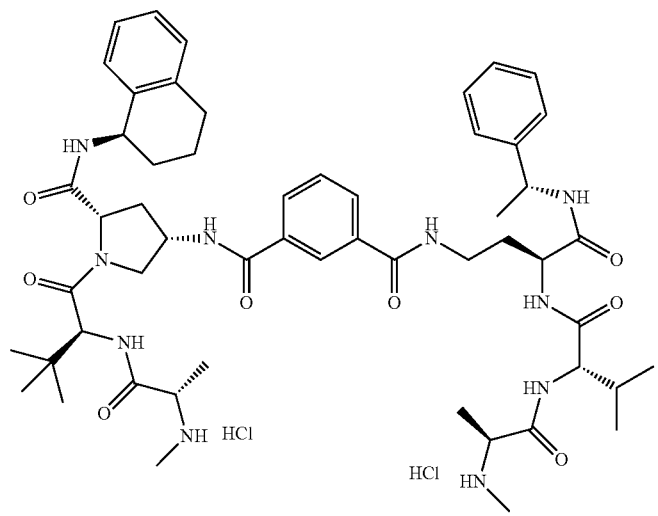 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)c1ccccc1)C(C)C ; Cl ; Cl]
175
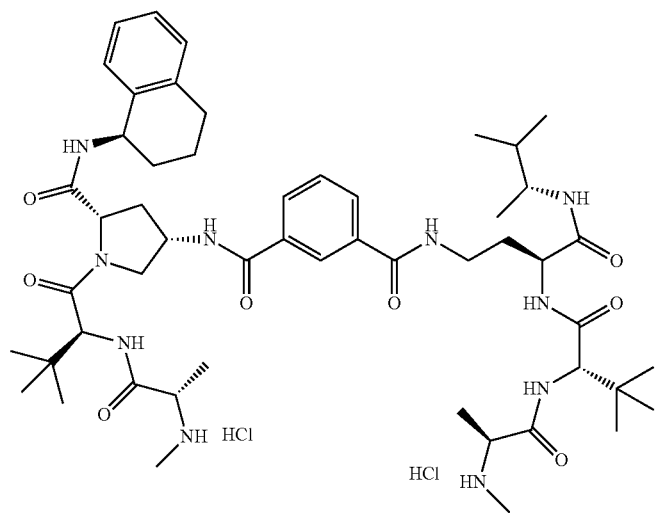 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)C(C)C)C(C)(C)C ; Cl ; Cl]
176

TABLE 4-continued
177
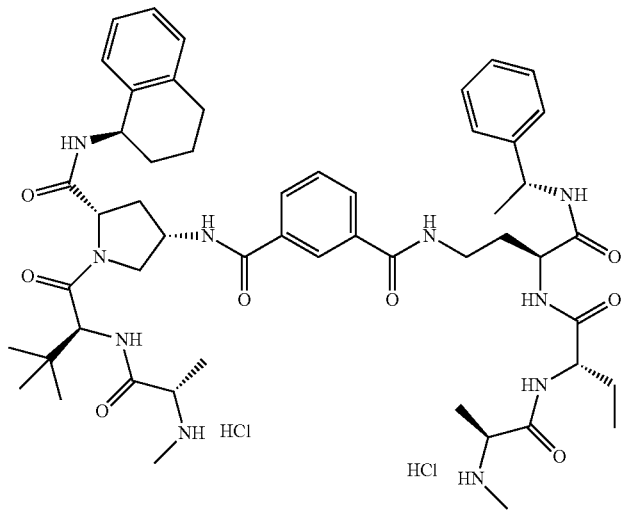 [SMILES: CC[C@H](NC(=O)[C@H](C)NC)C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)c1ccccc1 ; Cl ; Cl]
178
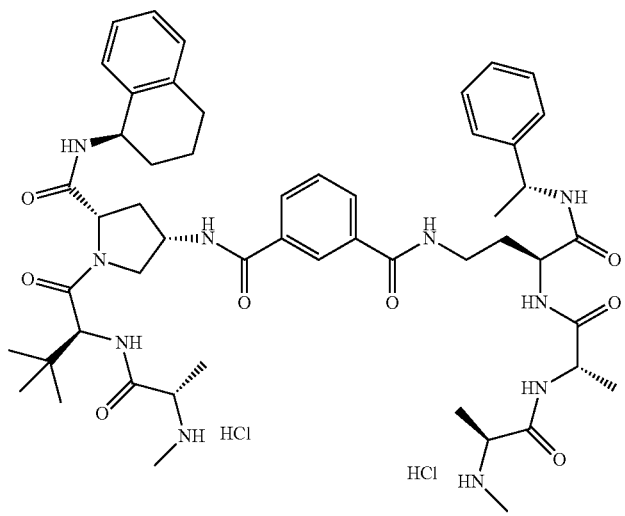 [SMILES: CN[C@@H](C)C(=O)N[C@@H](C)C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)c1ccccc1 ; Cl ; Cl]
179
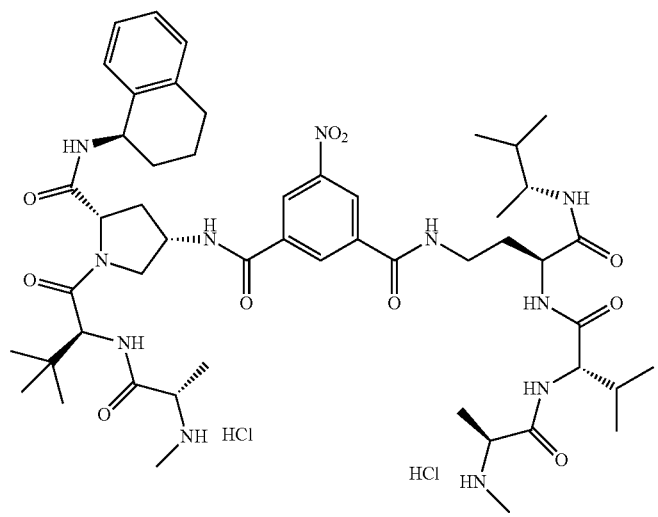 [SMILES: CN[C@@H](C)C(=O)N[C@H](C(=O)N[C@@H](CCNC(=O)c1cc(C(=O)N[C@H]2C[C@@H](C(=O)N[C@@H]3CCCc4ccccc43)N(C(=O)[C@@H](NC(=O)[C@H](C)NC)C(C)(C)C)C2)cc([N+](=O)[O-])c1)C(=O)N[C@H](C)C(C)C)C(C)C ; Cl ; Cl]

TABLE 4-continued
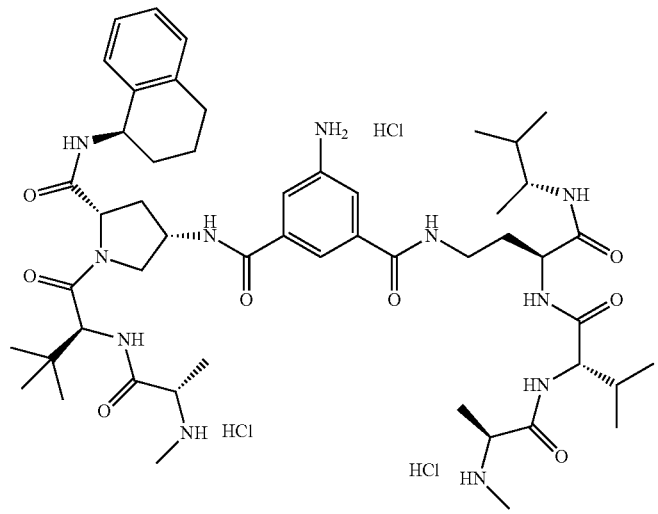 [SMILES: CN[C@@H](C)C(=O)N[C@H](C(=O)N[C@@H](CCNC(=O)c1cc(N)cc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@H](C)C(C)C)C(C)C ; Cl ; Cl ; Cl]
180
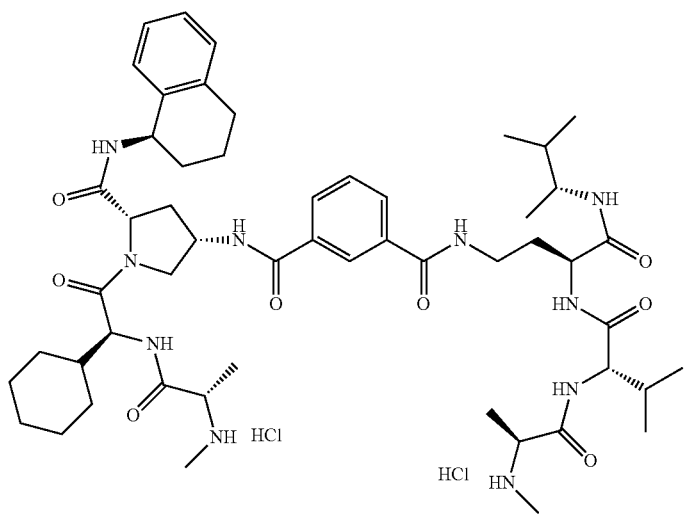 [SMILES: CN[C@@H](C)C(=O)N[C@H](C(=O)N[C@@H](CCNC(=O)c1cccc(C(=O)N[C@H]2C[C@@H](C(=O)N[C@@H]3CCCc4ccccc43)N(C(=O)[C@@H](NC(=O)[C@H](C)NC)C3CCCCC3)C2)c1)C(=O)N[C@H](C)C(C)C)C(C)C ; Cl ; Cl]
181
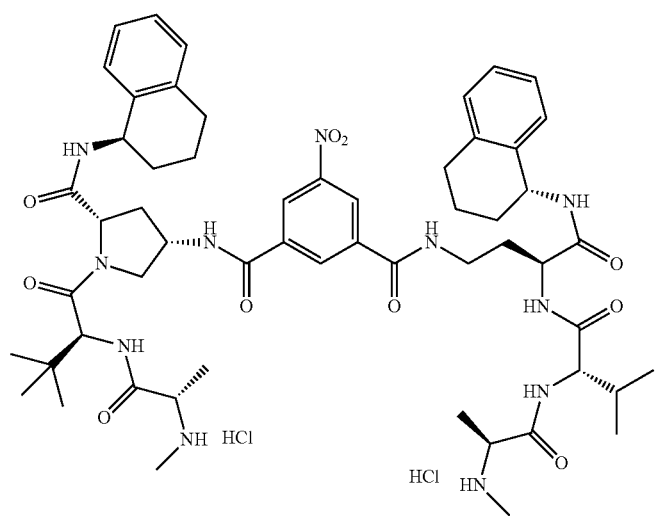 [SMILES: CN[C@@H](C)C(=O)N[C@H](C(=O)N[C@@H](CCNC(=O)c1cc(C(=O)N[C@H]2C[C@@H](C(=O)N[C@@H]3CCCc4ccccc43)N(C(=O)[C@@H](NC(=O)[C@H](C)NC)C(C)(C)C)C2)cc([N+](=O)[O-])c1)C(=O)N[C@@H]1CCCc2ccccc21)C(C)C ; Cl ; Cl]
182

TABLE 4-continued
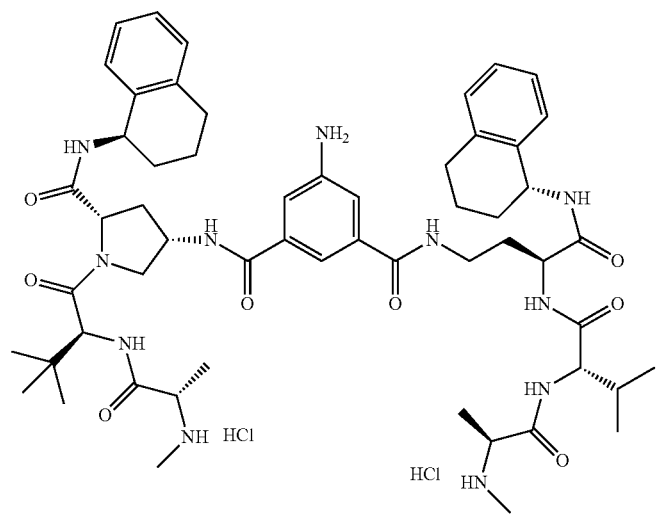 [SMILES: CN[C@@H](C)C(=O)N[C@H](C(=O)N[C@@H](CCNC(=O)c1cc(N)cc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N[C@@H]1CCCc2ccccc21)C(C)C ; Cl ; Cl]
183
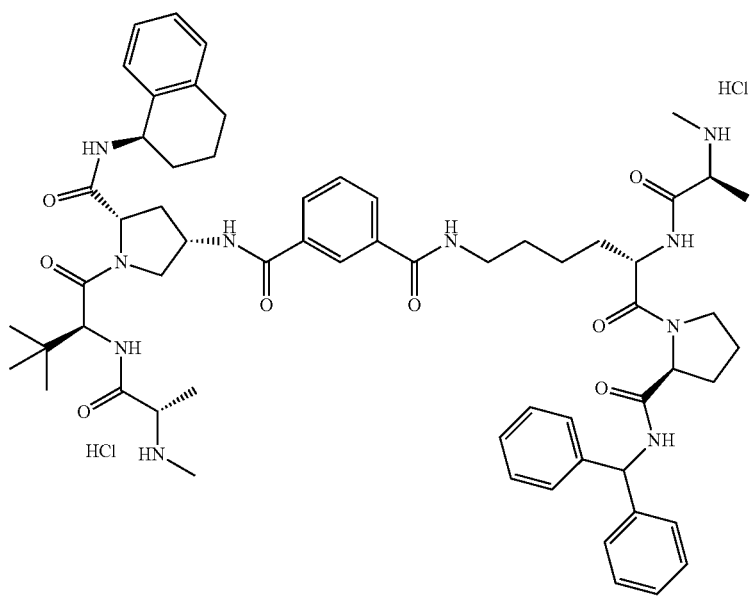 [SMILES: CN[C@@H](C)C(=O)N[C@@H](CCCCNC(=O)c1cccc(C(=O)N[C@H]2C[C@@H](C(=O)N[C@@H]3CCCc4ccccc43)N(C(=O)[C@@H](NC(=O)[C@H](C)NC)C(C)(C)C)C2)c1)C(=O)N1CCC[C@H]1C(=O)NC(c1ccccc1)c1ccccc1 ; Cl ; Cl]
184

TABLE 4-continued
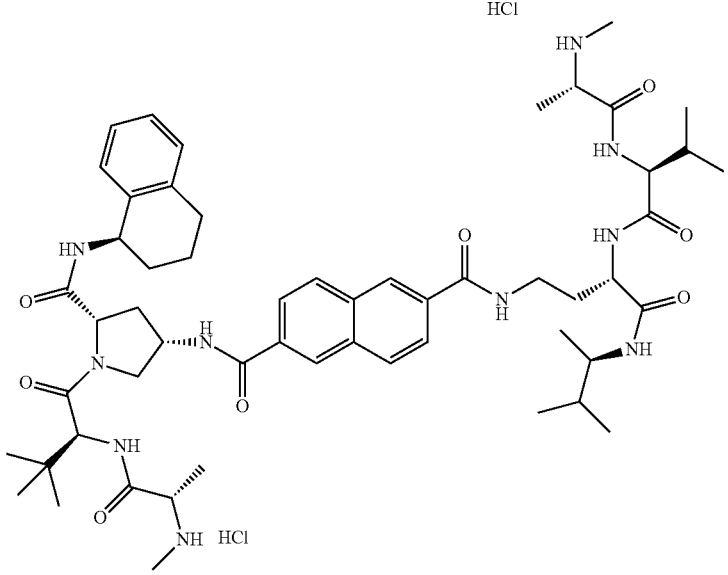 [SMILES: Cl ; CN[C@@H](C)C(=O)N[C@H](C(=O)N[C@@H](CCNC(=O)c1ccc2cc(C(=O)N[C@H]3C[C@@H](C(=O)N[C@@H]4CCCc5ccccc54)N(C(=O)[C@@H](NC(=O)[C@H](C)NC)C(C)(C)C)C3)ccc2c1)C(=O)N[C@H](C)C(C)C)C(C)C ; Cl]
185
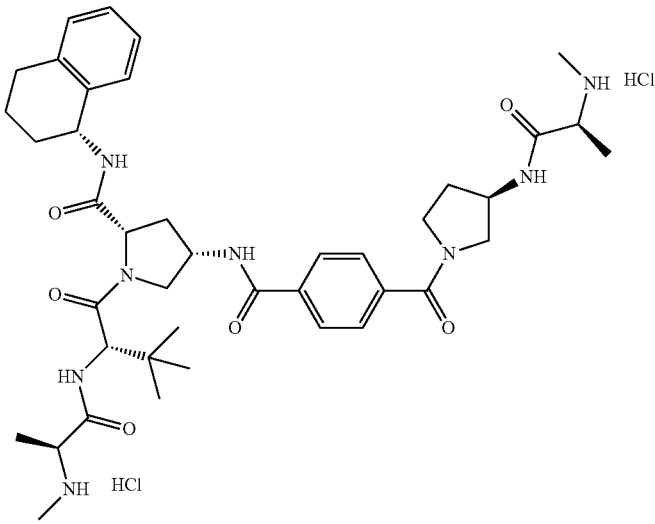 [SMILES: CN[C@@H](C)C(=O)N[C@@H]1CCN(C(=O)c2ccc(C(=O)N[C@H]3C[C@@H](C(=O)N[C@@H]4CCCc5ccccc54)N(C(=O)[C@@H](NC(=O)[C@H](C)NC)C(C)(C)C)C3)cc2)C1 ; Cl ; Cl]
186

TABLE 4-continued
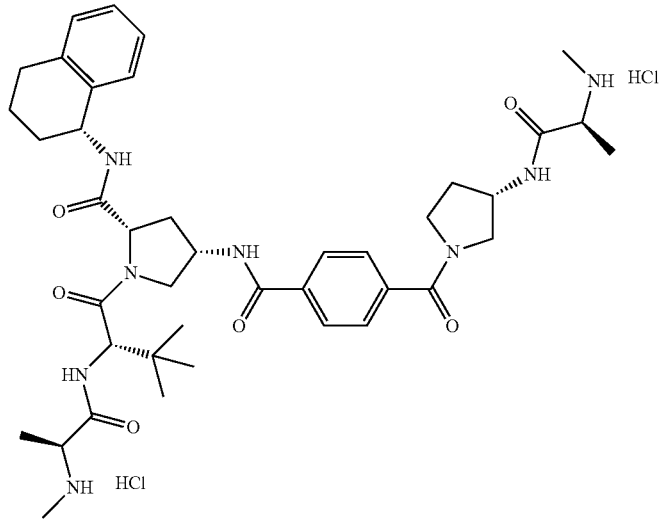 [SMILES: CN[C@@H](C)C(=O)N[C@H]1CCN(C(=O)c2ccc(C(=O)N[C@H]3C[C@@H](C(=O)N[C@@H]4CCCc5ccccc54)N(C(=O)[C@@H](NC(=O)[C@H](C)NC)C(C)(C)C)C3)cc2)C1 ; Cl ; Cl]
187
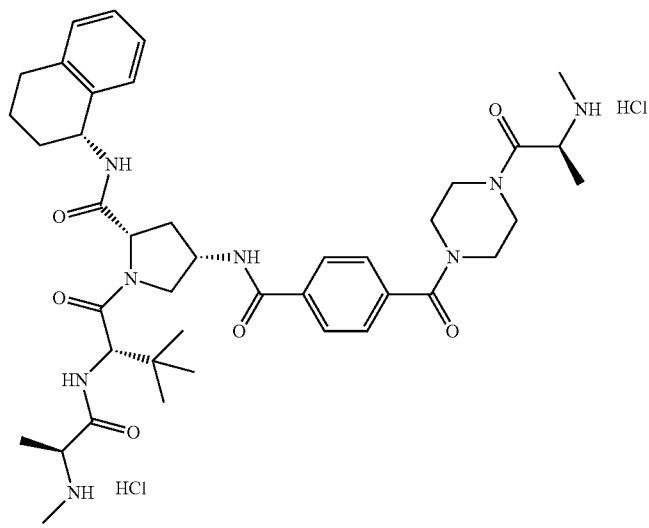 [SMILES: CN[C@@H](C)C(=O)N[C@H](C(=O)N1C[C@@H](NC(=O)c2ccc(C(=O)N3CCN(C(=O)[C@H](C)NC)CC3)cc2)C[C@H]1C(=O)N[C@@H]1CCCc2ccccc21)C(C)(C)C ; Cl ; Cl]
188
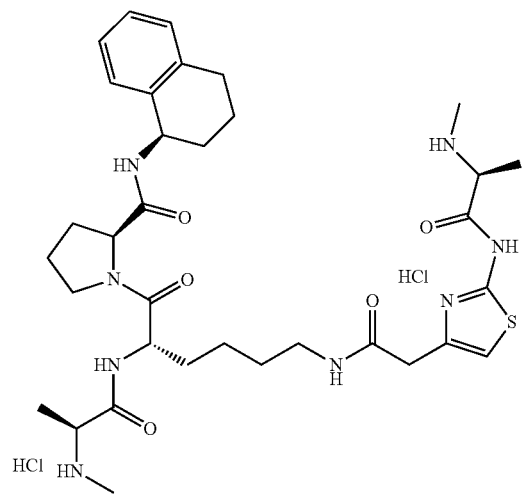 [SMILES: Cl ; CN[C@@H](C)C(=O)Nc1nc(CC(=O)NCCCC[C@H](NC(=O)[C@H](C)NC)C(=O)N2CCC[C@H]2C(=O)N[C@@H]2CCCc3ccccc32)cs1 ; Cl]
189

TABLE 4-continued
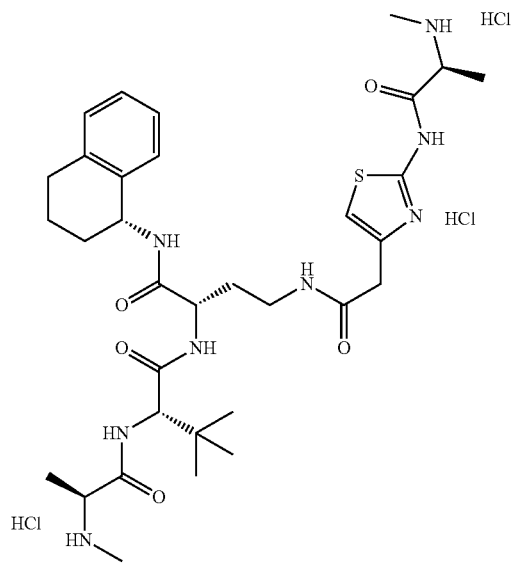 [SMILES: Cl ; CN[C@@H](C)C(=O)Nc1nc(CC(=O)NCC[C@H](NC(=O)[C@@H](NC(=O)[C@H](C)NC)C(C)(C)C)C(=O)N[C@@H]2CCCc3ccccc32)cs1 ; Cl ; Cl]
190
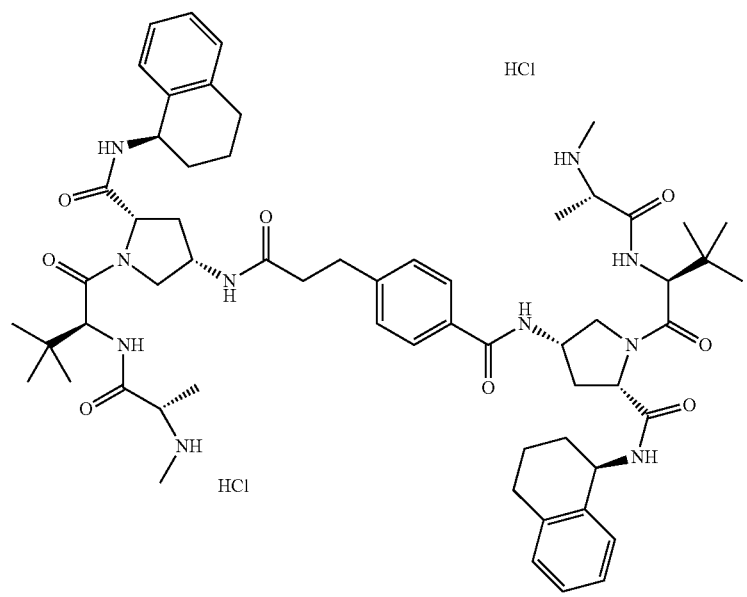 [SMILES: CN[C@@H](C)C(=O)N[C@H](C(=O)N1C[C@@H](NC(=O)CCc2ccc(C(=O)N[C@H]3C[C@@H](C(=O)N[C@@H]4CCCc5ccccc54)N(C(=O)[C@@H](NC(=O)[C@H](C)NC)C(C)(C)C)C3)cc2)C[C@H]1C(=O)N[C@@H]1CCCc2ccccc21)C(C)(C)C ; Cl ; Cl]
191

TABLE 4-continued
192
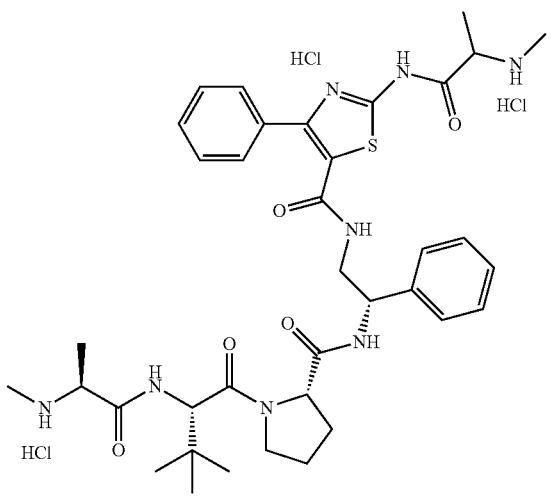
193
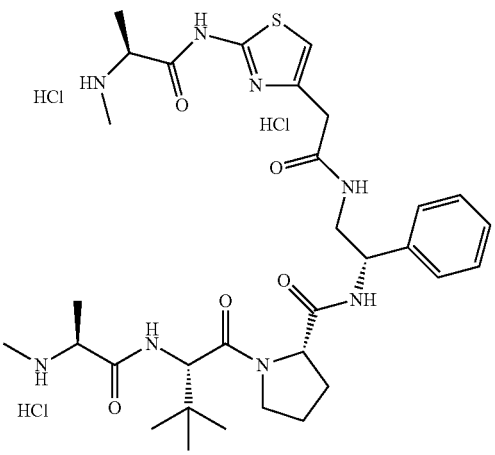 [SMILES: CN[C@@H](C)C(=O)Nc1nc(CC(=O)NC[C@@H](NC(=O)[C@@H]2CCCN2C(=O)[C@@H](NC(=O)[C@H](C)NC)C(C)(C)C)c2ccccc2)cs1 ; Cl ; Cl ; Cl]
194
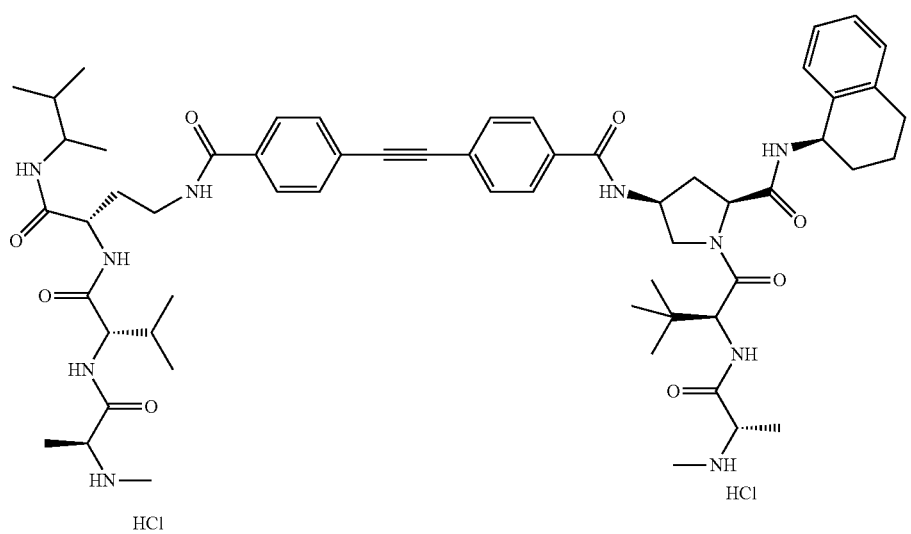 [SMILES: CN[C@@H](C)C(=O)N[C@H](C(=O)N[C@@H](CCNC(=O)c1ccc(C#Cc2ccc(C(=O)N[C@H]3C[C@@H](C(=O)N[C@@H]4CCCc5ccccc54)N(C(=O)[C@@H](NC(=O)[C@H](C)NC)C(C)(C)C)C3)cc2)cc1)C(=O)NC(C)C(C)C)C(C)C ; Cl ; Cl]
195
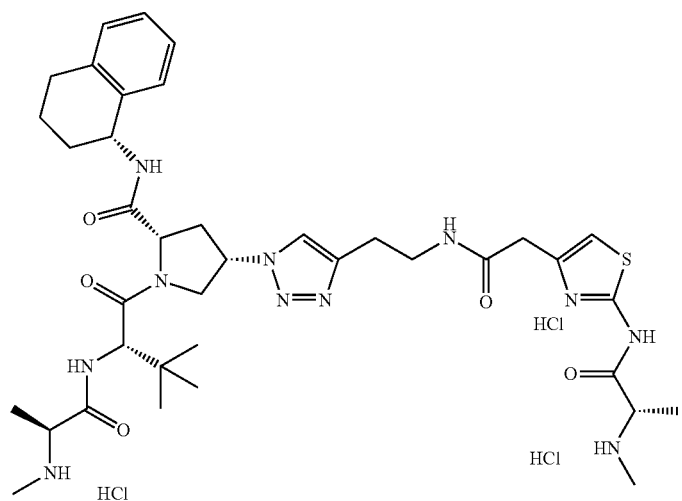 [SMILES: CN[C@@H](C)C(=O)Nc1nc(CC(=O)NCCc2cn([C@H]3C[C@@H](C(=O)N[C@@H]4CCCc5ccccc54)N(C(=O)[C@@H](NC(=O)[C@H](C)NC)C(C)(C)C)C3)nn2)cs1 ; Cl ; Cl ; Cl]

TABLE 4-continued
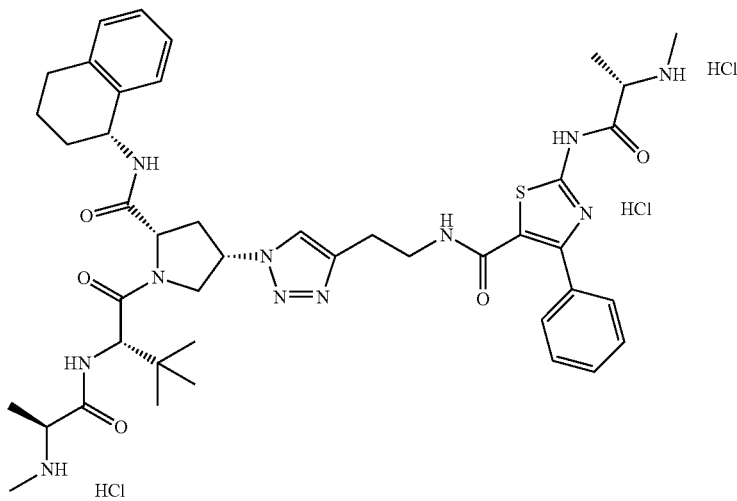
196
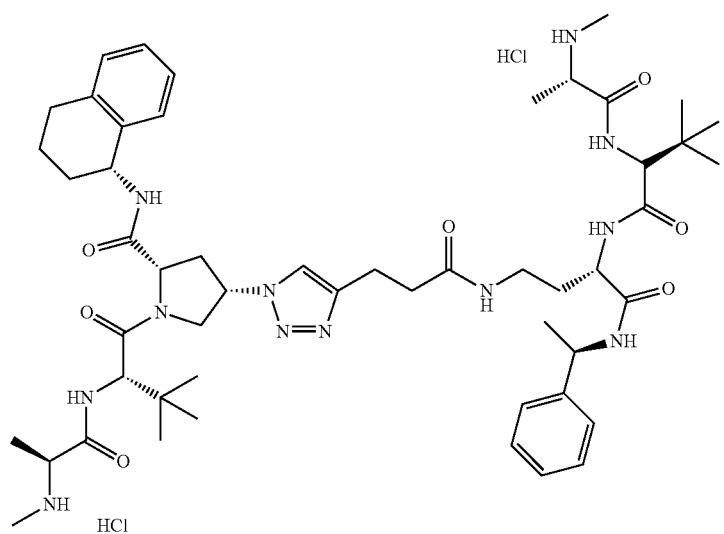
197
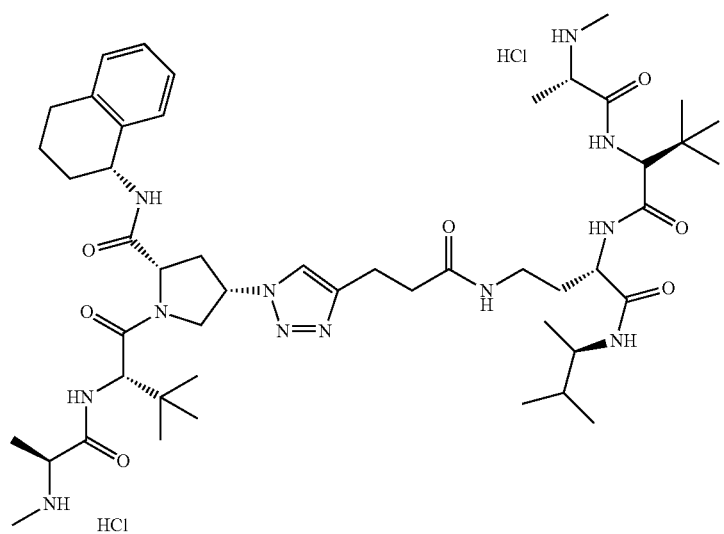
198

TABLE 4-continued
199
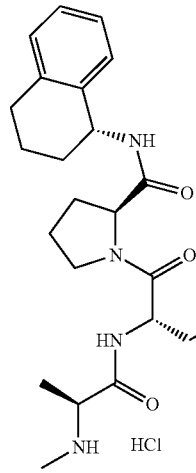
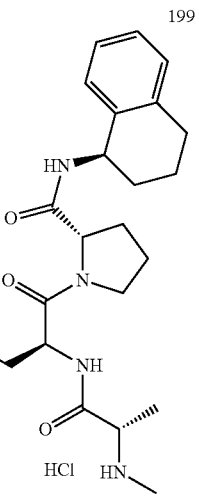
200
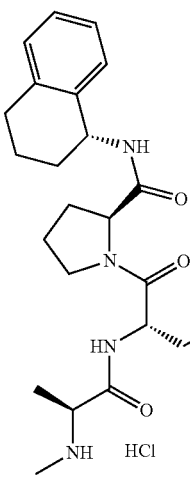
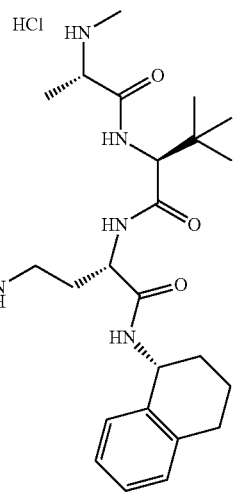
201
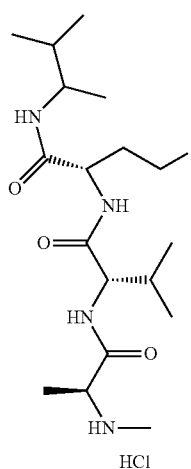
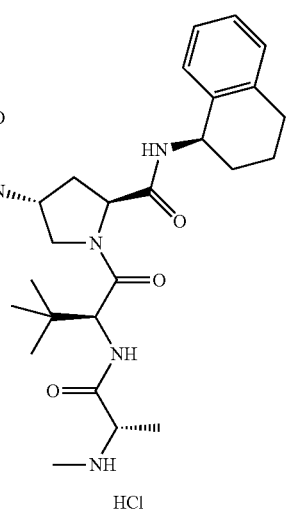
202
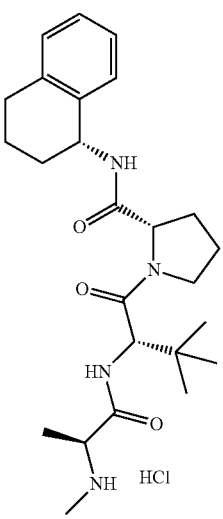
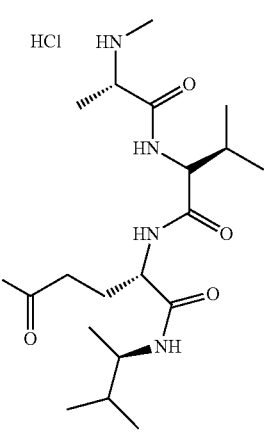

TABLE 4-continued
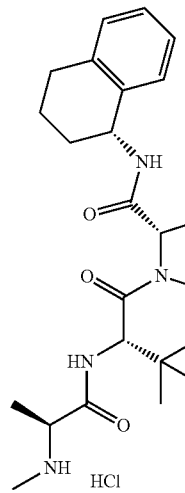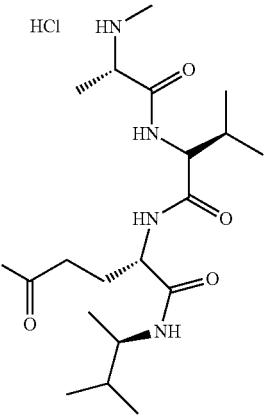
203
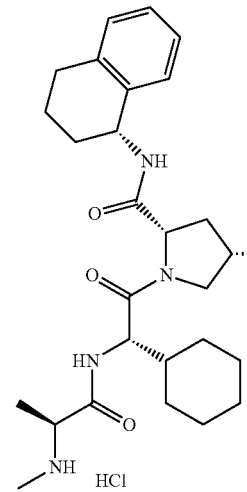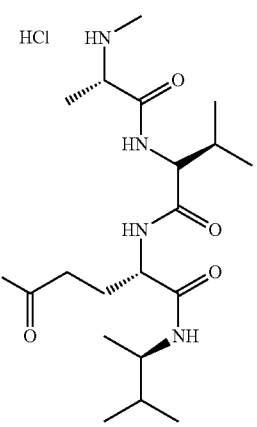
204
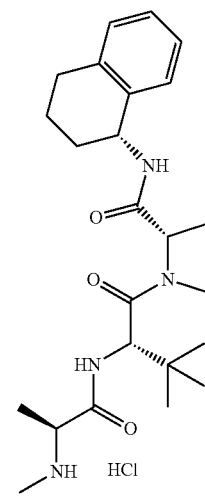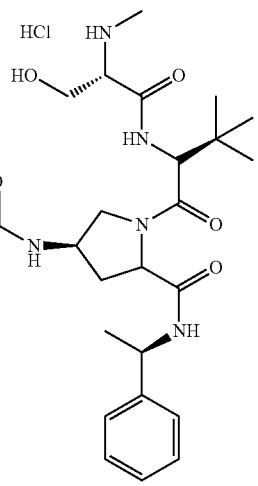
205

TABLE 5
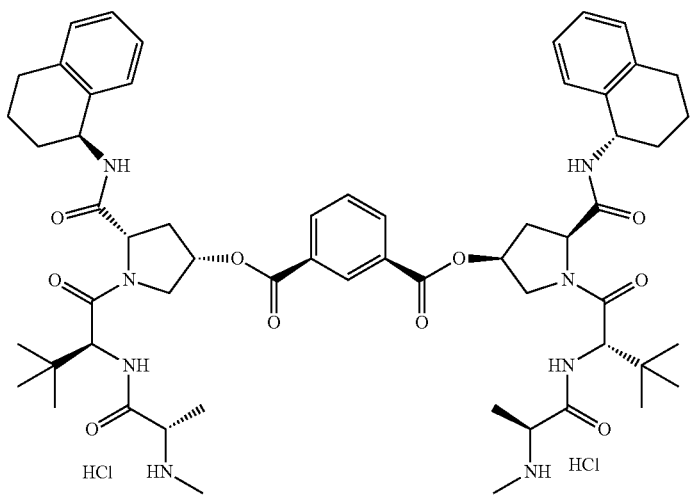
206
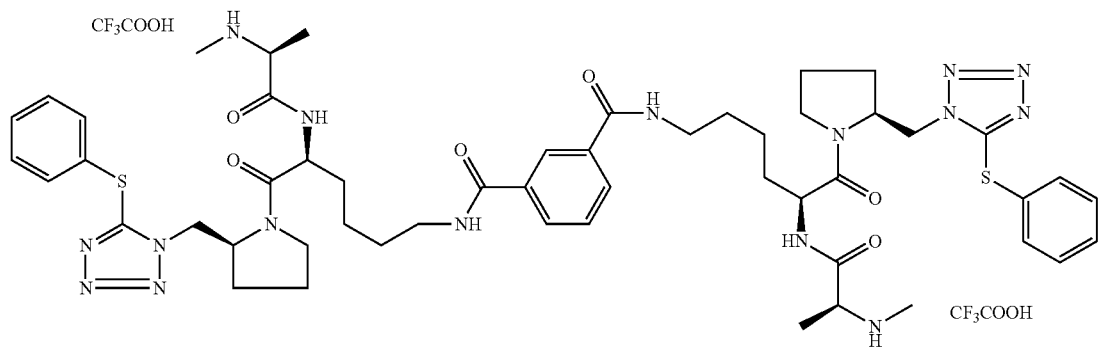 [SMILES: CN[C@@H](C)C(=O)N[C@@H](CCCCNC(=O)c1cccc(C(=O)NCCCC[C@H](NC(=O)[C@H](C)NC)C(=O)N2CCC[C@H]2Cn2nnnc2Sc2ccccc2)c1)C(=O)N1CCC[C@H]1Cn1nnnc1Sc1ccccc1 ; "CF3COOH" ; "CF3COOH"]
207
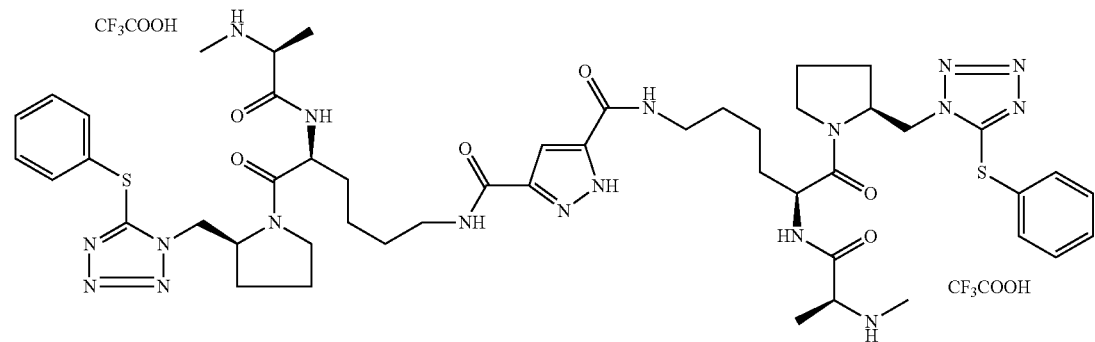 [SMILES: CN[C@@H](C)C(=O)N[C@@H](CCCCNC(=O)c1cc(C(=O)NCCCC[C@H](NC(=O)[C@H](C)NC)C(=O)N2CCC[C@H]2Cn2nnnc2Sc2ccccc2)[nH]n1)C(=O)N1CCC[C@H]1Cn1nnnc1Sc1ccccc1 ; "CF3COOH" ; "CF3COOH"]
208
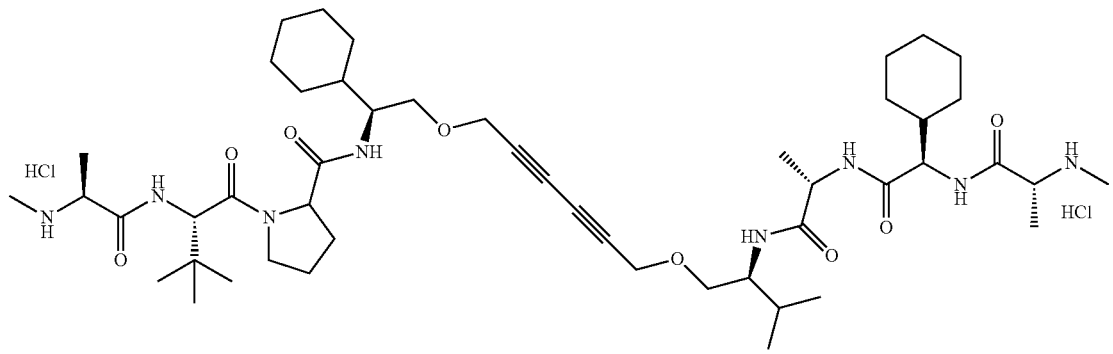
209

TABLE 5-continued
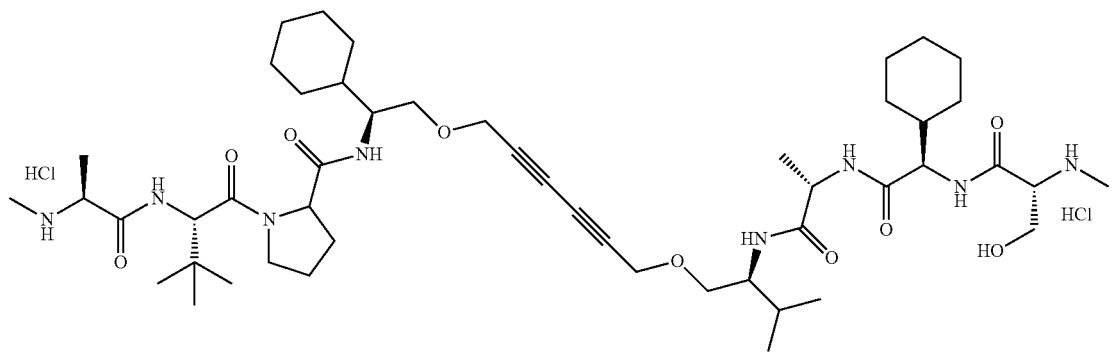
210
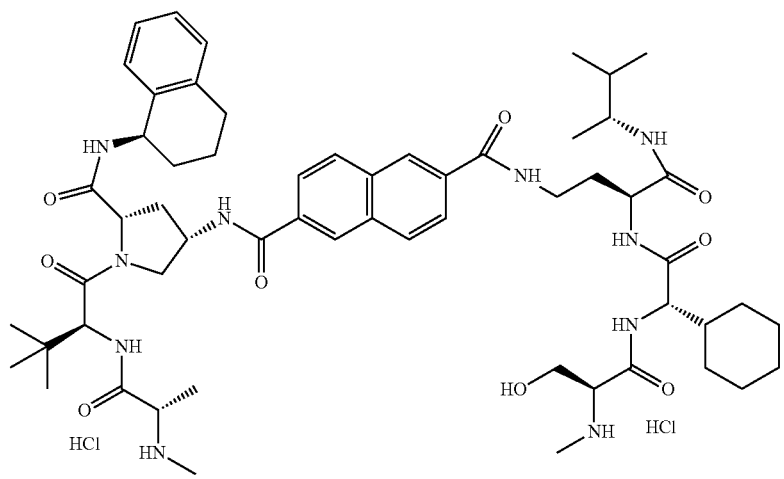 [SMILES: CN[C@@H](C)C(=O)N[C@H](C(=O)N1C[C@@H](NC(=O)c2ccc3cc(C(=O)NCC[C@H](NC(=O)[C@@H](NC(=O)[C@H](CO)NC)C4CCCCC4)C(=O)N[C@H](C)C(C)C)ccc3c2)C[C@H]1C(=O)N[C@@H]1CCCc2ccccc21)C(C)(C)C ; Cl ; Cl]
211
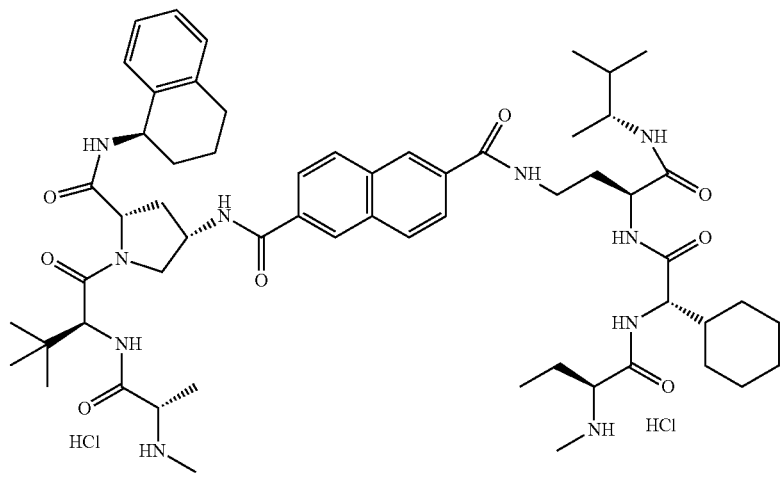 [SMILES: CC[C@H](NC)C(=O)N[C@H](C(=O)N[C@@H](CCNC(=O)c1ccc2cc(C(=O)N[C@H]3C[C@@H](C(=O)N[C@@H]4CCCc5ccccc54)N(C(=O)[C@@H](NC(=O)[C@H](C)NC)C(C)(C)C)C3)ccc2c1)C(=O)N[C@H](C)C(C)C)C1CCCCC1 ; Cl ; Cl]
212

TABLE 5-continued

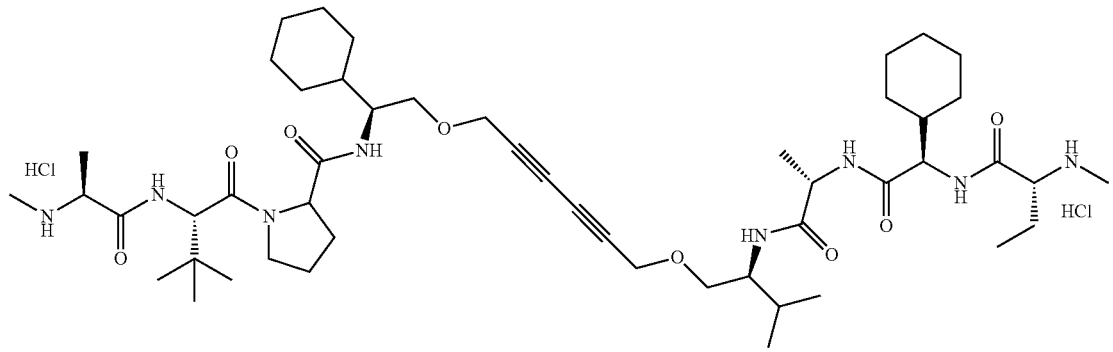

Representative Biological Data
Biological data for the compounds presented in Tables 1-5 is provided in Tables 6-10, respectively.

TABLE 6

Biological Data for Compounds in Table 1.

| Cpd. No. | IC50 (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells | | |
|---|---|---|---|---|---|---|
| | | | | Compound alone | Compound + 100 ng/ml TNFa (μM) | Compound + 300 ng/ml TRAIL (μM) |
| 1 | | | | >1 | 0.0023 | 0.0019 |
| 2 | | | | >1 | 0.062 | 0.054 |
| 3 | | | | >1 | 0.50 | 0.42 |
| 4 | | | | >1 | >1 | 0.739 |
| 5 | | | | >1 | 0.706 | 0.982 |
| 6 | | | | >1 | 0.471 | 0.310 |
| 7 | | | | >1 | 0.383 | 0.217 |
| 8 | | | | >1 | >1 | >1 |
| 9 | | | | >1 | >1 | >1 |
| 10 | | | | >1 | 0.065 | 0.085 |
| 11 | | | | >1 | 0.834 | 0.545 |
| 12 | | | | | | |
| 13 | | | | | | |
| 14 | | | | >1 | >1 | >1 |
| 15 | | | | >1 | 0.209 | 0.235 |
| 16 | | | | >1 | >1 | >1 |
| 17 | | | | >1 | >1 | >1 |
| 18 | | | | | | |
| 19 | | | | | | |
| 20 | | | | >1 | >1 | >1 |
| 21 | | | | | | |
| 22 | | | | | | |
| 23 | | | | >1 | >1 | >1 |
| 24 | | | | | | |
| 25 | | | | >1 | 0.375 | 0.293 |
| 26 | | | | >1 | >1 | >1 |
| 27 | | | | | | |
| 28 | | | | | | |
| 29 | | | | | | |
| 30 | | | | >1 | >1 | >1 |
| 31 | | | | | | |
| 32 | | | | | | |
| 33 | | | | | | |
| 34 | | | | | | |
| 35 | | | | >1 | >1 | >1 |
| 36 | | | | | | |
| 37 | | | | | | |
| 38 | | | | >1 | >1 | >1 |
| 39 | | | | >1 | >1 | >1 |
| 40 | | | | >1 | 0.555 | 0.517 |
| 41 | | | | >1 | 0.452 | 0.434 |
| 42 | | | | >1 | 0.753 | 0.645 |
| 43 | | | | >1 | 0.050 | 0.048 |

TABLE 6-continued

Biological Data for Compounds in Table 1.

| Cpd. No. | IC50 (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells |  |  |
|---|---|---|---|---|---|---|
|  |  |  |  | Compound alone | Compound + 100 ng/ml TNFa (μM) | Compound + 300 ng/ml TRAIL (μM) |
| 44 |  |  |  | >1 | 0.215 | 0.198 |
| 45 |  |  |  | >1 | 0.008 | 0.014 |
| 46 |  |  |  | >1 | 0.048 | 0.014 |
| 47 |  |  |  | >1 | 0.012 | 0.011 |
| 48 |  |  |  |  |  |  |
| 49 |  |  |  |  |  |  |
| 50 |  |  |  | >1 | 0.236 | 0.122 |
| 51 |  |  |  | >1 | 0.104 | 0.081 |
| 52 |  |  |  | >1 | 0.046 | 0.052 |
| 53 |  |  |  | >1 | 0.466 | 0.227 |
| 54 |  |  |  |  |  |  |
| 55 |  |  |  |  |  |  |
| 56 |  |  |  |  |  |  |
| 57 |  |  |  |  |  |  |
| 58 |  |  |  | >1 | >1 | >1 |
| 59 |  |  |  | >1 | >1 | >1 |
| 60 |  |  |  | >1 | 0.044 | 0.049 |
| 61 |  |  |  | >1 | 0.324 | 0.439 |
| 62 |  |  |  | >1 | 0.107 | 0.099 |
| 63 |  |  |  | >1 | 0.143 | 0.162 |
| 64 |  |  |  | >1 | 0.180 | 0.151 |
| 65 |  |  |  | >1 | 0.265 | 0.328 |
| 66 |  |  |  | >1 | 0.012 | 0.013 |
| 67 |  |  |  | >1 | 0.191 | 0.220 |
| 68 |  |  |  | >1 | 0.029 | 0.019 |
| 69 |  |  |  | >1 | >1 | >1 |
| 70 |  |  |  | >1 | 0.0011 | 0.0033 |
| 71 |  |  |  | >1 | 0.0050 | 0.0091 |
| 72 |  |  |  | >1 | 0.0018 | 0.0033 |
| 73 |  |  |  | >1 | 0.0698 | 0.0730 |
| 74 |  |  |  | >1 | >1 | >1 |
| 75 |  |  |  | >1 | 0.0180 | 0.0130 |
| 76 |  |  |  |  |  |  |
| 77 |  |  |  | >1 | >1 | >1 |
| 78 |  |  |  |  |  |  |
| 79 |  |  |  | >1 | >1 | >1 |
| 80 |  |  |  | >1 | >1 | >1 |
| 81 |  |  |  | >1 | 0.155 | 0.196 |
| 82 |  |  |  | >1 | 0.536 | 0.564 |
| 83 |  |  |  | >1 | 0.494 | 0.437 |
| 84 |  |  |  | >1 | >1 | >1 |
| 85 |  |  |  | >1 | >1 | >1 |
| 86 |  |  |  | >1 | >1 | >1 |

TABLE 7

Biological Data for Compounds in Table 2

| Cpd. No. | IC$_{50}$ (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells |  |  |
|---|---|---|---|---|---|---|
|  |  |  |  | Compound alone | Compound + 100 ng/ml TNFa (μM) | Compound + 300 ng/ml TRAIL (μM) |
| 87 | 0.404 | >2400 | 547.5 |  |  |  |
| 88 | 0.188 | >2400 | 112.8 |  |  |  |
| 89 | 0.414 | >2400 | 266.6 |  |  |  |
| 90 |  |  |  |  |  |  |
| 91 |  |  |  |  |  |  |
| 92 |  |  |  | >1 | 0.547 | 0.798 |
| 93 |  |  |  | >1 | 0.299 | 0.327 |
| 94 |  |  |  | >1 | 0.014 | 0.049 |
| 95 |  |  |  | >1 | >1 | >1 |
| 96 |  |  |  | >1 | 0.2108 | 0.4170 |
| 97 |  |  |  |  |  |  |

TABLE 7-continued

Biological Data for Compounds in Table 2

| Cpd No. | IC$_{50}$ (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells Compound alone | Compound + 100 ng/ml TNFa (μM) | Compound + 300 ng/ml TRAIL (μM) |
|---|---|---|---|---|---|---|
| 98 | | | | | | |
| 99 | | | | | | |
| 100 | | | | >1 | 0.0570 | 0.0520 |
| 101 | | | | | | |
| 102 | | | | >1 | 0.0640 | 0.0690 |
| 103 | | | | | | |
| 104 | | | | | | |
| 105 | | | | | | |
| 106 | | | | >1 | 0.006 | 0.006 |
| 107 | | | | | | |
| 108 | | | | | | |
| 109 | | | | >1 | 0.004 | 0.003 |

TABLE 8

Biological Data for Compounds in Table 3

| Cpd No. | IC$_{50}$ (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells Compound alone | Compound + 100 ng/ml TNFa (μM) | Compound + 300 ng/ml TRAIL (μM) |
|---|---|---|---|---|---|---|
| 110 | 0.059 | >2400 | 65.3 | | | |
| 111 | >30 | >2400 | >2400 | | | |
| 112 | >30 | >2400 | >2400 | | | |
| 113 | | | | >1 | 0.2080 | 0.2030 |
| 114 | | | | >1 | 0.1990 | 0.1840 |
| 115 | | | | >1 | 0.0570 | 0.0630 |
| 116 | | | | >1 | 0.0046 | 0.0059 |
| 117 | | | | >1 | 0.020 | 0.025 |
| 118 | | | | >1 | 0.0007 | 0.0008 |
| 119 | | | | >1 | 0.0014 | 0.0018 |
| 120 | | | | >1 | 0.0006 | 0.0006 |
| 121 | | | | >1 | 0.0013 | 0.0015 |
| 122 | | | | >1 | 0.0015 | 0.0014 |
| 123 | | | | >1 | 0.069 | 0.067 |
| 124 | | | | >1 | 0.061 | 0.066 |
| 125 | | | | >1 | 0.0007 | 0.0008 |
| 126 | | | | >1 | 0.023 | 0.028 |
| 127 | | | | >1 | 0.032 | 0.028 |
| 128 | | | | >1 | 0.010 | 0.014 |
| 129 | | | | >1 | 0.006 | 0.004 |
| 130 | | | | >1 | 0.018 | 0.019 |

TABLE 9

Biological Data for Compounds in Table 4

| Cpd No. | IC$_{50}$ (μM) in cell viability assay in HCC461 | Synergy with TRAIL in PANC-1 ng/ml IC$_{50}$ for TRAIL | IC$_{50}$ for TRAIL + 100 nm compound | IC$_{50}$ (μM) in cell viability assay in PANC-1 cells Compound alone | Compound + 100 ng/ml TNFa (μM) | Compound + 300 ng/ml TRAIL (μM) |
|---|---|---|---|---|---|---|
| 131 | 0.642 | >2400 | 63.6 | | | |
| 132 | 0.017 | >2400 | 71.0 | | | |
| 133 | 0.016 | >2400 | 62.2 | | | |
| 134 | 0.058 | >2400 | 100.7 | | | |
| 135 | 12.100 | >2400 | 440.6 | | | |
| 136 | >30 | >2400 | 402.8 | | | |

TABLE 9-continued

Biological Data for Compounds in Table 4

| | IC$_{50}$ (µM) in cell viability assay in HCC461 | Synergy with TRAIL in PANC-1 ng/ml IC$_{50}$ for TRAIL | IC$_{50}$ for TRAIL + 100 nm compound | IC$_{50}$ (µM) in cell viability assay in PANC-1 cells | | |
|---|---|---|---|---|---|---|
| | | | | Compound alone | Compound + 100 ng/ml TNFa (µM) | Compound + 300 ng/ml TRAIL (µM) |
| 137 | 6.970 | >2400 | 1436.0 | | | |
| 138 | >30 | >2400 | 186.4 | | | |
| 139 | 0.849 | >2400 | 530.4 | | | |
| 140 | 0.280 | >2400 | 141.4 | | | |
| 141 | 0.109 | >2400 | 97.4 | | | |
| 142 | >30 | >2400 | 2011.7 | | | |
| 143 | 0.027 | >2400 | 46.4 | | | |
| 144 | 0.043 | >2400 | 221.1 | | | |
| 145 | >30 | >2400 | 1888.9 | | | |
| 146 | >30 | >2400 | 744.7 | | | |
| 147 | 0.185 | >2400 | 145.0 | | | |
| 148 | 0.622 | >2400 | 304.8 | | | |
| 149 | 0.072 | >2400 | 235.8 | | | |
| 150 | 0.121 | >2400 | 150.5 | | | |
| 151 | 0.297 | >2400 | 1538.8 | | | |
| 152 | 0.447 | >2400 | 710.5 | | | |
| 153 | 27.6 | >2400 | >2400 | | | |
| 154 | 3.6 | >2400 | 187.2 | | | |
| 155 | 0.467 | >2400 | 1586.8 | | | |
| 156 | 0.083 | >2400 | 331.8 | | | |
| 157 | 0.030 | >2400 | 68.0 | | | |
| 158 | >30 | >2400 | >2400 | | | |
| 159 | 0.221 | >2400 | >2400 | | | |
| 160 | 29.4 | >2400 | >2400 | | | |
| 161 | 2.5 | >2400 | 236.9 | | | |
| 162 | >30 | >2400 | >2400 | | | |
| 163 | >30 | >2400 | >2400 | | | |
| 164 | >30 | >2400 | >2400 | | | |
| 165 | >30 | >2400 | >2400 | | | |
| 166 | | | | >1 | 0.994 | >1 |
| 167 | | | | >1 | 0.060 | 0.100 |
| 168 | | | | >1 | >1 | >1 |
| 169 | | | | >1 | 0.010 | 0.028 |
| 170 | | | | >1 | 0.015 | 0.015 |
| 171 | | | | >1 | 0.044 | 0.063 |
| 172 | | | | >1 | 0.025 | 0.028 |
| 173 | | | | >1 | 0.010 | 0.019 |
| 174 | | | | >1 | 0.0069 | 0.0107 |
| 175 | | | | >1 | 0.0163 | 0.0357 |
| 176 | | | | >1 | 0.0199 | 0.0388 |
| 177 | | | | >1 | 0.035 | 0.050 |
| 178 | | | | >1 | 0.054 | 0.089 |
| 179 | | | | >1 | 0.056 | 0.048 |
| 180 | | | | >1 | 0.124 | 0.201 |
| 181 | | | | >1 | 0.037 | 0.072 |
| 182 | | | | >1 | 0.043 | 0.080 |
| 183 | | | | >1 | 0.044 | 0.061 |
| 184 | | | | >1 | 0.027 | 0.076 |
| 185 | | | | >1 | 0.008 | 0.004 |
| 186 | | | | >1 | 0.5600 | 0.5500 |
| 187 | | | | >1 | 0.620 | 0.600 |
| 188 | | | | >1 | 0.56 | 0.55 |
| 189 | | | | >1 | >1 | >1 |
| 190 | | | | >1 | >1 | >1 |
| 191 | | | | >1 | 0.013 | 0.012 |
| 192 | | | | >1 | 0.659 | >1 |
| 193 | | | | >1 | >1 | >1 |
| 194 | | | | >1 | 0.057 | 0.060 |
| 195 | | | | >1 | >1 | >1 |
| 196 | | | | >1 | 0.577 | 0.622 |
| 197 | | | | >1 | 0.128 | 0.180 |
| 198 | | | | >1 | 0.109 | 0.069 |
| 199 | | | | >1 | 0.046 | 0.074 |
| 200 | | | | >1 | 0.046 | 0.084 |
| 201 | | | | >1 | 0.027 | 0.057 |
| 202 | | | | >1 | 0.679 | 0.674 |
| 203 | | | | >1 | 0.683 | 0.616 |
| 204 | | | | >1 | 0.392 | 0.564 |
| 205 | | | | >1 | 0.040 | 0.059 |

TABLE 10
Biological Data for Compounds in Table 5
| | IC$_{50}$ (μM) in cell viability assay in PANC-1 cells | | |
|---|---|---|---|
| Cpd. No. | Compound alone | Compound + 100 ng/ml TNFa (μM) | Compound + 300 ng/ml TRAIL (μM) |
| 206 | >1 | 0.0006 | 0.0006 |
| 207 | >1 | 0.263 | 0.398 |
| 208 | >1 | 0.614 | >1 |
| 209 | | 0.0007 | 0.0007 |
| 210 | 0.0170 | 0.0330 | 0.108 |
| 211 | 0.001 | 0.0009 | 0.024 |
| 212 | 0.0006 | 0.0006 | 0.022 |
| 213 | 0.005 | 0.004 | 0.137 |
TABLE 11
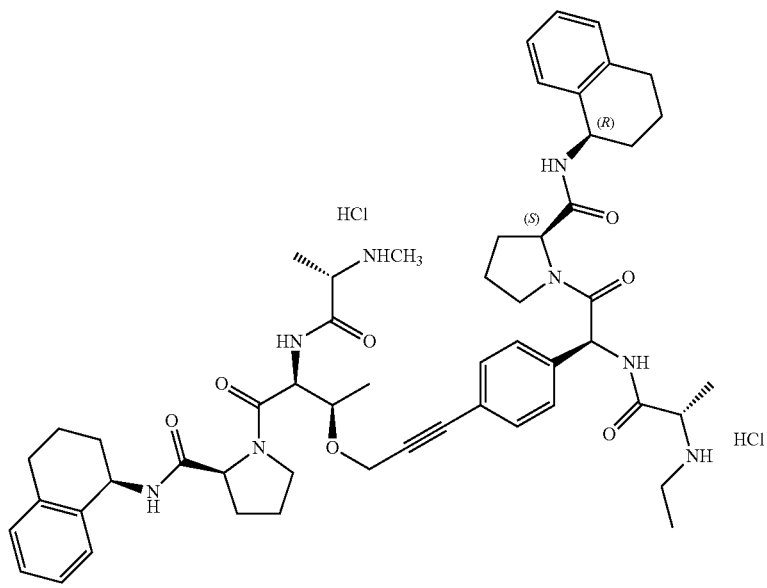
H1
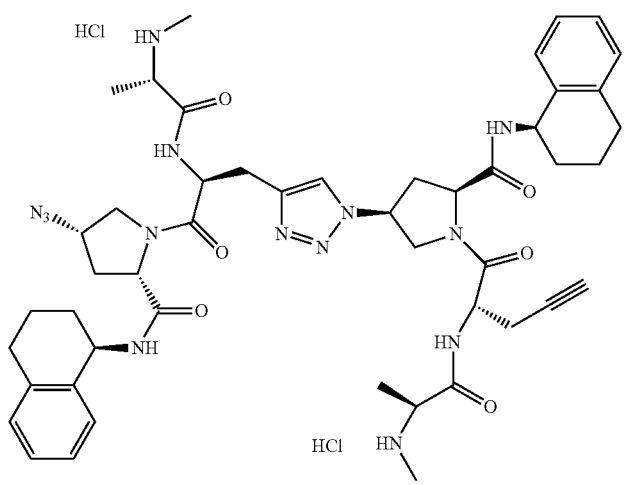 [SMILES: C#CC[C@H](NC(=O)[C@H](C)NC)C(=O)N1C[C@@H](n2cc(C[C@H](NC(=O)[C@H](C)NC)C(=O)N3C[C@@H](N=[N+]=[N-])C[C@H]3C(=O)N[C@@H]3CCCc4ccccc43)nn2)C[C@H]1C(=O)N[C@@H]1CCCc2ccccc21 ; Cl ; Cl]
H2

TABLE 11-continued
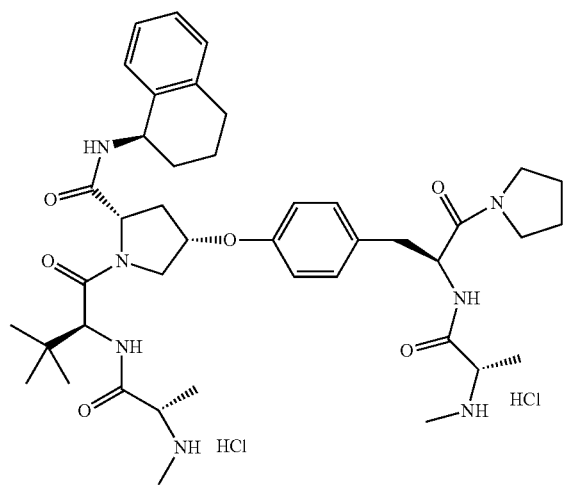 [SMILES: CN[C@@H](C)C(=O)N[C@@H](Cc1ccc(O[C@H]2C[C@@H](C(=O)N[C@@H]3CCCc4ccccc43)N(C(=O)[C@@H](NC(=O)[C@H](C)NC)C(C)(C)C)C2)cc1)C(=O)N1CCCC1 ; Cl ; Cl]
H3
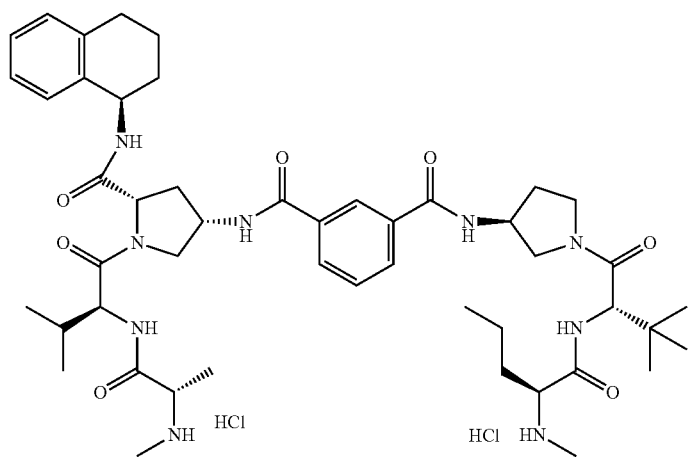 [SMILES: CCC[C@H](NC)C(=O)N[C@H](C(=O)N1CC[C@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)C)C3)c2)C1)C(C)(C)C ; Cl ; Cl]
H4
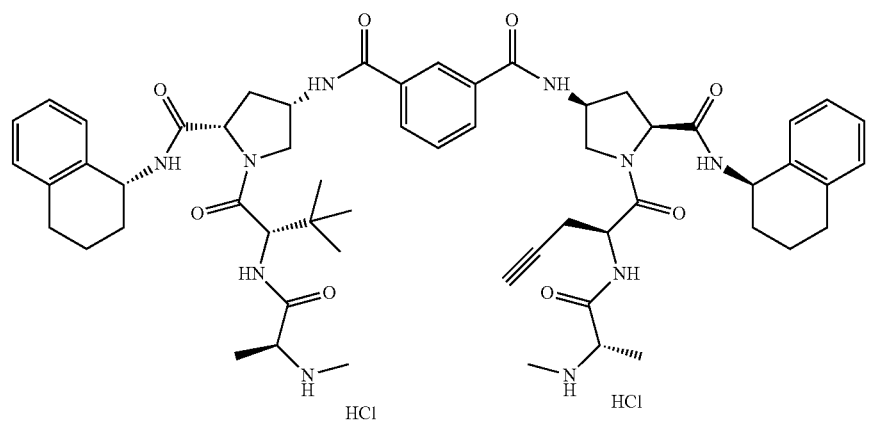 [SMILES: C#CC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21 ; Cl ; Cl]
H5

TABLE 11-continued
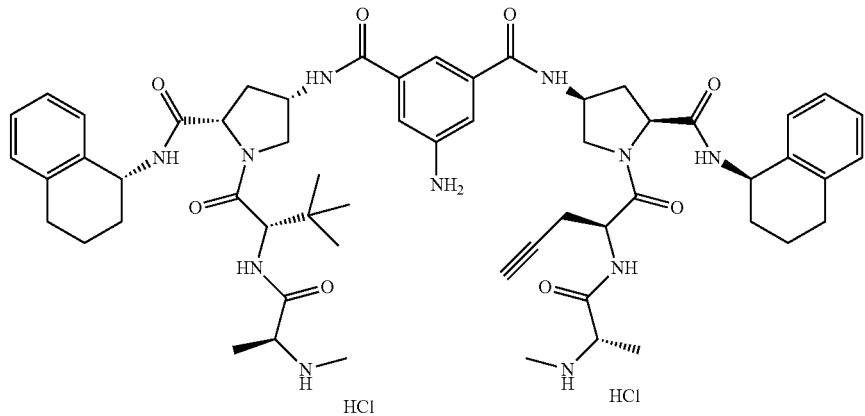 [SMILES: C#CC[C@H](NC(=O)[C@H](C)NC)C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21 ; Cl ; Cl]
H6
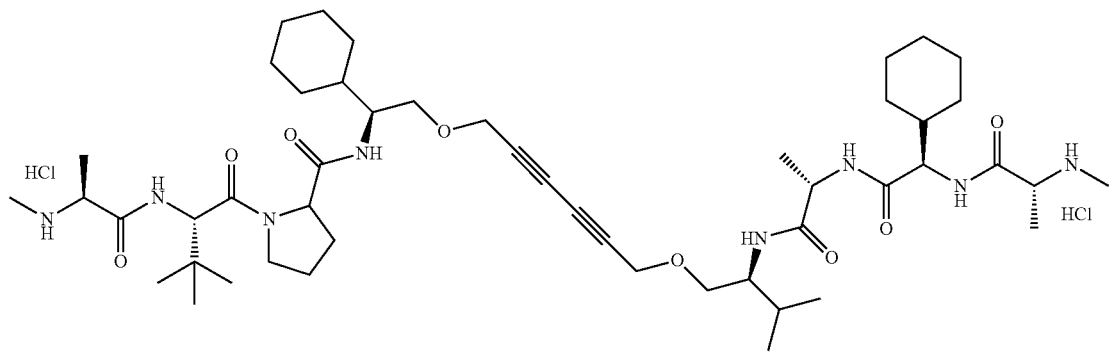
H7
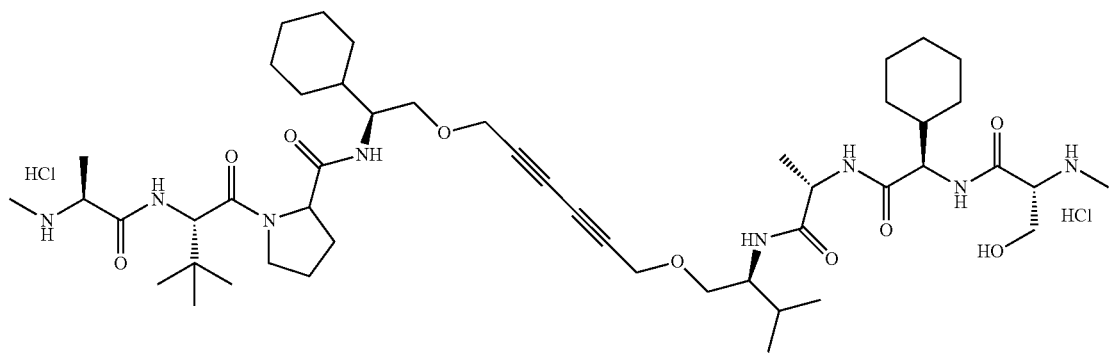
H8
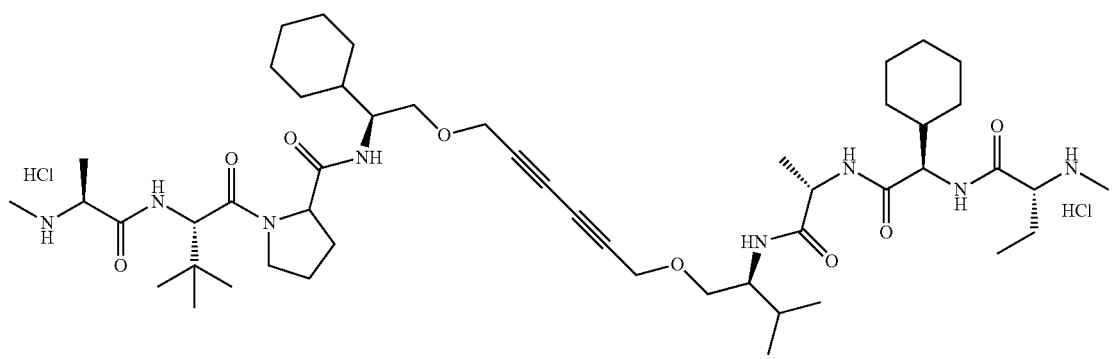
H9

TABLE 11-continued
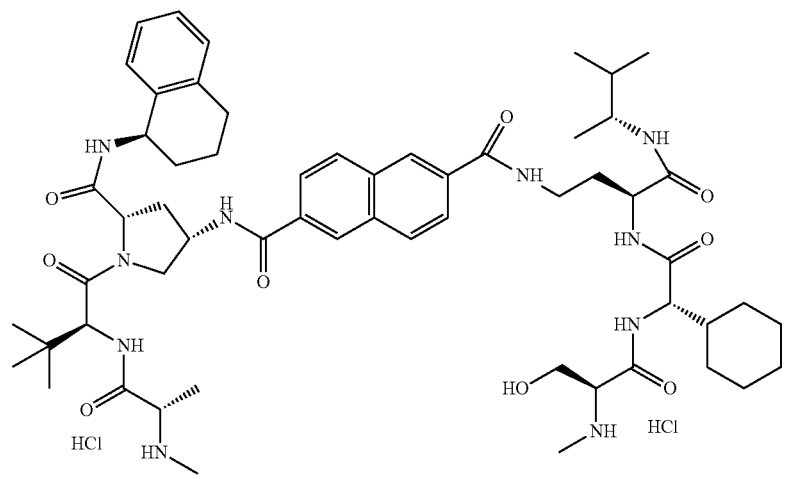 [SMILES: CN[C@@H](C)C(=O)N[C@H](C(=O)N1C[C@@H](NC(=O)c2ccc3cc(C(=O)NCC[C@H](NC(=O)[C@@H](NC(=O)[C@H](CO)NC)C4CCCCC4)C(=O)N[C@H](C)C(C)C)ccc3c2)C[C@H]1C(=O)N[C@@H]1CCCc2ccccc21)C(C)(C)C ; Cl ; Cl]
H10
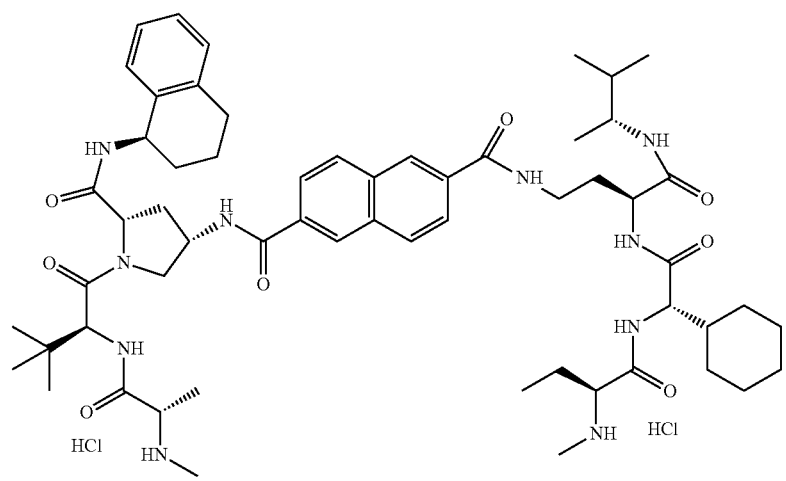 [SMILES: CC[C@H](NC)C(=O)N[C@H](C(=O)N[C@@H](CCNC(=O)c1ccc2cc(C(=O)N[C@H]3C[C@@H](C(=O)N[C@@H]4CCCc5ccccc54)N(C(=O)[C@@H](NC(=O)[C@H](C)NC)C(C)(C)C)C3)ccc2c1)C(=O)N[C@H](C)C(C)C)C1CCCCC1 ; Cl ; Cl]
H11
TABLE 12
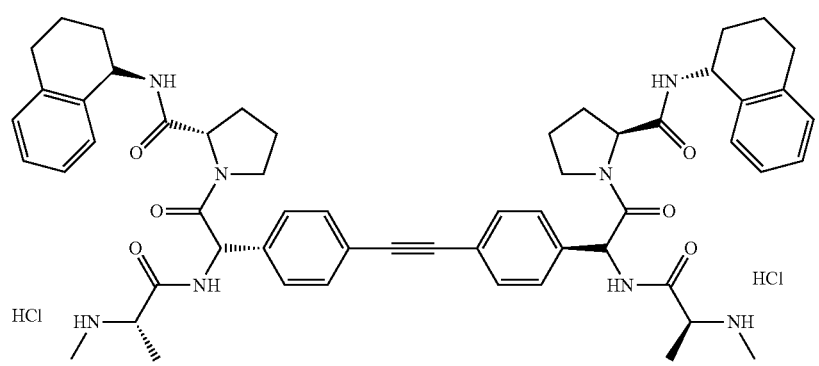
P2-1

TABLE 12-continued
P2-2
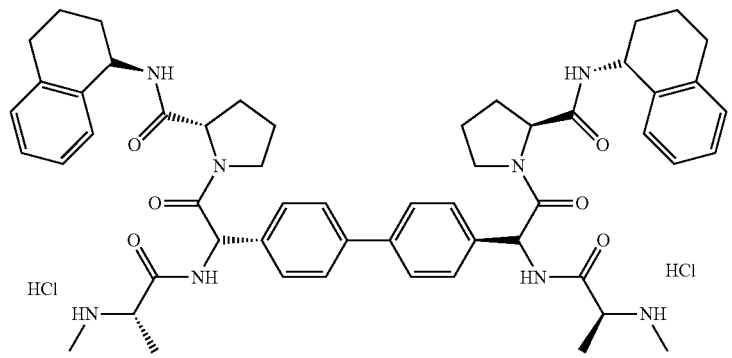
P2-3
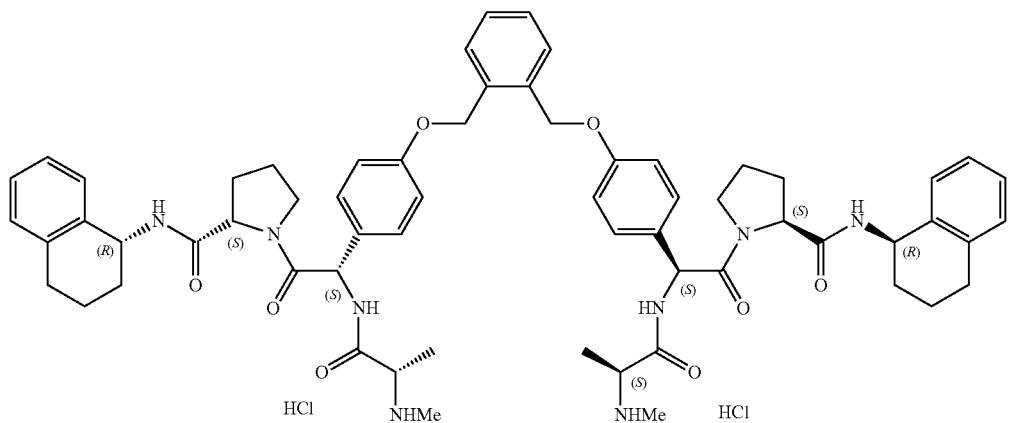
P2-4
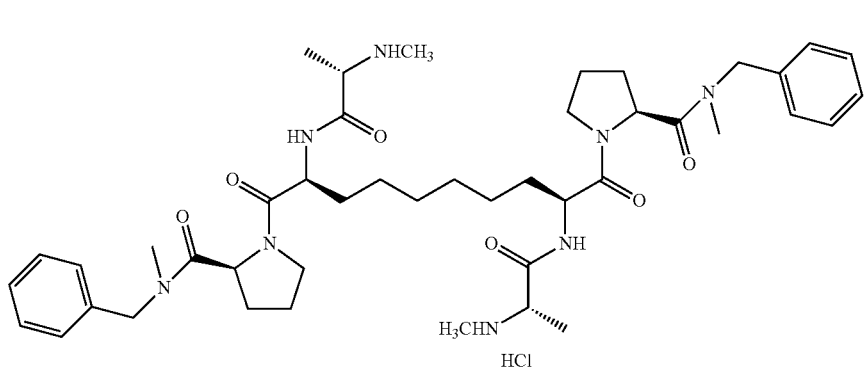
P2-5
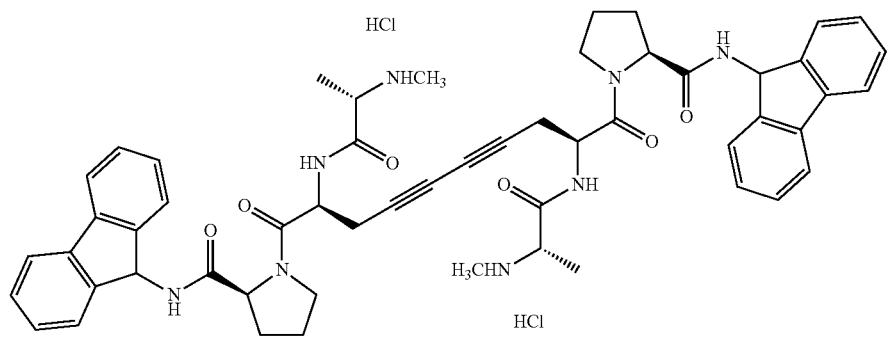

TABLE 12-continued
P2-6
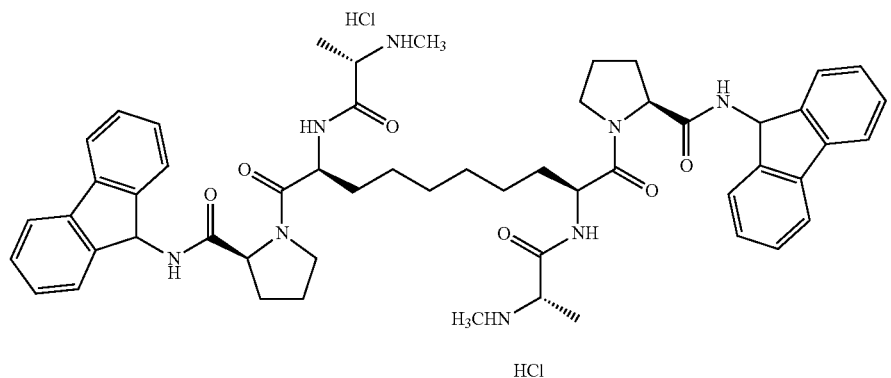
P2-7
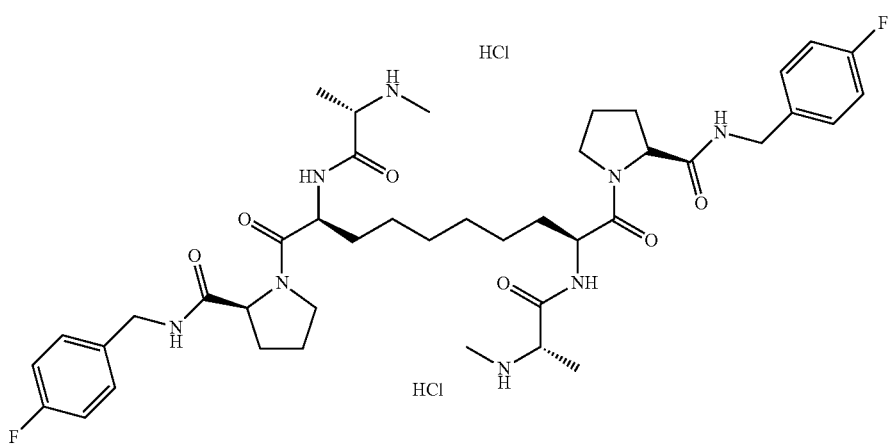
P2-8
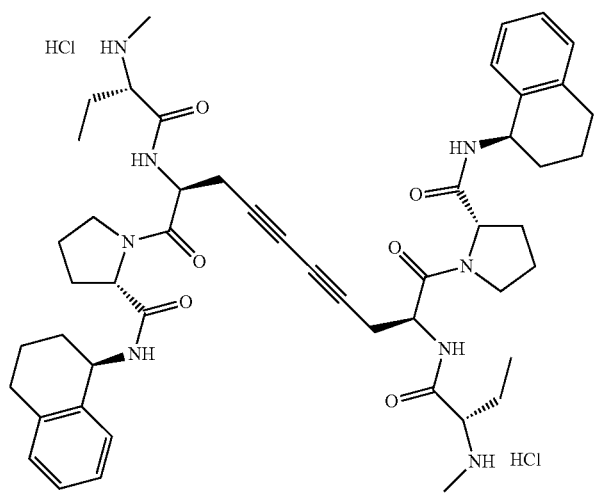 [SMILES: CC[C@H](NC)C(=O)N[C@@H](CC#CC#CC[C@H](NC(=O)[C@H](CC)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]

TABLE 12-continued
P2-9
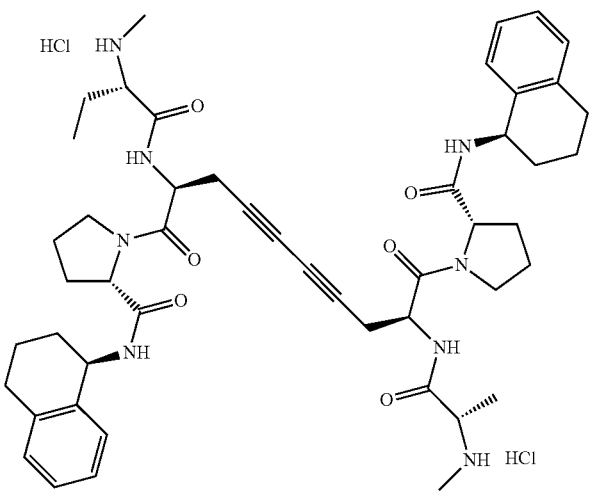 [SMILES: CC[C@H](NC)C(=O)N[C@@H](CC#CC#CC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-10
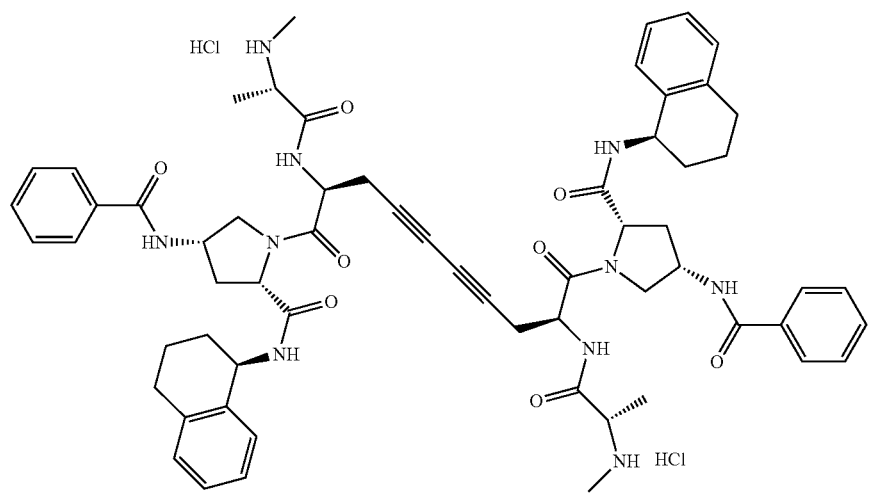 [SMILES: CN[C@@H](C)C(=O)N[C@@H](CC#CC#CC[C@H](NC(=O)[C@H](C)NC)C(=O)N1C[C@@H](NC(=O)c2ccccc2)C[C@H]1C(=O)N[C@@H]1CCCc2ccccc21)C(=O)N1C[C@@H](NC(=O)c2ccccc2)C[C@H]1C(=O)N[C@@H]1CCCc2ccccc21 ; Cl ; Cl]
P2-11
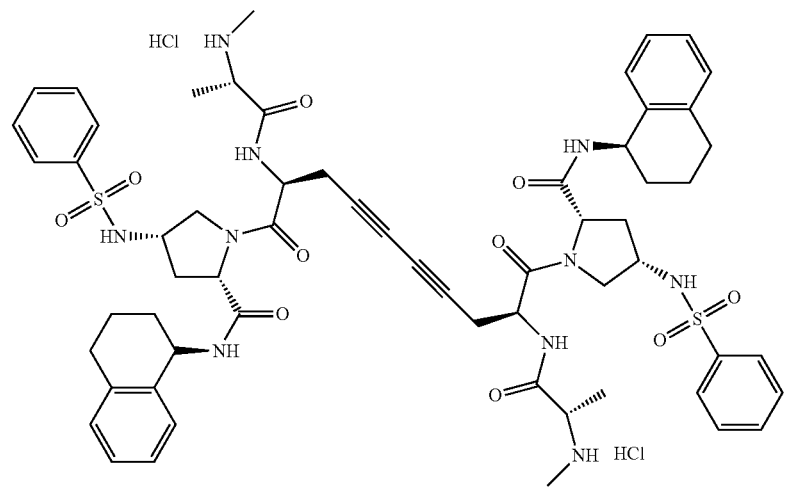

TABLE 12-continued
P2-12
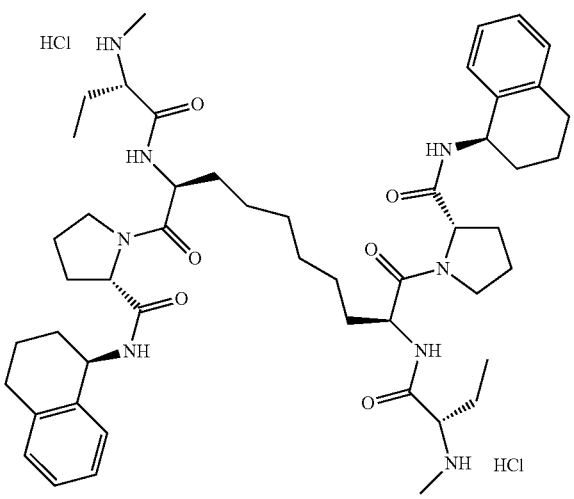 [SMILES: CC[C@H](NC)C(=O)N[C@@H](CCCCCC[C@H](NC(=O)[C@H](CC)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-13
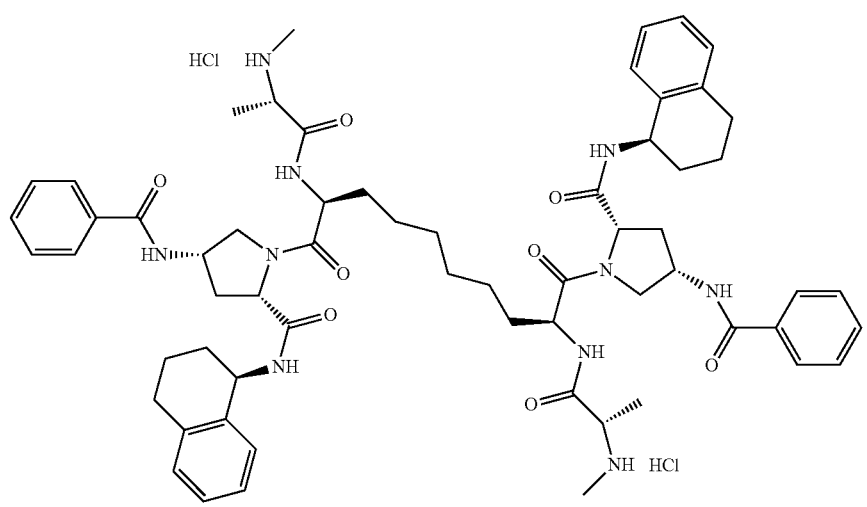 [SMILES: CN[C@@H](C)C(=O)N[C@@H](CCCCCC[C@H](NC(=O)[C@H](C)NC)C(=O)N1C[C@@H](NC(=O)c2ccccc2)C[C@H]1C(=O)N[C@@H]1CCCc2ccccc21)C(=O)N1C[C@@H](NC(=O)c2ccccc2)C[C@H]1C(=O)N[C@@H]1CCCc2ccccc21 ; Cl ; Cl]
P2-14
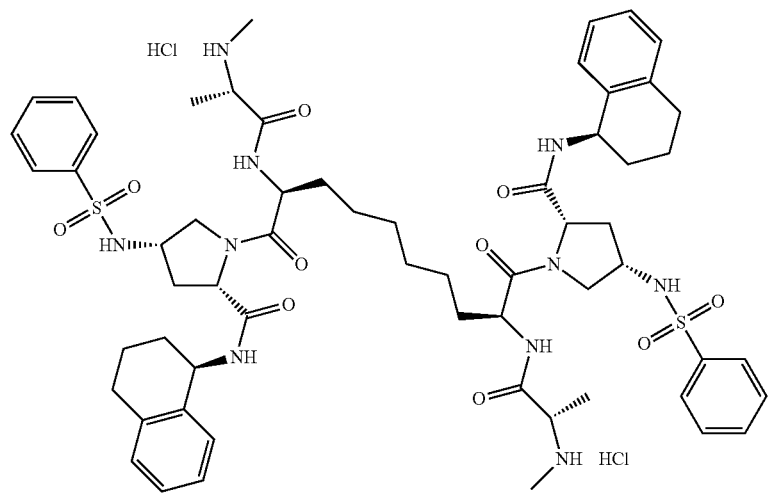 [SMILES: CN[C@@H](C)C(=O)N[C@@H](CCCCCC[C@H](NC(=O)[C@H](C)NC)C(=O)N1C[C@@H](NS(=O)(=O)c2ccccc2)C[C@H]1C(=O)N[C@@H]1CCCc2ccccc21)C(=O)N1C[C@@H](NS(=O)(=O)c2ccccc2)C[C@H]1C(=O)N[C@@H]1CCCc2ccccc21 ; Cl ; Cl]

TABLE 12-continued
P2-15
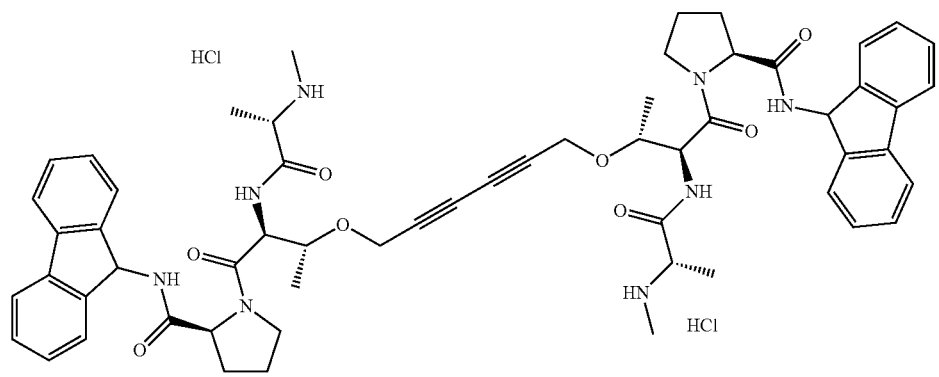 [SMILES: CN[C@@H](C)C(=O)N[C@H](C(=O)N1CCC[C@H]1C(=O)NC1c2ccccc2-c2ccccc21)[C@@H](C)OCC#CC#CCO[C@H](C)[C@H](NC(=O)[C@H](C)NC)C(=O)N1CCC[C@H]1C(=O)NC1c2ccccc2-c2ccccc21 ; Cl ; Cl]
P2-16
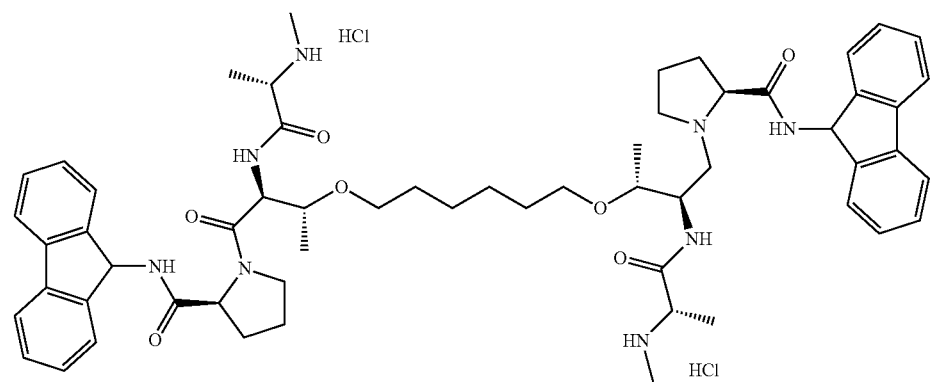 [SMILES: CN[C@@H](C)C(=O)N[C@H](C(=O)N1CCC[C@H]1C(=O)NC1c2ccccc2-c2ccccc21)[C@@H](C)OCCCCCCO[C@H](C)[C@@H](CN1CCC[C@H]1C(=O)NC1c2ccccc2-c2ccccc21)NC(=O)[C@H](C)NC ; Cl ; Cl]
P2-17
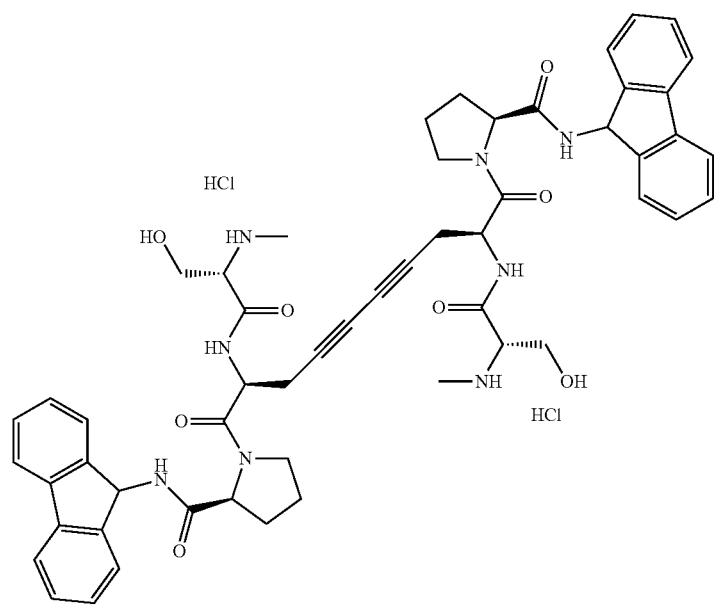 [SMILES: CN[C@@H](CO)C(=O)N[C@@H](CC#CC#CC[C@H](NC(=O)[C@H](CO)NC)C(=O)N1CCC[C@H]1C(=O)NC1c2ccccc2-c2ccccc21)C(=O)N1CCC[C@H]1C(=O)NC1c2ccccc2-c2ccccc21 ; Cl ; Cl]

TABLE 12-continued
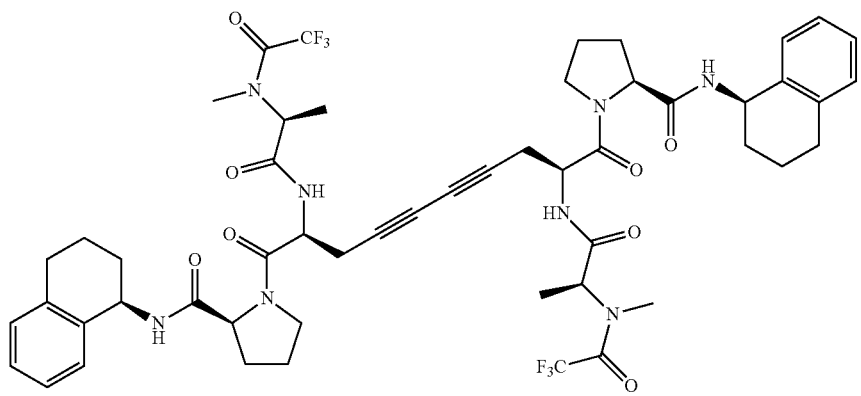 [SMILES: C[C@@H](C(=O)N[C@@H](CC#CC#CC[C@H](NC(=O)[C@H](C)N(C)C(=O)C(F)(F)F)C(=O)N1CCC[C@H]1C(=O)N[C@@H]1CCCc2ccccc21)C(=O)N1CCC[C@H]1C(=O)N[C@@H]1CCCc2ccccc21)N(C)C(=O)C(F)(F)F]
P2-18
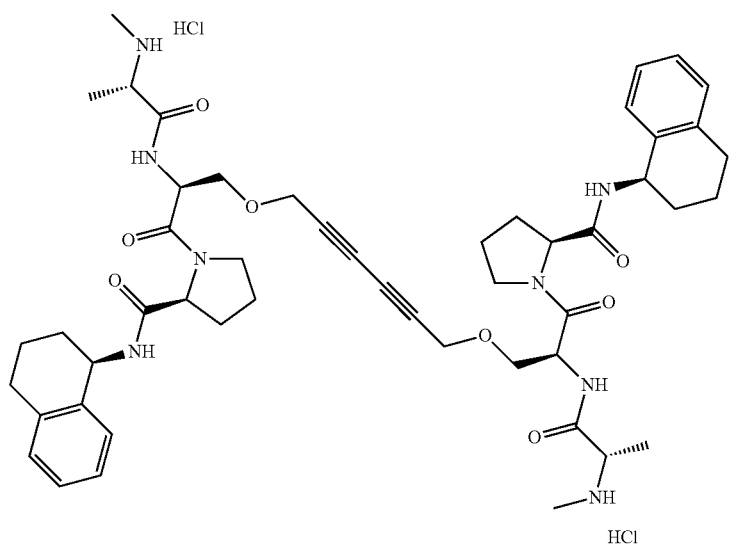 [SMILES: CN[C@@H](C)C(=O)N[C@@H](COCC#CC#CCOC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-19
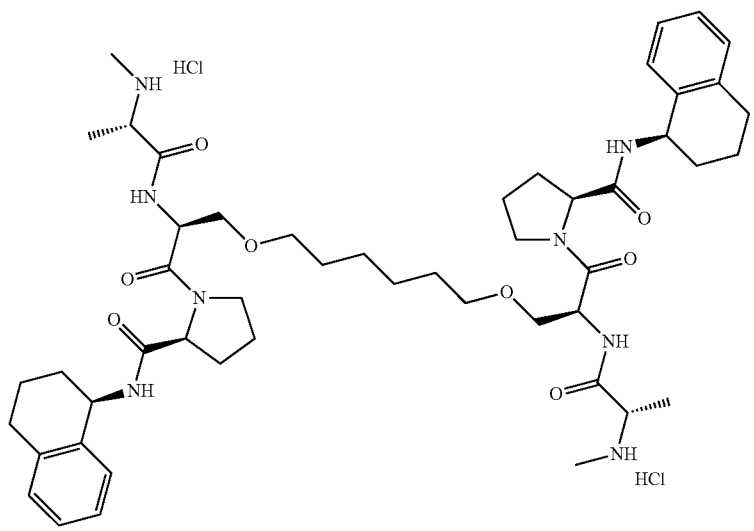 [SMILES: CN[C@@H](C)C(=O)N[C@@H](COCCCCCCOC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-20

TABLE 12-continued
P2-21
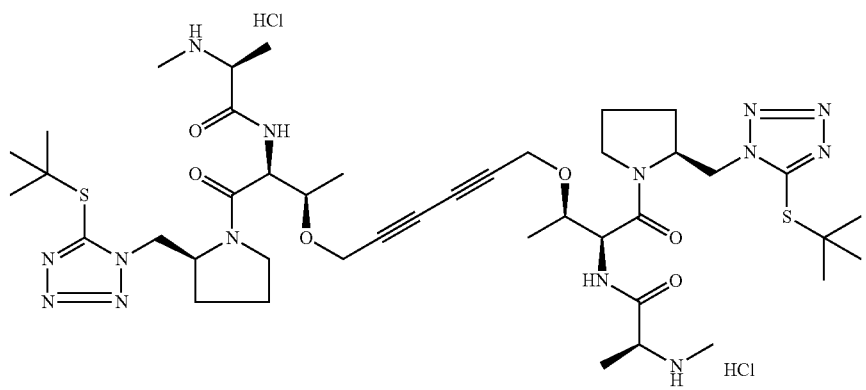 [SMILES: Cl ; CN[C@@H](C)C(=O)N[C@H](C(=O)N1CCC[C@H]1Cn1nnnc1SC(C)(C)C)[C@@H](C)OCC#CC#CCO[C@H](C)[C@H](NC(=O)[C@H](C)NC)C(=O)N1CCC[C@H]1Cn1nnnc1SC(C)(C)C ; Cl]
P2-22
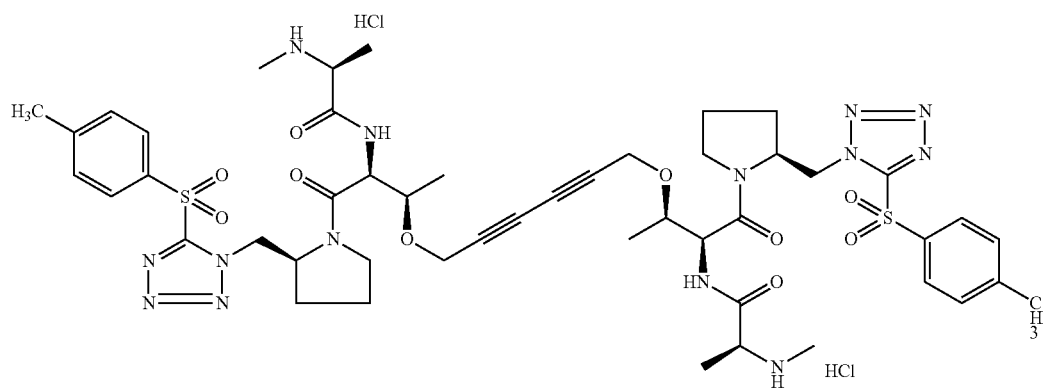
P2-23
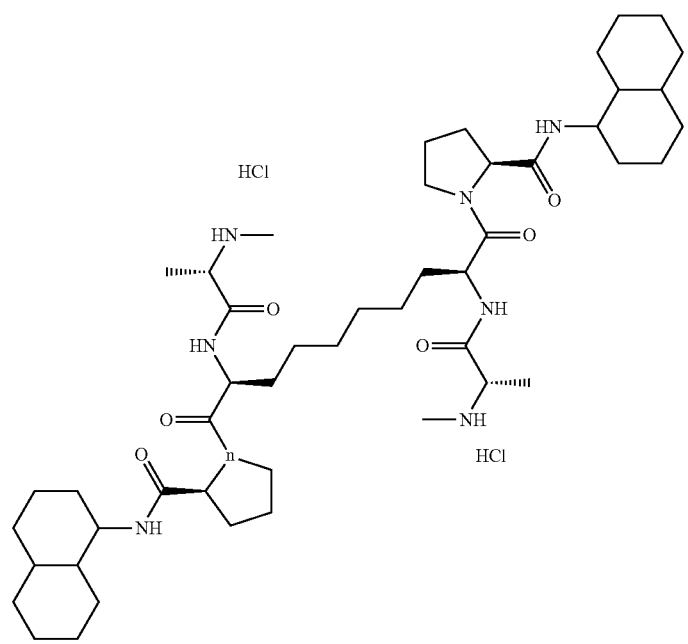

TABLE 12-continued
P2-24
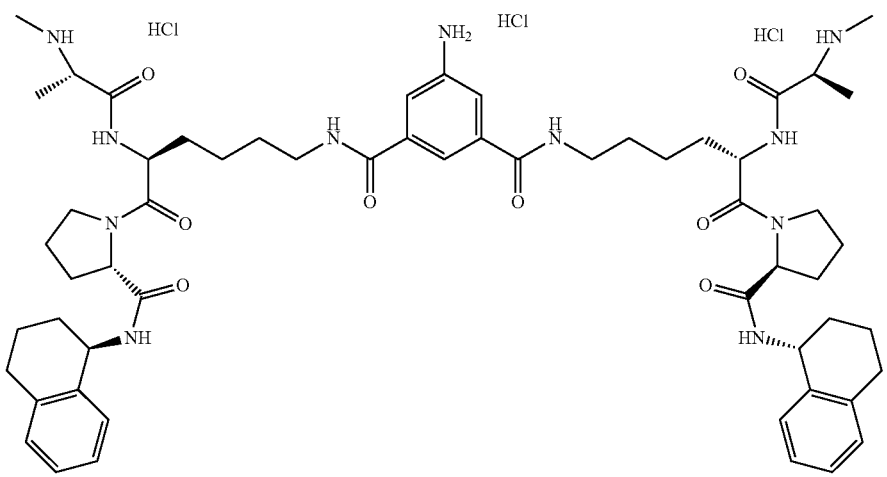 [SMILES: CN[C@@H](C)C(=O)N[C@@H](CCCCNC(=O)c1cc(N)cc(C(=O)NCCCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21 ; Cl ; Cl ; Cl]
P2-25
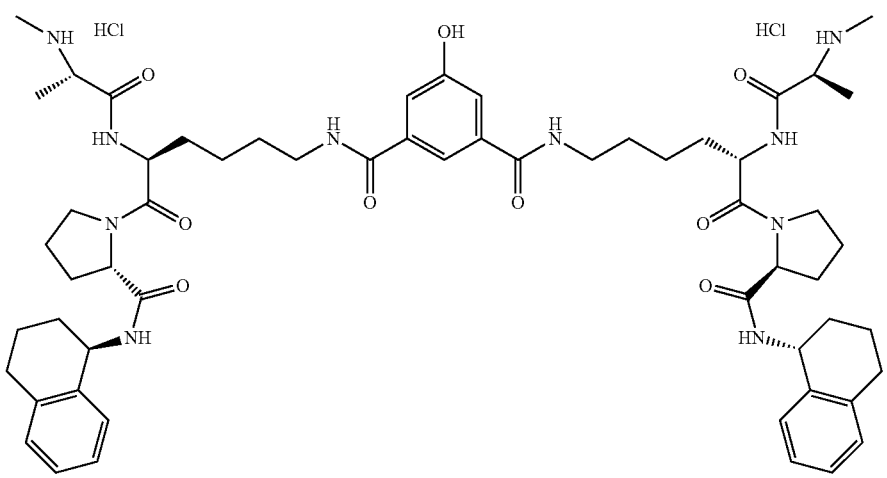 [SMILES: CN[C@@H](C)C(=O)N[C@@H](CCCCNC(=O)c1cc(O)cc(C(=O)NCCCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21 ; Cl ; Cl]
P2-26
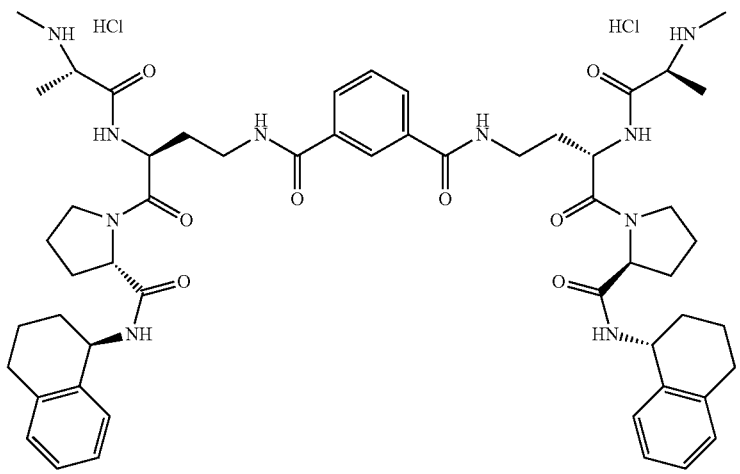 [SMILES: CN[C@@H](C)C(=O)N[C@@H](CCNC(=O)c1cccc(C(=O)NCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21 ; Cl ; Cl]

TABLE 12-continued
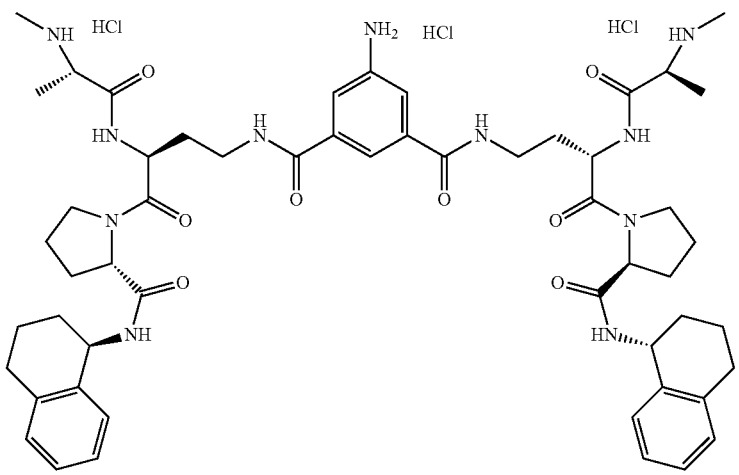 [SMILES: CN[C@@H](C)C(=O)N[C@@H](CCNC(=O)c1cc(N)cc(C(=O)NCC[C@H](NC(=O)[C@H](C)NC)C(=O)N2CCC[C@H]2C(=O)N[C@@H]2CCCc3ccccc32)c1)C(=O)N1CCC[C@H]1C(=O)N[C@@H]1CCCc2ccccc21 ; Cl ; Cl ; Cl]
P2-27
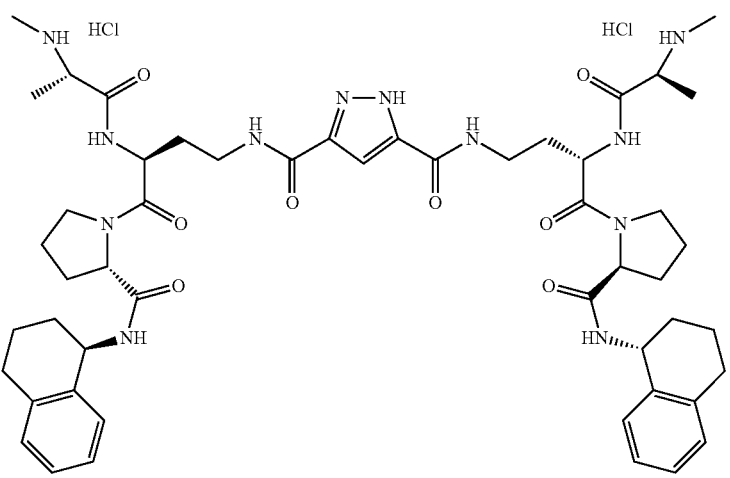 [SMILES: CN[C@@H](C)C(=O)N[C@@H](CCNC(=O)c1cc(C(=O)NCC[C@H](NC(=O)[C@H](C)NC)C(=O)N2CCC[C@H]2C(=O)N[C@@H]2CCCc3ccccc32)[nH]n1)C(=O)N1CCC[C@H]1C(=O)N[C@@H]1CCCc2ccccc21 ; Cl ; Cl]
P2-28
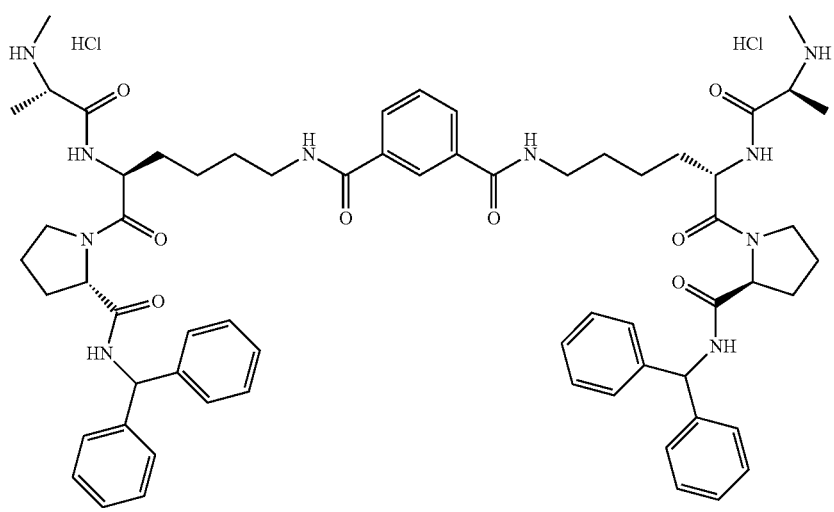 [SMILES: CN[C@@H](C)C(=O)N[C@@H](CCCCNC(=O)c1cccc(C(=O)NCCCC[C@H](NC(=O)[C@H](C)NC)C(=O)N2CCC[C@H]2C(=O)NC(c2ccccc2)c2ccccc2)c1)C(=O)N1CCC[C@H]1C(=O)NC(c1ccccc1)c1ccccc1 ; Cl ; Cl]
P2-29

TABLE 12-continued
P2-30
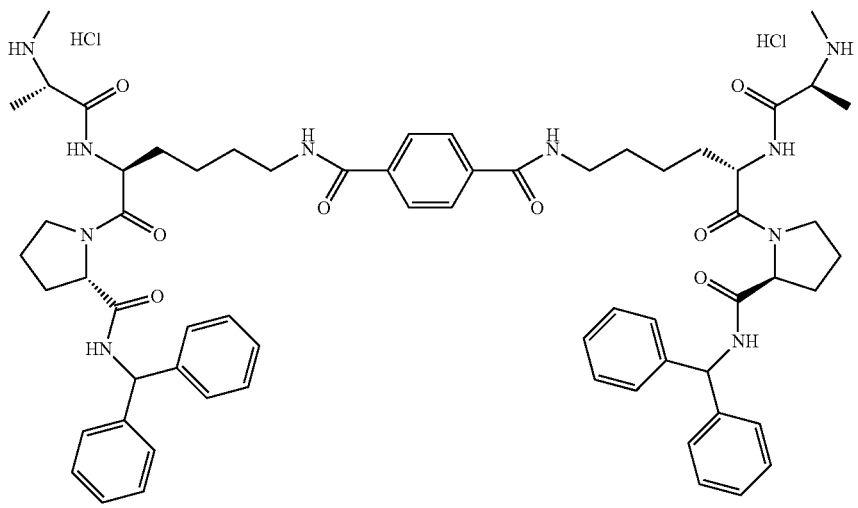 [SMILES: CN[C@@H](C)C(=O)N[C@@H](CCCCNC(=O)c1ccc(C(=O)NCCCC[C@H](NC(=O)[C@H](C)NC)C(=O)N2CCC[C@H]2C(=O)NC(c2ccccc2)c2ccccc2)cc1)C(=O)N1CCC[C@H]1C(=O)NC(c1ccccc1)c1ccccc1 ; Cl ; Cl]
P2-31
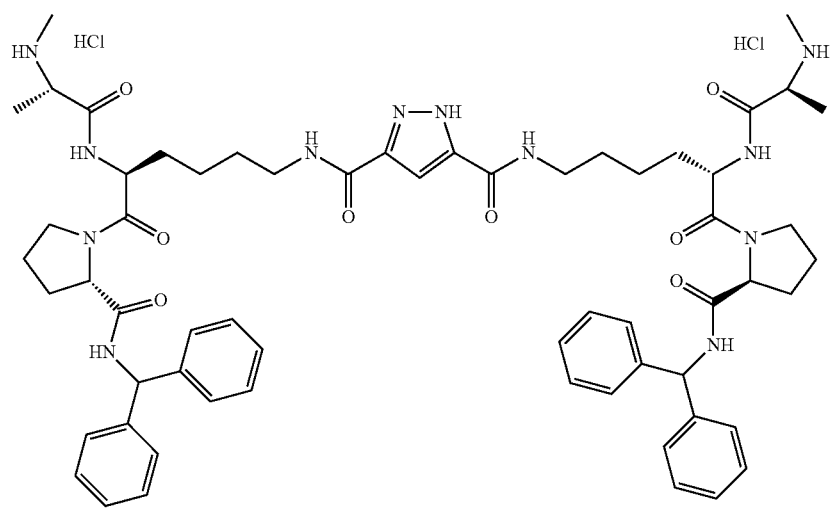 [SMILES: CN[C@@H](C)C(=O)N[C@@H](CCCCNC(=O)c1cc(C(=O)NCCCC[C@H](NC(=O)[C@H](C)NC)C(=O)N2CCC[C@H]2C(=O)NC(c2ccccc2)c2ccccc2)[nH]n1)C(=O)N1CCC[C@H]1C(=O)NC(c1ccccc1)c1ccccc1 ; Cl ; Cl]
P2-32
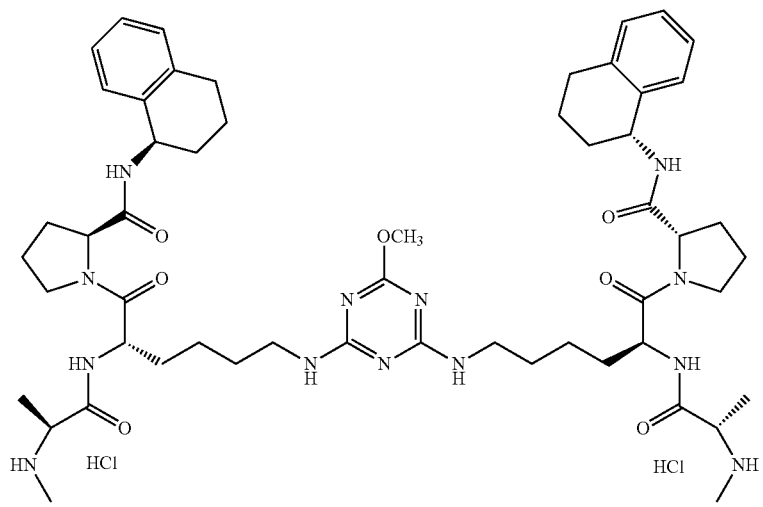 [SMILES: CN[C@@H](C)C(=O)N[C@@H](CCCCNc1nc(NCCCC[C@H](NC(=O)[C@H](C)NC)C(=O)N2CCC[C@H]2C(=O)N[C@@H]2CCCc3ccccc32)nc(OC)n1)C(=O)N1CCC[C@H]1C(=O)N[C@@H]1CCCc2ccccc21 ; Cl ; Cl]

TABLE 12-continued
P2-33
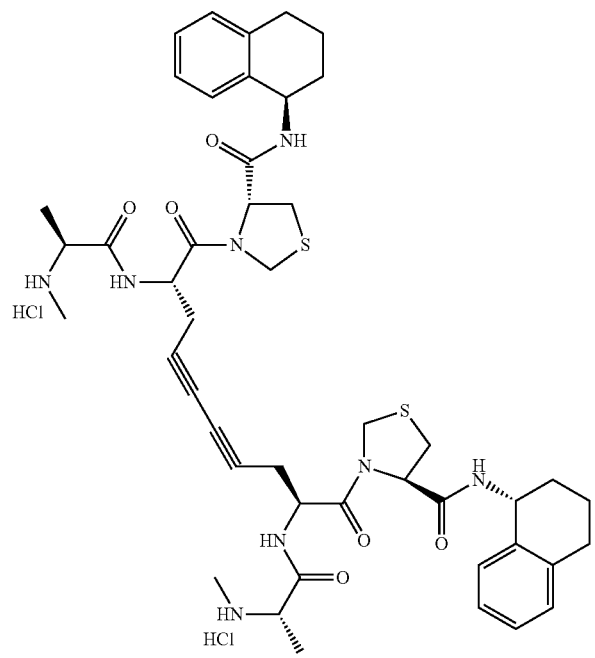 [SMILES: Cl ; CN[C@@H](C)C(=O)N[C@@H](CC#CC#CC[C@H](NC(=O)[C@H](C)NC)C(=O)N1CSC[C@H]1C(=O)N[C@@H]1CCCc2ccccc21)C(=O)N1CSC[C@H]1C(=O)N[C@@H]1CCCc2ccccc21 ; Cl]
P2-34
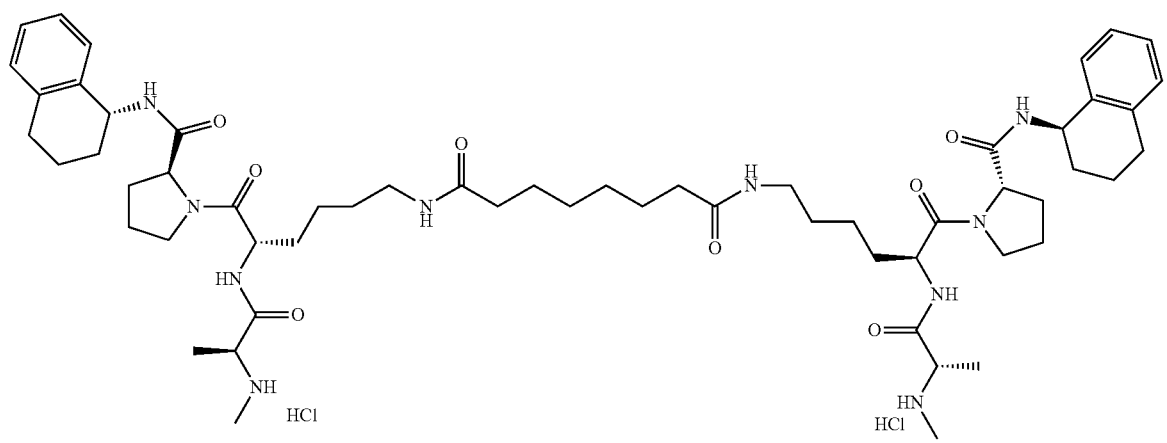 [SMILES: CN[C@@H](C)C(=O)N[C@@H](CCCCNC(=O)CCCCCCC(=O)NCCCC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-35
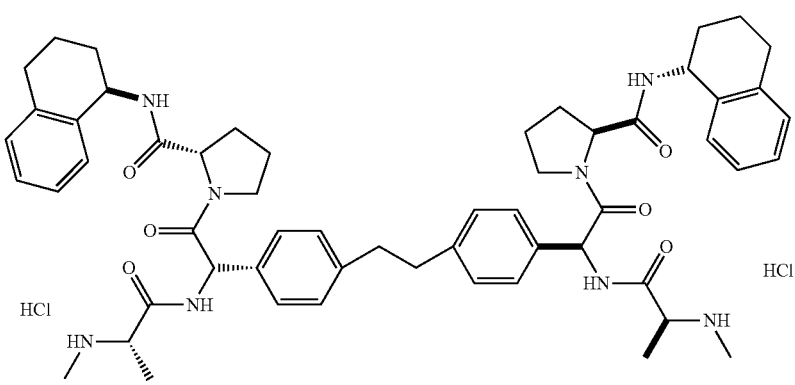

TABLE 12-continued
P2-36
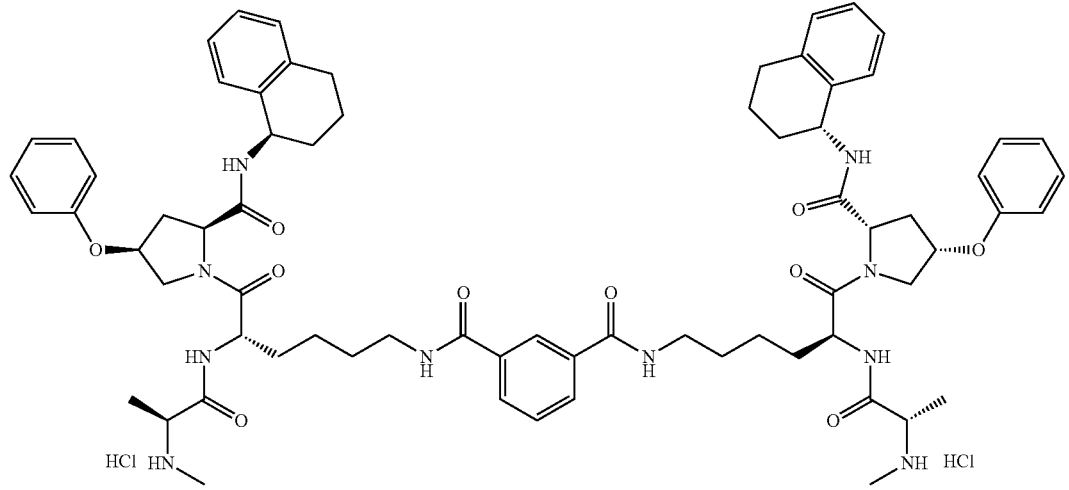 [SMILES: CN[C@@H](C)C(=O)N[C@@H](CCCCNC(=O)c1cccc(C(=O)NCCCC[C@H](NC(=O)[C@H](C)NC)C(=O)N2C[C@@H](Oc3ccccc3)C[C@H]2C(=O)N[C@@H]2CCCc3ccccc32)c1)C(=O)N1C[C@@H](Oc2ccccc2)C[C@H]1C(=O)N[C@@H]1CCCc2ccccc21 ; Cl ; Cl]
P2-37
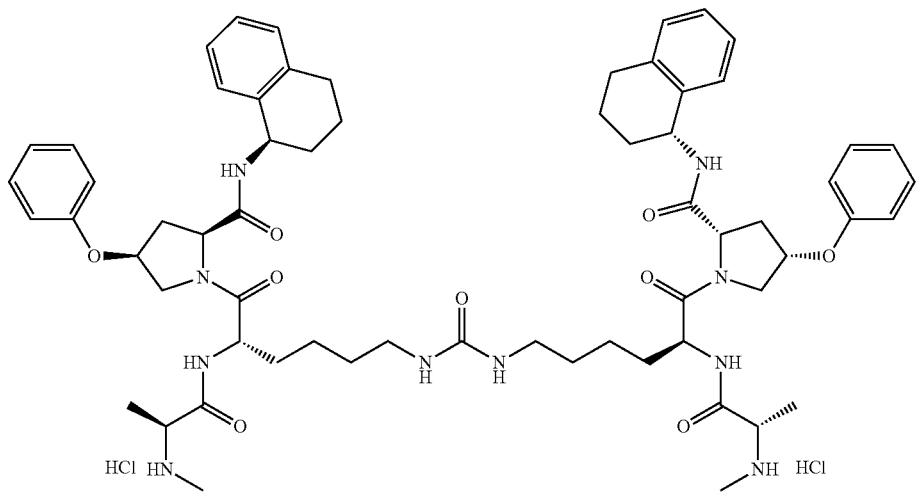 [SMILES: CN[C@@H](C)C(=O)N[C@@H](CCCCNC(=O)NCCCC[C@H](NC(=O)[C@H](C)NC)C(=O)N1C[C@@H](Oc2ccccc2)C[C@H]1C(=O)N[C@@H]1CCCc2ccccc21)C(=O)N1C[C@@H](Oc2ccccc2)C[C@H]1C(=O)N[C@@H]1CCCc2ccccc21 ; Cl ; Cl]
P2-38
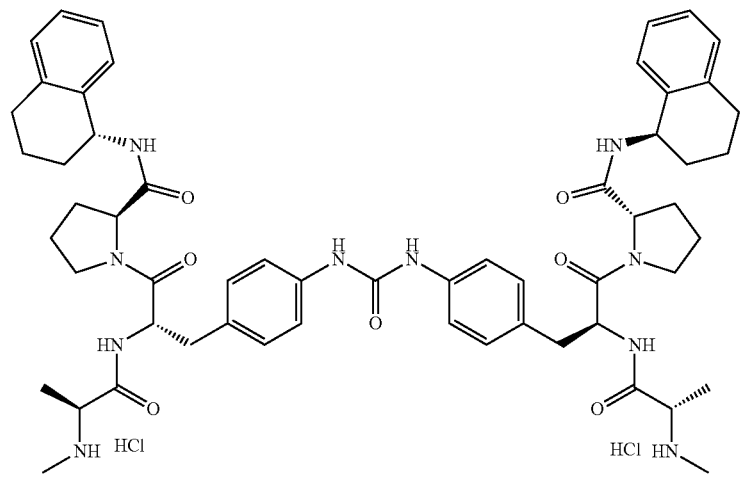 [SMILES: CN[C@@H](C)C(=O)N[C@@H](Cc1ccc(NC(=O)Nc2ccc(C[C@H](NC(=O)[C@H](C)NC)C(=O)N3CCC[C@H]3C(=O)N[C@@H]3CCCc4ccccc43)cc2)cc1)C(=O)N1CCC[C@H]1C(=O)N[C@@H]1CCCc2ccccc21 ; Cl ; Cl]

TABLE 12-continued
P2-39
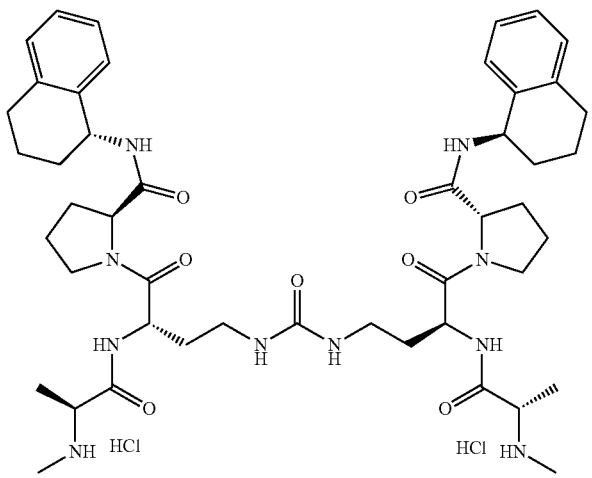 [SMILES: CN[C@@H](C)C(=O)N[C@@H](CCNC(=O)NCC[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-40
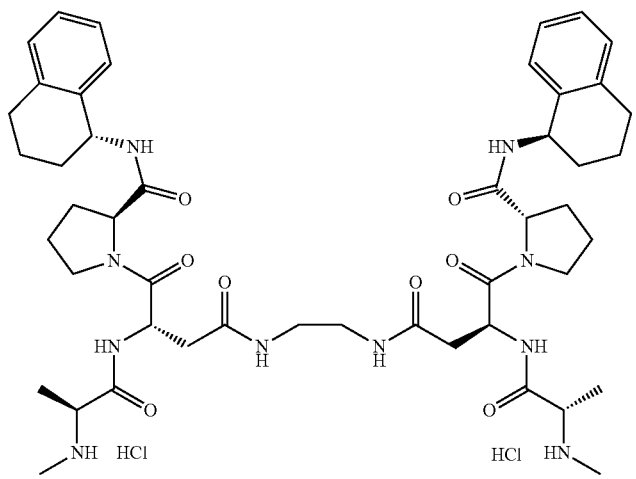 [SMILES: CN[C@@H](C)C(=O)N[C@@H](CC(=O)NCCNC(=O)C[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-41
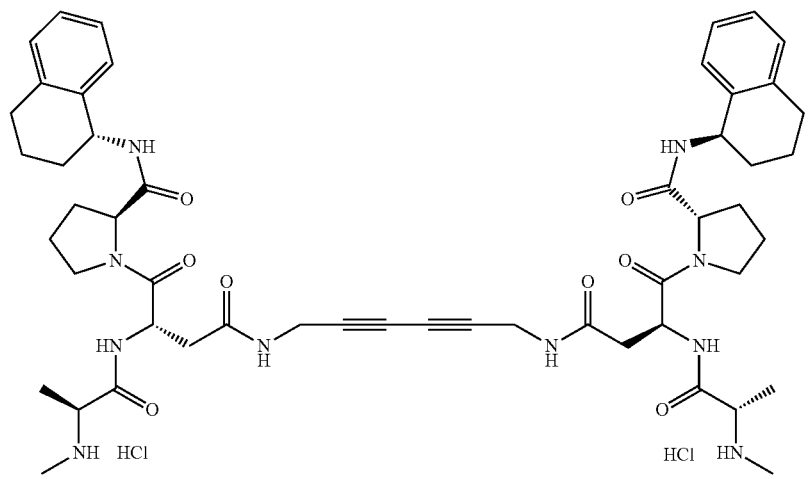 [SMILES: CN[C@@H](C)C(=O)N[C@@H](CC(=O)NCC#CC#CCNC(=O)C[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]

TABLE 12-continued
P2-42
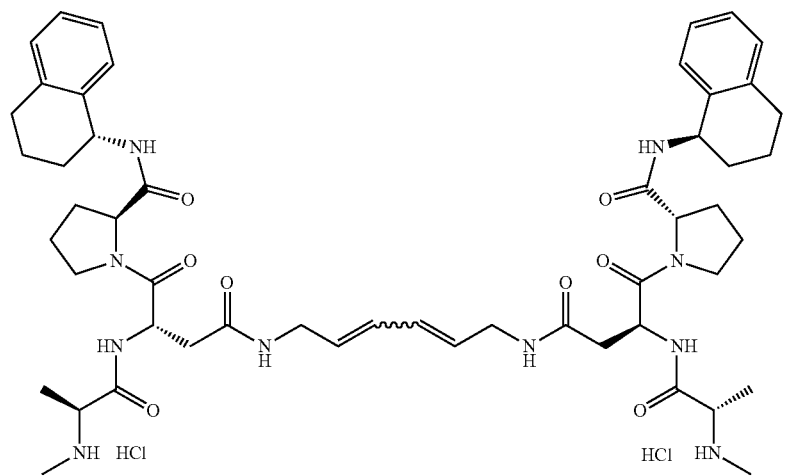 [SMILES: CN[C@@H](C)C(=O)N[C@@H](CC(=O)NCC=CC=CCNC(=O)C[C@H](NC(=O)[C@H](C)NC)C(=O)N1CCC[C@H]1C(=O)N[C@@H]1CCCc2ccccc21)C(=O)N1CCC[C@H]1C(=O)N[C@@H]1CCCc2ccccc21 ; Cl ; Cl]
P2-43
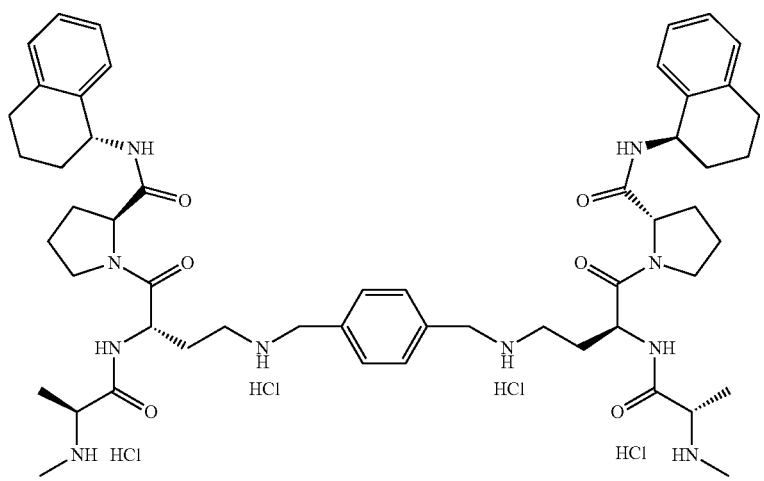 [SMILES: CN[C@@H](C)C(=O)N[C@@H](CCNCc1ccc(CNCC[C@H](NC(=O)[C@H](C)NC)C(=O)N2CCC[C@H]2C(=O)N[C@@H]2CCCc3ccccc32)cc1)C(=O)N1CCC[C@H]1C(=O)N[C@@H]1CCCc2ccccc21 ; Cl ; Cl ; Cl ; Cl]
P2-44
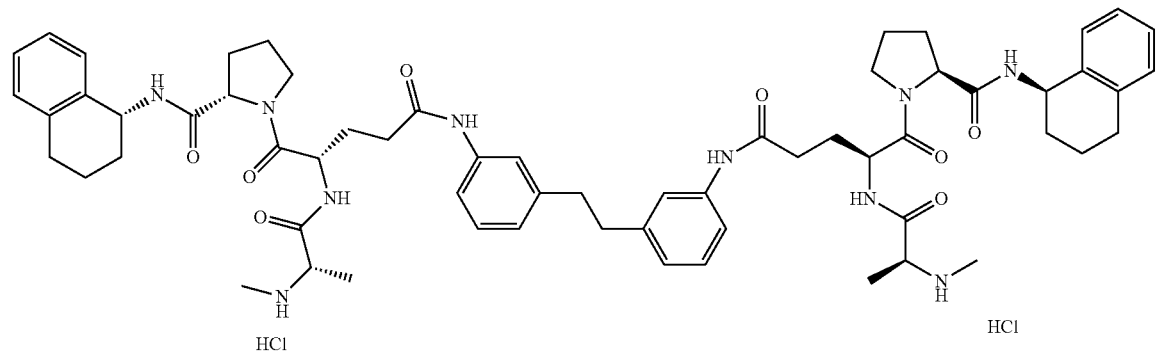 [SMILES: CN[C@@H](C)C(=O)N[C@@H](CCC(=O)Nc1cccc(CCc2cccc(NC(=O)CC[C@H](NC(=O)[C@H](C)NC)C(=O)N3CCC[C@H]3C(=O)N[C@@H]3CCCc4ccccc43)c2)c1)C(=O)N1CCC[C@H]1C(=O)N[C@@H]1CCCc2ccccc21 ; Cl ; Cl]

TABLE 12-continued
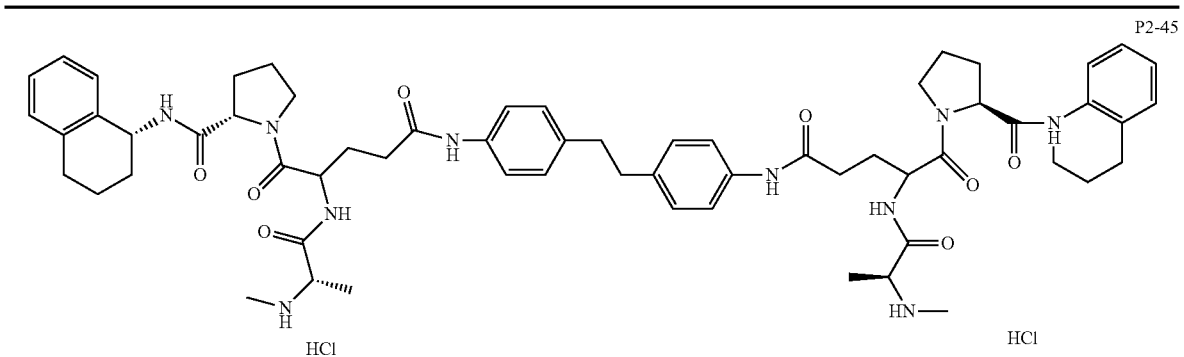
P2-45
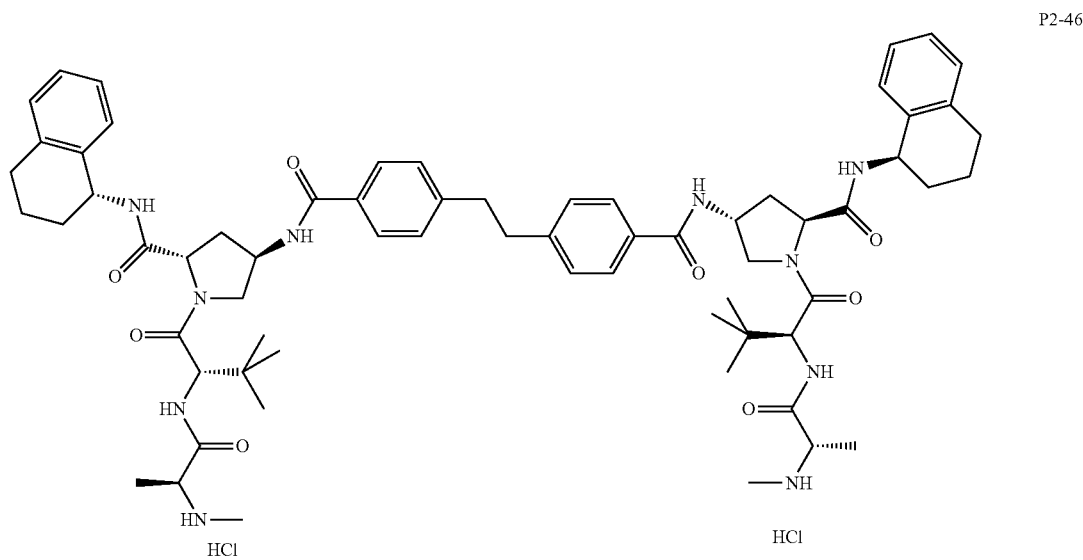
P2-46
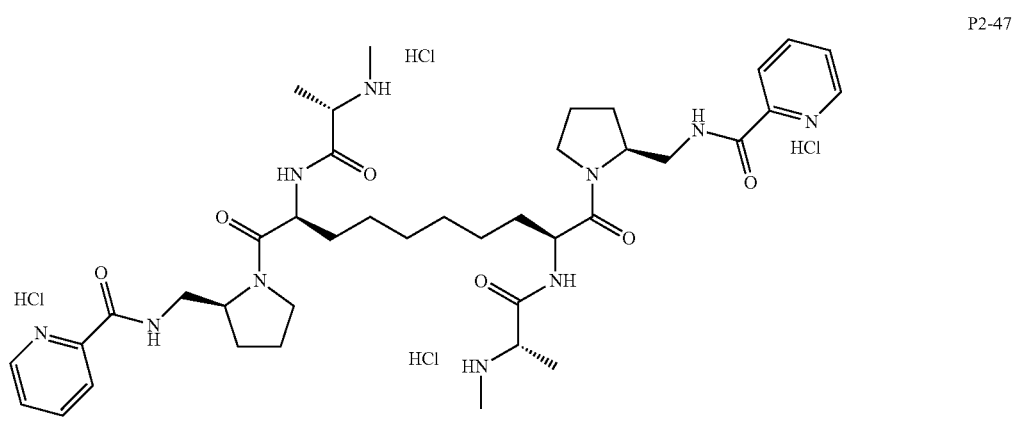
P2-47
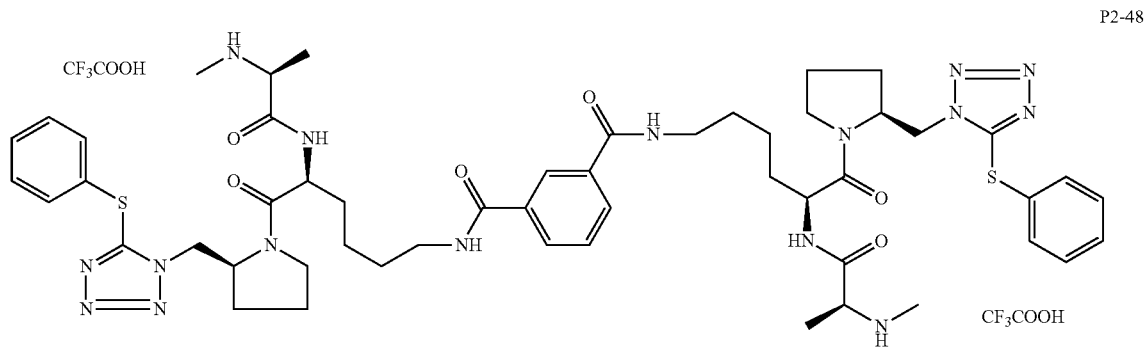
P2-48

TABLE 12-continued
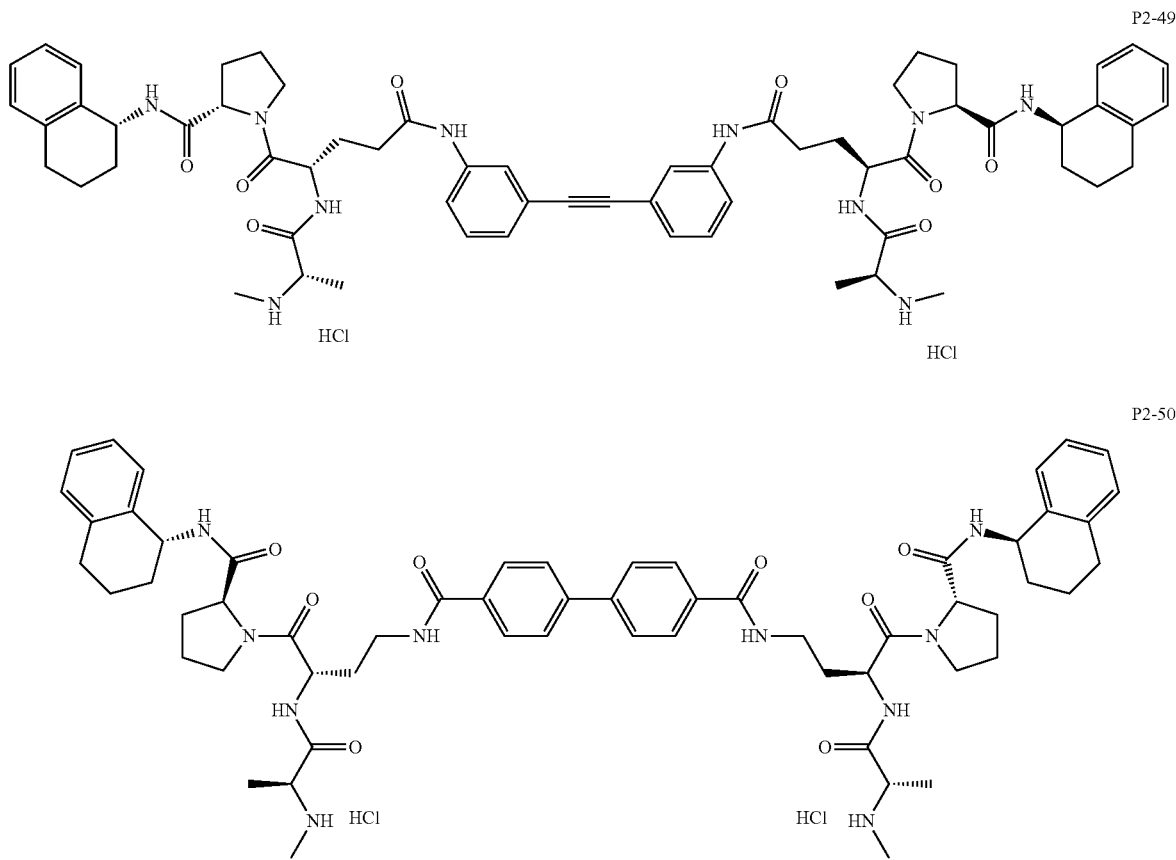
P2-49
P2-50
TABLE 13
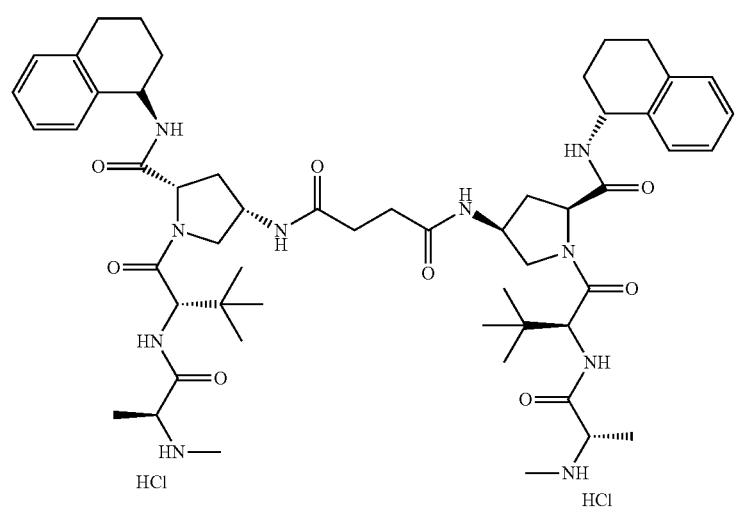
P3-1

TABLE 13-continued
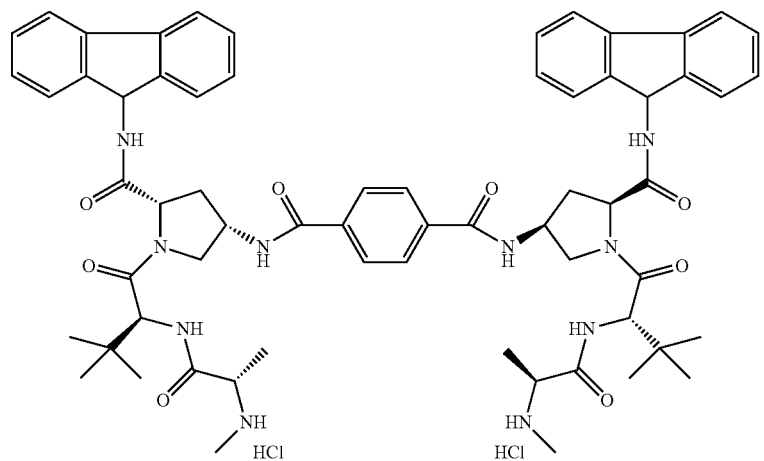 [SMILES: CN[C@@H](C)C(=O)N[C@H](C(=O)N1C[C@@H](NC(=O)c2ccc(C(=O)N[C@H]3C[C@@H](C(=O)NC4c5ccccc5-c5ccccc54)N(C(=O)[C@@H](NC(=O)[C@H](C)NC)C(C)(C)C)C3)cc2)C[C@H]1C(=O)NC1c2ccccc2-c2ccccc21)C(C)(C)C ; Cl ; Cl]
P3-2
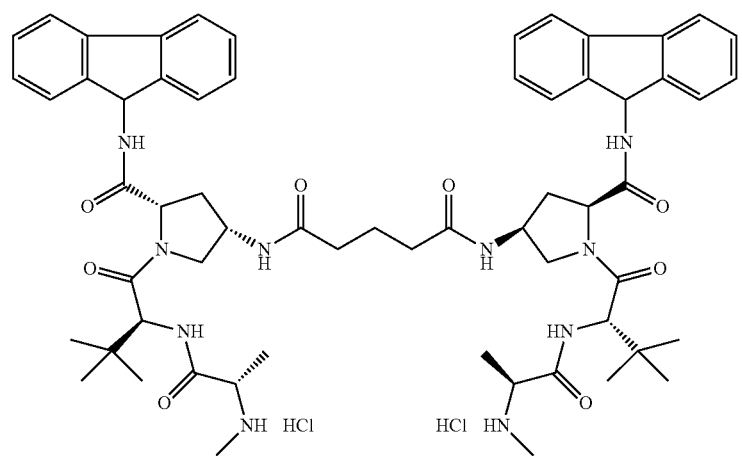 [SMILES: CN[C@@H](C)C(=O)N[C@H](C(=O)N1C[C@@H](NC(=O)CCCC(=O)N[C@H]2C[C@@H](C(=O)NC3c4ccccc4-c4ccccc43)N(C(=O)[C@@H](NC(=O)[C@H](C)NC)C(C)(C)C)C2)C[C@H]1C(=O)NC1c2ccccc2-c2ccccc21)C(C)(C)C ; Cl ; Cl]
P3-3
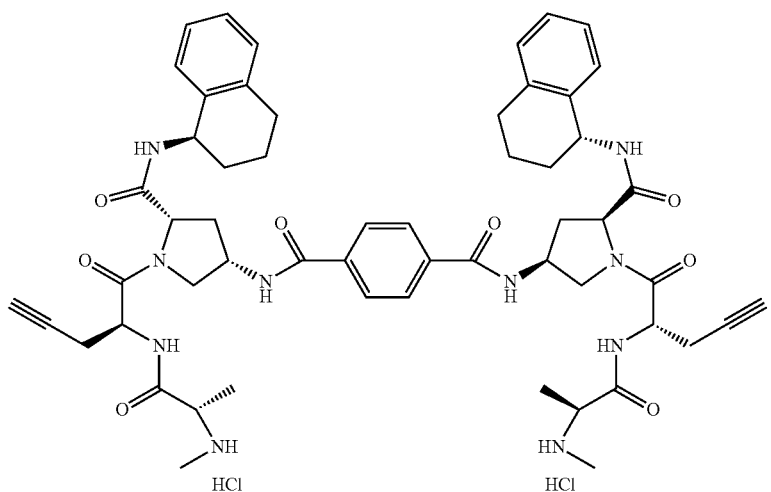 [SMILES: C#CC[C@H](NC(=O)[C@H](C)NC)C(=O)N1C[C@@H](NC(=O)c2ccc(C(=O)N[C@H]3C[C@@H](C(=O)N[C@@H]4CCCc5ccccc54)N(C(=O)[C@H](CC#C)NC(=O)[C@H](C)NC)C3)cc2)C[C@H]1C(=O)N[C@@H]1CCCc2ccccc21 ; Cl ; Cl]
P3-4

TABLE 13-continued
P3-5
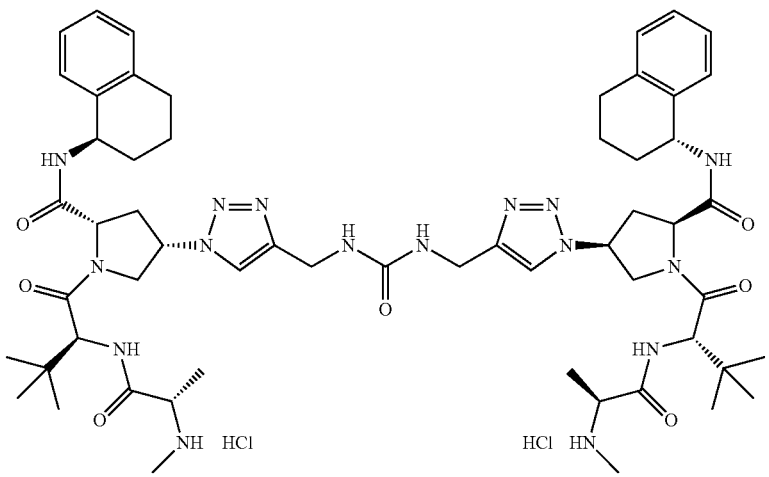 [SMILES: CN[C@@H](C)C(=O)N[C@H](C(=O)N1C[C@@H](n2cc(CNC(=O)NCc3cn([C@H]4C[C@@H](C(=O)N[C@@H]5CCCc6ccccc65)N(C(=O)[C@@H](NC(=O)[C@H](C)NC)C(C)(C)C)C4)nn3)nn2)C[C@H]1C(=O)N[C@@H]1CCCc2ccccc21)C(C)(C)C ; Cl ; Cl]
P3-6
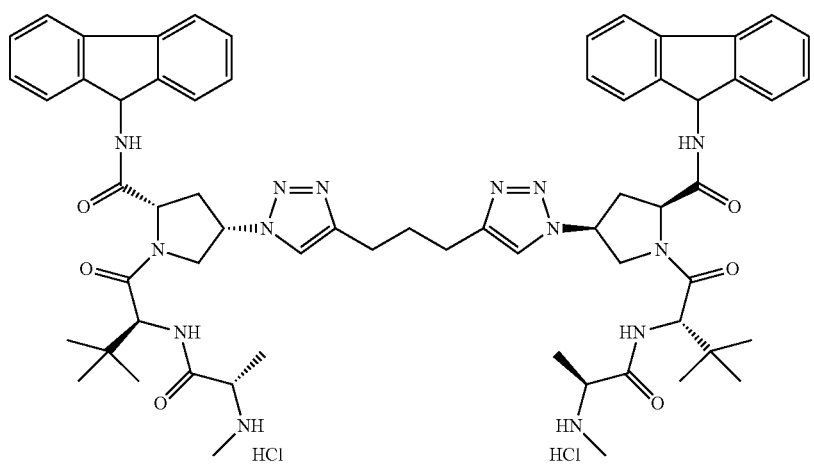 [SMILES: CN[C@@H](C)C(=O)N[C@H](C(=O)N1C[C@@H](n2cc(CCCc3cn([C@H]4C[C@@H](C(=O)NC5c6ccccc6-c6ccccc65)N(C(=O)[C@@H](NC(=O)[C@H](C)NC)C(C)(C)C)C4)nn3)nn2)C[C@H]1C(=O)NC1c2ccccc2-c2ccccc21)C(C)(C)C ; Cl ; Cl]
P3-7
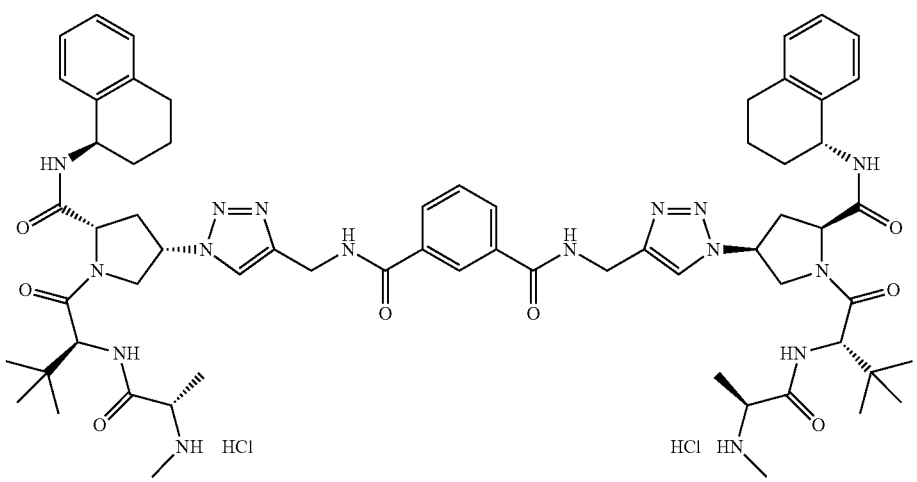 [SMILES: CN[C@@H](C)C(=O)N[C@H](C(=O)N1C[C@@H](n2cc(CNC(=O)c3cccc(C(=O)NCc4cn([C@H]5C[C@@H](C(=O)N[C@@H]6CCCc7ccccc76)N(C(=O)[C@@H](NC(=O)[C@H](C)NC)C(C)(C)C)C5)nn4)c3)nn2)C[C@H]1C(=O)N[C@@H]1CCCc2ccccc21)C(C)(C)C ; Cl ; Cl]

TABLE 13-continued
P3-8
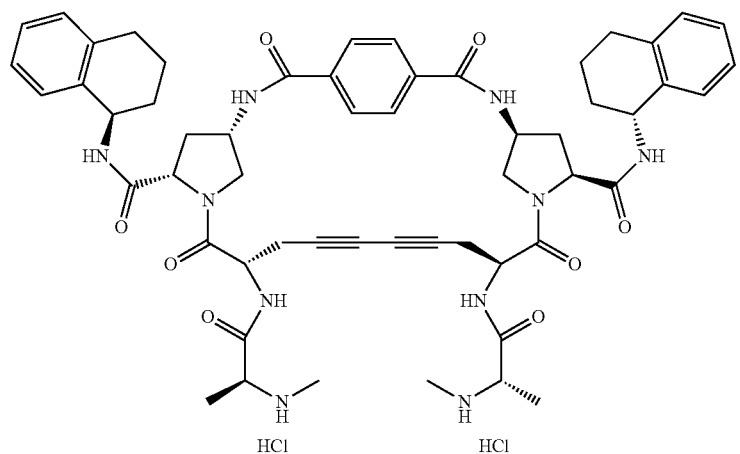 [SMILES: CN[C@@H](C)C(=O)N[C@H]1CC#CC#CC[C@H](NC(=O)[C@H](C)NC)C(=O)N2C[C@H](C[C@H]2C(=O)N[C@@H]2CCCc3ccccc32)NC(=O)c2ccc(cc2)C(=O)N[C@H]2C[C@@H](C(=O)N[C@@H]3CCCc4ccccc43)N(C2)C1=O ; Cl ; Cl]
P3-9
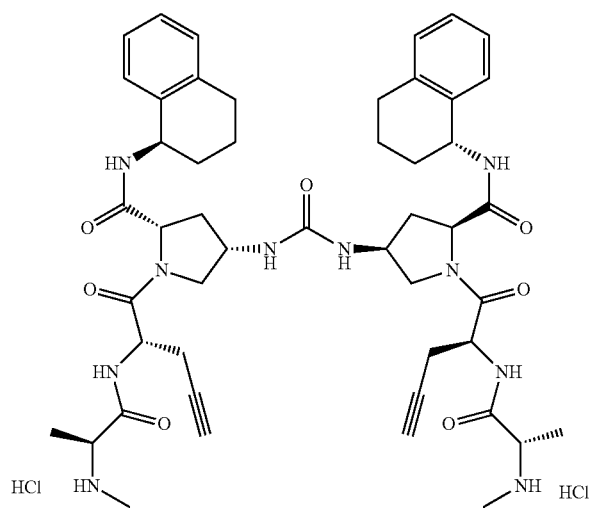 [SMILES: Cl ; C#CC[C@H](NC(=O)[C@H](C)NC)C(=O)N1C[C@@H](NC(=O)N[C@H]2C[C@@H](C(=O)N[C@@H]3CCCc4ccccc43)N(C(=O)[C@H](CC#C)NC(=O)[C@H](C)NC)C2)C[C@H]1C(=O)N[C@@H]1CCCc2ccccc21 ; Cl]
P3-10
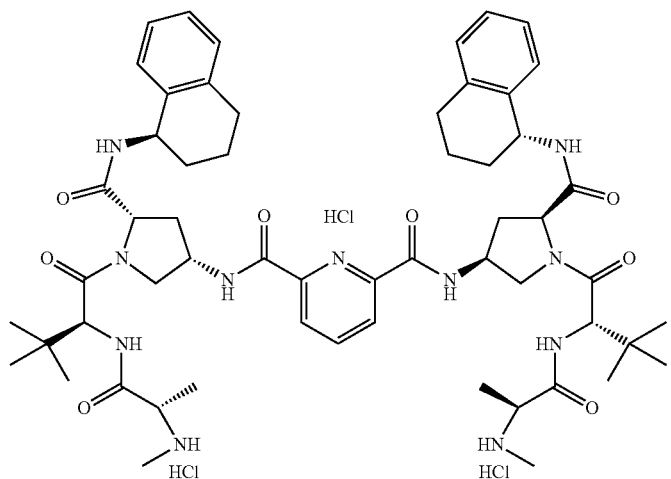 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)(C)C)C3)n2)C[C@H]1C(=O)N[C@@H]1CCCc2ccccc21)C(C)(C)C ; Cl ; Cl ; Cl]

TABLE 13-continued
P3-11
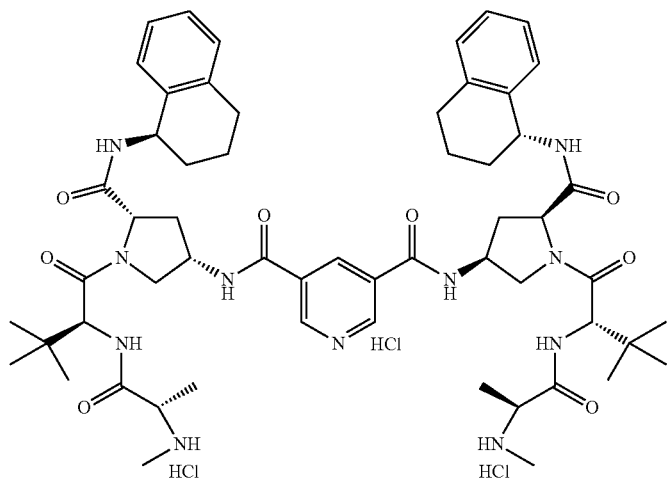 [SMILES: CN[C@@H](C)C(=O)N[C@H](C(=O)N1C[C@@H](NC(=O)c2cncc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl ; Cl]
P3-12
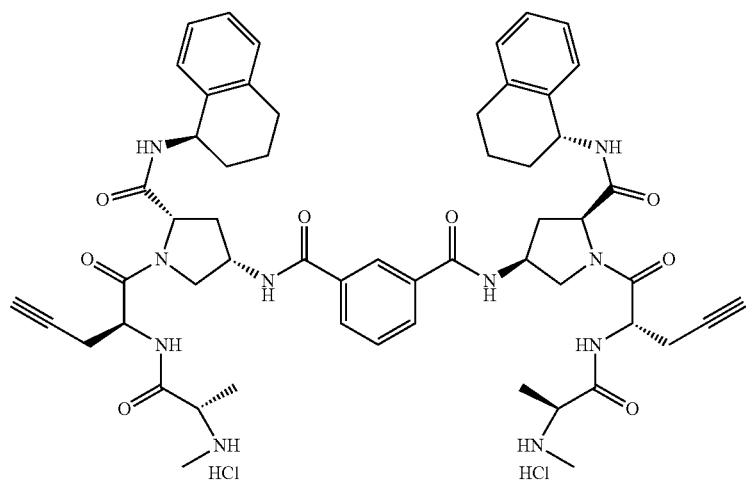 [SMILES: C#CC[C@H](NC(=O)[C@H](C)NC)C(=O)N1C[C@@H](NC(=O)c2cccc(C(=O)N[C@H]3C[C@@H](C(=O)N[C@@H]4CCCc5ccccc54)N(C(=O)[C@H](CC#C)NC(=O)[C@H](C)NC)C3)c2)C[C@H]1C(=O)N[C@@H]1CCCc2ccccc21 ; Cl ; Cl]
P3-13
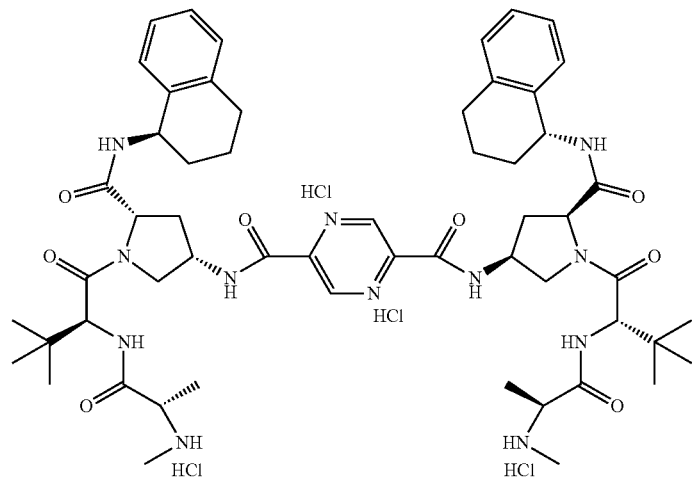 [SMILES: CN[C@@H](C)C(=O)N[C@H](C(=O)N1C[C@@H](NC(=O)c2cnc(C(=O)N[C@H]3C[C@@H](C(=O)N[C@@H]4CCCc5ccccc54)N(C(=O)[C@@H](NC(=O)[C@H](C)NC)C(C)(C)C)C3)cn2)C[C@H]1C(=O)N[C@@H]1CCCc2ccccc21)C(C)(C)C ; Cl ; Cl ; Cl ; Cl]

TABLE 13-continued
P3-14
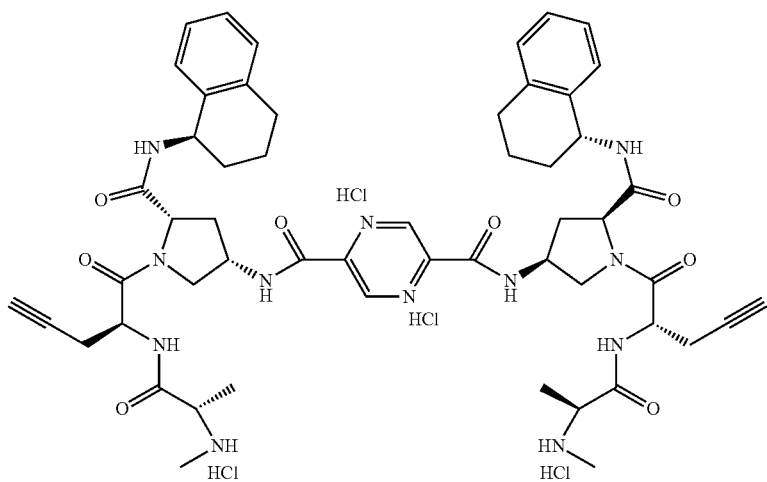 [SMILES: C#CC[C@H](NC(=O)[C@H](C)NC)C(=O)N1C[C@@H](NC(=O)c2cnc(C(=O)N[C@H]3C[C@@H](C(=O)N[C@@H]4CCCc5ccccc54)N(C(=O)[C@H](CC#C)NC(=O)[C@H](C)NC)C3)cn2)C[C@H]1C(=O)N[C@@H]1CCCc2ccccc21 ; Cl ; Cl ; Cl ; Cl]
P3-15
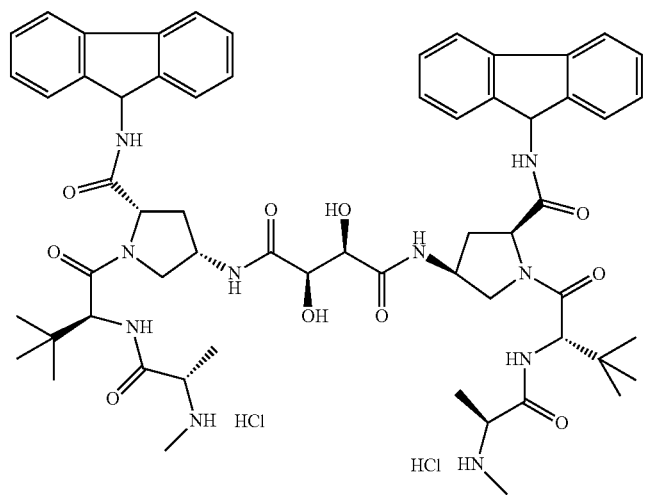 [SMILES: CN[C@@H](C)C(=O)N[C@H](C(=O)N1C[C@@H](NC(=O)[C@H](O)[C@@H](O)C(=O)N[C@H]2C[C@@H](C(=O)NC3c4ccccc4-c4ccccc43)N(C(=O)[C@@H](NC(=O)[C@H](C)NC)C(C)(C)C)C2)C[C@H]1C(=O)NC1c2ccccc2-c2ccccc21)C(C)(C)C ; Cl ; Cl]
P3-16
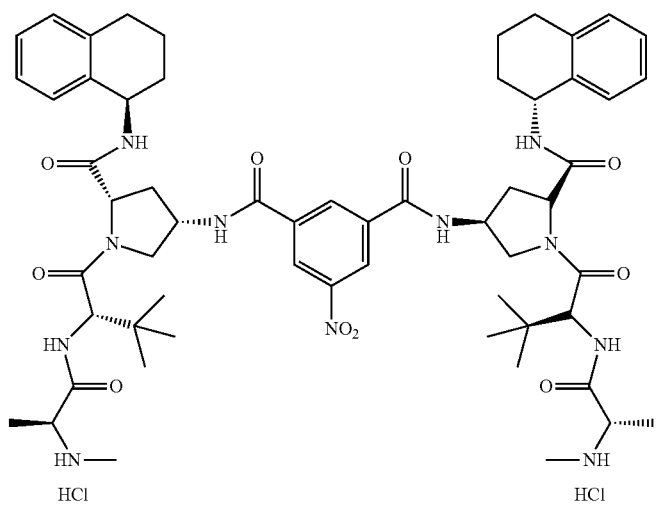

TABLE 13-continued
P3-17
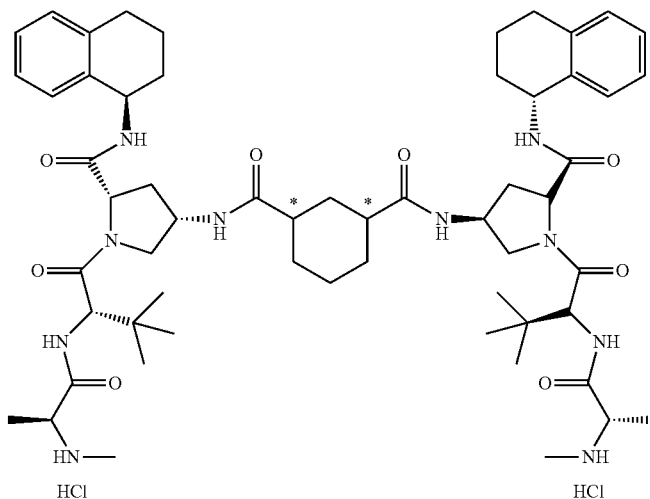
trans or cis A
P3-18
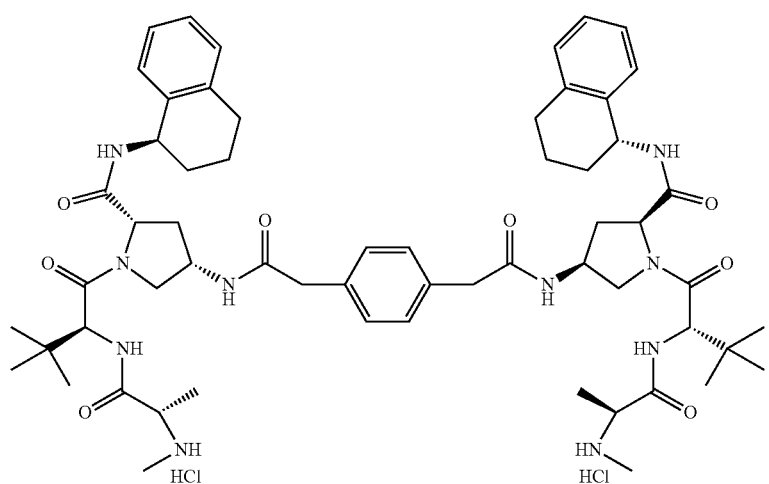 [SMILES: CN[C@@H](C)C(=O)N[C@H](C(=O)N1C[C@@H](NC(=O)Cc2ccc(CC(=O)N[C@H]3C[C@@H](C(=O)N[C@@H]4CCCc5ccccc54)N(C(=O)[C@@H](NC(=O)[C@H](C)NC)C(C)(C)C)C3)cc2)C[C@H]1C(=O)N[C@@H]1CCCc2ccccc21)C(C)(C)C ; Cl ; Cl]
P3-19
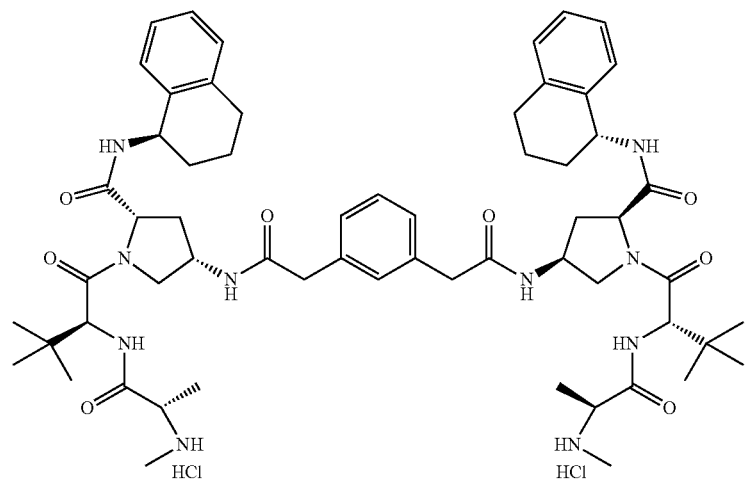 [SMILES: CN[C@@H](C)C(=O)N[C@H](C(=O)N1C[C@@H](NC(=O)Cc2cccc(CC(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl]

TABLE 13-continued
P3-20
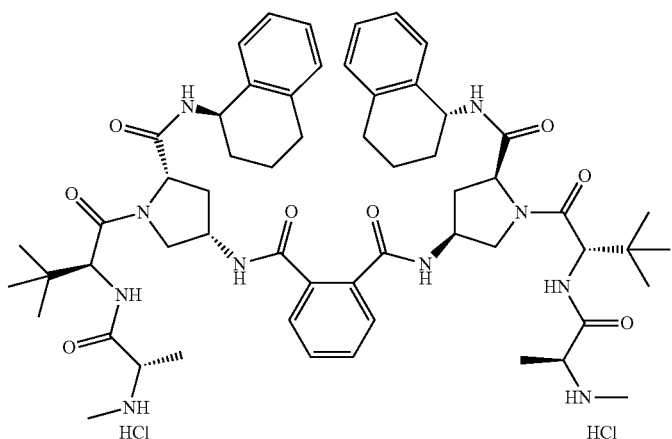 [SMILES: CN[C@@H](C)C(=O)N[C@H](C(=O)N1C[C@@H](NC(=O)c2ccccc2C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]
P3-21
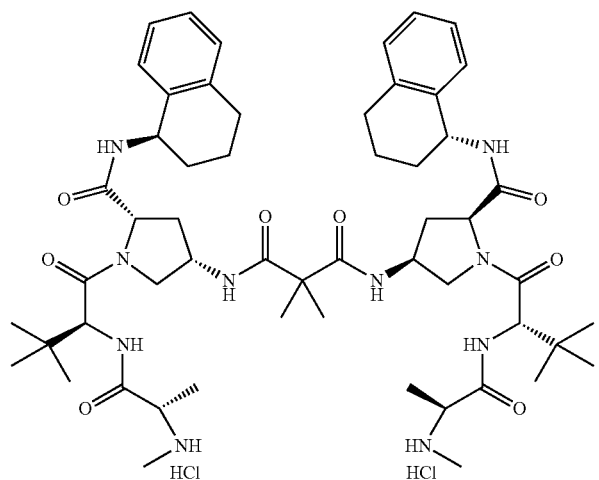 [SMILES: CN[C@@H](C)C(=O)N[C@H](C(=O)N1C[C@@H](NC(=O)C(C)(C)C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]
P3-22
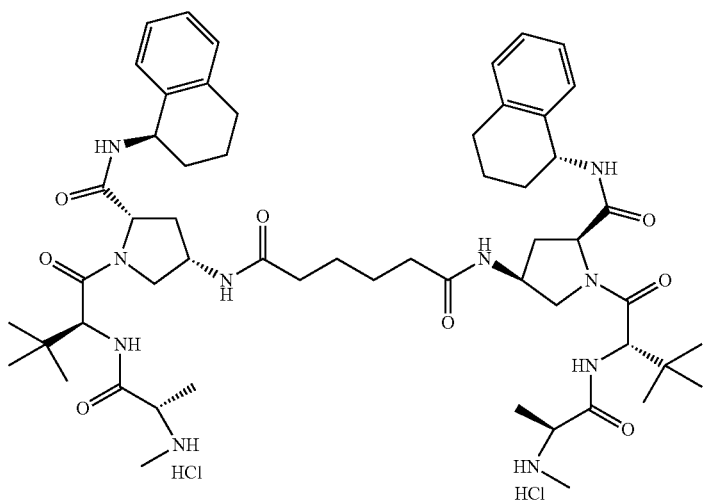 [SMILES: CN[C@@H](C)C(=O)N[C@H](C(=O)N1C[C@@H](NC(=O)CCCCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]

TABLE 13-continued
P3-23
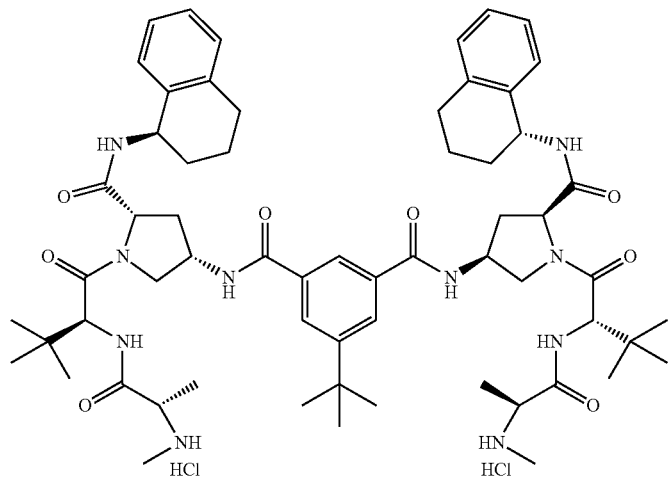 [SMILES: CN[C@@H](C)C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)NC)C(C)(C)C)C3)cc(C(C)(C)C)c2)C[C@H]1C(=O)N[C@@H]1CCCc2ccccc21)C(C)(C)C ; Cl ; Cl]
P3-24
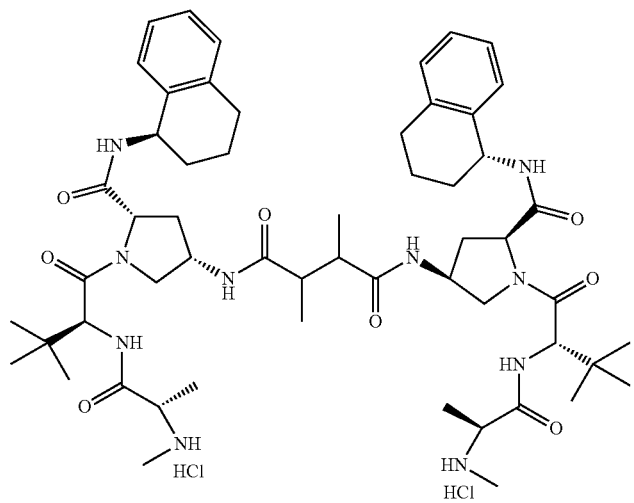
Meso Compound
P3-25
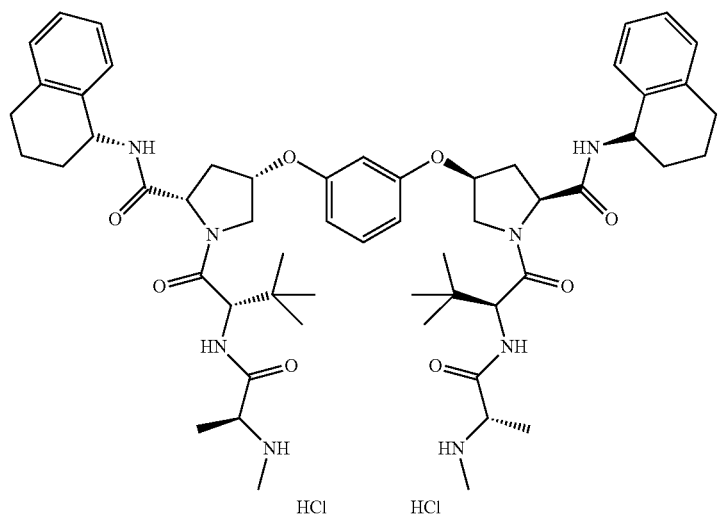

TABLE 13-continued
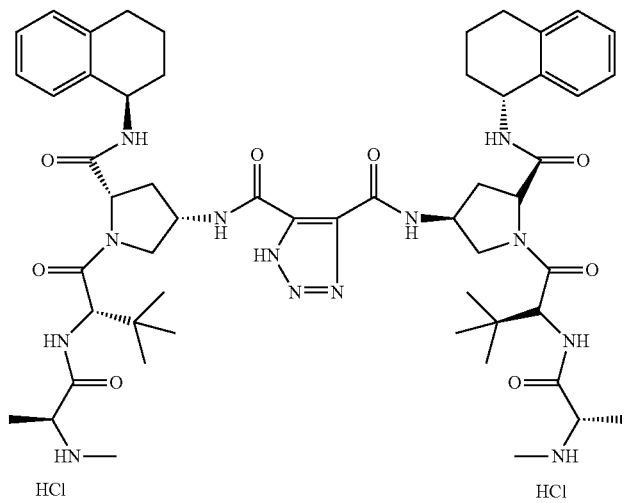
P3-26
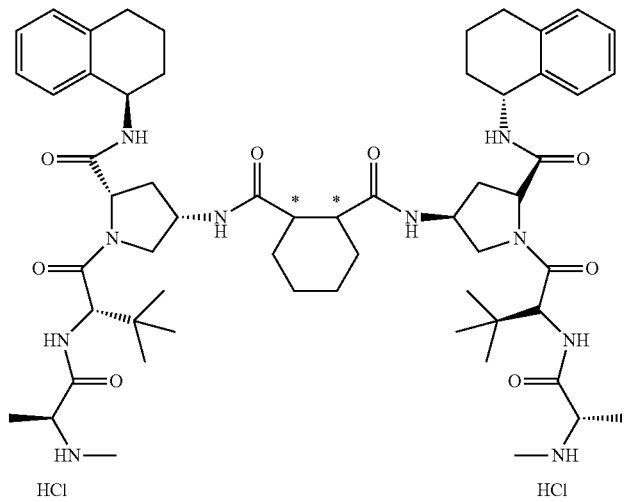
P3-27
trans A
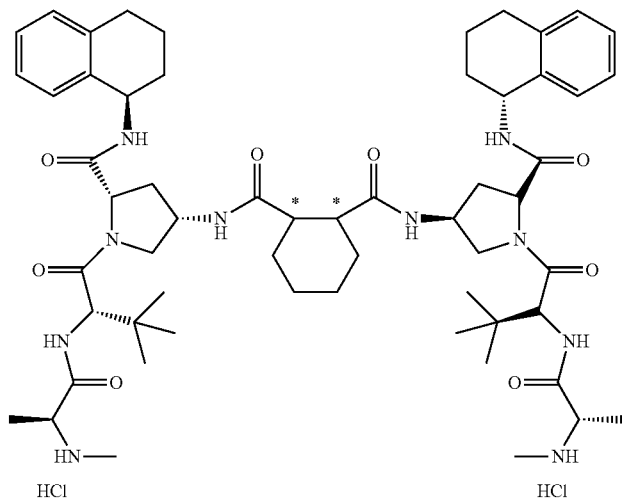
P3-28
trans B TABLE 13-continued
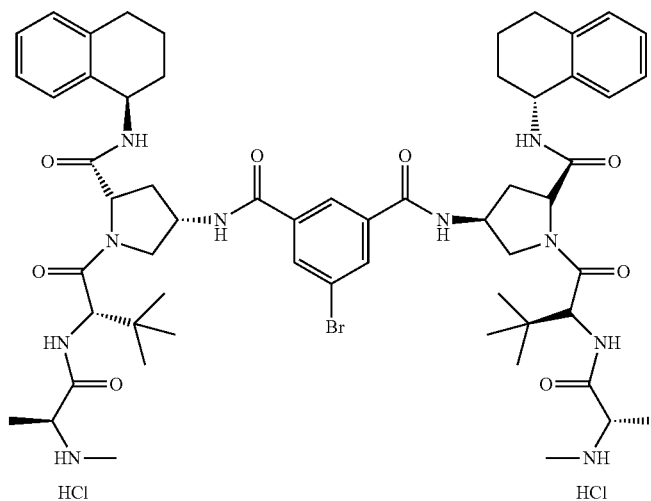
P3-29
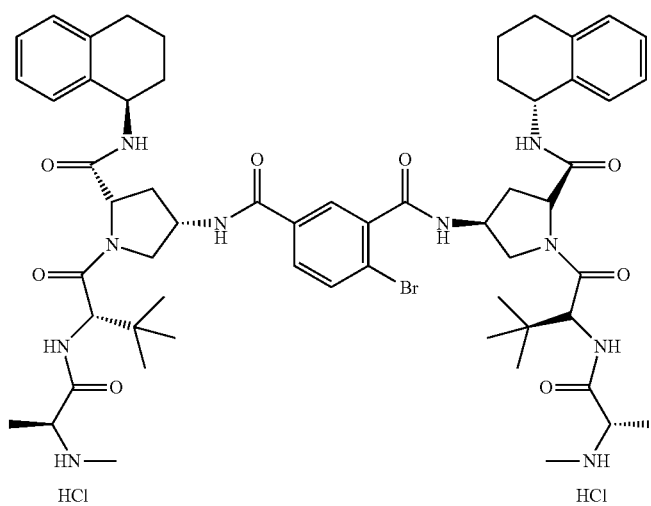
P3-30
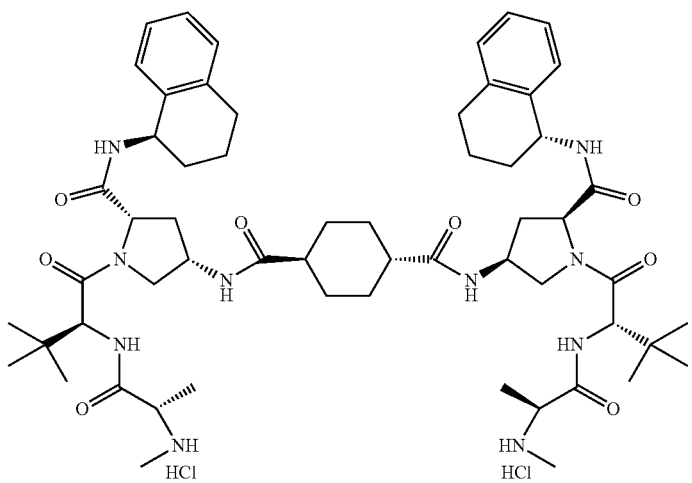 [SMILES: CN[C@@H](C)C(=O)N[C@H](C(=O)N1C[C@@H](NC(=O)[C@H]2CC[C@H](C(=O)N[C@H]3C[C@@H](C(=O)N[C@@H]4CCCc5ccccc54)N(C(=O)[C@@H](NC(=O)[C@H](C)NC)C(C)(C)C)C3)CC2)C[C@H]1C(=O)N[C@@H]1CCCc2ccccc21)C(C)(C)C ; Cl ; Cl]
P3-31

P3-32
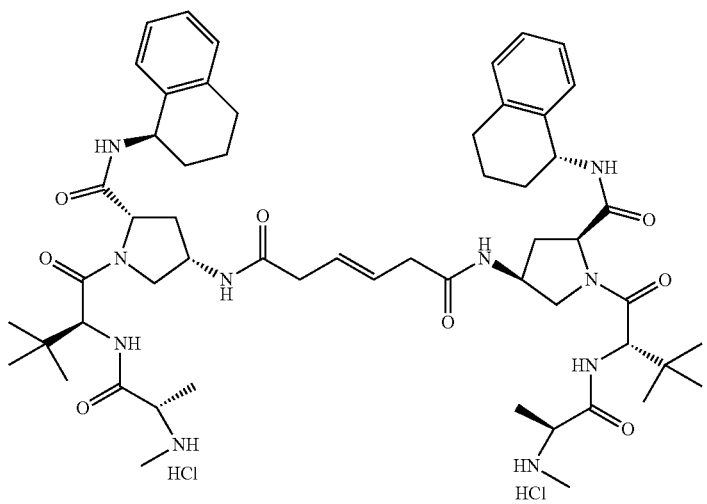 [SMILES: CN[C@@H](C)C(=O)N[C@H](C(=O)N1C[C@@H](NC(=O)C/C=C/CC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]
P3-33
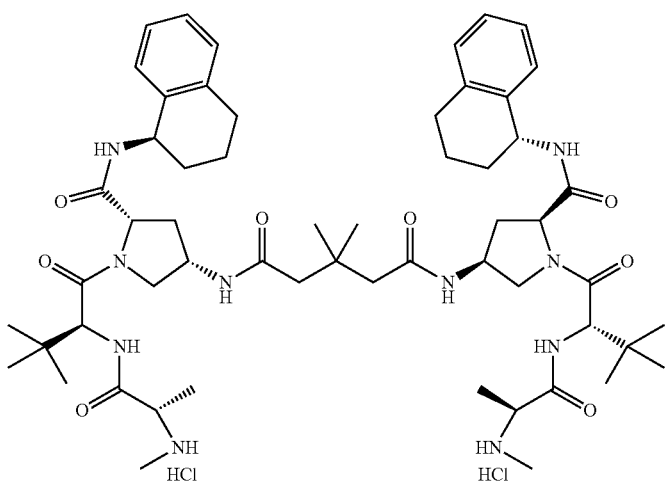 [SMILES: CN[C@@H](C)C(=O)N[C@H](C(=O)N1C[C@@H](NC(=O)CC(C)(C)CC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]
P3-34
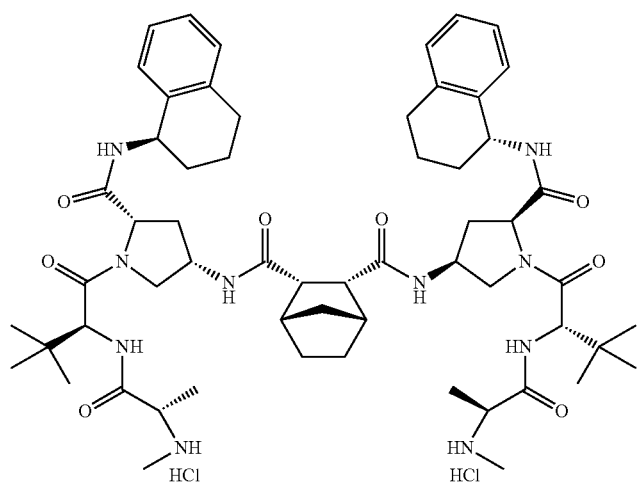 [SMILES: CN[C@@H](C)C(=O)N[C@H](C(=O)N1C[C@@H](NC(=O)[C@@H]2[C@@H]3CC[C@@H](C3)[C@@H]2C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]

TABLE 13-continued
P3-35
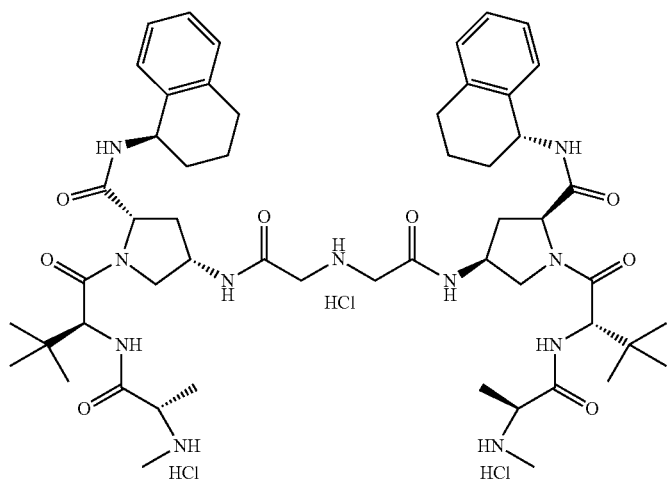 [SMILES: CN[C@@H](C)C(=O)N[C@H](C(=O)N1C[C@@H](NC(=O)CNCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl ; Cl]
P3-36
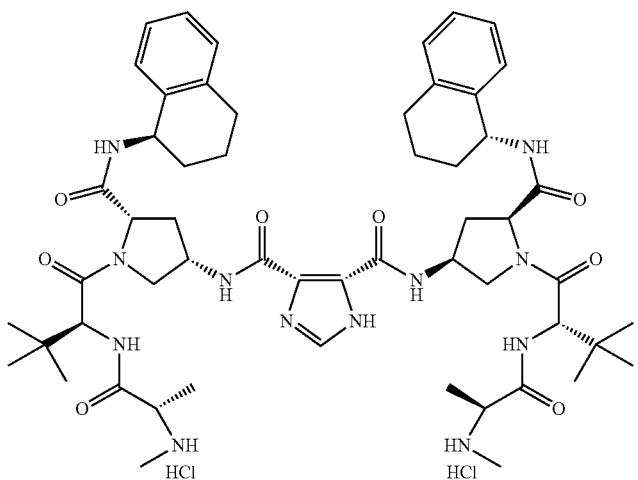
P3-37
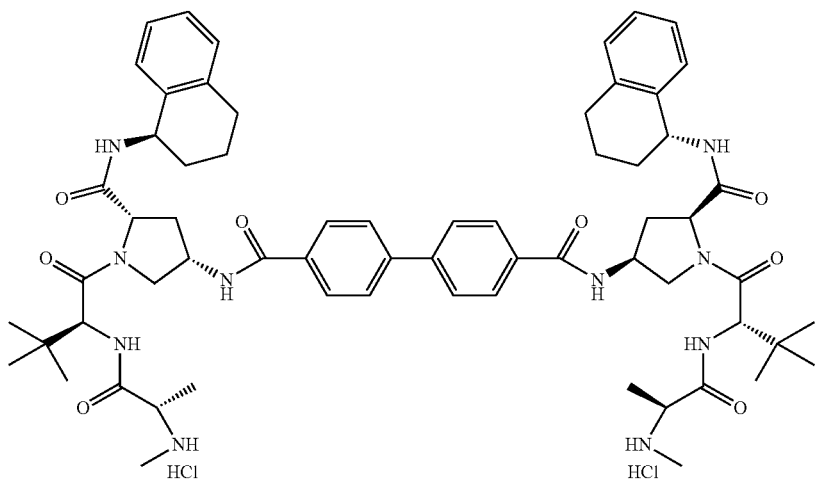 [SMILES: CN[C@@H](C)C(=O)N[C@H](C(=O)N1C[C@@H](NC(=O)c2ccc(-c3ccc(C(=O)N[C@H]4C[C@@H](C(=O)N[C@@H]5CCCc6ccccc65)N(C(=O)[C@@H](NC(=O)[C@H](C)NC)C(C)(C)C)C4)cc3)cc2)C[C@H]1C(=O)N[C@@H]1CCCc2ccccc21)C(C)(C)C ; Cl ; Cl]

TABLE 13-continued
P3-38
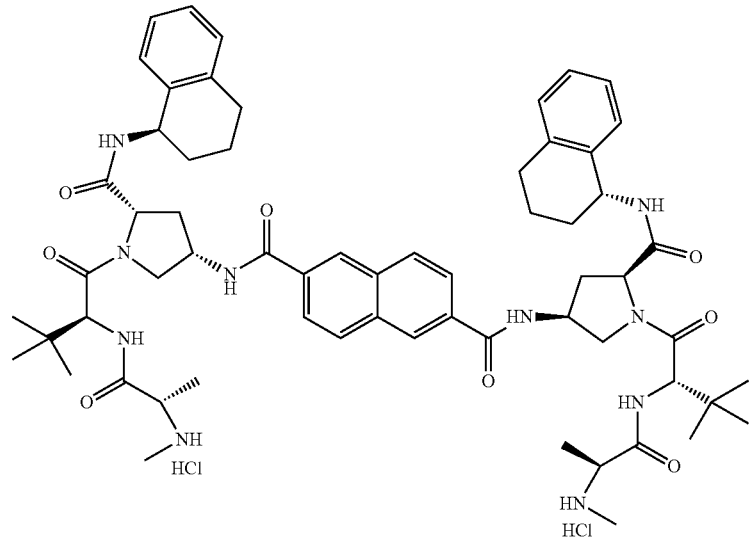 [SMILES: CN[C@@H](C)C(=O)N[C@H](C(=O)N1C[C@@H](NC(=O)c2ccc3cc(C(=O)N[C@H]4C[C@@H](C(=O)N[C@@H]5CCCc6ccccc65)N(C(=O)[C@@H](NC(=O)[C@H](C)NC)C(C)(C)C)C4)ccc3c2)C[C@H]1C(=O)N[C@@H]1CCCc2ccccc21)C(C)(C)C ; Cl ; Cl]
P3-39
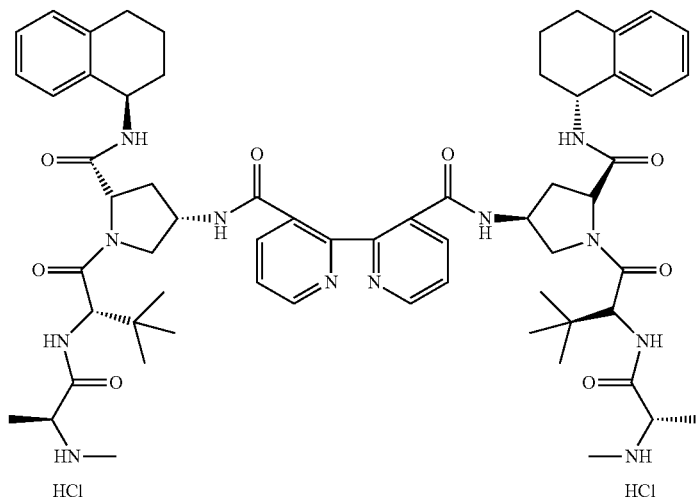
P3-40
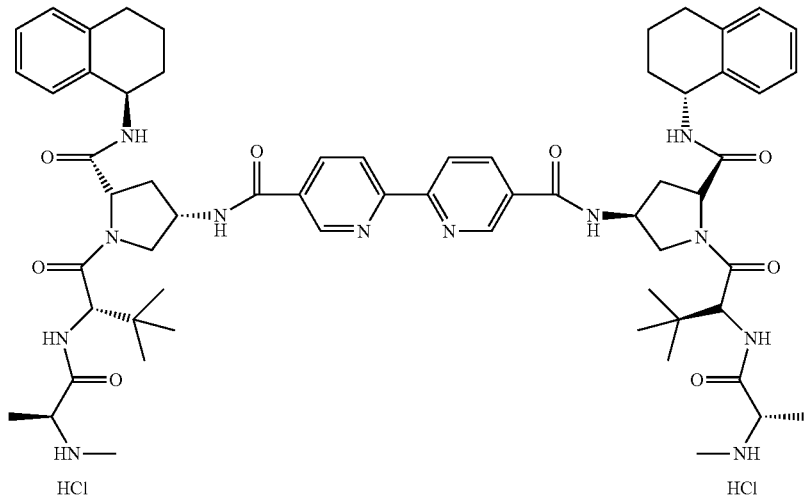

TABLE 13-continued
P3-41
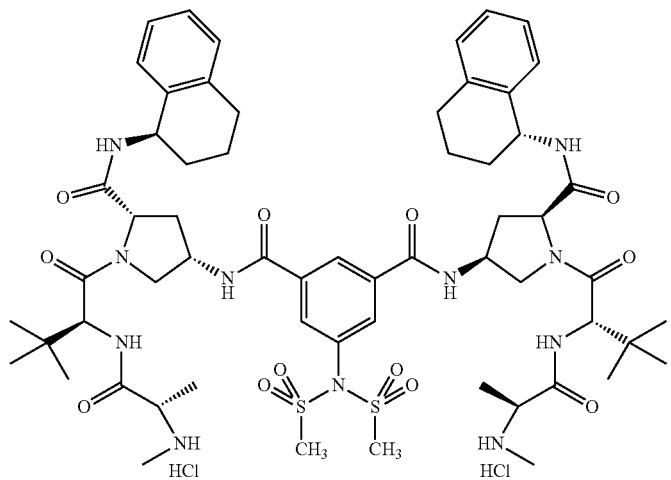 [SMILES: CN[C@@H](C)C(=O)N[C@H](C(=O)N1C[C@@H](NC(=O)c2cc(C(=O)N[C@H]3C[C@@H](C(=O)N[C@@H]4CCCc5ccccc54)N(C(=O)[C@@H](NC(=O)[C@H](C)NC)C(C)(C)C)C3)cc(N(S(C)(=O)=O)S(C)(=O)=O)c2)C[C@H]1C(=O)N[C@@H]1CCCc2ccccc21)C(C)(C)C ; Cl ; Cl]
P3-42
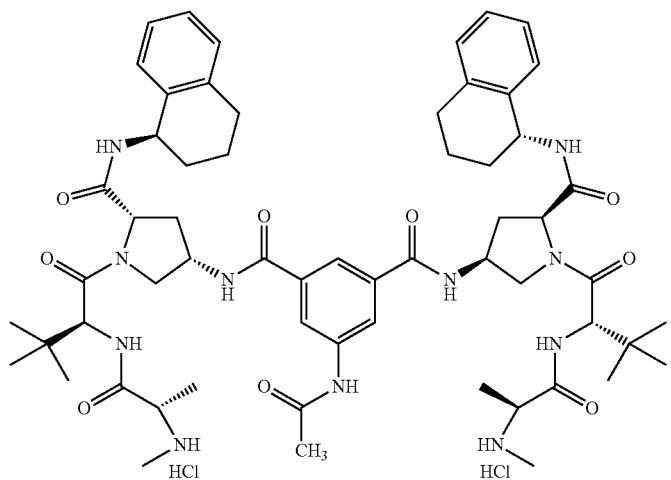 [SMILES: CN[C@@H](C)C(=O)N[C@H](C(=O)N1C[C@@H](NC(=O)c2cc(NC(C)=O)cc(C(=O)N[C@H]3C[C@@H](C(=O)N[C@@H]4CCCc5ccccc54)N(C(=O)[C@@H](NC(=O)[C@H](C)NC)C(C)(C)C)C3)c2)C[C@H]1C(=O)N[C@@H]1CCCc2ccccc21)C(C)(C)C ; Cl ; Cl]
P3-43
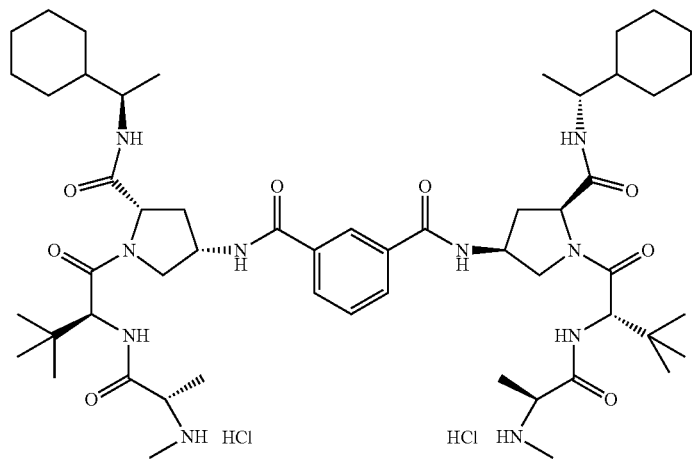 [SMILES: CN[C@@H](C)C(=O)N[C@H](C(=O)N1C[C@@H](NC(=O)c2cccc(C(=O)N[C@H]3C[C@@H](C(=O)N[C@H](C)C4CCCCC4)N(C(=O)[C@@H](NC(=O)[C@H](C)NC)C(C)(C)C)C3)c2)C[C@H]1C(=O)N[C@H](C)C1CCCCC1)C(C)(C)C ; Cl ; Cl]

TABLE 13-continued
P3-44
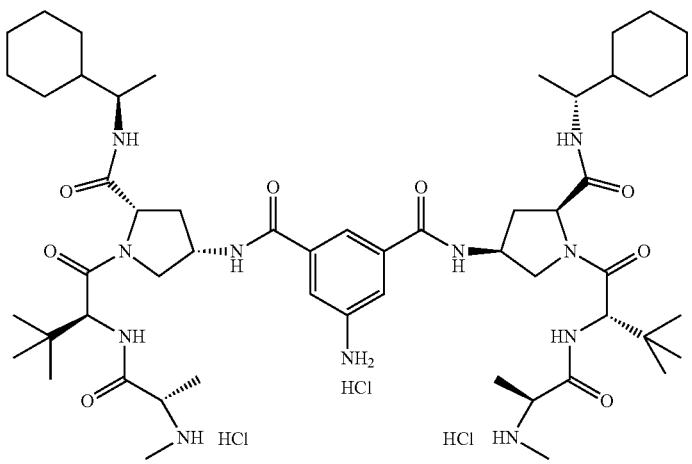 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)C4CCCCC4)N(C(=O)[C@@H](NC(=O)[C@H](C)NC)C(C)(C)C)C3)c2)C[C@H]1C(=O)N[C@H](C)C1CCCCC1)C(C)(C)C ; Cl ; Cl ; Cl]
P3-45
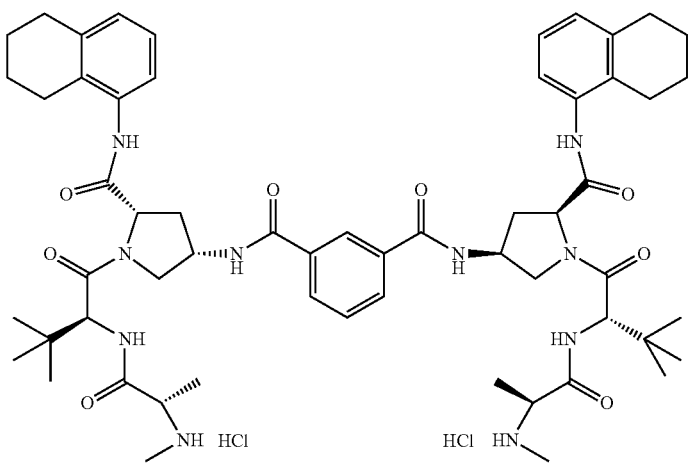 [SMILES: CN[C@@H](C)C(=O)N[C@H](C(=O)N1C[C@@H](NC(=O)c2cccc(C(=O)N[C@H]3C[C@@H](C(=O)Nc4cccc5c4CCCC5)N(C(=O)[C@@H](NC(=O)[C@H](C)NC)C(C)(C)C)C3)c2)C[C@H]1C(=O)Nc1cccc2c1CCCC2)C(C)(C)C ; Cl ; Cl]
P3-46
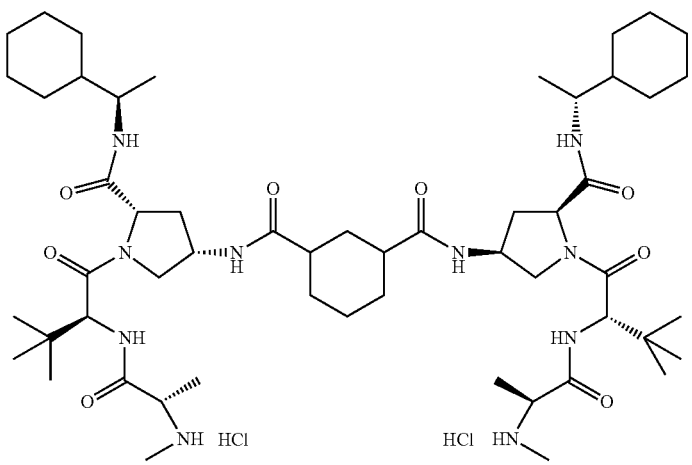 [SMILES: CN[C@@H](C)C(=O)N[C@H](C(=O)N1C[C@@H](NC(=O)C2CCCC(C(=O)N[C@H]3C[C@@H](C(=O)N[C@H](C)C4CCCCC4)N(C(=O)[C@@H](NC(=O)[C@H](C)NC)C(C)(C)C)C3)C2)C[C@H]1C(=O)N[C@H](C)C1CCCCC1)C(C)(C)C ; Cl ; Cl]

US 8,551,955 B2
TABLE 13-continued
P3-47
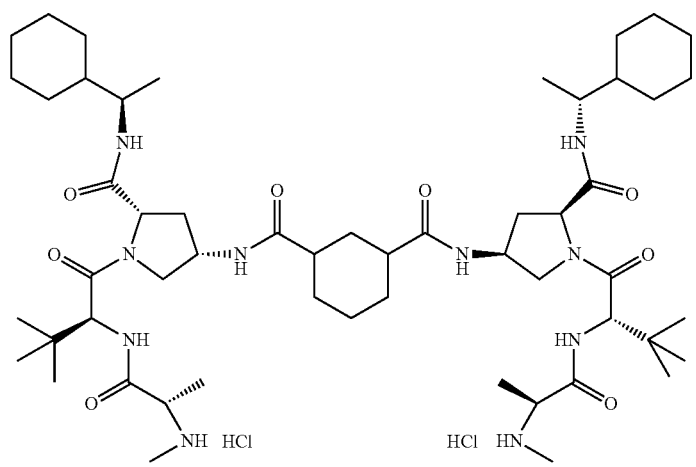 [SMILES: CN[C@@H](C)C(=O)N[C@H](C(=O)N1C[C@@H](NC(=O)C2CCCC(C(=O)N[C@H]3C[C@@H](C(=O)N[C@H](C)C4CCCCC4)N(C(=O)[C@@H](NC(=O)[C@H](C)NC)C(C)(C)C)C3)C2)C[C@H]1C(=O)N[C@H](C)C1CCCCC1)C(C)(C)C ; Cl ; Cl]
P3-48
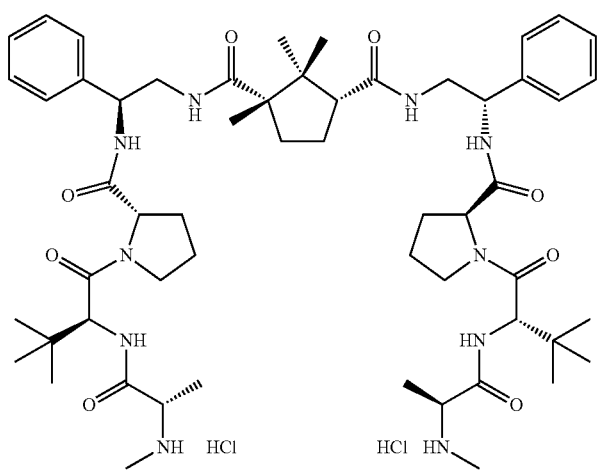
P3-49
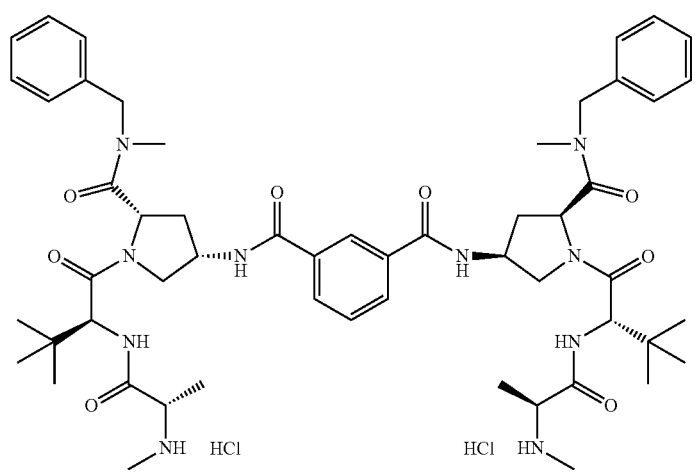 [SMILES: CN[C@@H](C)C(=O)N[C@H](C(=O)N1C[C@@H](NC(=O)c2cccc(C(=O)N[C@H]3C[C@@H](C(=O)N(C)Cc4ccccc4)N(C(=O)[C@@H](NC(=O)[C@H](C)NC)C(C)(C)C)C3)c2)C[C@H]1C(=O)N(C)Cc1ccccc1)C(C)(C)C ; Cl ; Cl]

TABLE 13-continued
P3-50
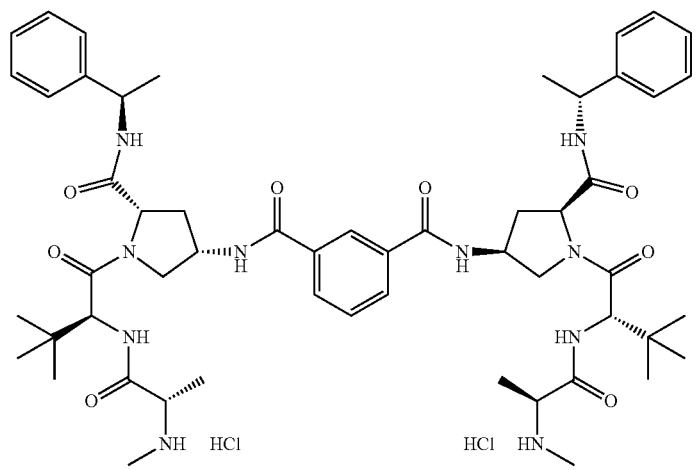 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1)C(C)(C)C ; Cl ; Cl]
P3-51
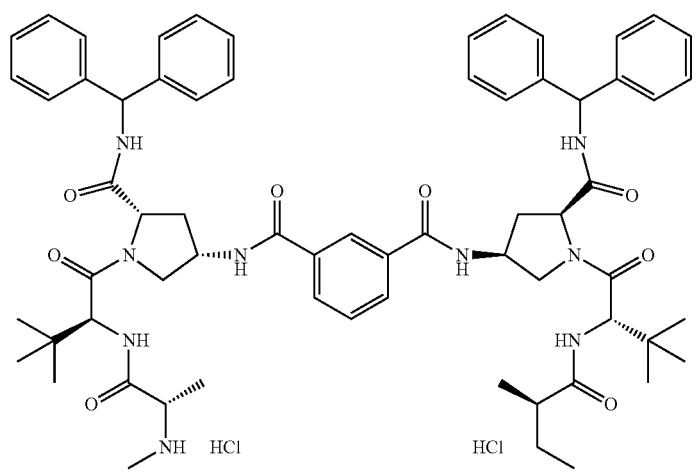 [SMILES: CC[C@@H](C)C(=O)N[C@H](C(=O)N1C[C@@H](NC(=O)c2cccc(C(=O)N[C@H]3C[C@@H](C(=O)NC(c4ccccc4)c4ccccc4)N(C(=O)[C@@H](NC(=O)[C@H](C)NC)C(C)(C)C)C3)c2)C[C@H]1C(=O)NC(c1ccccc1)c1ccccc1)C(C)(C)C ; Cl ; Cl]
P3-52
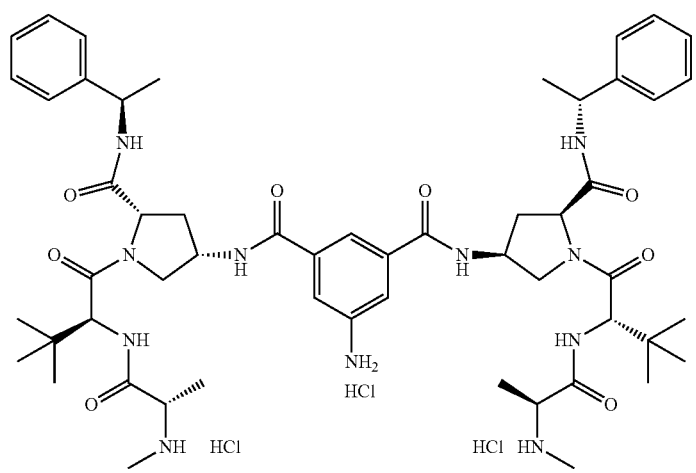 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1)C(C)(C)C ; Cl ; Cl ; Cl]

TABLE 13-continued
P3-53
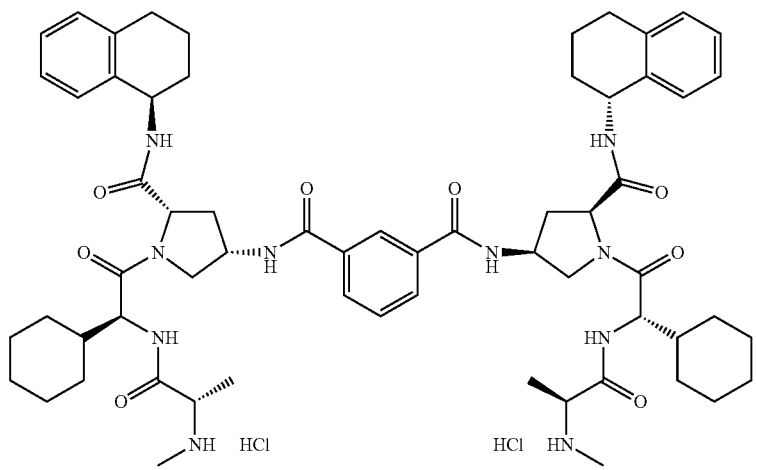 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C4CCCCC4)C3)c2)C[C@H]1C(=O)N[C@@H]1CCCc2ccccc21)C1CCCCC1 ; Cl ; Cl]
P3-54
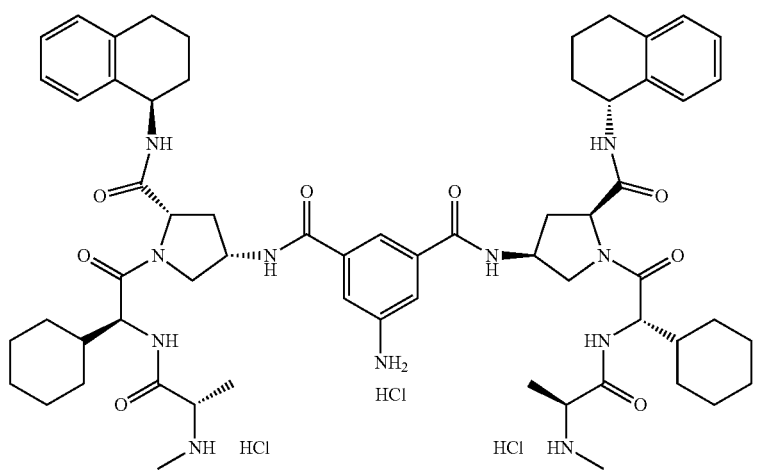 [SMILES: CN[C@@H](C)C(=O)N[C@H](C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)C4CCCCC4)C3)c2)C[C@H]1C(=O)N[C@@H]1CCCc2ccccc21)C1CCCCC1 ; Cl ; Cl ; Cl]
P3-55
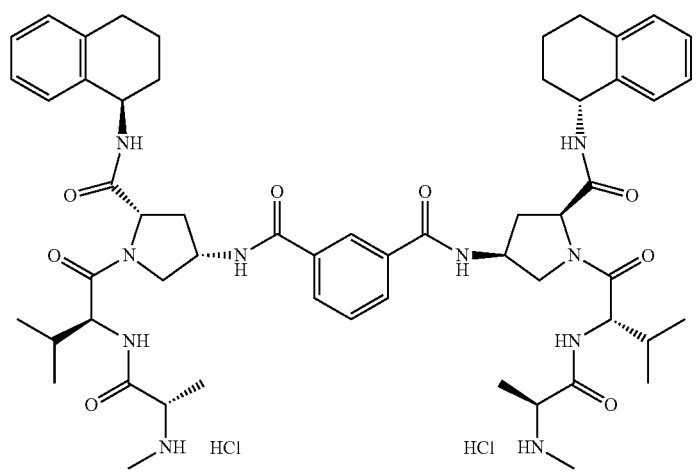 [SMILES: CN[C@@H](C)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](C)NC)C(C)C)C3)c2)C[C@H]1C(=O)N[C@@H]1CCCc2ccccc21)C(C)C ; Cl ; Cl]

TABLE 13-continued
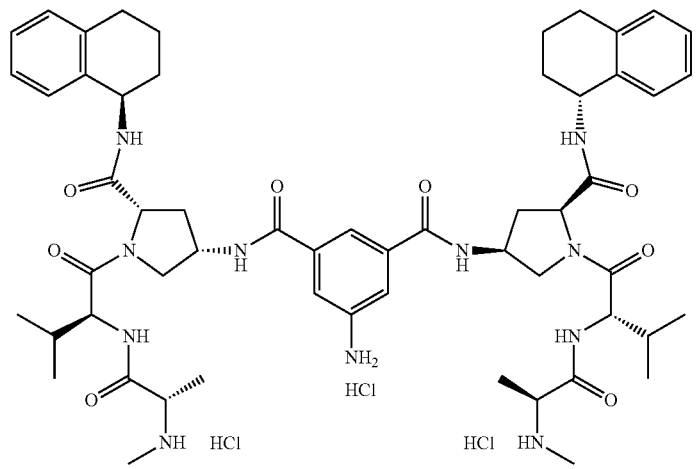 [SMILES: CN[C@@H](C)C(=O)N[C@H](C(=O)N1C[C@@H](NC(=O)c2cc(N)cc(C(=O)N[C@H]3C[C@@H](C(=O)N[C@@H]4CCCc5ccccc54)N(C(=O)[C@@H](NC(=O)[C@H](C)NC)C(C)C)C3)c2)C[C@H]1C(=O)N[C@@H]1CCCc2ccccc21)C(C)C ; Cl ; Cl ; Cl]
P3-56
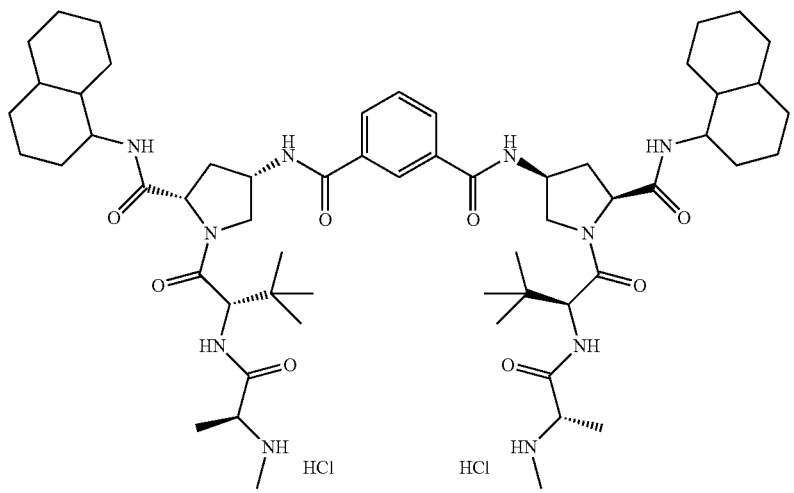
Trans isomer B1
P3-57
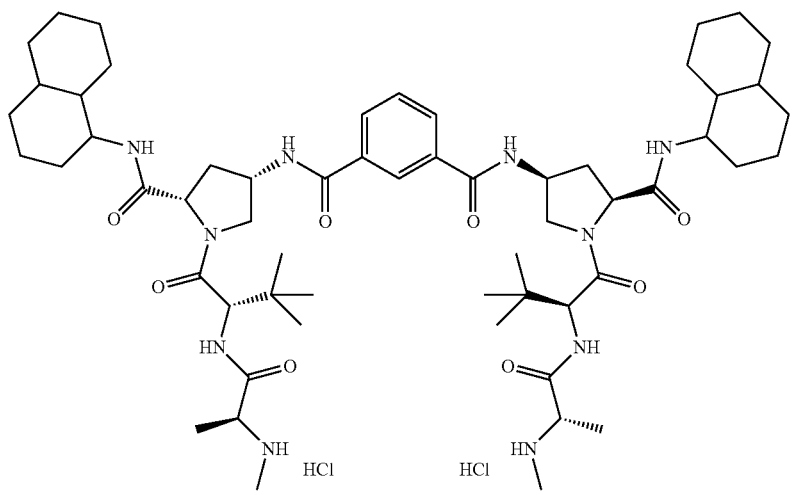
Trans isomer B2
P3-58

TABLE 13-continued
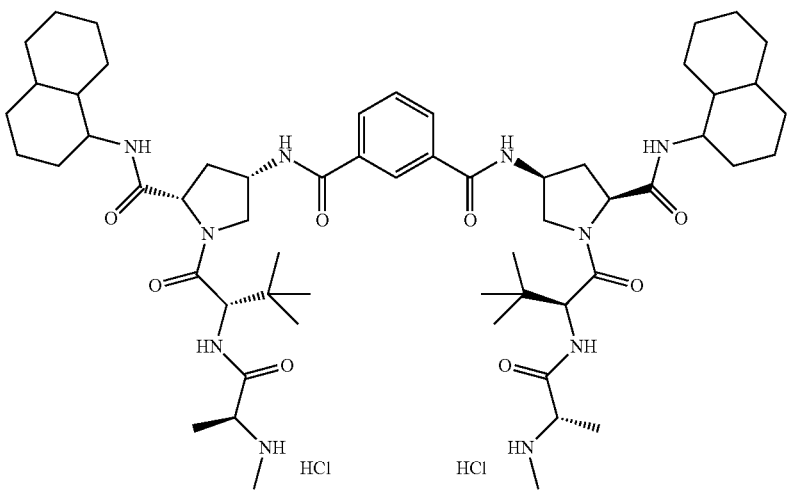
P3-59
Trans isomer A1
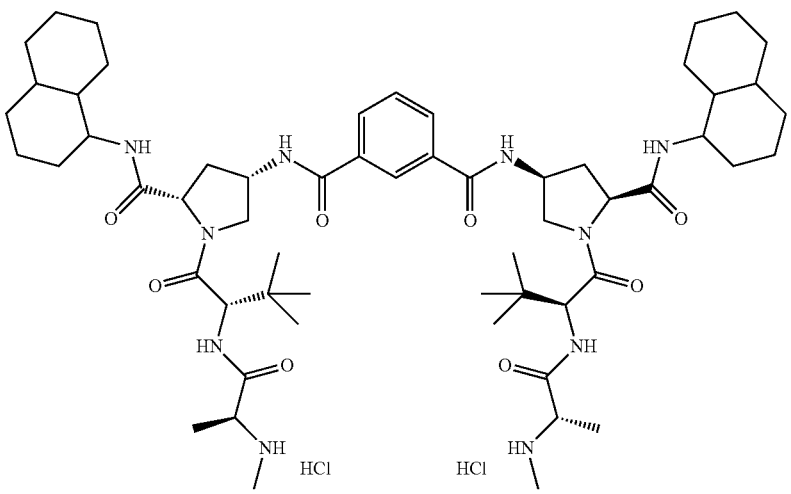
P3-60
Trans isomer A2
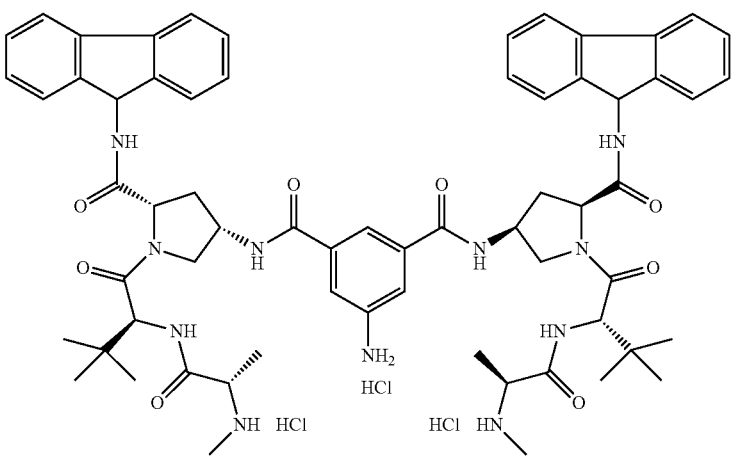 [SMILES: CN[C@@H](C)C(=O)N[C@H](C(=O)N1C[C@@H](NC(=O)c2cc(N)cc(C(=O)N[C@H]3C[C@@H](C(=O)NC4c5ccccc5-c5ccccc54)N(C(=O)[C@@H](NC(=O)[C@H](C)NC)C(C)(C)C)C3)c2)C[C@H]1C(=O)NC1c2ccccc2-c2ccccc21)C(C)(C)C ; Cl ; Cl ; Cl]
P3-61

TABLE 13-continued
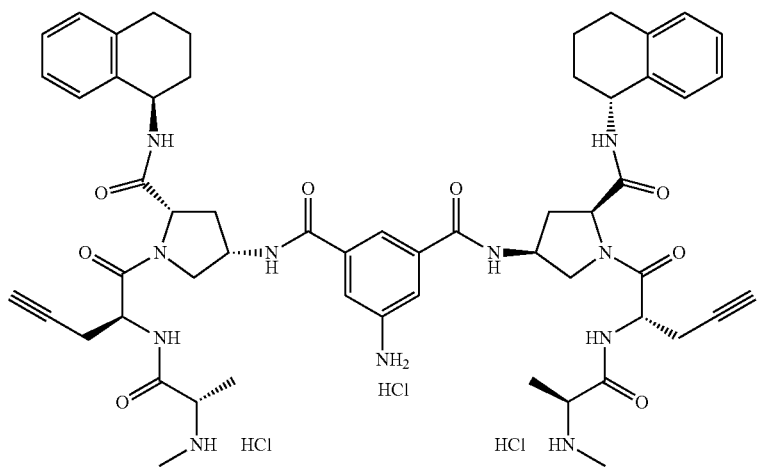 [SMILES: C#CC[C@H](NC(=O)[C@H](C)NC)C(=O)N1C[C@@H](NC(=O)c2cc(N)cc(C(=O)N[C@H]3C[C@@H](C(=O)N[C@@H]4CCCc5ccccc54)N(C(=O)[C@H](CC#C)NC(=O)[C@H](C)NC)C3)c2)C[C@H]1C(=O)N[C@@H]1CCCc2ccccc21 ; Cl ; Cl ; Cl]
P3-62
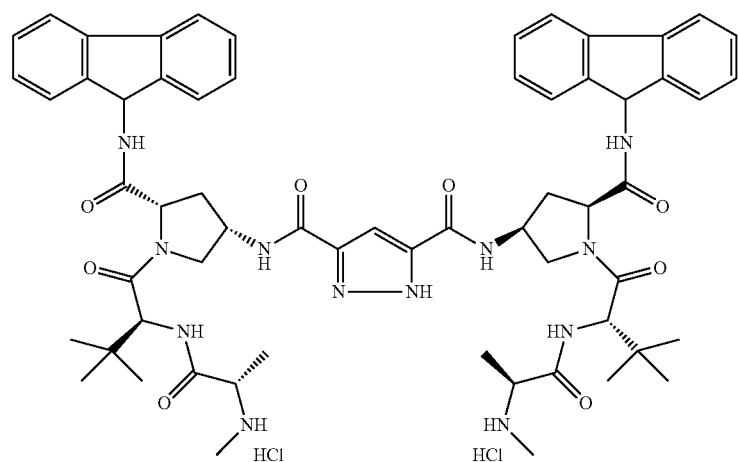 [SMILES: CN[C@@H](C)C(=O)N[C@H](C(=O)N1C[C@@H](NC(=O)c2cc(C(=O)N[C@H]3C[C@@H](C(=O)NC4c5ccccc5-c5ccccc54)N(C(=O)[C@@H](NC(=O)[C@H](C)NC)C(C)(C)C)C3)[nH]n2)C[C@H]1C(=O)NC1c2ccccc2-c2ccccc21)C(C)(C)C ; Cl ; Cl]
P3-63
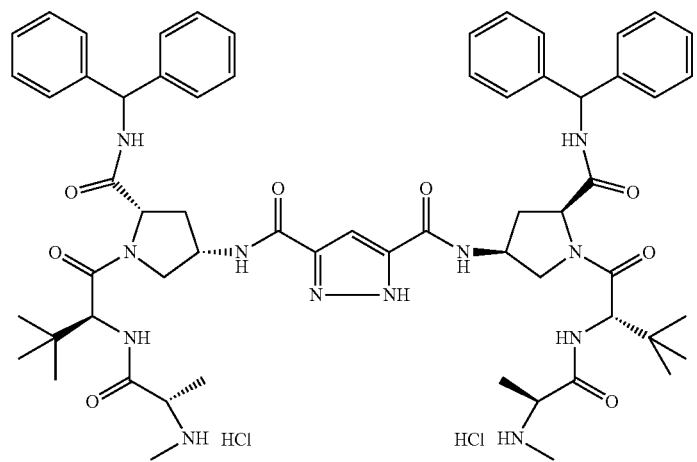 [SMILES: CN[C@@H](C)C(=O)N[C@H](C(=O)N1C[C@@H](NC(=O)c2cc(C(=O)N[C@H]3C[C@@H](C(=O)NC(c4ccccc4)c4ccccc4)N(C(=O)[C@@H](NC(=O)[C@H](C)NC)C(C)(C)C)C3)[nH]n2)C[C@H]1C(=O)NC(c1ccccc1)c1ccccc1)C(C)(C)C ; Cl ; Cl]
P3-64

TABLE 13-continued
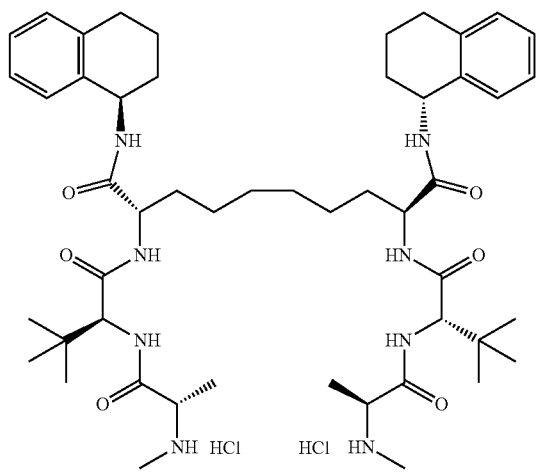 [SMILES: CN[C@@H](C)C(=O)N[C@H](C(=O)N[C@@H](CCCCCC[C@H](NC(=O)[C@@H](NC(=O)[C@H](C)NC)C(C)(C)C)C(=O)N[C@@H]1CCCc2ccccc21)C(=O)N[C@@H]1CCCc2ccccc21)C(C)(C)C ; Cl ; Cl]
P3-65
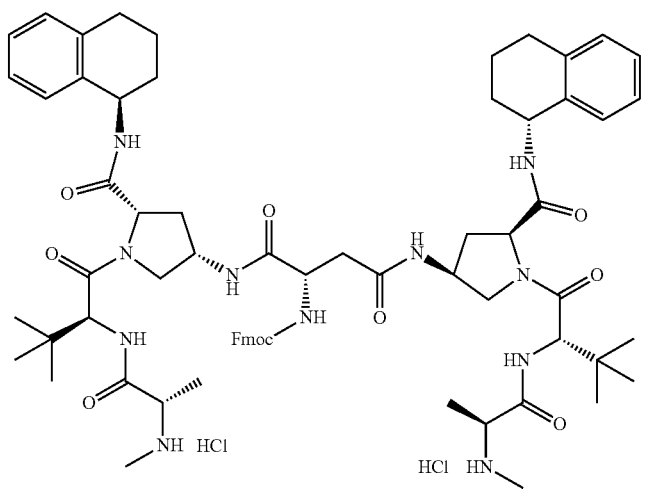
P3-66
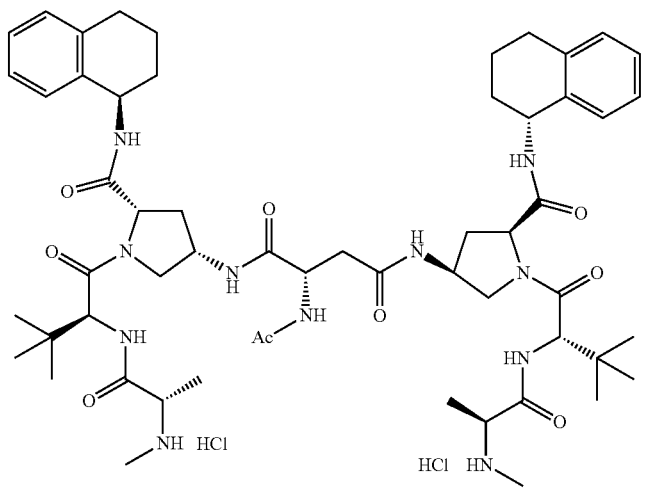 [SMILES: CN[C@@H](C)C(=O)N[C@H](C(=O)N1C[C@@H](NC(=O)C[C@H](NC(C)=O)C(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]
P3-67

TABLE 13-continued
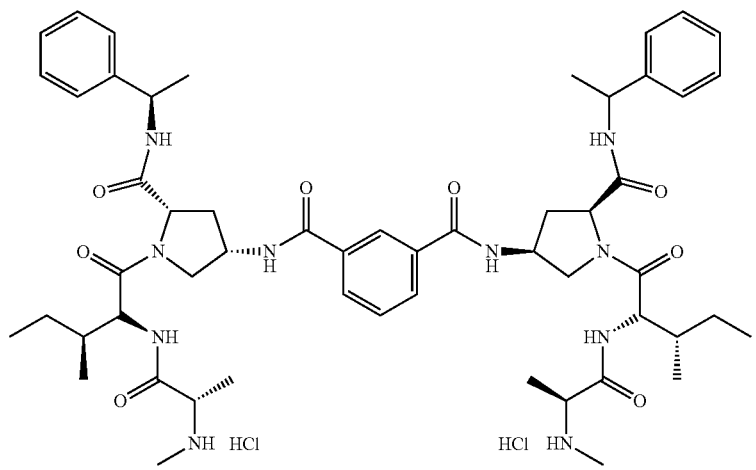
P3-68
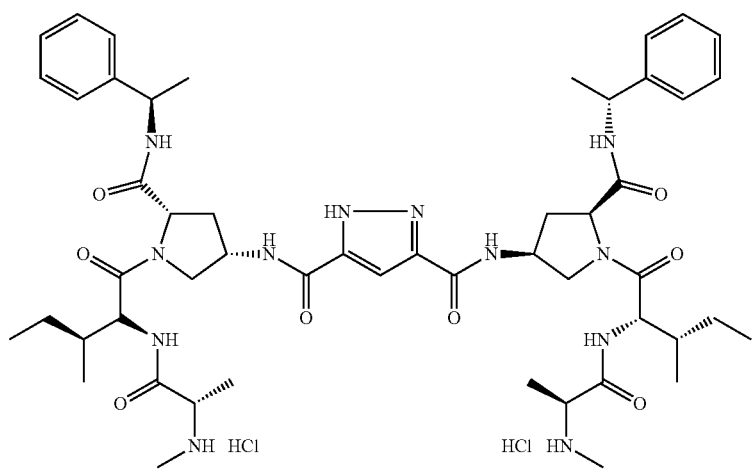
P3-69
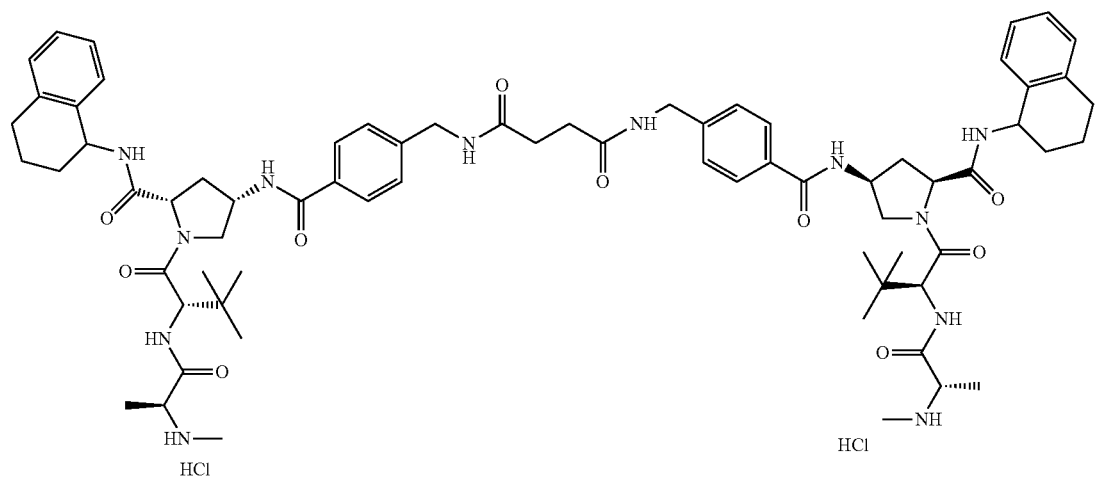
P3-70
Isomer B TABLE 13-continued
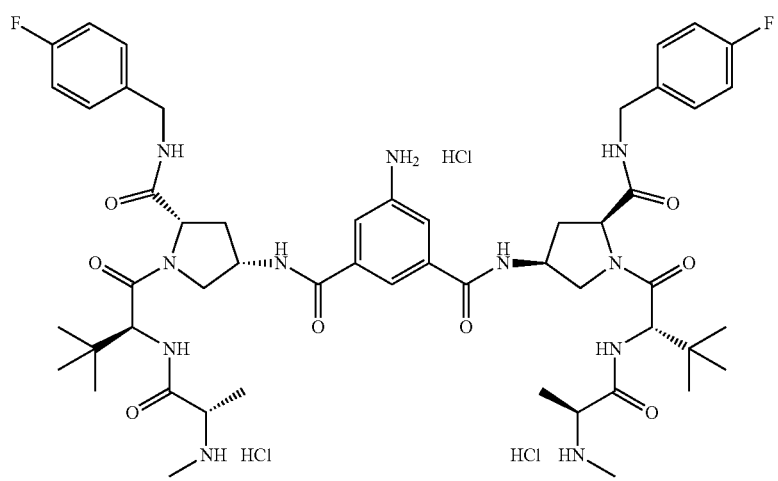 [SMILES: CN[C@@H](C)C(=O)N[C@H](C(=O)N1C[C@@H](NC(=O)c2cc(N)cc(C(=O)N[C@H]3C[C@@H](C(=O)NCc4ccc(F)cc4)N(C(=O)[C@@H](NC(=O)[C@H](C)NC)C(C)(C)C)C3)c2)C[C@H]1C(=O)NCc1ccc(F)cc1)C(C)(C)C ; Cl ; Cl ; Cl]
P3-71
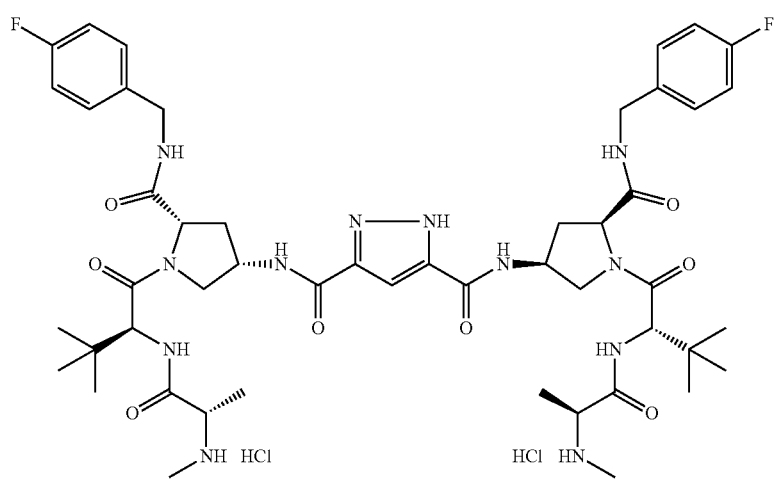 [SMILES: CN[C@@H](C)C(=O)N[C@H](C(=O)N1C[C@@H](NC(=O)c2cc(C(=O)N[C@H]3C[C@@H](C(=O)NCc4ccc(F)cc4)N(C(=O)[C@@H](NC(=O)[C@H](C)NC)C(C)(C)C)C3)[nH]n2)C[C@H]1C(=O)NCc1ccc(F)cc1)C(C)(C)C ; Cl ; Cl]
P3-72
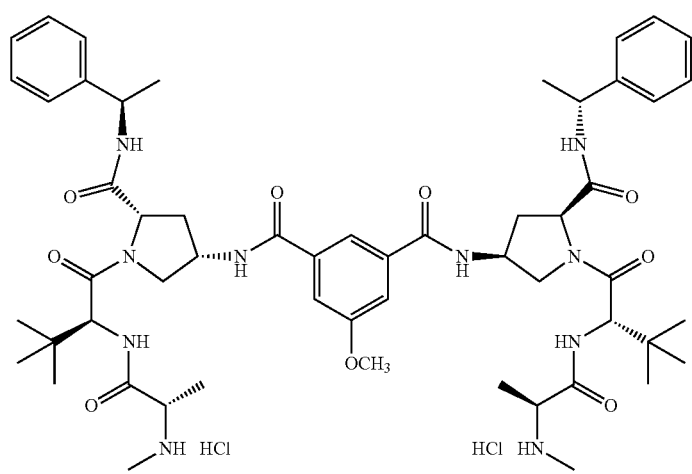 [SMILES: CN[C@@H](C)C(=O)N[C@H](C(=O)N1C[C@@H](NC(=O)c2cc(OC)cc(C(=O)N[C@H]3C[C@@H](C(=O)N[C@H](C)c4ccccc4)N(C(=O)[C@@H](NC(=O)[C@H](C)NC)C(C)(C)C)C3)c2)C[C@H]1C(=O)N[C@H](C)c1ccccc1)C(C)(C)C ; Cl ; Cl]
P3-73

TABLE 13-continued
P3-74
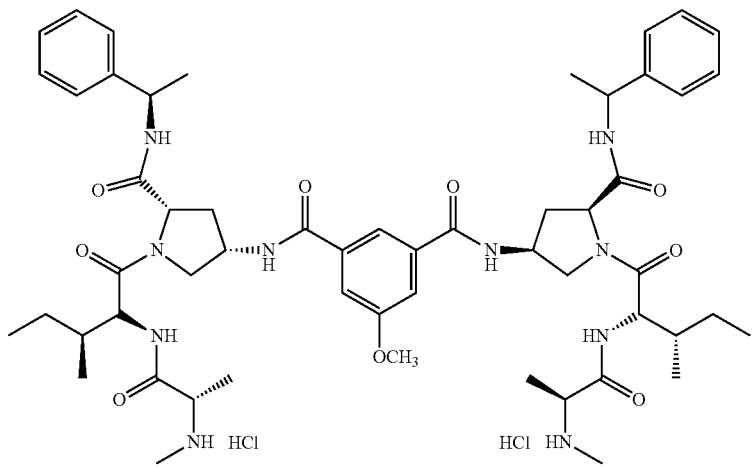
P3-75
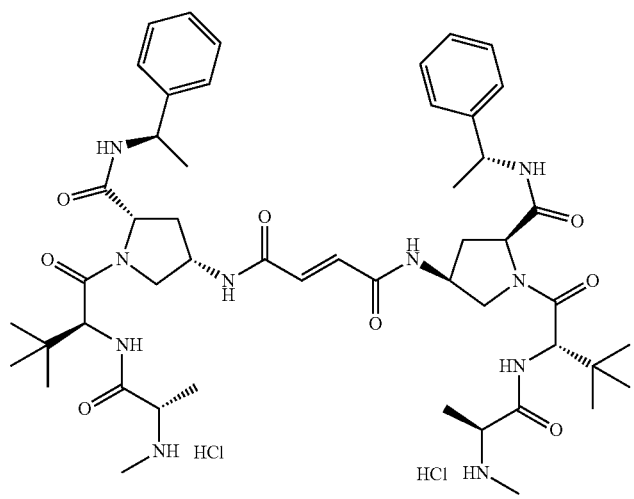 [SMILES: CN[C@@H](C)C(=O)N[C@H](C(=O)N1C[C@@H](NC(=O)/C=C/C(=O)N[C@H]2C[C@@H](C(=O)N[C@H](C)c3ccccc3)N(C(=O)[C@@H](NC(=O)[C@H](C)NC)C(C)(C)C)C2)C[C@H]1C(=O)N[C@H](C)c1ccccc1)C(C)(C)C ; Cl ; Cl]
P3-76
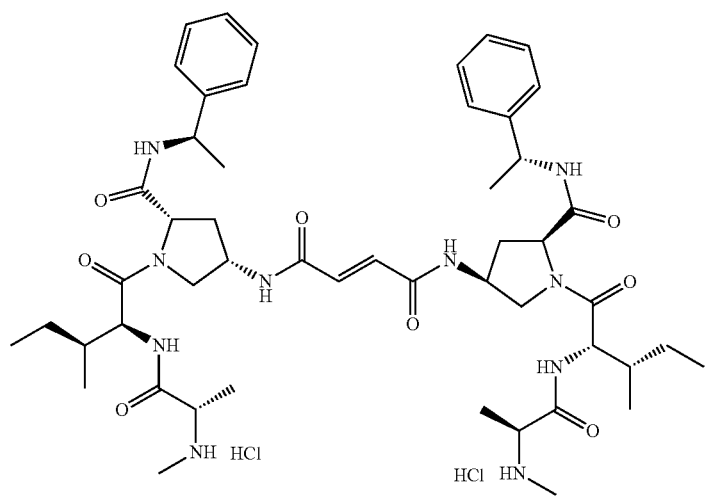 [SMILES: CC[C@H](C)[C@H](NC(=O)[C@H](C)NC)C(=O)N1C[C@@H](NC(=O)/C=C/C(=O)N[C@H]2C[C@@H](C(=O)N[C@H](C)c3ccccc3)N(C(=O)[C@@H](NC(=O)[C@H](C)NC)[C@@H](C)CC)C2)C[C@H]1C(=O)N[C@H](C)c1ccccc1 ; Cl ; Cl]

TABLE 13-continued
P3-77
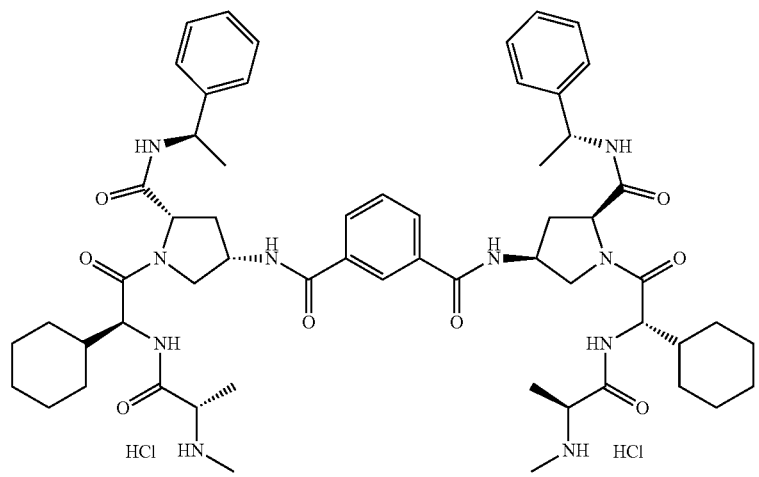 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C4CCCCC4)C3)c2)C[C@H]1C(=O)N[C@H](C)c1ccccc1)C1CCCCC1 ; Cl ; Cl]
P3-78
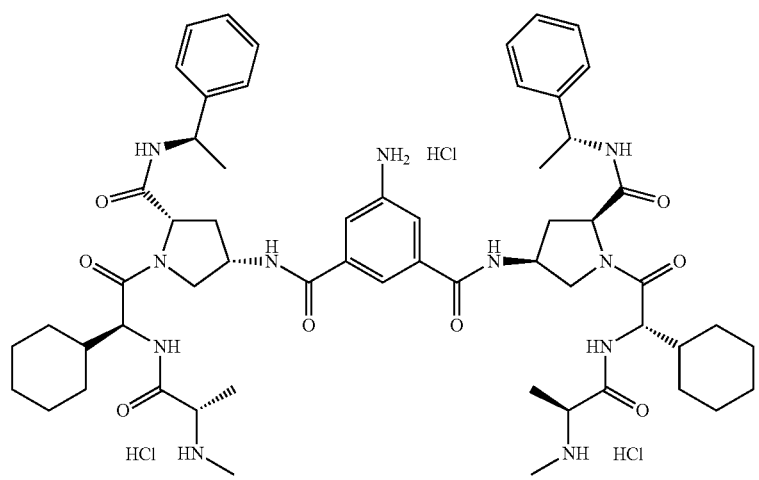 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)C4CCCCC4)C3)c2)C[C@H]1C(=O)N[C@H](C)c1ccccc1)C1CCCCC1 ; Cl ; Cl ; Cl]
P3-79
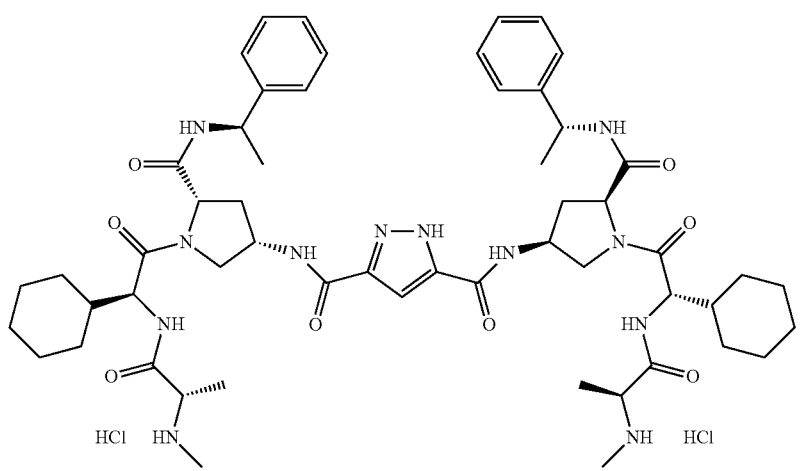 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)C4CCCCC4)C3)[nH]n2)C[C@H]1C(=O)N[C@H](C)c1ccccc1)C1CCCCC1 ; Cl ; Cl]

TABLE 13-continued
P3-80
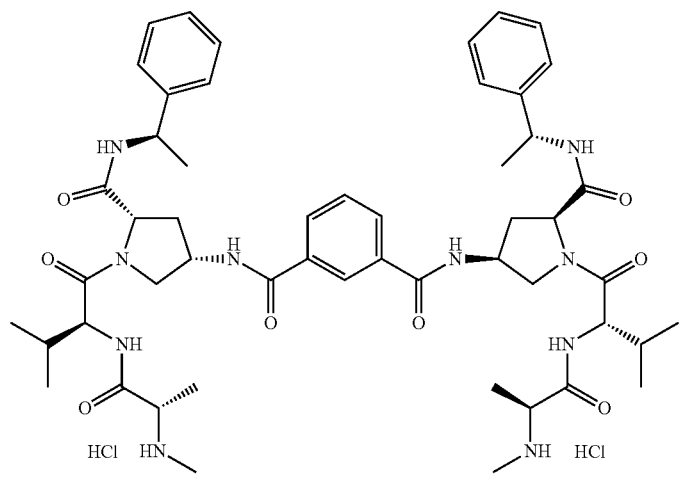 [SMILES: CN[C@@H](C)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](C)NC)C(C)C)C3)c2)C[C@H]1C(=O)N[C@H](C)c1ccccc1)C(C)C ; Cl ; Cl]
P3-81
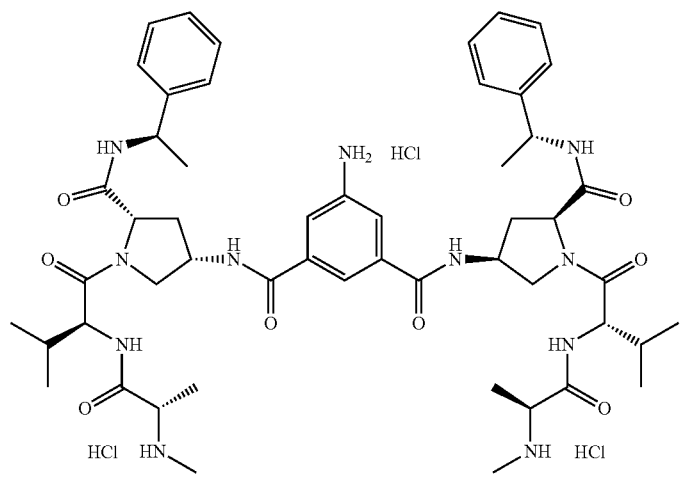 [SMILES: CN[C@@H](C)C(=O)N[C@H](C(=O)N1C[C@@H](NC(=O)c2cc(N)cc(C(=O)N[C@H]3C[C@@H](C(=O)N[C@H](C)c4ccccc4)N(C(=O)[C@@H](NC(=O)[C@H](C)NC)C(C)C)C3)c2)C[C@H]1C(=O)N[C@H](C)c1ccccc1)C(C)C ; Cl ; Cl ; Cl]
P3-82
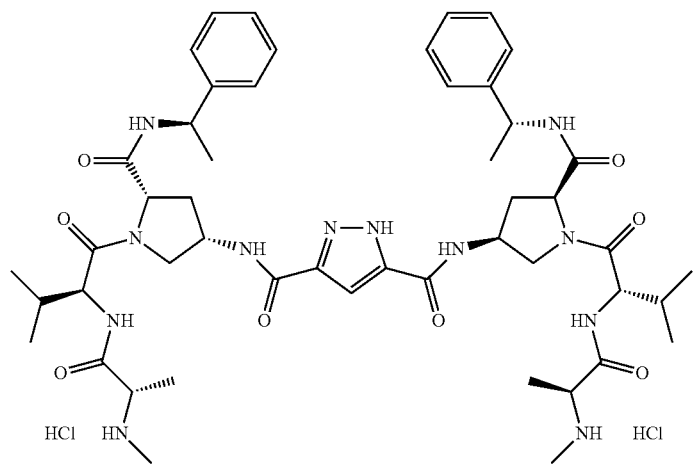 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)C(C)C)C3)[nH]n2)C[C@H]1C(=O)N[C@H](C)c1ccccc1)C(C)C ; Cl ; Cl]

TABLE 13-continued
P3-83
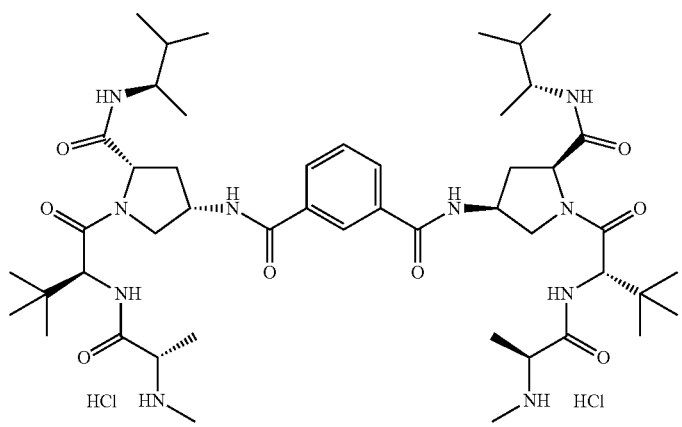 [SMILES: CN[C@@H](C)C(=O)N[C@H](C(=O)N1C[C@@H](NC(=O)c2cccc(C(=O)N[C@H]3C[C@@H](C(=O)N[C@H](C)C(C)C)N(C(=O)[C@@H](NC(=O)[C@H](C)NC)C(C)(C)C)C3)c2)C[C@H]1C(=O)N[C@H](C)C(C)C)C(C)(C)C ; Cl ; Cl]
P3-84
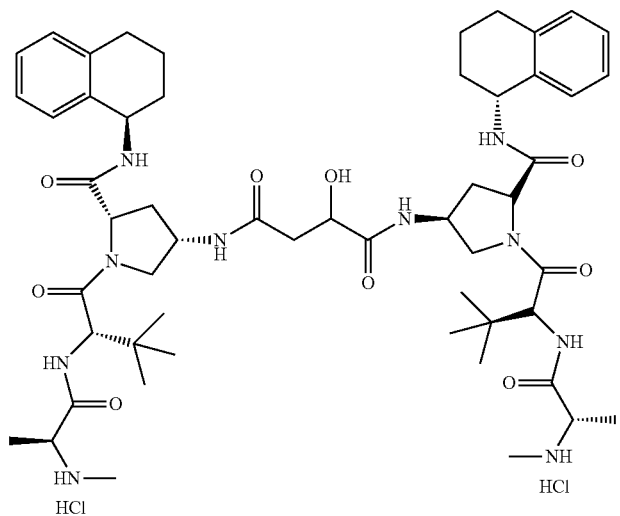
P3-85
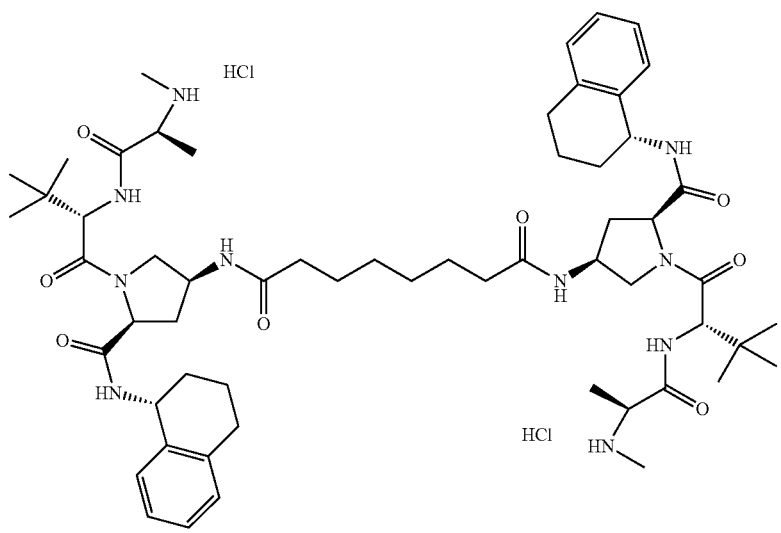 [SMILES: CN[C@@H](C)C(=O)N[C@H](C(=O)N1C[C@@H](NC(=O)CCCCCCC(=O)N[C@H]2C[C@@H](C(=O)N[C@@H]3CCCc4ccccc43)N(C(=O)[C@@H](NC(=O)[C@H](C)NC)C(C)(C)C)C2)C[C@H]1C(=O)N[C@@H]1CCCc2ccccc21)C(C)(C)C ; Cl ; Cl]

P3-86
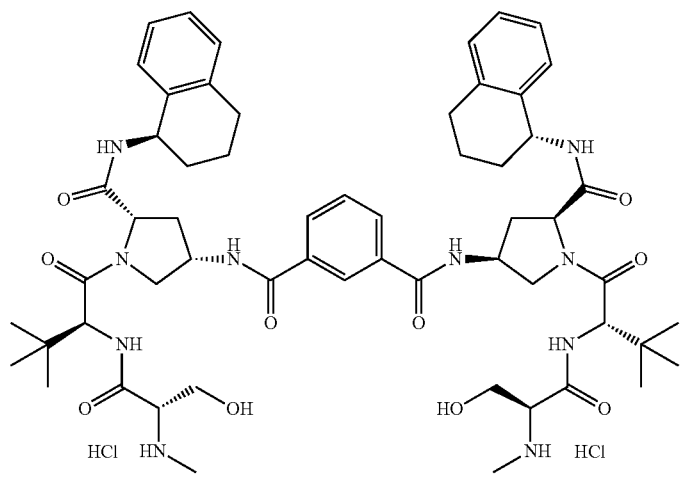 [SMILES: CN[C@@H](CO)C(=O)N[C@H](C(=O)N1C[C@@H](NC(=O)c2cccc(C(=O)N[C@H]3C[C@@H](C(=O)N[C@@H]4CCCc5ccccc54)N(C(=O)[C@@H](NC(=O)[C@H](CO)NC)C(C)(C)C)C3)c2)C[C@H]1C(=O)N[C@@H]1CCCc2ccccc21)C(C)(C)C ; Cl ; Cl]
P3-87
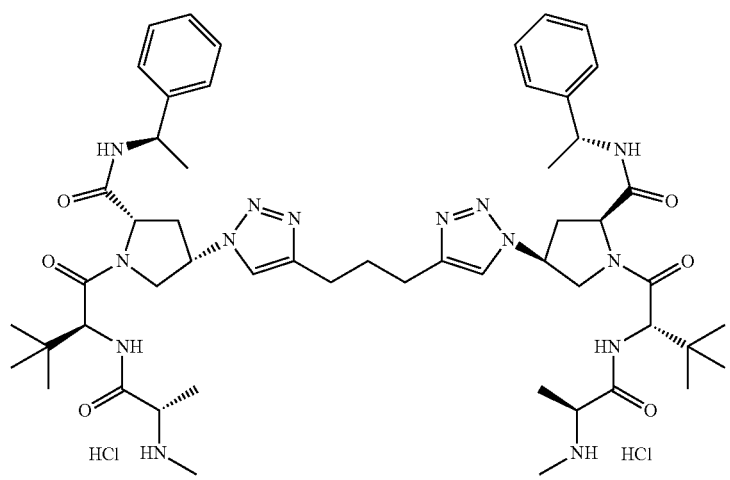 [SMILES: CN[C@@H](C)C(=O)N[C@H](C(=O)N1C[C@@H](n2cc(CCCc3cn([C@H]4C[C@@H](C(=O)N[C@H](C)c5ccccc5)N(C(=O)[C@@H](NC(=O)[C@H](C)NC)C(C)(C)C)C4)nn3)nn2)C[C@H]1C(=O)N[C@H](C)c1ccccc1)C(C)(C)C ; Cl ; Cl]
P3-88
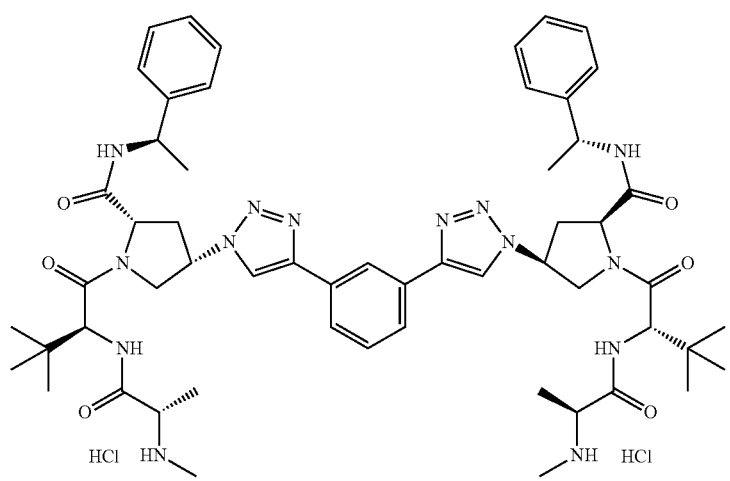 [SMILES: CN[C@@H](C)C(=O)N[C@H](C(=O)N1C[C@@H](n2cc(-c3cccc(-c4cn([C@H]5C[C@@H](C(=O)N[C@H](C)c6ccccc6)N(C(=O)[C@@H](NC(=O)[C@H](C)NC)C(C)(C)C)C5)nn4)c3)nn2)C[C@H]1C(=O)N[C@H](C)c1ccccc1)C(C)(C)C ; Cl ; Cl]

TABLE 13-continued
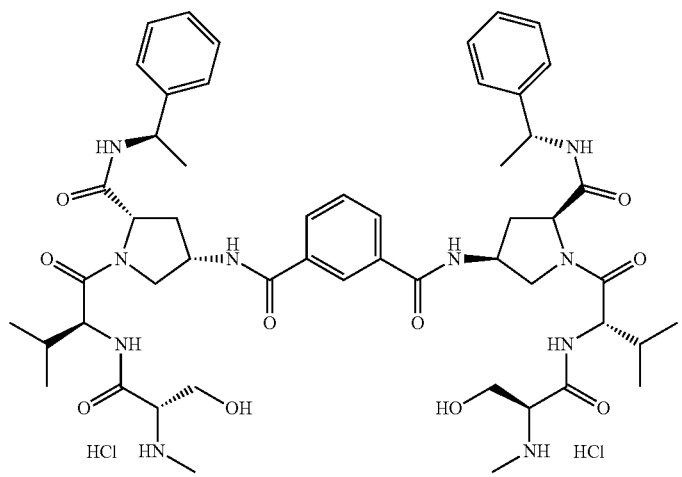 [SMILES: CN[C@@H](CO)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](CO)NC)C(C)C)C3)c2)C[C@H]1C(=O)N[C@H](C)c1ccccc1)C(C)C ; Cl ; Cl]
P3-89
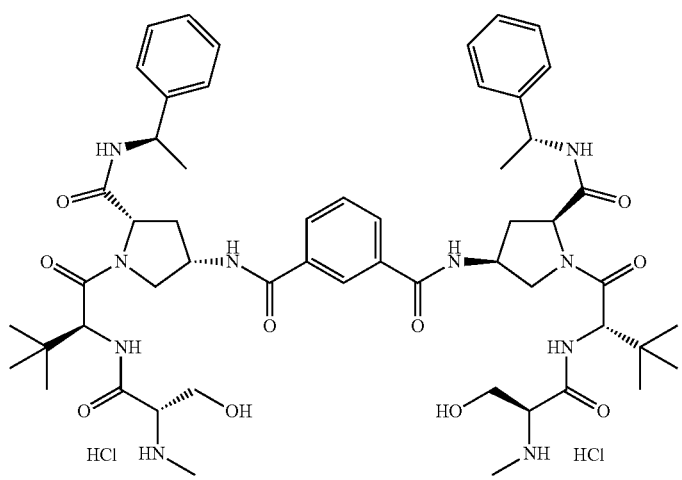 [SMILES: CN[C@@H](CO)C(=O)N[C@H](C(=O)N1C[C@@H](NC(=O)c2cccc(C(=O)N[C@H]3C[C@@H](C(=O)N[C@H](C)c4ccccc4)N(C(=O)[C@@H](NC(=O)[C@H](CO)NC)C(C)(C)C)C3)c2)C[C@H]1C(=O)N[C@H](C)c1ccccc1)C(C)(C)C ; Cl ; Cl]
P3-90
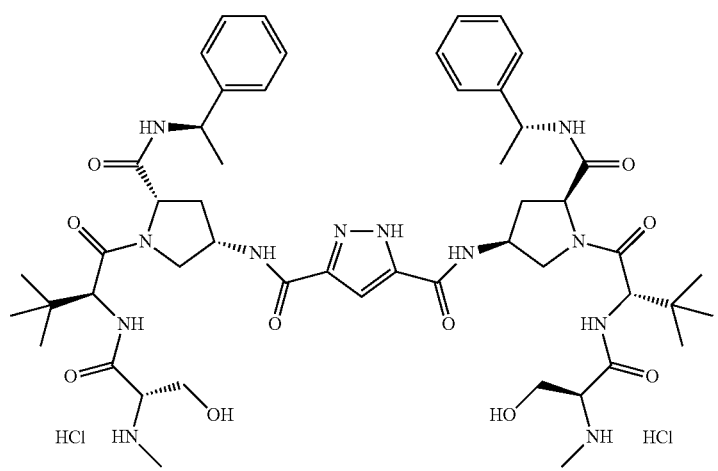 [SMILES: CN[C@@H](CO)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](CO)NC)C(C)(C)C)C3)[nH]n2)C[C@H]1C(=O)N[C@H](C)c1ccccc1)C(C)(C)C ; Cl ; Cl]
P3-91

TABLE 13-continued
P3-92
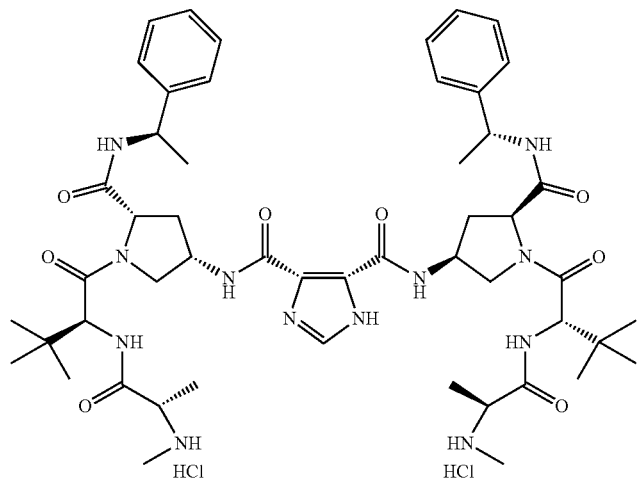
P3-93
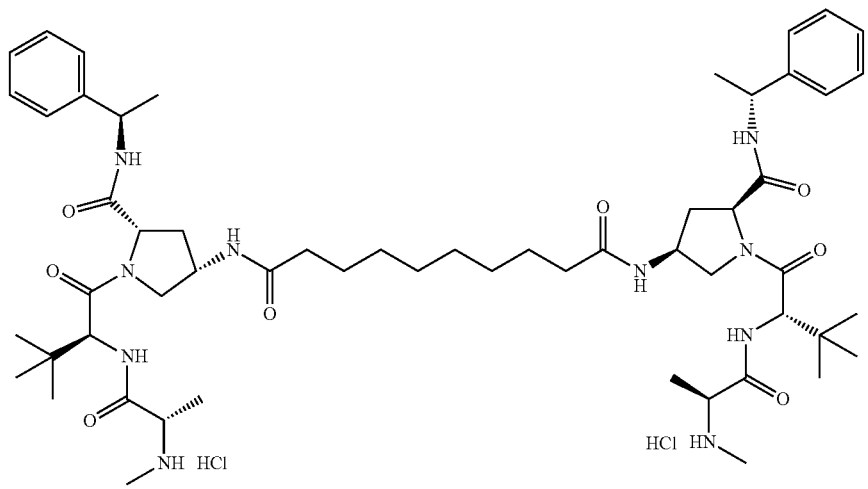 [SMILES: CN[C@@H](C)C(=O)N[C@H](C(=O)N1C[C@@H](NC(=O)CCCCCCCCC(=O)N[C@H]2C[C@@H](C(=O)N[C@H](C)c3ccccc3)N(C(=O)[C@@H](NC(=O)[C@H](C)NC)C(C)(C)C)C2)C[C@H]1C(=O)N[C@H](C)c1ccccc1)C(C)(C)C ; Cl ; Cl]
P3-94
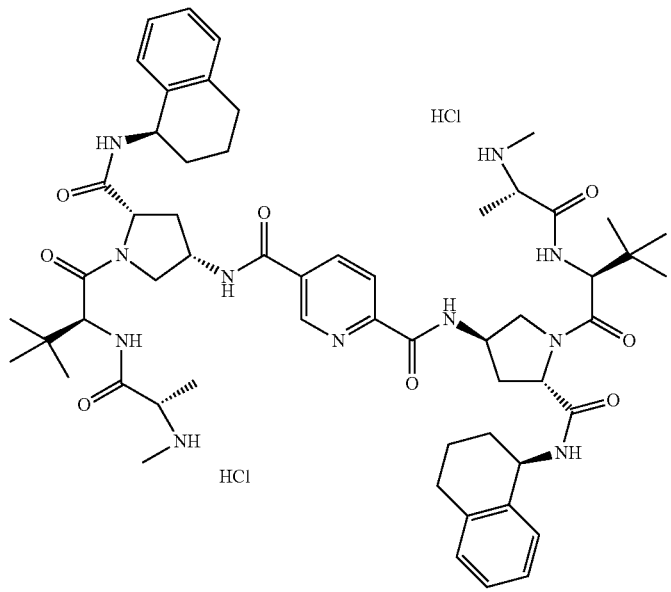 [SMILES: CN[C@@H](C)C(=O)N[C@H](C(=O)N1C[C@@H](NC(=O)c2ccc(C(=O)N[C@@H]3C[C@@H](C(=O)N[C@@H]4CCCc5ccccc54)N(C(=O)[C@@H](NC(=O)[C@H](C)NC)C(C)(C)C)C3)nc2)C[C@H]1C(=O)N[C@@H]1CCCc2ccccc21)C(C)(C)C ; Cl ; Cl]

TABLE 13-continued
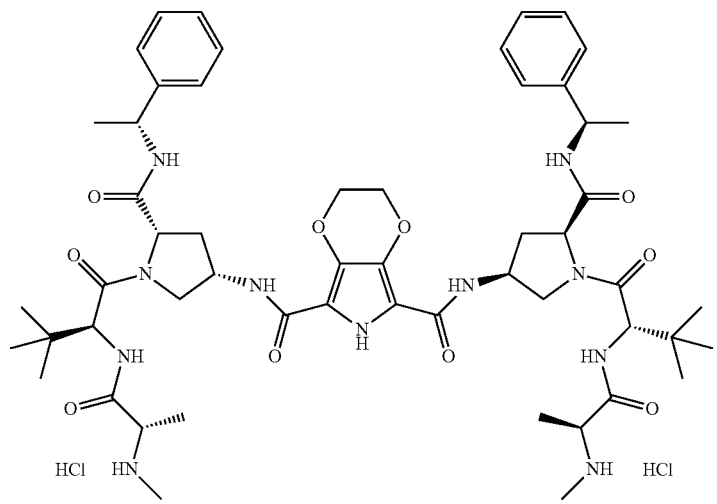 [SMILES: CN[C@@H](C)C(=O)N[C@H](C(=O)N1C[C@@H](NC(=O)c2[nH]c(C(=O)N[C@H]3C[C@@H](C(=O)N[C@H](C)c4ccccc4)N(C(=O)[C@@H](NC(=O)[C@H](C)NC)C(C)(C)C)C3)c3c2OCCO3)C[C@H]1C(=O)N[C@H](C)c1ccccc1)C(C)(C)C ; Cl ; Cl]
P3-95
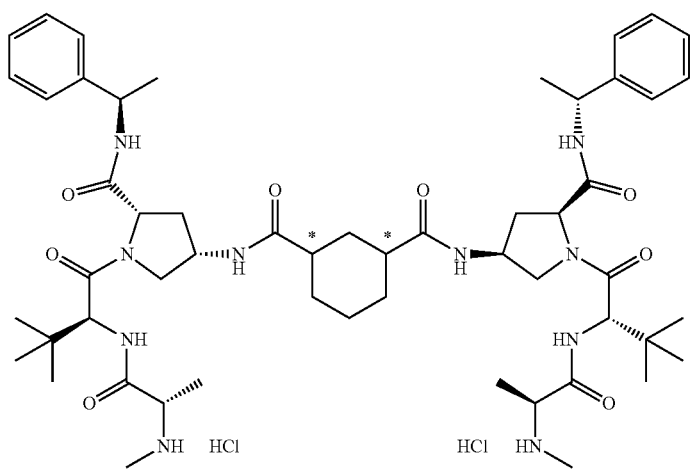 [SMILES: CN[C@@H](C)C(=O)N[C@H](C(=O)N1C[C@@H](NC(=O)C2CCCC(C(=O)N[C@H]3C[C@@H](C(=O)N[C@H](C)c4ccccc4)N(C(=O)[C@@H](NC(=O)[C@H](C)NC)C(C)(C)C)C3)C2)C[C@H]1C(=O)N[C@H](C)c1ccccc1)C(C)(C)C ; Cl ; Cl]
P3-96
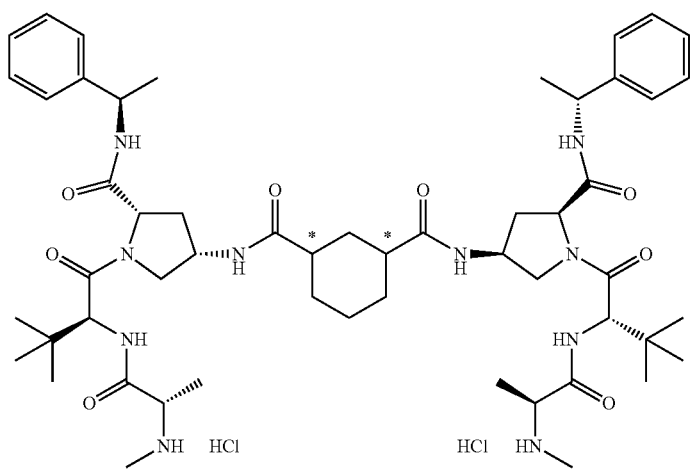 [SMILES: CN[C@@H](C)C(=O)N[C@H](C(=O)N1C[C@@H](NC(=O)C2CCCC(C(=O)N[C@H]3C[C@@H](C(=O)N[C@H](C)c4ccccc4)N(C(=O)[C@@H](NC(=O)[C@H](C)NC)C(C)(C)C)C3)C2)C[C@H]1C(=O)N[C@H](C)c1ccccc1)C(C)(C)C ; Cl ; Cl]
P3-97

TABLE 13-continued
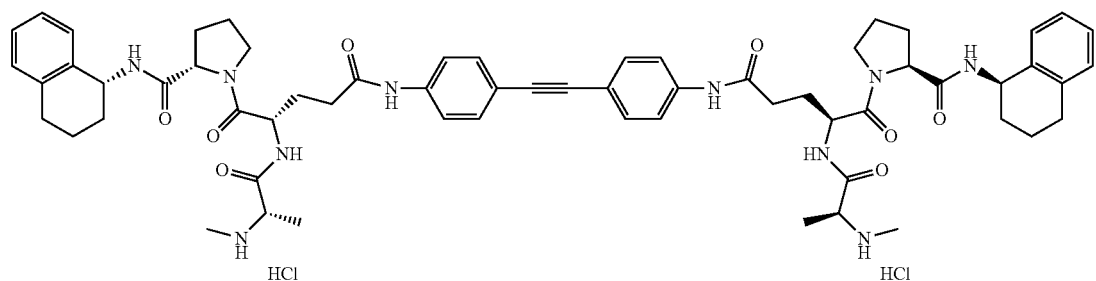 [SMILES: CN[C@@H](C)C(=O)N[C@@H](CCC(=O)Nc1ccc(C#Cc2ccc(NC(=O)CC[C@H](NC(=O)[C@H](C)NC)C(=O)N3CCC[C@H]3C(=O)N[C@@H]3CCCc4ccccc43)cc2)cc1)C(=O)N1CCC[C@H]1C(=O)N[C@@H]1CCCc2ccccc21 ; Cl ; Cl]
P3-98
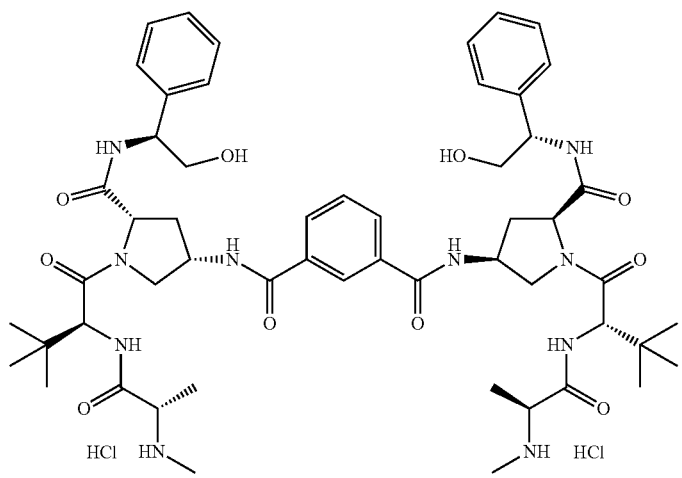 [SMILES: CN[C@@H](C)C(=O)N[C@H](C(=O)N1C[C@@H](NC(=O)c2cccc(C(=O)N[C@H]3C[C@@H](C(=O)N[C@H](CO)c4ccccc4)N(C(=O)[C@@H](NC(=O)[C@H](C)NC)C(C)(C)C)C3)c2)C[C@H]1C(=O)N[C@H](CO)c1ccccc1)C(C)(C)C ; Cl ; Cl]
P3-99
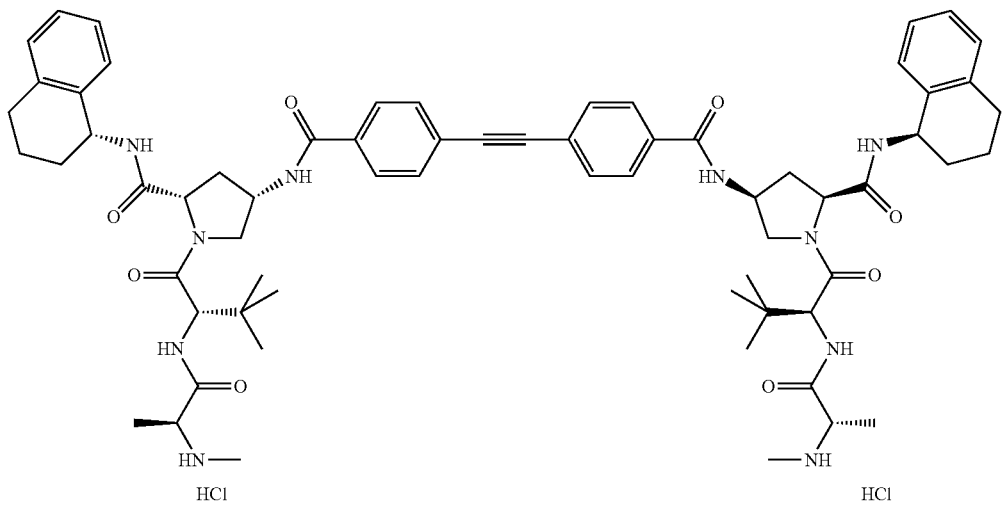 [SMILES: CN[C@@H](C)C(=O)N[C@H](C(=O)N1C[C@@H](NC(=O)c2ccc(C#Cc3ccc(C(=O)N[C@H]4C[C@@H](C(=O)N[C@@H]5CCCc6ccccc65)N(C(=O)[C@@H](NC(=O)[C@H](C)NC)C(C)(C)C)C4)cc3)cc2)C[C@H]1C(=O)N[C@@H]1CCCc2ccccc21)C(C)(C)C ; Cl ; Cl]
P3-100

TABLE 13-continued
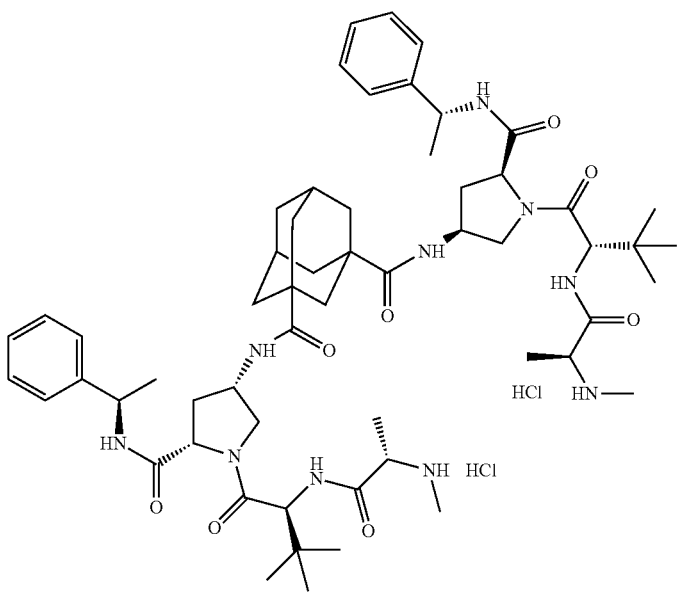 [SMILES: CN[C@@H](C)C(=O)N[C@H](C(=O)N1C[C@@H](NC(=O)C23CC4CC(C2)CC(C(=O)N[C@H]2C[C@@H](C(=O)N[C@H](C)c5ccccc5)N(C(=O)[C@@H](NC(=O)[C@H](C)NC)C(C)(C)C)C2)(C4)C3)C[C@H]1C(=O)N[C@H](C)c1ccccc1)C(C)(C)C ; Cl ; Cl]
P3-101
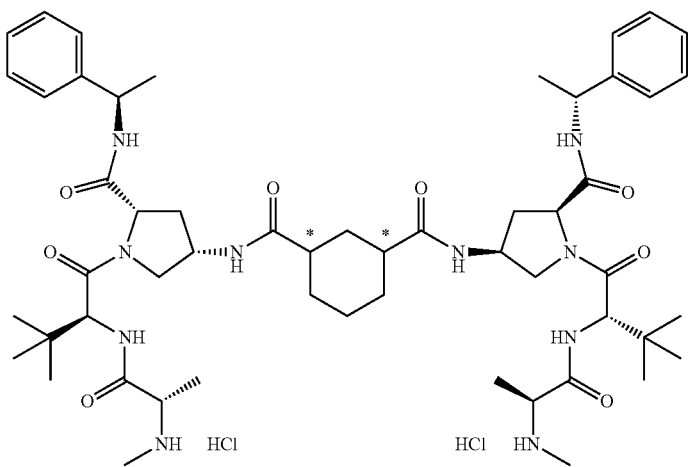 [SMILES: CN[C@@H](C)C(=O)N[C@H](C(=O)N1C[C@@H](NC(=O)C2CCCC(C(=O)N[C@H]3C[C@@H](C(=O)N[C@H](C)c4ccccc4)N(C(=O)[C@@H](NC(=O)[C@H](C)NC)C(C)(C)C)C3)C2)C[C@H]1C(=O)N[C@H](C)c1ccccc1)C(C)(C)C ; Cl ; Cl]
P3-102
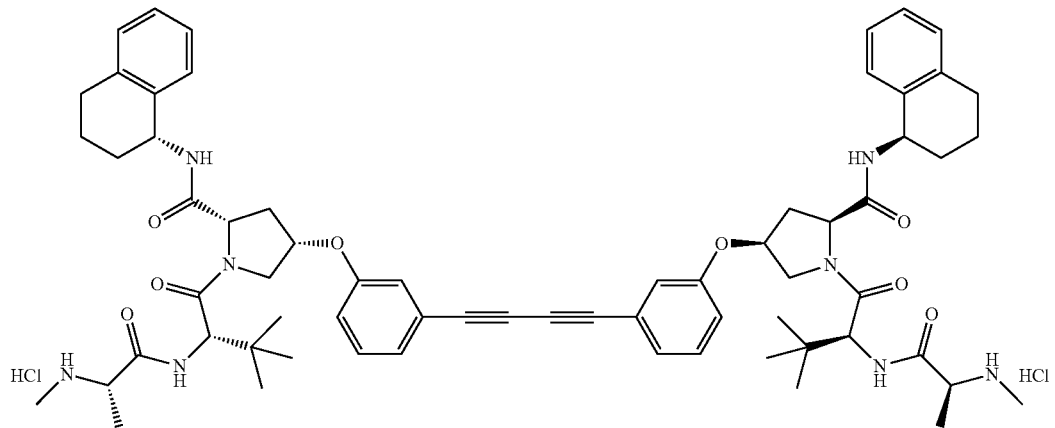
P3-103

TABLE 13-continued
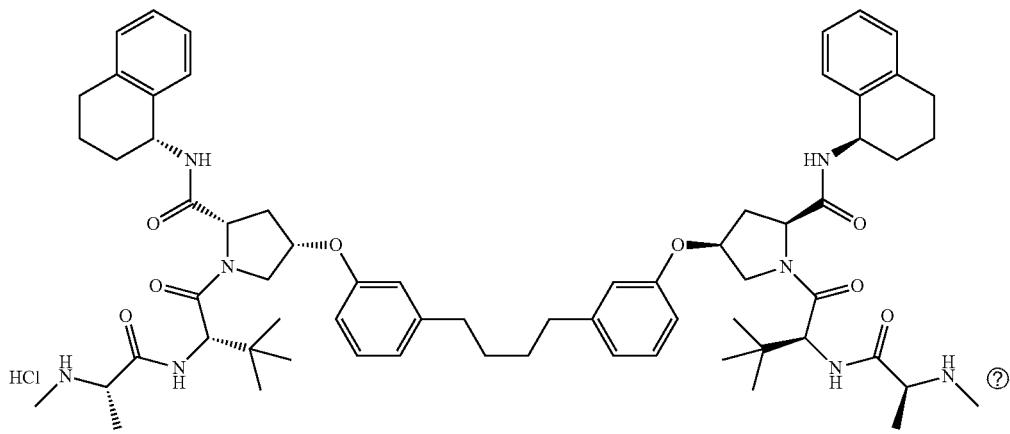
P3-104
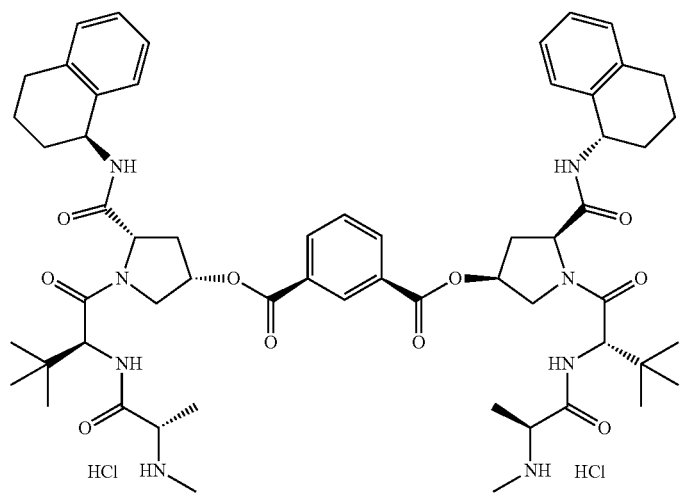
P3-105
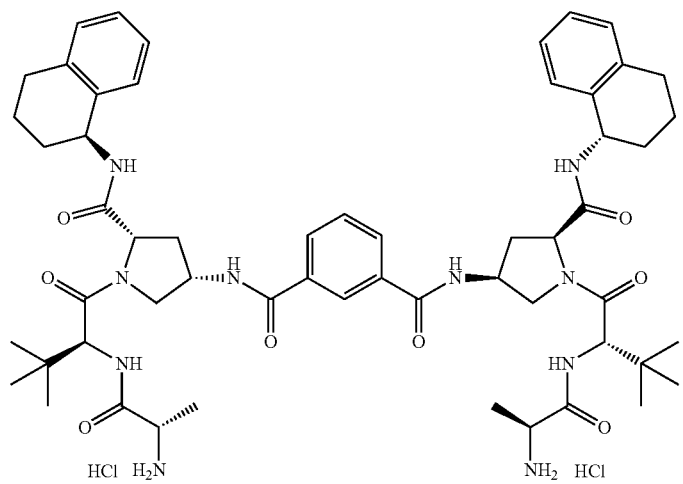 [SMILES: C[C@H](N)C(=O)N[C@H](C(=O)N1C[C@@H](NC(=O)c2cccc(C(=O)N[C@H]3C[C@@H](C(=O)N[C@H]4CCCc5ccccc54)N(C(=O)[C@@H](NC(=O)[C@H](C)N)C(C)(C)C)C3)c2)C[C@H]1C(=O)N[C@H]1CCCc2ccccc21)C(C)(C)C ; Cl ; Cl]
P3-106

TABLE 13-continued
P3-107
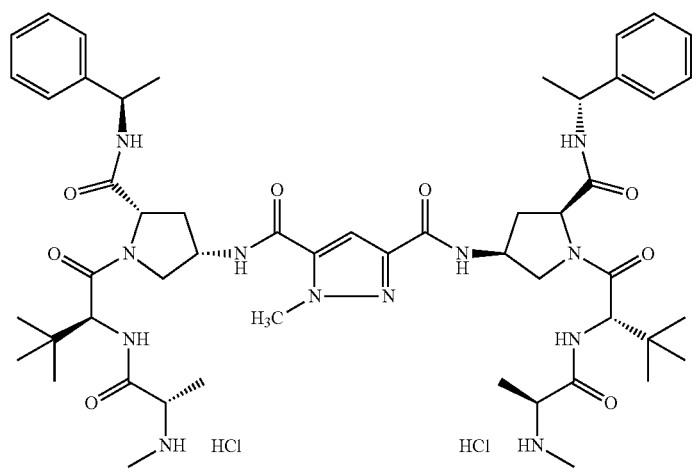 [SMILES: CN[C@@H](C)C(=O)N[C@H](C(=O)N1C[C@@H](NC(=O)c2cc(C(=O)N[C@H]3C[C@@H](C(=O)N[C@H](C)c4ccccc4)N(C(=O)[C@@H](NC(=O)[C@H](C)NC)C(C)(C)C)C3)n(C)n2)C[C@H]1C(=O)N[C@H](C)c1ccccc1)C(C)(C)C ; Cl ; Cl]
P3-108
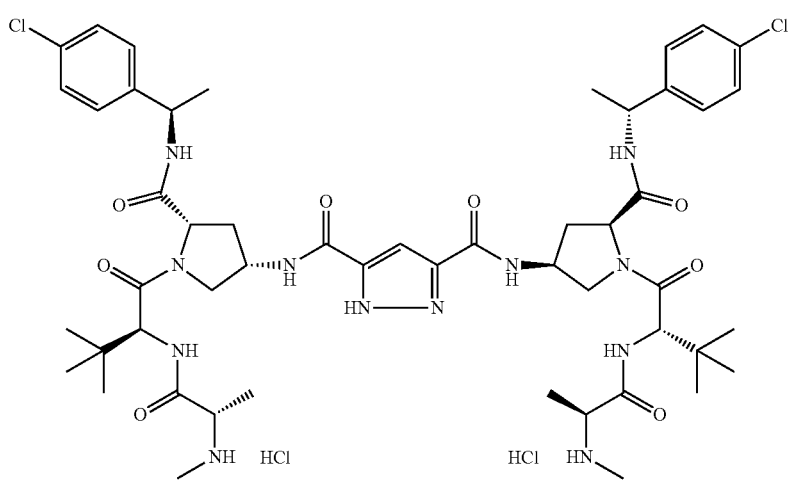 [SMILES: CN[C@@H](C)C(=O)N[C@H](C(=O)N1C[C@@H](NC(=O)c2cc(C(=O)N[C@H]3C[C@@H](C(=O)N[C@H](C)c4ccc(Cl)cc4)N(C(=O)[C@@H](NC(=O)[C@H](C)NC)C(C)(C)C)C3)[nH]n2)C[C@H]1C(=O)N[C@H](C)c1ccc(Cl)cc1)C(C)(C)C ; Cl ; Cl]
P3-109
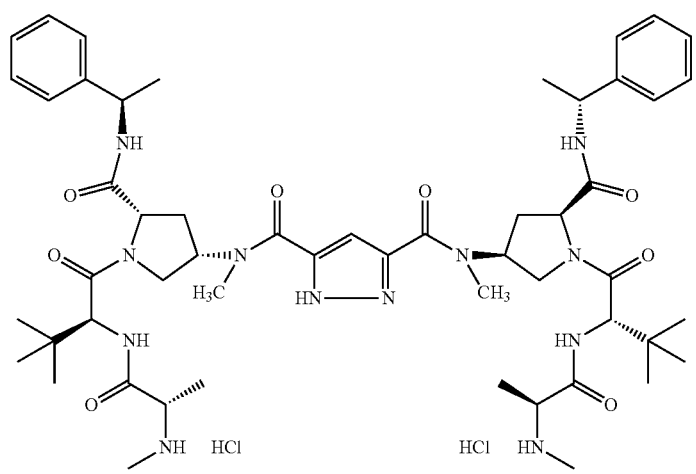 [SMILES: CN[C@@H](C)C(=O)N[C@H](C(=O)N1C[C@@H](N(C)C(=O)c2cc(C(=O)N(C)[C@H]3C[C@@H](C(=O)N[C@H](C)c4ccccc4)N(C(=O)[C@@H](NC(=O)[C@H](C)NC)C(C)(C)C)C3)[nH]n2)C[C@H]1C(=O)N[C@H](C)c1ccccc1)C(C)(C)C ; Cl ; Cl]

TABLE 13-continued
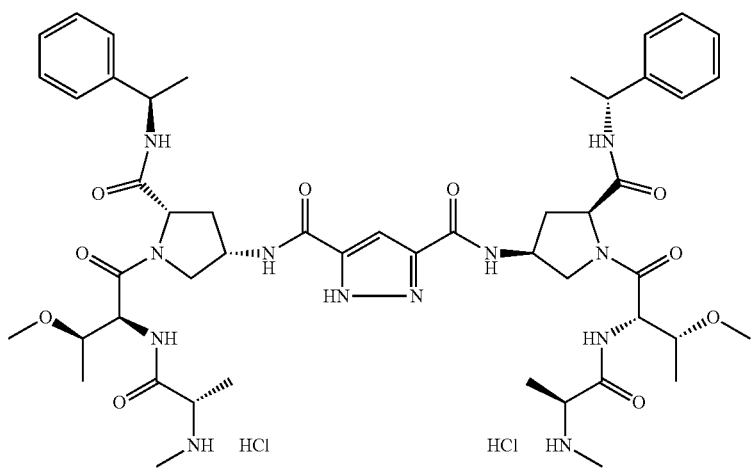
P3-110
TABLE 14
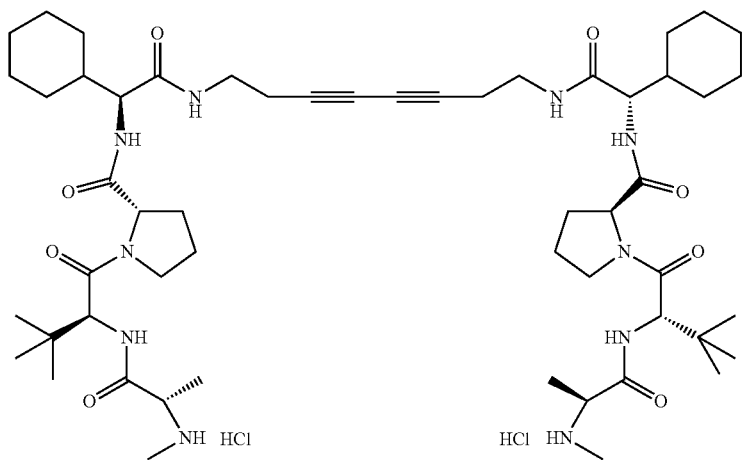 [SMILES: CN[C@@H](C)C(=O)N[C@H](C(=O)N1CCC[C@H]1C(=O)N[C@H](C(=O)NCCC#CC#CCCNC(=O)[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl]
P4-1
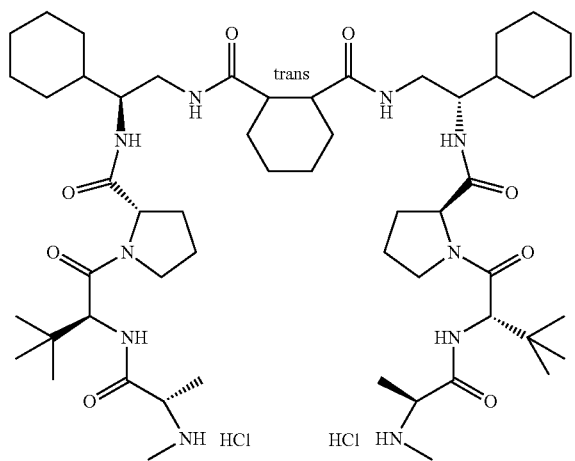
P4-2

TABLE 14-continued
P4-3
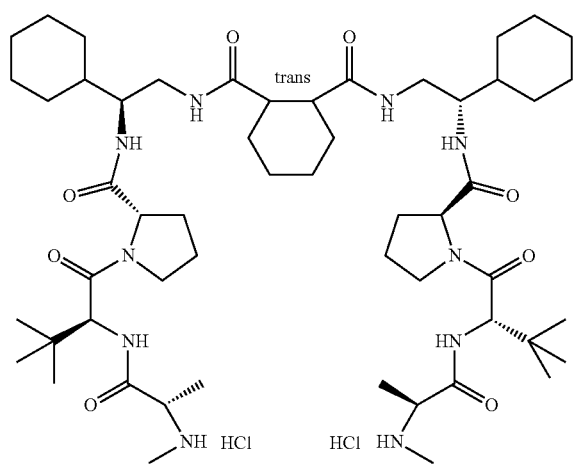 [SMILES: CN[C@@H](C)C(=O)N[C@H](C(=O)N1CCC[C@H]1C(=O)N[C@H](CNC(=O)C1CCCCC1C(=O)NC[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl]
Trans Isomer 2
P4-4
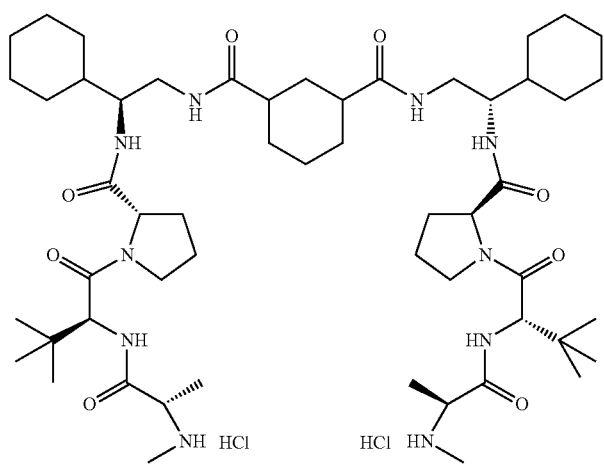 [SMILES: CN[C@@H](C)C(=O)N[C@H](C(=O)N1CCC[C@H]1C(=O)N[C@H](CNC(=O)C1CCCC(C(=O)NC[C@@H](NC(=O)[C@@H]2CCCN2C(=O)[C@@H](NC(=O)[C@H](C)NC)C(C)(C)C)C2CCCCC2)C1)C1CCCCC1)C(C)(C)C ; Cl ; Cl]
P4-5
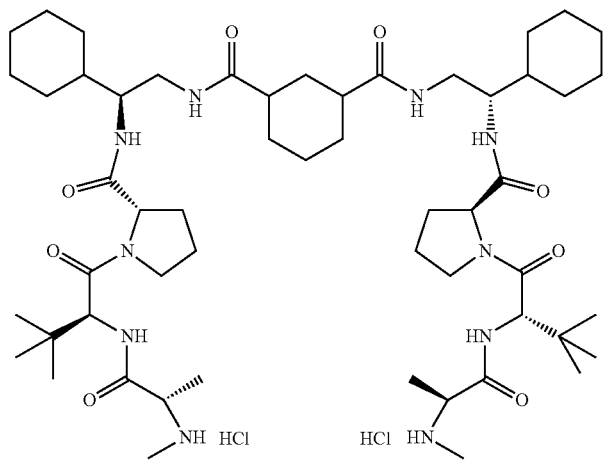 [SMILES: CN[C@@H](C)C(=O)N[C@H](C(=O)N1CCC[C@H]1C(=O)N[C@H](CNC(=O)C1CCCC(C(=O)NC[C@@H](NC(=O)[C@@H]2CCCN2C(=O)[C@@H](NC(=O)[C@H](C)NC)C(C)(C)C)C2CCCCC2)C1)C1CCCCC1)C(C)(C)C ; Cl ; Cl]

TABLE 14-continued
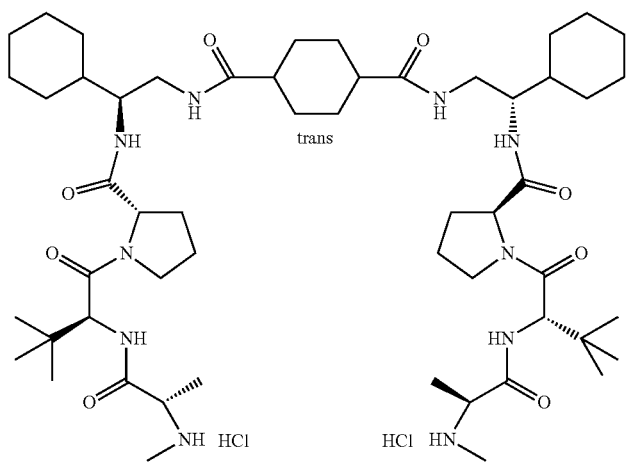 [SMILES: CN[C@@H](C)C(=O)N[C@H](C(=O)N1CCC[C@H]1C(=O)N[C@H](CNC(=O)C1CCC(C(=O)NC[C@@H](NC(=O)[C@@H]2CCCN2C(=O)[C@@H](NC(=O)[C@H](C)NC)C(C)(C)C)C2CCCCC2)CC1)C1CCCCC1)C(C)(C)C ; Cl ; Cl]
P4-6
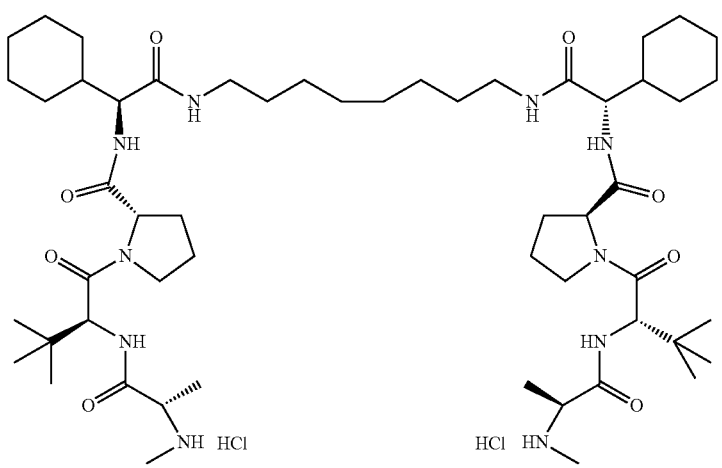 [SMILES: CN[C@@H](C)C(=O)N[C@H](C(=O)N1CCC[C@H]1C(=O)N[C@H](C(=O)NCCCCCCCCNC(=O)[C@@H](NC(=O)[C@@H]1CCCN1C(=O)[C@@H](NC(=O)[C@H](C)NC)C(C)(C)C)C1CCCCC1)C1CCCCC1)C(C)(C)C ; Cl ; Cl]
P4-7
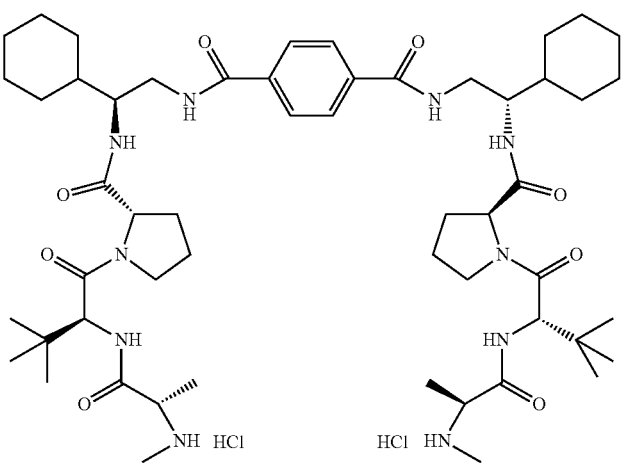 [SMILES: CN[C@@H](C)C(=O)N[C@H](C(=O)N1CCC[C@H]1C(=O)N[C@H](CNC(=O)c1ccc(C(=O)NC[C@@H](NC(=O)[C@@H]2CCCN2C(=O)[C@@H](NC(=O)[C@H](C)NC)C(C)(C)C)C2CCCCC2)cc1)C1CCCCC1)C(C)(C)C ; Cl ; Cl]
P4-8

TABLE 14-continued
P4-9
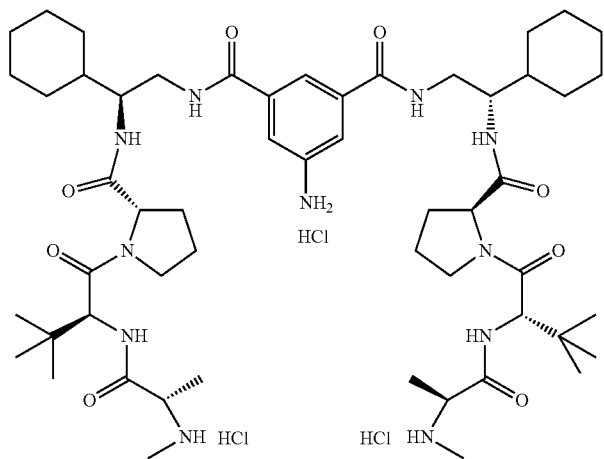 [SMILES: CN[C@@H](C)C(=O)N[C@H](C(=O)N1CCC[C@H]1C(=O)N[C@H](CNC(=O)c1cc(N)cc(C(=O)NC[C@@H](NC(=O)[C@@H]2CCCN2C(=O)[C@@H](NC(=O)[C@H](C)NC)C(C)(C)C)C2CCCCC2)c1)C1CCCCC1)C(C)(C)C ; Cl ; Cl ; Cl]
P4-10
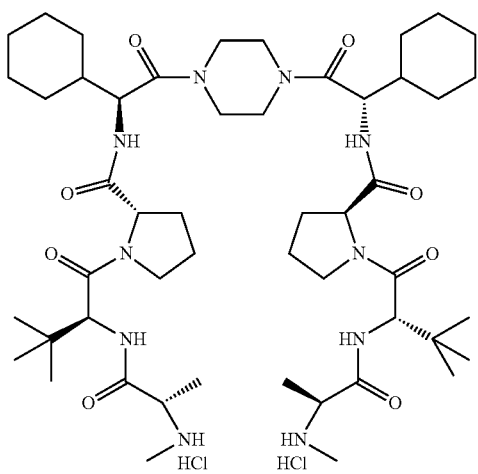 [SMILES: CN[C@@H](C)C(=O)N[C@H](C(=O)N1CCC[C@H]1C(=O)N[C@H](C(=O)N1CCN(C(=O)[C@@H](NC(=O)[C@@H]2CCCN2C(=O)[C@@H](NC(=O)[C@H](C)NC)C(C)(C)C)C2CCCCC2)CC1)C1CCCCC1)C(C)(C)C ; Cl ; Cl]
P4-11
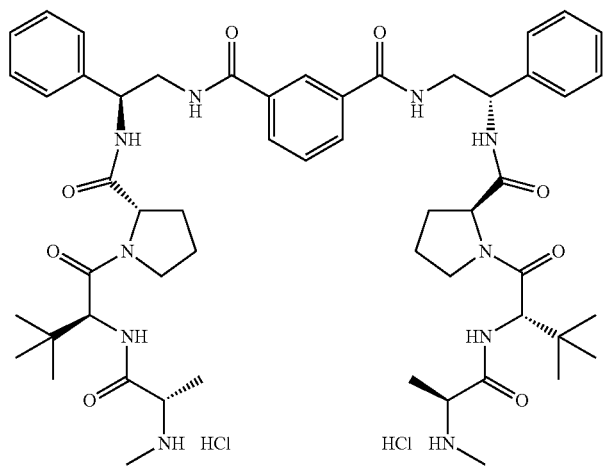 [SMILES: CN[C@@H](C)C(=O)N[C@H](C(=O)N1CCC[C@H]1C(=O)N[C@H](CNC(=O)c1cccc(C(=O)NC[C@@H](NC(=O)[C@@H]2CCCN2C(=O)[C@@H](NC(=O)[C@H](C)NC)C(C)(C)C)c2ccccc2)c1)c1ccccc1)C(C)(C)C ; Cl ; Cl]

TABLE 14-continued
P4-12
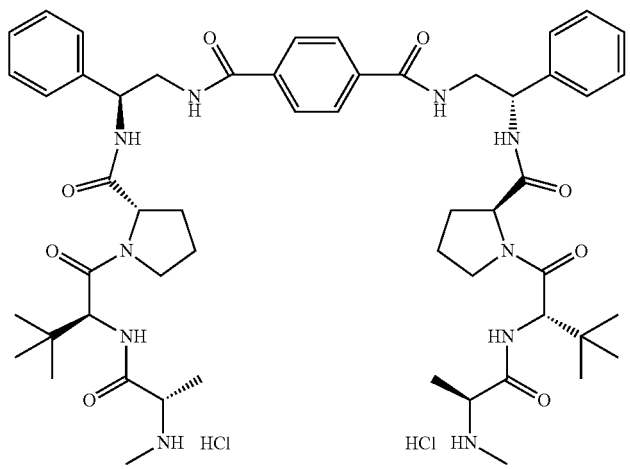 [SMILES: CN[C@@H](C)C(=O)N[C@H](C(=O)N1CCC[C@H]1C(=O)N[C@H](CNC(=O)c1ccc(C(=O)NC[C@@H](NC(=O)[C@@H]2CCCN2C(=O)[C@@H](NC(=O)[C@H](C)NC)C(C)(C)C)c2ccccc2)cc1)c1ccccc1)C(C)(C)C ; Cl ; Cl]
P4-13
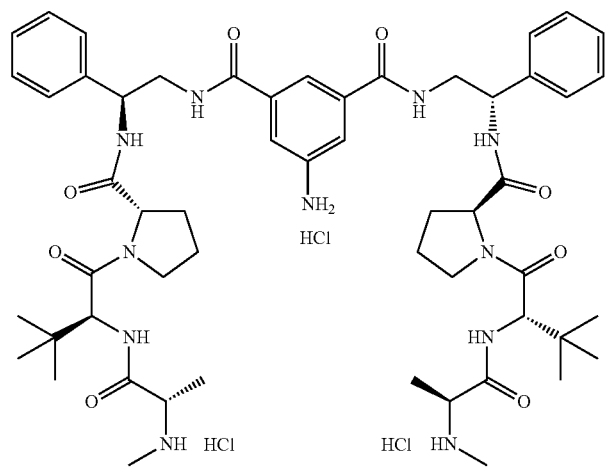 [SMILES: CN[C@@H](C)C(=O)N[C@H](C(=O)N1CCC[C@H]1C(=O)N[C@H](CNC(=O)c1cc(N)cc(C(=O)NC[C@@H](NC(=O)[C@@H]2CCCN2C(=O)[C@@H](NC(=O)[C@H](C)NC)C(C)(C)C)c2ccccc2)c1)c1ccccc1)C(C)(C)C ; Cl ; Cl ; Cl]
P4-14
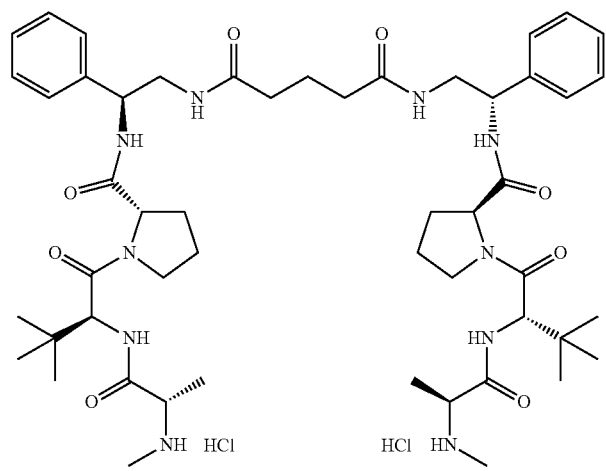 [SMILES: CN[C@@H](C)C(=O)N[C@H](C(=O)N1CCC[C@H]1C(=O)N[C@H](CNC(=O)CCCC(=O)NC[C@@H](NC(=O)[C@@H]1CCCN1C(=O)[C@@H](NC(=O)[C@H](C)NC)C(C)(C)C)c1ccccc1)c1ccccc1)C(C)(C)C ; Cl ; Cl]

TABLE 14-continued
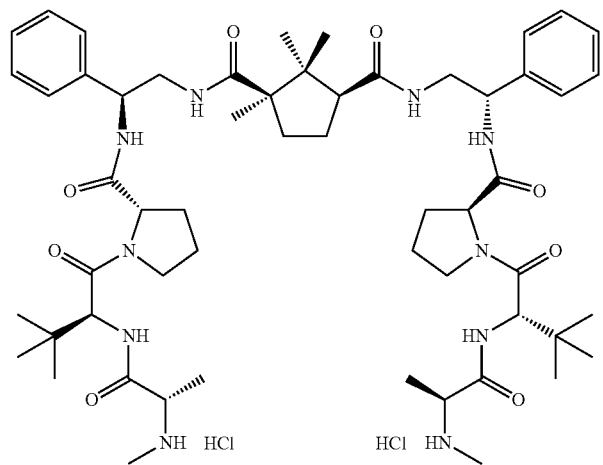
P4-15
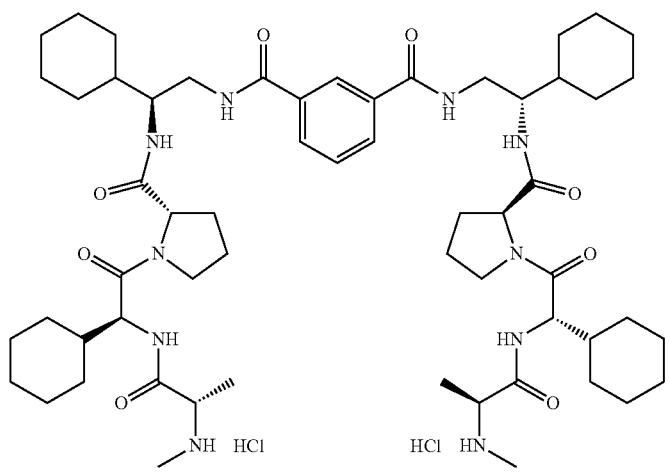 [SMILES: CN[C@@H](C)C(=O)N[C@H](C(=O)N1CCC[C@H]1C(=O)N[C@H](CNC(=O)c1cccc(C(=O)NC[C@@H](NC(=O)[C@@H]2CCCN2C(=O)[C@@H](NC(=O)[C@H](C)NC)C2CCCCC2)C2CCCCC2)c1)C1CCCCC1)C1CCCCC1 ; Cl ; Cl]
P4-16
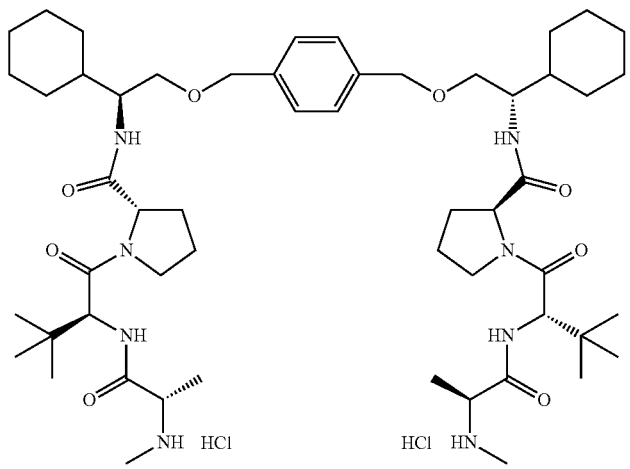 [SMILES: CN[C@@H](C)C(=O)N[C@H](C(=O)N1CCC[C@H]1C(=O)N[C@H](COCc1ccc(COC[C@@H](NC(=O)[C@@H]2CCCN2C(=O)[C@@H](NC(=O)[C@H](C)NC)C(C)(C)C)C2CCCCC2)cc1)C1CCCCC1)C(C)(C)C ; Cl ; Cl]
P4-17

TABLE 14-continued
P4-18
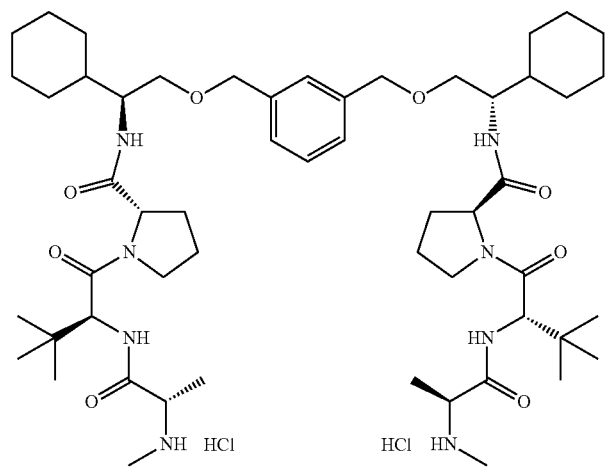 [SMILES: CN[C@@H](C)C(=O)N[C@H](C(=O)N1CCC[C@H]1C(=O)N[C@H](COCc1cccc(COC[C@@H](NC(=O)[C@@H]2CCCN2C(=O)[C@@H](NC(=O)[C@H](C)NC)C(C)(C)C)C2CCCCC2)c1)C1CCCCC1)C(C)(C)C ; Cl ; Cl]
P4-19
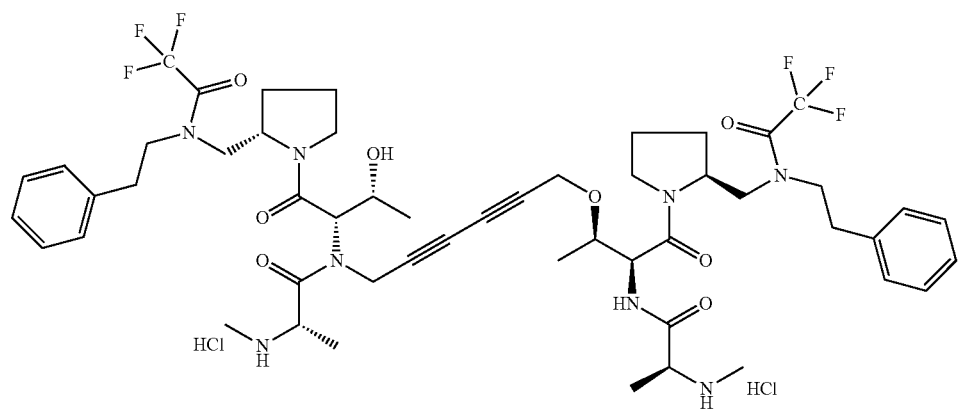 [SMILES: CN[C@@H](C)C(=O)N[C@H](C(=O)N1CCC[C@H]1CN(CCc1ccccc1)C(=O)C(F)(F)F)[C@@H](C)OCC#CC#CCN(C(=O)[C@H](C)NC)[C@H](C(=O)N1CCC[C@H]1CN(CCc1ccccc1)C(=O)C(F)(F)F)[C@@H](C)O ; Cl ; Cl]
P4-20
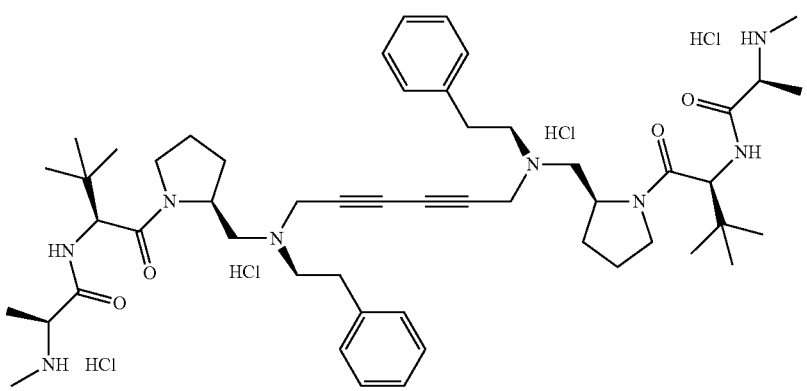

TABLE 14-continued
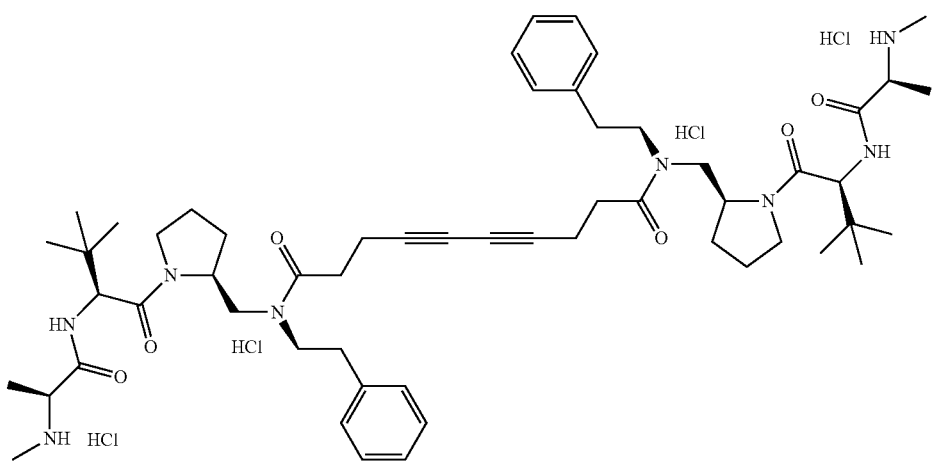
P4-21
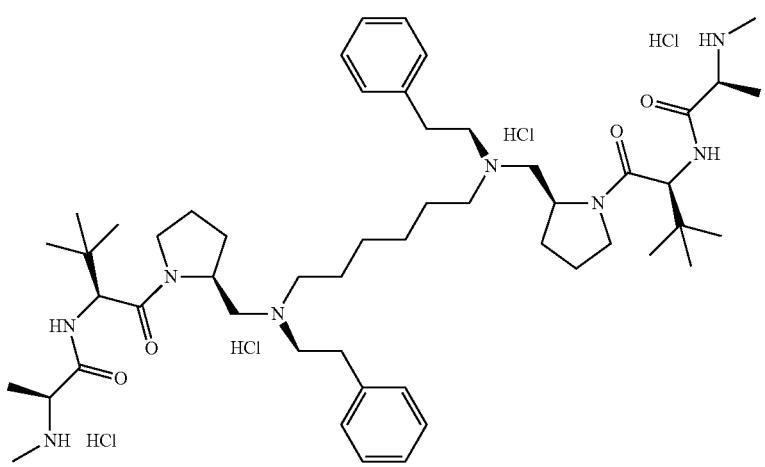
P4-22
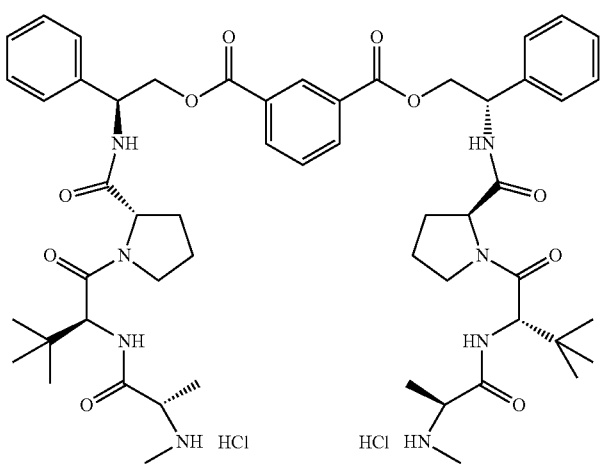 [SMILES: CN[C@@H](C)C(=O)N[C@H](C(=O)N1CCC[C@H]1C(=O)N[C@H](COC(=O)c1cccc(C(=O)OC[C@@H](NC(=O)[C@@H]2CCCN2C(=O)[C@@H](NC(=O)[C@H](C)NC)C(C)(C)C)c2ccccc2)c1)c1ccccc1)C(C)(C)C ; Cl ; Cl]
P4-23

P4-24
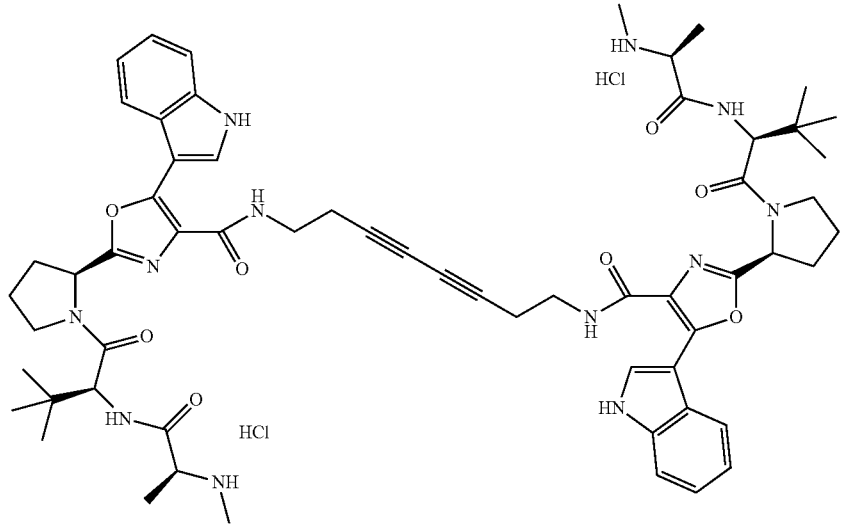 [SMILES: CN[C@@H](C)C(=O)N[C@H](C(=O)N1CCC[C@H]1c1nc(C(=O)NCCC#CC#CCCNC(=O)c2nc([C@@H]3CCCN3C(=O)[C@@H](NC(=O)[C@H](C)NC)C(C)(C)C)oc2-c2c[nH]c3ccccc23)c(-c2c[nH]c3ccccc23)o1)C(C)(C)C ; Cl ; Cl]
P4-25
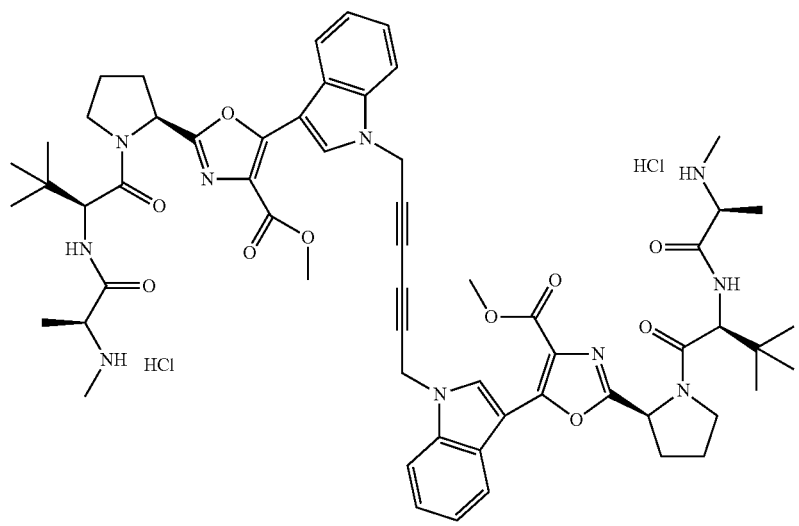 [SMILES: CN[C@@H](C)C(=O)N[C@H](C(=O)N1CCC[C@H]1c1nc(C(=O)OC)c(-c2cn(CC#CC#CCn3cc(-c4oc([C@@H]5CCCN5C(=O)[C@@H](NC(=O)[C@H](C)NC)C(C)(C)C)nc4C(=O)OC)c4ccccc43)c3ccccc23)o1)C(C)(C)C ; Cl ; Cl]

TABLE 14-continued

P4-26
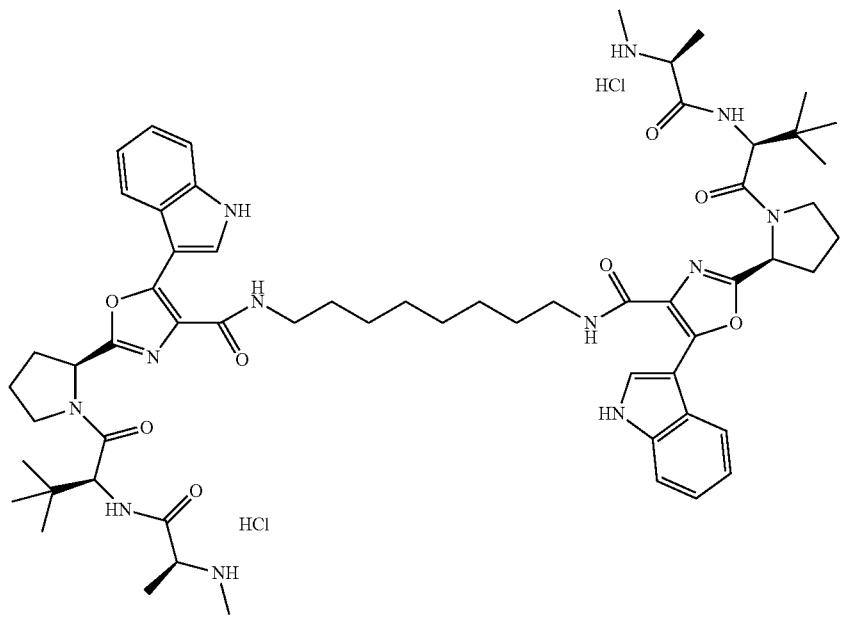 [SMILES: CN[C@@H](C)C(=O)N[C@H](C(=O)N1CCC[C@H]1c1nc(C(=O)NCCCCCCCCNC(=O)c2nc([C@@H]3CCCN3C(=O)[C@@H](NC(=O)[C@H](C)NC)C(C)(C)C)oc2-c2c[nH]c3ccccc23)c(-c2c[nH]c3ccccc23)o1)C(C)(C)C ; Cl ; Cl]

P4-27
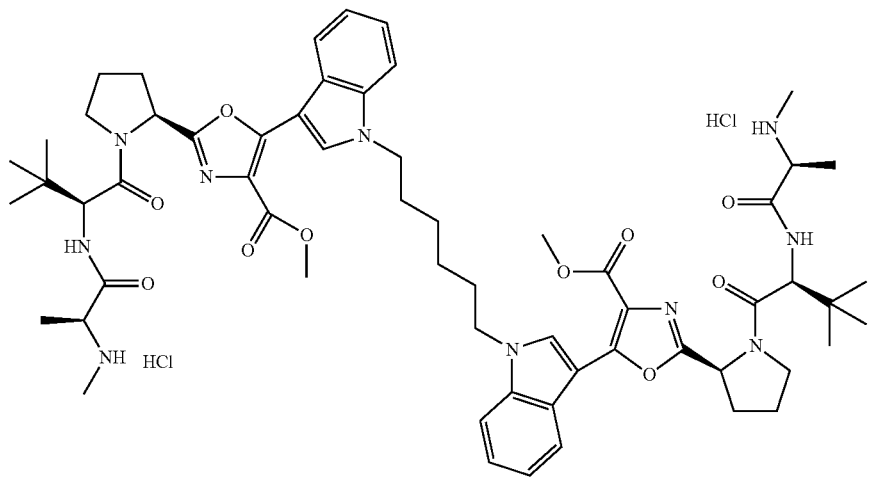 [SMILES: CN[C@@H](C)C(=O)N[C@H](C(=O)N1CCC[C@H]1c1nc(C(=O)OC)c(-c2cn(CCCCCCn3cc(-c4oc([C@@H]5CCCN5C(=O)[C@@H](NC(=O)[C@H](C)NC)C(C)(C)C)nc4C(=O)OC)c4ccccc43)c3ccccc23)o1)C(C)(C)C ; Cl ; Cl]

Representative Biological Data
Biological data for the compounds presented in Tables 11-14 is provided in Tables 15-18.

TABLE 15

| Hetero-dimer Cmpnd # | IC50 (uM) in cell viability assay in HCC461 | Synergy with TRAIL in PANC-1 or T98G ng/ml (H-1-2 use T98G Cells, H-3-11 use PANC-1 Cells) | | IC50 (uM) in cell viability assay in PANC-1 cells | | |
|---|---|---|---|---|---|---|
| | | IC50 for TRAIL | IC50 for TRAIL + 100 nm cmpnd | Cmpnd alone | Cmpnd + 100 ng/ml TNFa (uM) | Cmpnd + 300 ng/ml TRAIL (uM) |
| H-1 | 0.01710 | 540.9 | 26.4 | | | |
| H-2 | 0.114 | 199.24 | 200.31 | | | |
| H-3 | 0.088 | >2400 | 103.38 | | | |
| H-4 | 1.689 | >2400 | 150.6 | | | |
| H-5 | | | | >1 | 0.008 | 0.009 |

TABLE 15-continued

| | IC50 (uM) in | | Synergy with TRAIL in PANC-1 or T98G ng/ml (H-1-2 use T98G Cells, H-3-11 use PANC-1 Cells) | IC50 (uM) in cell viability assay in PANC-1 cells | | |
|---|---|---|---|---|---|---|
| Hetero-dimer Cmpnd # | cell viability assay in HCC461 | IC50 for TRAIL | IC50 for TRAIL + 100 nm cmpnd | Cmpnd alone | Cmpnd + 100 ng/ml TNFa (uM) | Cmpnd + 300 ng/ml TRAIL (uM) |
| H-6 | | | | >1 | 0.0229 | 0.0611 |
| H-7 | | | | >1 | 0.0007 | 0.0007 |
| H-8 | | | | >1 | 0.0170 | 0.0330 |
| H-9 | | | | >1 | 0.005 | 0.004 |
| H-10 | | | | >1 | 0.001 | 0.0009 |
| H-11 | | | | >1 | 0.0006 | 0.0006 |

TABLE 16

| | IC50 (uM) in | | Synergy with TRAIL in PANC-1 or T98G ng/ml (P2-1-15 use T98G Cells, P2-16-48 use PANC1 Cells) | IC50 (uM) in cell viability assay in PANC-1 cells | | |
|---|---|---|---|---|---|---|
| P2-linked Dimer Cmpnd# | cell viability assay in HCC461 | IC50 for TRAIL | IC50 for TRAIL + 100 nm compound | Compound alone | Compound + 100 ng/ml TNFa (uM) | Compound + 300 ng/ml TRAIL (uM) |
| P2-1 | 0.018 | 58.800 | 9.07 | | | |
| P2-2 | 0.098 | 58.800 | 12.8 | | | |
| P2-3 | 0.072 | 58.800 | 19 | | | |
| P2-4 | 0.037 | 116.4 | 91.5 | | | |
| P2-5 | 0.091 | 120.7 | 12.8 | | | |
| P2-6 | 0.024 | 120.7 | 6.3 | | | |
| P2-7 | 0.17 | >2400 | 196.28 | | | |
| P2-8 | 0.009 | 160.88 | 14.18 | | | |
| P2-9 | 0.025 | 160.88 | 13.95 | | | |
| P2-10 | 0.109 | 199.24 | 117.86 | | | |
| P2-11 | 0.171 | 199.24 | 124.56 | | | |
| P2-12 | 0.021 | 199.24 | 5.91 | | | |
| P2-13 | 0.168 | 199.24 | 171.08 | | | |
| P2-14 | 0.092 | 199.24 | 59.74 | | | |
| P2-15 | 0.07 | 489.0 | 16.2 | | | |
| P2-16 | 0.03 | >2400 | 3.7 | | | |
| P2-17 | 0.134 | >2400 | 192.16 | | | |
| P2-18 | 0.031 | >2400 | 24.77 | | | |
| P2-19 | 0.025 | >2400 | 99.1 | | | |
| P2-20 | 0.043 | >2400 | 41.9 | | | |
| P2-21 | 0.24 | >2400 | 629.00 | | | |
| P2-22 | 0.18 | >2400 | 115.00 | | | |
| P2-23 | 0.055 | >2400 | 17.4 | | | |
| P2-24 | 0.121 | >2400 | 83.1 | | | |
| P2-25 | 0.086 | >2400 | 88.1 | | | |
| P2-26 | 0.080 | >2400 | 50.1 | | | |
| P2-27 | 0.165 | >2400 | 270.8 | | | |
| P2-28 | 0.163 | >2400 | 796.4 | | | |
| P2-29 | 0.324 | >2400 | 230.7 | | | |
| P2-30 | 0.189 | >2400 | 58.4 | | | |
| P2-31 | 0.268 | >2400 | 48.8 | | | |
| P2-32 | 0.038 | >2400 | 4.97 | | | |
| P2-33 | 0.188 | >2400 | 112.8 | | | |
| P2-34 | | | | >1 | 0.040 | 0.064 |
| P2-35 | | | | >1 | 0.007 | 0.007 |
| P2-36 | | | | >1 | 0.079 | 0.090 |
| P2-37 | | | | >1 | 0.174 | 0.527 |
| P2-38 | | | | >1 | 0.021 | 0.037 |
| P2-39 | | | | >1 | 0.349 | 0.225 |
| P2-40 | | | | >1 | 0.190 | 0.250 |
| P2-41 | | | | >1 | 0.094 | 0.092 |
| P2-42 | | | | >1 | 0.091 | 0.148 |
| P2-43 | | | | >1 | 0.012 | 0.016 |
| P2-44 | | | | >1 | 0.017 | 0.010 |
| P2-45 | | | | >1 | 0.002 | 0.004 |
| P2-46 | | | | >1 | 0.0007 | 0.0009 |

TABLE 16-continued

| | Synergy with TRAIL in PANC-1 or T98G ng/ml (P2-1-15 use T98G Cells, P2-16-48 use PANC1 Cells) | | IC50 (uM) in cell viability assay in PANC-1 cells | | |
|---|---|---|---|---|---|
| P2-linked Dimer Cmpnd# | IC50 (uM) in cell viability assay in HCC461 | IC50 for TRAIL | IC50 for TRAIL + 100 nm compound | Compound alone | Compound + 100 ng/ml TNFa (uM) | Compound + 300 ng/ml TRAIL (uM) |
| P2-47 | | | | >1 | 0.108 | 0.153 |
| P2-48 | | | | >1 | 0.263 | 0.398 |
| P2-49 | | | | >1 | 0.033 | 0.033 |
| P2-50 | | | | >1 | 0.067 | 0.019 |

TABLE 17

| | Synergy with TRAIL in PANC-1 or T98G ng/ml (P3-1 use T98G Cells, P3-2-112 use PANC-1 Cells) | | IC50 (uM) in cell viability assay in PANC-1 cells | | |
|---|---|---|---|---|---|
| P3-linked Dimer Cmpnd# | IC50 (uM) in cell viability assay in HCC461 | IC50 for TRAIL | IC50 for TRAIL + 100 nm cmpnd | Cmpnd alone | Cmpnd + 100 ng/ml TNFa (uM) | Cmpnd + 300 ng/ml TRAIL (uM) |
| P3-1 | 0.022 | 541.42 | 11.25 | | | |
| P3-2 | 0.02 | >2400 | 2.6 | | | |
| P3-3 | 0.07 | >2400 | 4.6 | | | |
| P3-4 | 0.006 | >2400 | 0.08 | | | |
| P3-5 | 0.061 | >2400 | 5.16 | | | |
| P3-6 | 0.007 | >2400 | 8.76 | | | |
| P3-7 | 0.007 | >2400 | 24.67 | | | |
| P3-8 | 0.081 | >2400 | 39.32 | | | |
| P3-9 | 0.086 | >2400 | 21.57 | | | |
| P3-10 | 0.046 | >2400 | 31.97 | | | |
| P3-11 | 0.003 | >2400 | 8.75 | | | |
| P3-12 | 0.047 | >2400 | 37.99 | | | |
| P3-13 | 0.028 | >2400 | 23.45 | | | |
| P3-14 | 0.023 | >2400 | 59.02 | | | |
| P3-15 | 0.017 | >2400 | 135.06 | | | |
| P3-16 | 0.007 | >2400 | 26.95 | | | |
| P3-17 | 0.002 | >2400 | 6.05 | | | |
| P3-18 | 0.008 | >2400 | 33.6 | | | |
| P3-19 | 0.002 | >2400 | 18.1 | | | |
| P3-20 | 0.008 | >2400 | 143.2 | | | |
| P3-21 | 0.005 | >2400 | 19.6 | | | |
| P3-22 | 0.003 | >2400 | 12.1 | | | |
| P3-23 | 0.007 | >2400 | 94.6 | | | |
| P3-24 | 0.006 | >2400 | 13.4 | | | |
| P3-25 | 0.007 | >2400 | 37.5 | | | |
| P3-26 | 0.058 | >2400 | 34.7 | | | |
| P3-27 | 0.031 | >2400 | 50.5 | | | |
| P3-28 | 0.019 | >2400 | 11.2 | | | |
| P3-29 | 0.016 | >2400 | 12.3 | | | |
| P3-30 | 0.013 | >2400 | 16.9 | | | |
| P3-31 | 0.002 | >2400 | 3.1 | | | |
| P3-32 | 0.006 | >2400 | 10.5 | | | |
| P3-33 | 0.017 | >2400 | 6.1 | | | |
| P3-34 | 0.080 | >2400 | 51.0 | | | |
| P3-35 | 0.048 | >2400 | 45.61 | | | |
| P3-36 | 2.376 | >2400 | 208.58 | | | |
| P3-37 | 0.008 | >2400 | 8.77 | | | |
| P3-38 | 0.007 | >2400 | 8.29 | | | |
| P3-39 | 0.006 | >2400 | 82.02 | | | |
| P3-40 | 0.005 | >2400 | 10.61 | | | |
| P3-41 | 0.016 | 1656.00 | 49.67 | | | |
| P3-42 | 0.011 | 1656.00 | 9.65 | | | |
| P3-43 | 0.057 | >2400 | 22.6 | | | |
| P3-44 | 0.040 | >2400 | 12.5 | | | |
| P3-45 | 0.181 | >2400 | 88.1 | | | |
| P3-46 | 0.024 | >2400 | 15.2 | | | |
| P3-47 | 0.022 | >2400 | 8.3 | | | |
| P3-48 | 0.183 | >2400 | 150.4 | | | |

TABLE 17-continued

| | IC50 (uM) in | Synergy with TRAIL in PANC-1 or T98G ng/ml (P3-1 use T98G Cells, P3-2-112 use PANC-1 Cells) | | IC50 (uM) in cell viability assay in PANC-1 cells | | |
|---|---|---|---|---|---|---|
| | | | IC50 for | | | |
| P3-linked Dimer Cmpnd# | cell viability assay in HCC461 | IC50 for TRAIL | TRAIL + 100 nm cmpnd | Cmpnd alone | Cmpnd + 100 ng/ml TNFa (uM) | Cmpnd + 300 ng/ml TRAIL (uM) |
| P3-49 | 0.141 | >2400 | 37.8 | | | |
| P3-50 | 0.063 | >2400 | 7.4 | | | |
| P3-51 | 0.026 | >2400 | 5.3 | | | |
| P3-52 | 0.044 | >2400 | 16.3 | | | |
| P3-53 | 0.010 | >2400 | 2.7 | | | |
| P3-54 | 0.051 | >2400 | 35.9 | | | |
| P3-55 | 0.017 | >2400 | 8.5 | | | |
| P3-56 | 0.091 | >2400 | 43.6 | | | |
| P3-57 | 1.690 | >2400 | >2400 | | | |
| P3-58 | 0.211 | >2400 | 37.5 | | | |
| P3-59 | 0.450 | >2400 | 124.6 | | | |
| P3-60 | 0.311 | >2400 | 68.3 | | | |
| P3-61 | 0.020 | >2400 | 47.0 | | | |
| P3-62 | 0.198 | >2400 | 175.1 | | | |
| P3-63 | 0.016 | >2400 | 51.2 | | | |
| P3-64 | 0.008 | >2400 | 38.4 | | | |
| P3-65 | 0.002 | >2400 | 13.1 | | | |
| P3-66 | 0.258 | >2400 | 12.1 | | | |
| P3-67 | 0.214 | >2400 | 9.8 | | | |
| P3-68 | 0.025 | >2400 | 4.1 | | | |
| P3-69 | 0.017 | >2400 | 8.3 | | | |
| P3-70 | 0.06 | >2400 | 53.1 | | | |
| P3-71 | 0.035 | >2400 | 36.9 | | | |
| P3-72 | 0.023 | >2400 | 130.6 | | | |
| P3-73 | 0.075 | >2400 | 74.8 | | | |
| P3-74 | 0.072 | >2400 | 105.8 | | | |
| P3-75 | 0.057 | 1882.0 | 195.4 | | | |
| P3-76 | 0.036 | 1882.0 | 180.3 | | | |
| P3-77 | 0.014 | >2400 | 131.8 | | | |
| P3-78 | 0.049 | >2400 | 122.7 | | | |
| P3-79 | 0.057 | >2400 | 195.0 | | | |
| P3-80 | 0.053 | >2400 | 225.0 | | | |
| P3-81 | 0.058 | >2400 | 181.0 | | | |
| P3-82 | 0.063 | >2400 | 138.3 | | | |
| P3-83 | 0.196 | >2400 | 131.2 | | | |
| P3-84 | 0.1 | >2400 | 35.1 | | | |
| P3-85 | 0.099 | >2400 | 147.8 | | | |
| P3-86 | 0.077 | >2400 | 157.7 | | | |
| P3-87 | 0.028 | >2400 | 184.6 | | | |
| P3-88 | 0.033 | >2400 | 138.6 | | | |
| P3-89 | 0.073 | >2400 | >2400 | | | |
| P3-90 | | | | >1 | 0.007 | 0.021 |
| P3-91 | | | | >1 | 0.152 | 0.225 |
| P3-92 | | | | >1 | 0.099 | 0.072 |
| P3-93 | | | | >1 | 0.012 | 0.043 |
| P3-94 | | | | >1 | 0.003 | 0.006 |
| P3-95 | | | | >1 | 0.006 | 0.006 |
| P3-96 | | | | >1 | 0.055 | 0.006 |
| P3-97 | | | | >1 | 0.059 | 0.065 |
| P3-98 | | | | >1 | 0.010 | 0.012 |
| P3-99 | | | | >1 | 0.062 | 0.054 |
| P3-100 | | | | >1 | 0.054 | 0.055 |
| P3-101 | | | | >1 | 0.001 | 0.001 |
| P3-102 | | | | >1 | 0.017 | 0.023 |
| P3-103 | | | | >1 | 0.0316 | 0.0370 |
| P3-104 | | | | >1 | 0.042 | 0.042 |
| P3-105 | | | | >1 | 0.0006 | 0.0006 |

TABLE 17-continued

|  | | Synergy with TRAIL in PANC-1 or T98G ng/ml (P3-1 use T98G Cells, P3-2-112 use PANC-1 Cells) | | IC50 (uM) in cell viability assay | | |
|---|---|---|---|---|---|---|
|  | IC50 (uM) in | | IC50 for | in PANC-1 cells | | |
| P3-linked Dimer Cmpnd# | cell viability assay in HCC461 | IC50 for TRAIL | TRAIL + 100 nm cmpnd | Cmpnd alone | Cmpnd + 100 ng/ml TNFa (uM) | Cmpnd + 300 ng/ml TRAIL (uM) |
| P3-106 |  |  |  | >1 | 0.193 | 0.115 |
| P3-107 |  |  |  | >1 | 0.015 | 0.020 |
| P3-108 |  |  |  | >1 | 0.012 | 0.036 |
| P3-109 |  |  |  | >1 | 0.028 | 0.049 |
| P3-110 |  |  |  | >1 | 0.056 | 0.073 |

TABLE 18

|  | | Synergy with TRAIL in PANC-1 cells ng/ml | | IC50 (uM) in cell viability assay | | |
|---|---|---|---|---|---|---|
|  | IC50 (uM) in | | IC50 for | in PANC-1 cells | | |
| P4-linked Dimer Cmpnd# | cell viability assay in HCC461 | IC50 for TRAIL | TRAIL + 100 nm cmpnd | Cmpnd alone | Cmpnd + 100 ng/ml TNFa (uM) | Cmpnd + 300 ng/ml TRAIL (uM) |
| P4-1 | 0.080 | >2400 | 169.48 |  |  |  |
| P4-2 | 0.120 | >2400 | 238.1 |  |  |  |
| P4-3 | 0.030 | >2400 | 39.0 |  |  |  |
| P4-4 | 0.004 | >2400 | 176.1 |  |  |  |
| P4-5 | 0.011 | >2400 | 54.2 |  |  |  |
| P4-6 | 0.070 | >2400 | 336.4 |  |  |  |
| P4-7 | 0.205 | >2400 | 50.3 |  |  |  |
| P4-8 | 0.200 | >2400 | 5.0 |  |  |  |
| P4-9 | 0.530 | >2400 | 140.5 |  |  |  |
| P4-10 | 0.26 | >2400 | 63.3 |  |  |  |
| P4-11 | 0.068 | >2400 | 21.7 |  |  |  |
| P4-12 | 0.038 | >2400 | 21.2 |  |  |  |
| P4-13 | 0.089 | >2400 | 43.1 |  |  |  |
| P4-14 | 0.093 | >2400 | 127.9 |  |  |  |
| P4-15 | 0.085 | >2400 | 59.9 |  |  |  |
| P4-16 | 0.130 | >2400 | 31.2 |  |  |  |
| P4-17 | 0.015 | >2400 | 14.7 |  |  |  |
| P4-18 | 0.013 | >2400 | 13.1 |  |  |  |
| P4-19 |  |  |  | >1 | 0.005 | 0.006 |
| P4-20 |  |  |  | >1 | 0.061 | 0.041 |
| P4-21 |  |  |  | >1 | 0.151 | 0.175 |
| P4-22 |  |  |  | >1 | 0.022 | 0.040 |
| P4-23 |  |  |  | >1 | 0.014 | 0.006 |
| P4-24 |  |  |  | >1 | 0.0006 | 0.0006 |
| P4-25 |  |  |  | >1 | 0.0342 | 0.0408 |
| P4-26 |  |  |  | >1 | 0.0007 | 0.0007 |
| P4-27 |  |  |  | >1 | 0.0243 | 0.0294 |

The invention claimed is:
1. A compound selected from the group consisting of the following compounds, including a free base form thereof, or any pharmaceutically acceptable salt thereof, and including any stereoisomeric forms thereof:
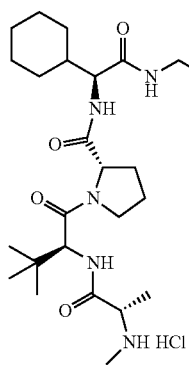
P4-1
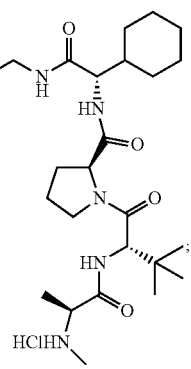
P4-2
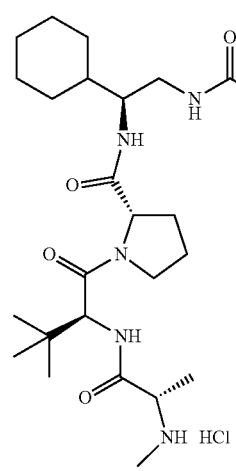
P4-3
Trans Isomer 2
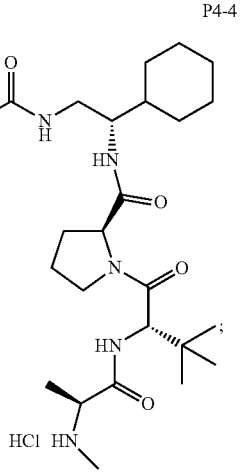
P4-4
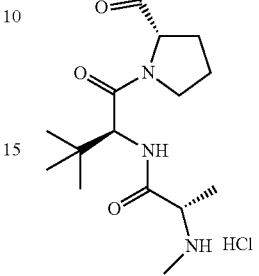
P4-5
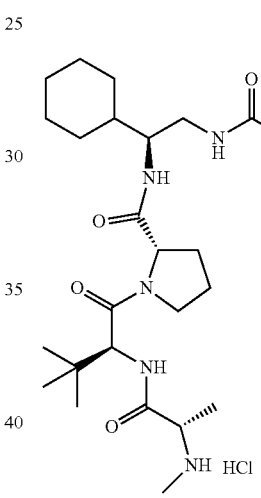
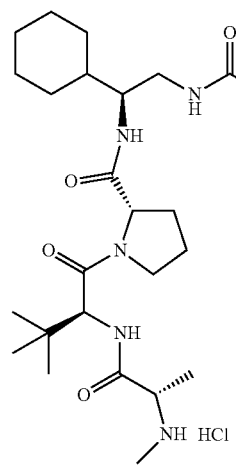
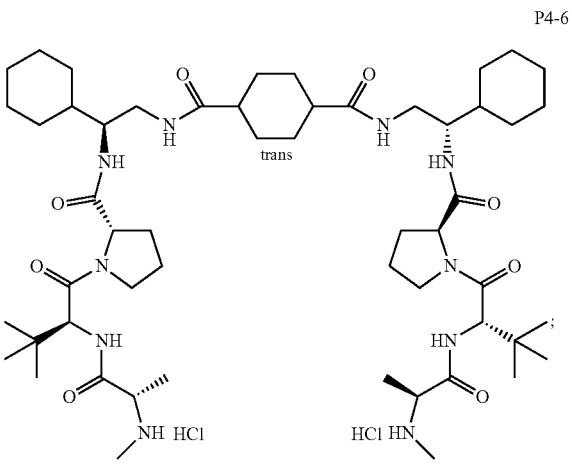
P4-6

337
-continued
P4-7
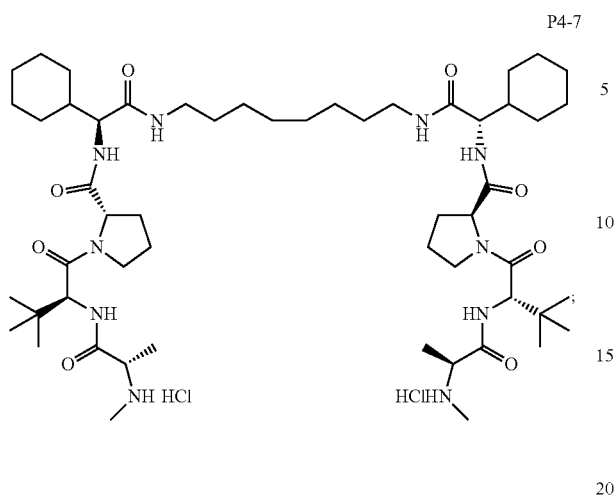
P4-8
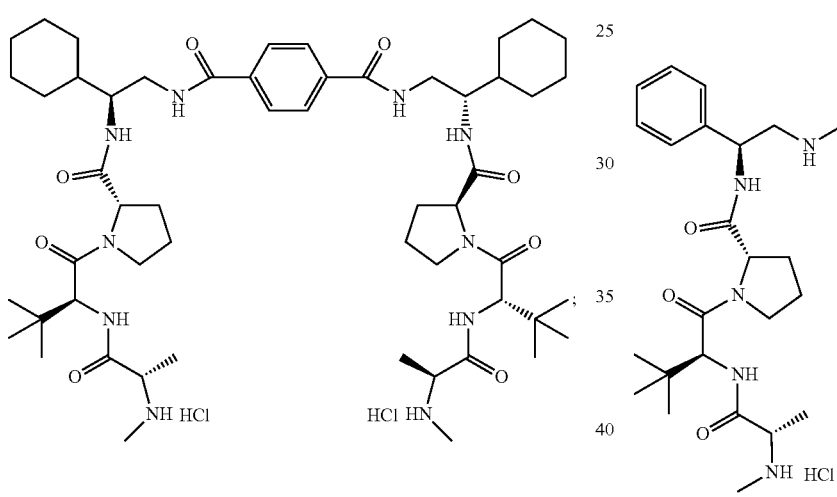
P4-9
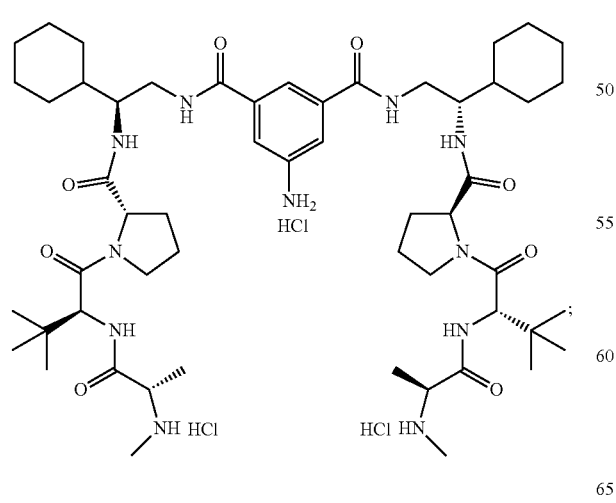
338
-continued
P4-10
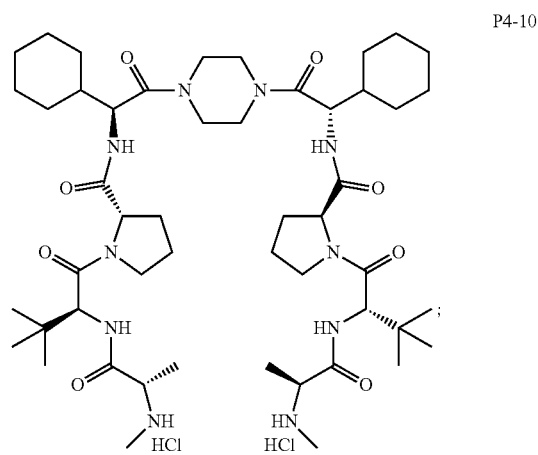
P4-11
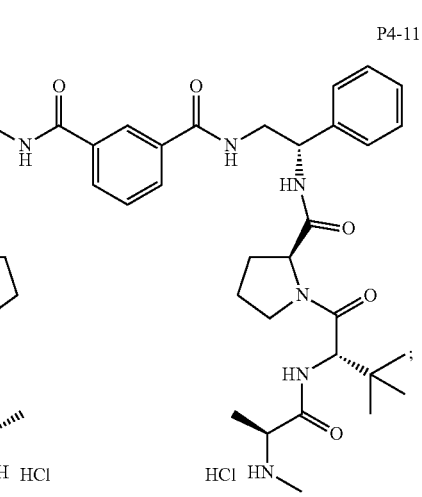
P4-12
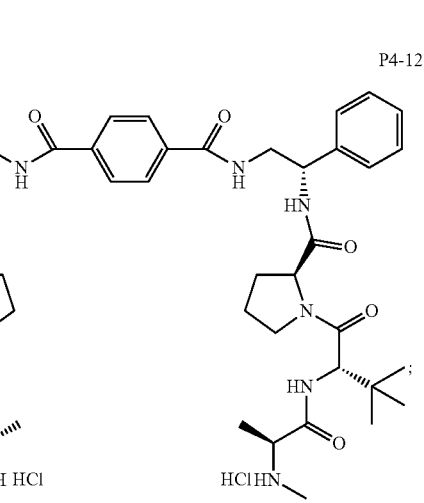

P4-13
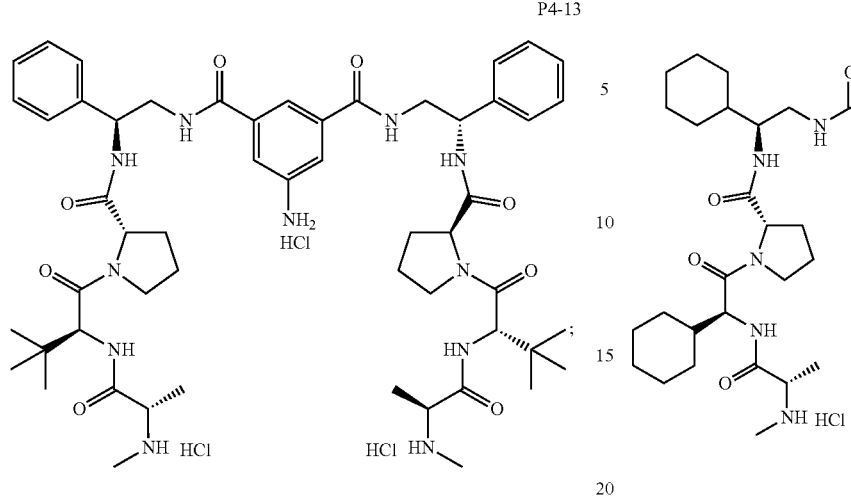
P4-16
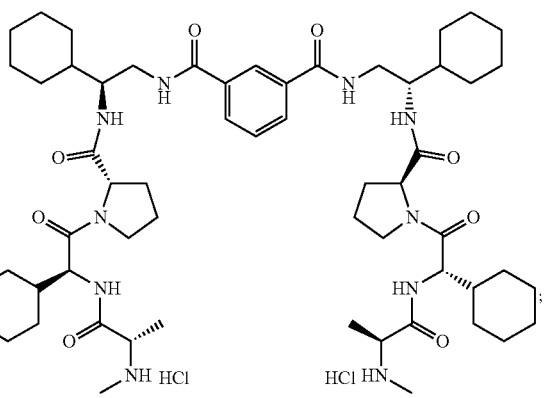
P4-14
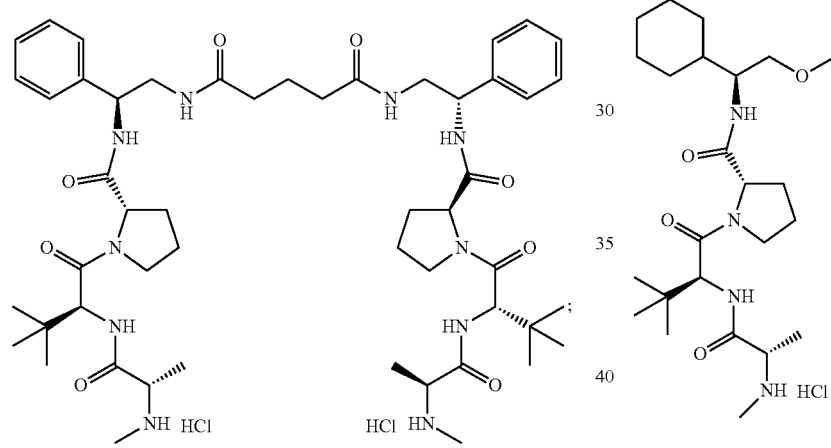
P4-17
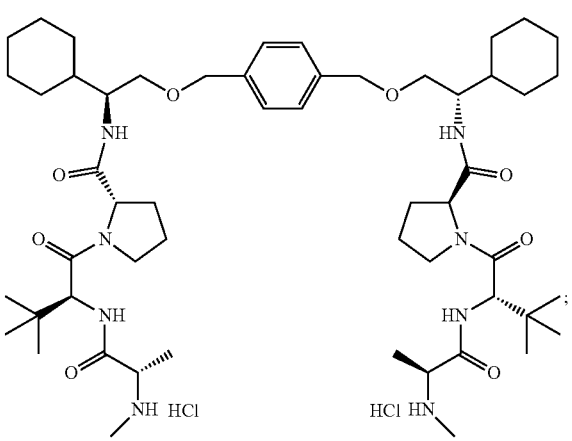
P4-15
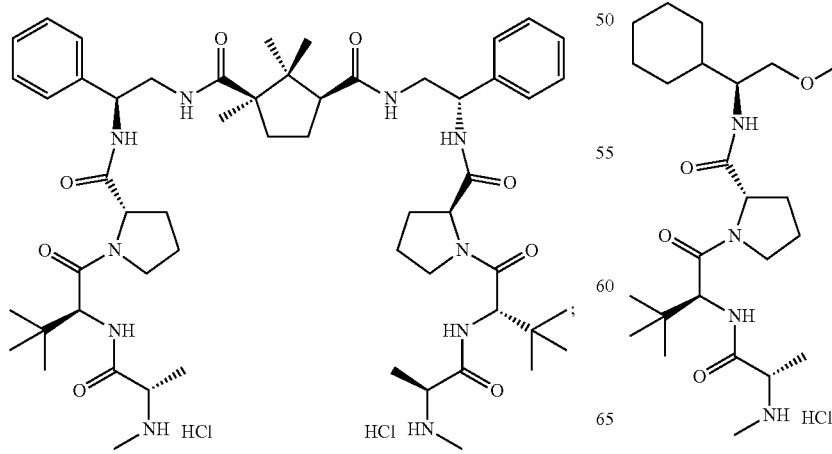
P4-18
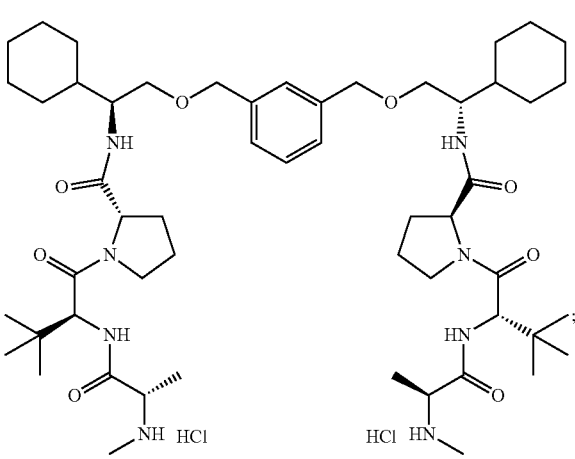

P4-19
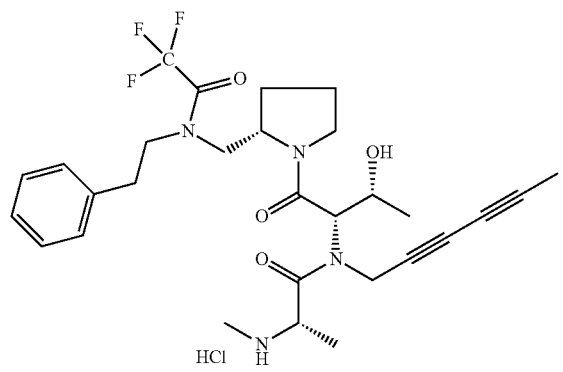
P4-20
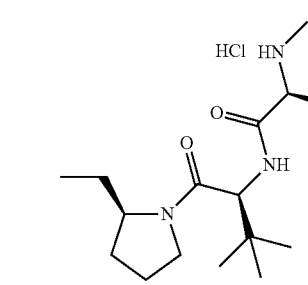
P4-21
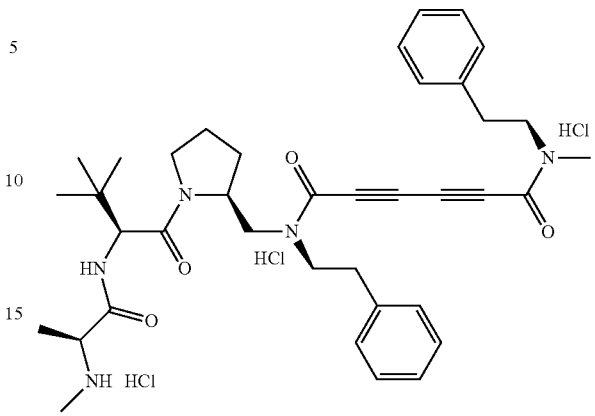
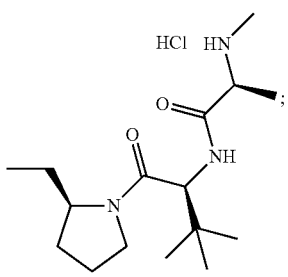
P4-22
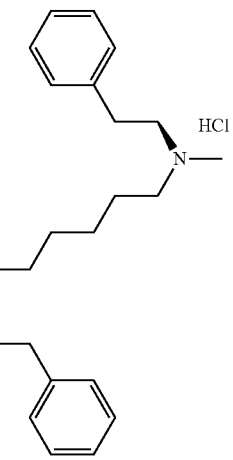
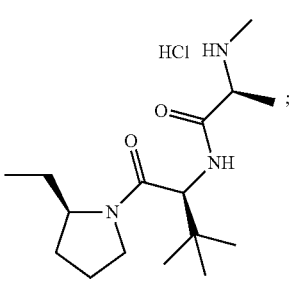

343
-continued
P4-23
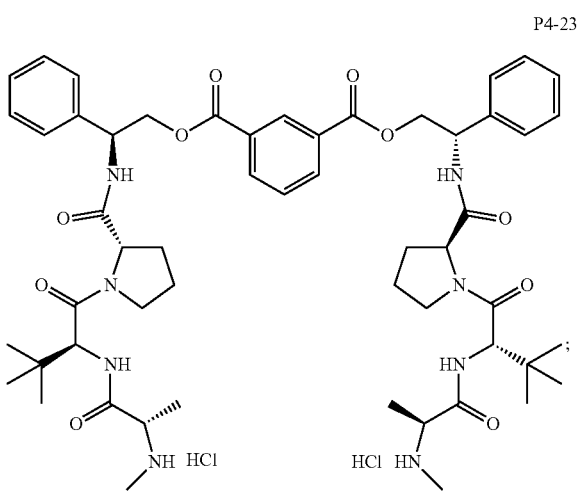
P4-24
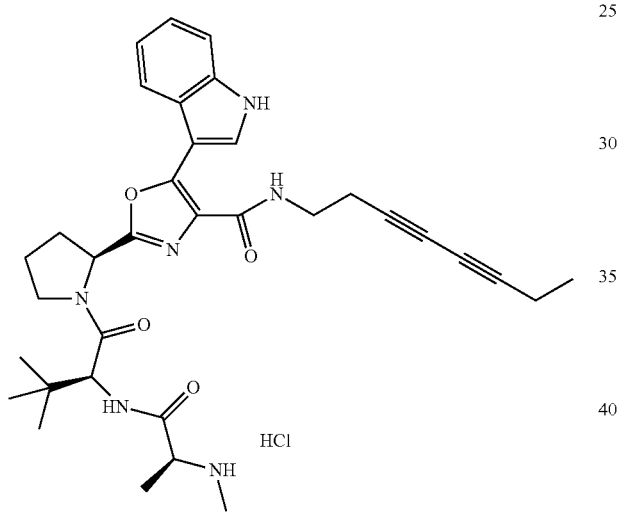
344
-continued
P4-25
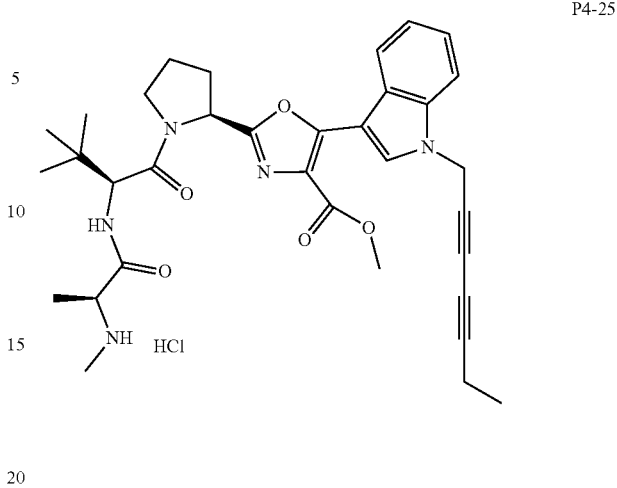
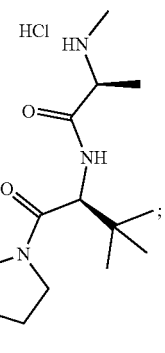
P4-26
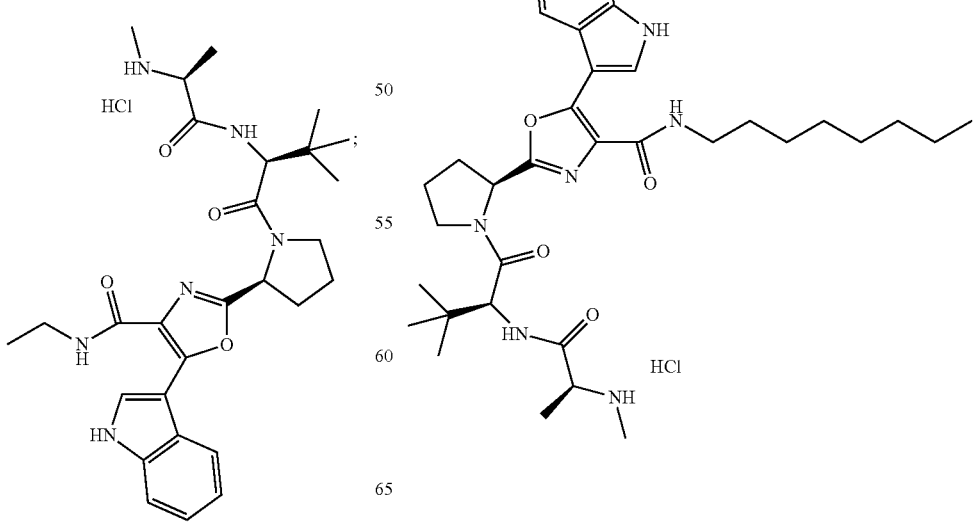

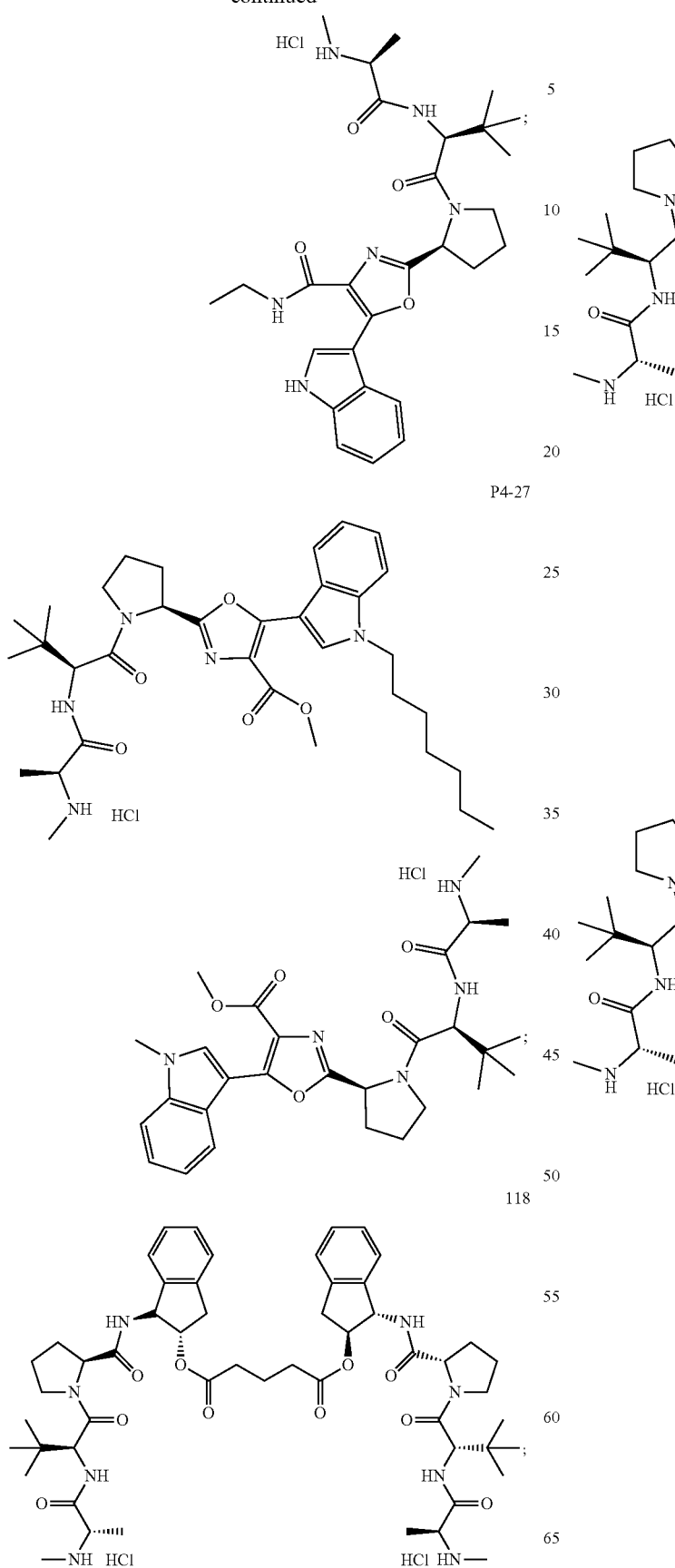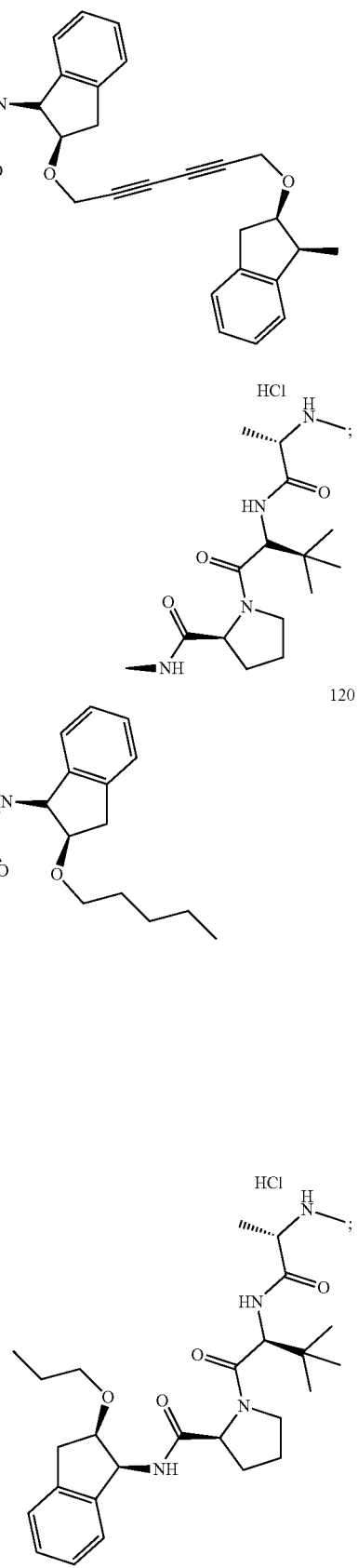

347
-continued
121
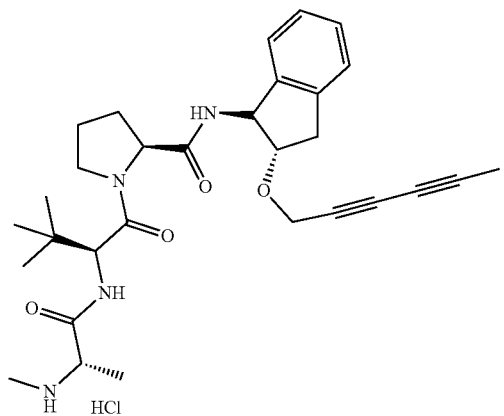
122
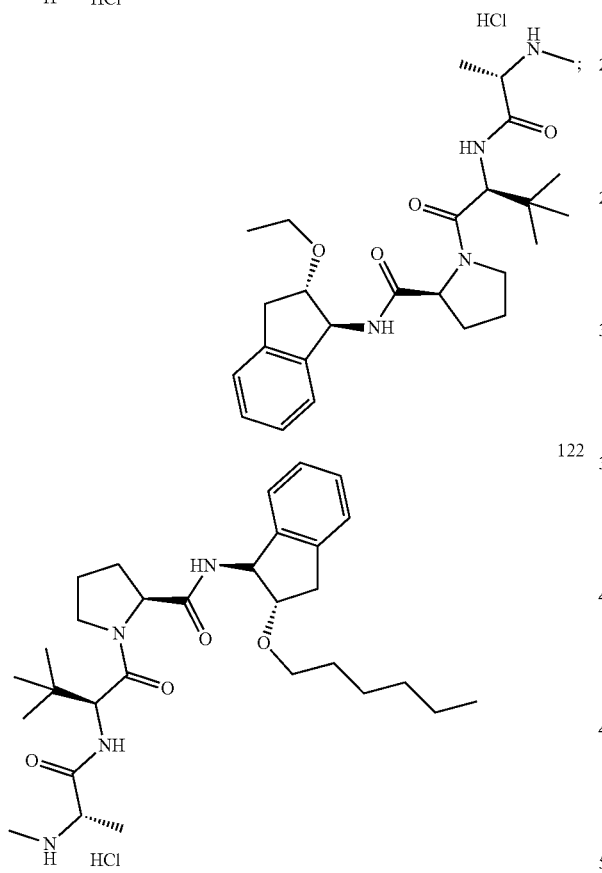
348
-continued
123
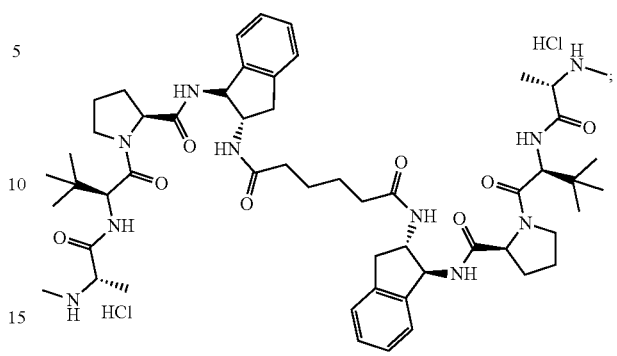
124
and
125
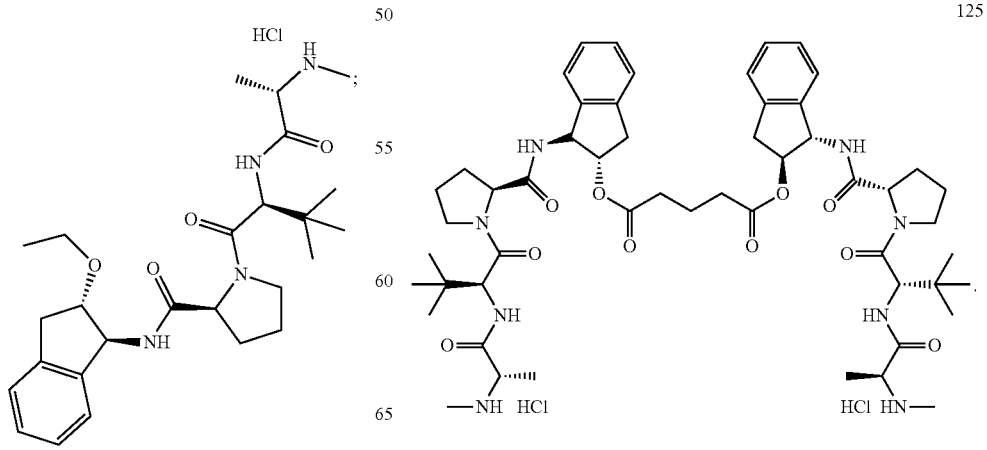

2. The compound according to claim 1 of structure:
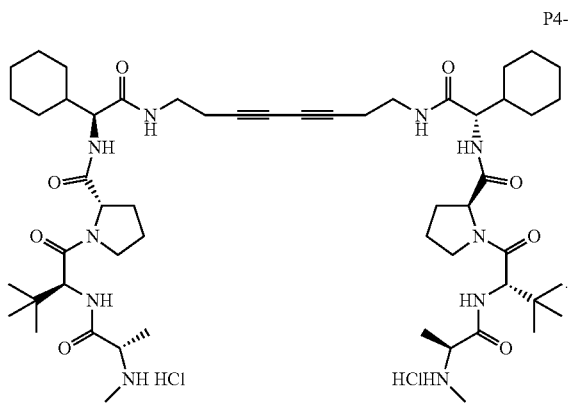
P4-1
3. The compound according to claim 1 of structure:
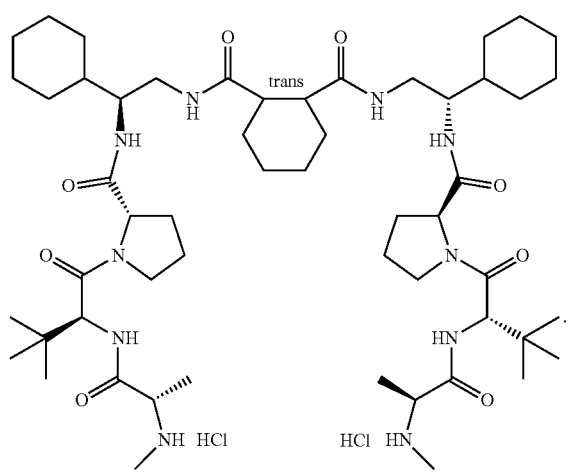
P4-2
4. The compound according to claim 1 of structure:
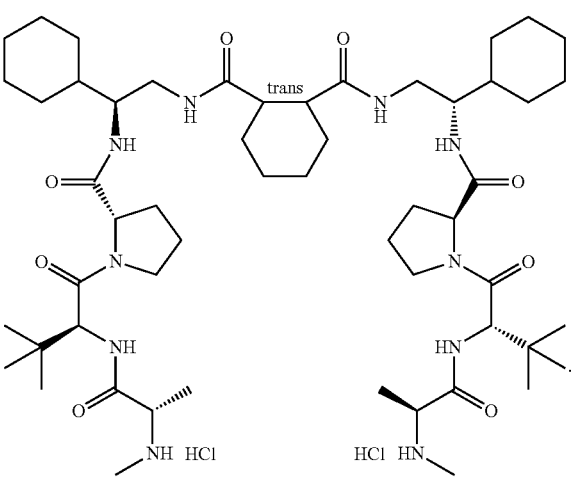
P4-3
Trans Isomer 2
5. The compound according to claim 1 of structure:
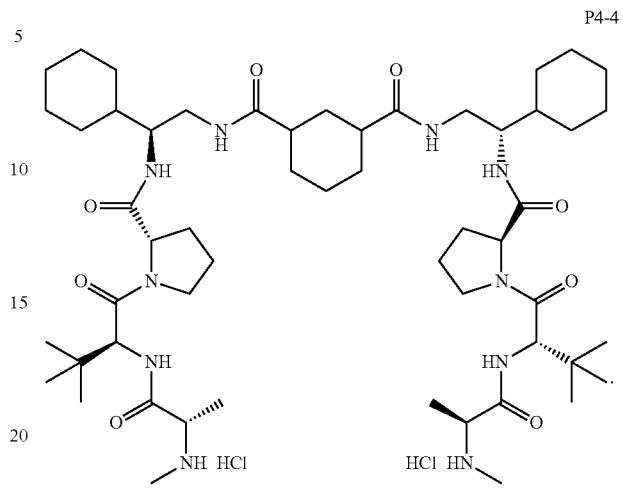
P4-4
6. The compound according to claim 1 of structure:
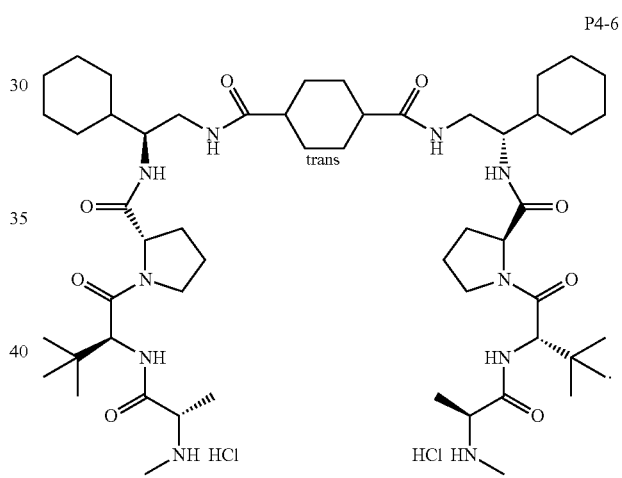
P4-6
7. The compound according to claim 1 of structure:
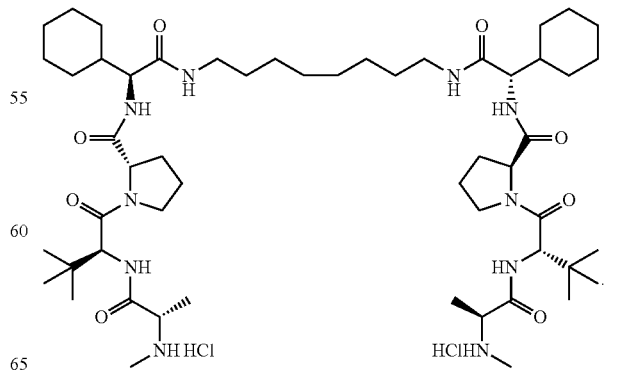
P4-7

8. The compound according to claim 1 of structure:
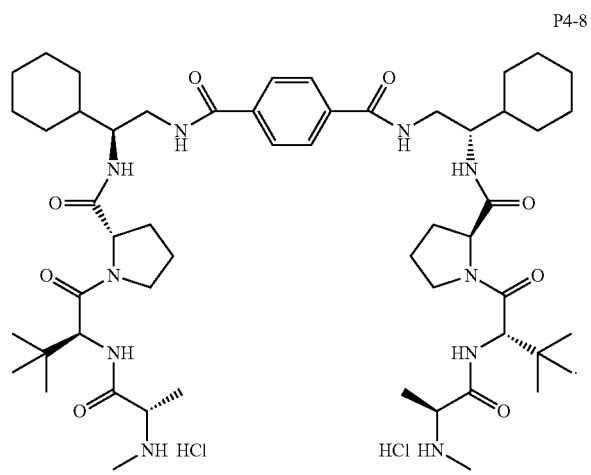 [SMILES: CN[C@@H](C)C(=O)N[C@H](C(=O)N1CCC[C@H]1C(=O)N[C@H](CNC(=O)c1ccc(C(=O)NC[C@@H](NC(=O)[C@@H]2CCCN2C(=O)[C@@H](NC(=O)[C@H](C)NC)C(C)(C)C)C2CCCCC2)cc1)C1CCCCC1)C(C)(C)C ; Cl ; Cl]
P4-8
9. The compound according to claim 1 of structure:
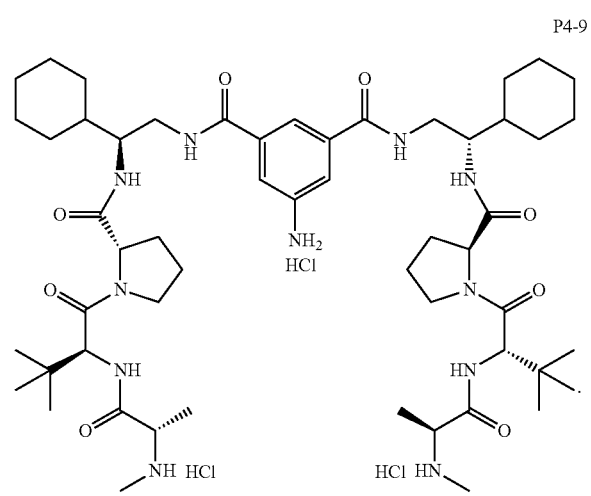 [SMILES: CN[C@@H](C)C(=O)N[C@H](C(=O)N1CCC[C@H]1C(=O)N[C@H](CNC(=O)c1cc(N)cc(C(=O)NC[C@@H](NC(=O)[C@@H]2CCCN2C(=O)[C@@H](NC(=O)[C@H](C)NC)C(C)(C)C)C2CCCCC2)c1)C1CCCCC1)C(C)(C)C ; Cl ; Cl ; Cl]
P4-9
10. The compound according to claim 1 of structure:
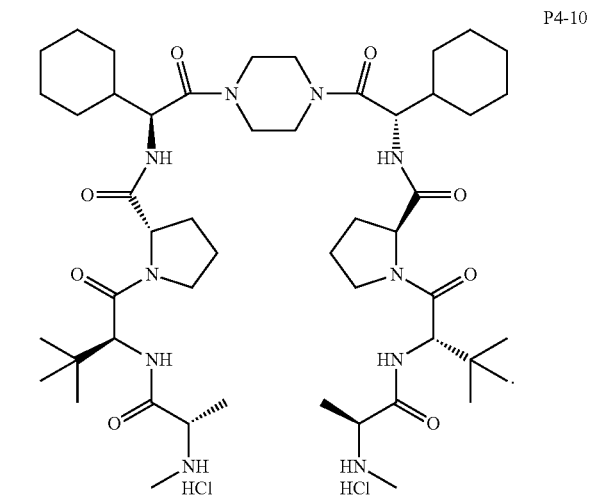 [SMILES: CN[C@@H](C)C(=O)N[C@H](C(=O)N1CCC[C@H]1C(=O)N[C@H](C(=O)N1CCN(C(=O)[C@@H](NC(=O)[C@@H]2CCCN2C(=O)[C@@H](NC(=O)[C@H](C)NC)C(C)(C)C)C2CCCCC2)CC1)C1CCCCC1)C(C)(C)C ; Cl ; Cl]
P4-10
11. The compound according to claim 1 of structure:
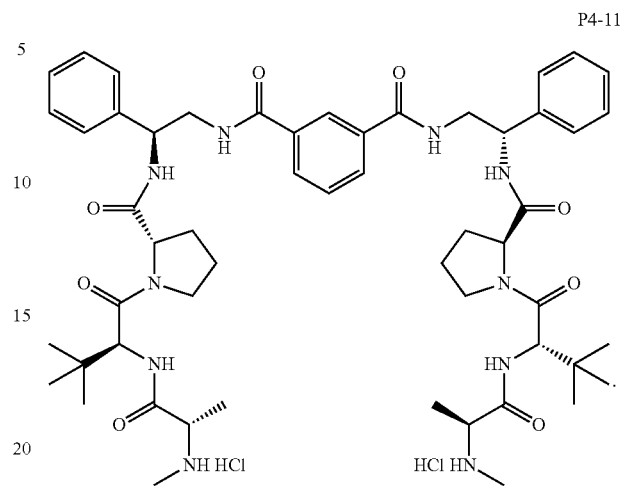
P4-11
12. The compound according to claim 1 of structure:
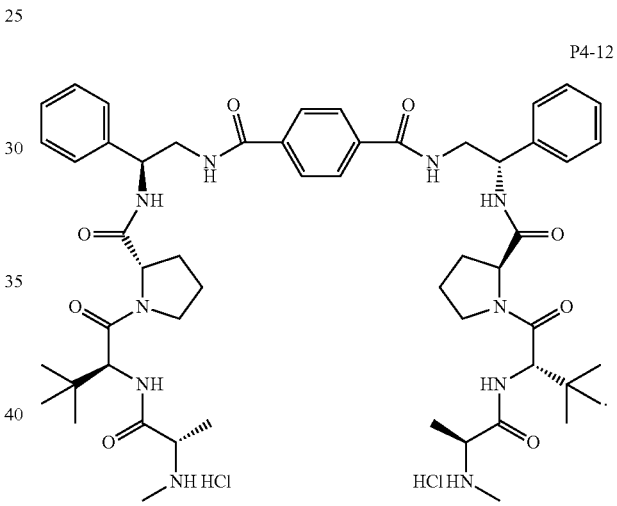
P4-12
13. The compound according to claim 1 of structure:
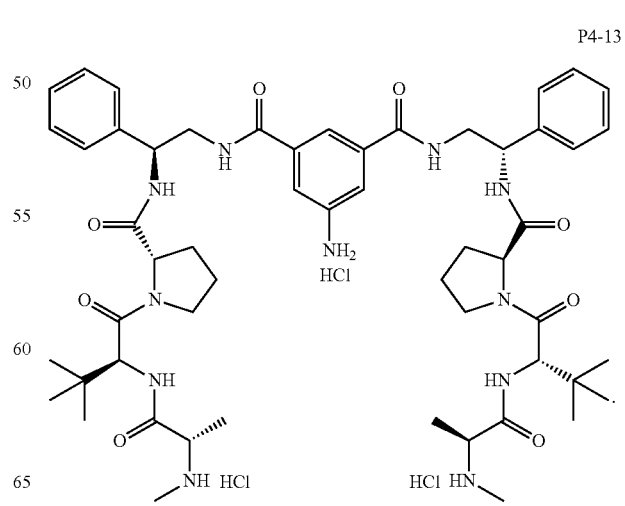
P4-13

14. The compound according to claim 1 of structure:

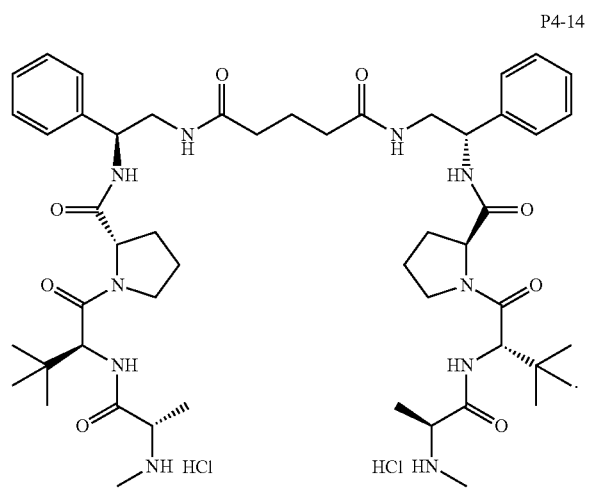 [SMILES: CN[C@@H](C)C(=O)N[C@H](C(=O)N1CCC[C@H]1C(=O)N[C@H](CNC(=O)CCCC(=O)NC[C@@H](NC(=O)[C@@H]1CCCN1C(=O)[C@@H](NC(=O)[C@H](C)NC)C(C)(C)C)c1ccccc1)c1ccccc1)C(C)(C)C ; Cl ; Cl]

P4-14

15. The compound according to claim 1 of structure:

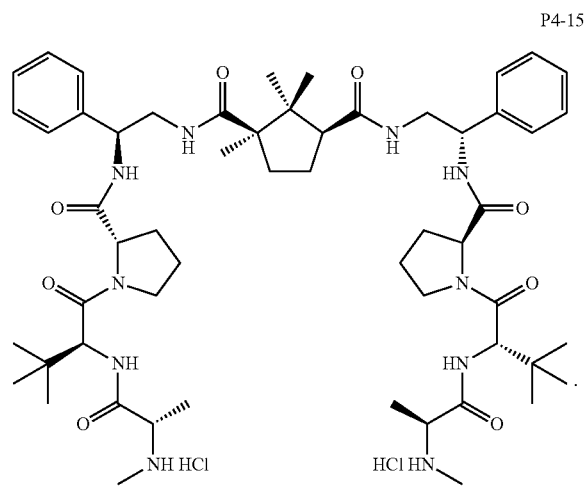

P4-15

16. The compound according to claim 1 of structure:

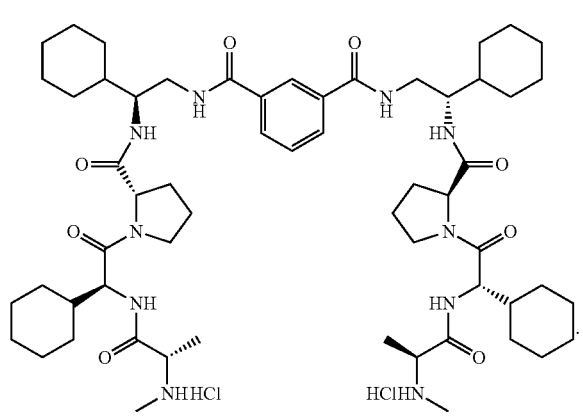

P4-16

17. The compound according to claim 1 of structure:

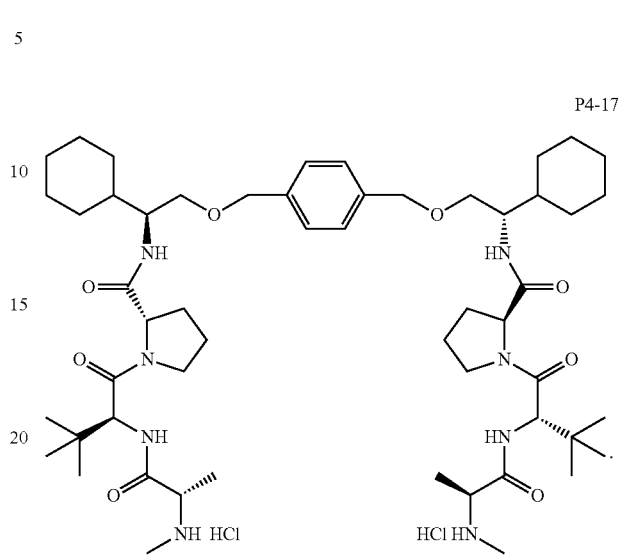

P4-17

18. The compound according to claim 1 of structure:

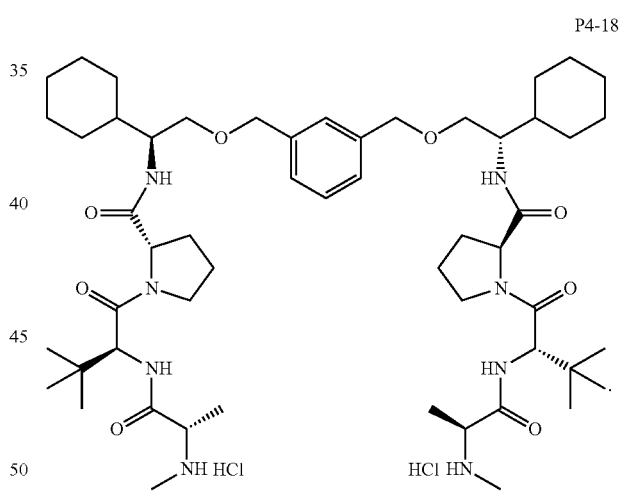

P4-18

19. A pharmaceutical composition comprising the compound of claim 1, and at least one pharmaceutically acceptable excipient, and further comprising at least one additional therapeutic agent that is tumor necrosis factor related apoptosis-inducing ligand (TRAIL).

20. A method for reducing cell proliferation or inducing cell death, comprising contacting a cell with an effective amount of the compound according to claim 1, thereby reducing cell proliferation or inducing cell death.

* * * * *

UNITED STATES PATENT AND TRADEMARK OFFICE
CERTIFICATE OF CORRECTION

PATENT NO. : 8,551,955 B2
APPLICATION NO. : 12/914840
DATED : October 8, 2013
INVENTOR(S) : Haizhou Sun et al.

It is certified that error appears in the above-identified patent and that said Letters Patent is hereby corrected as shown below:

In the Claims

Column 335 thru 348, Claim 1 should read:

1. A compound selected from the group consisting of the following compounds, including a free base form thereof, or any pharmaceutically acceptable salt thereof, and including any stereoisomeric forms thereof:

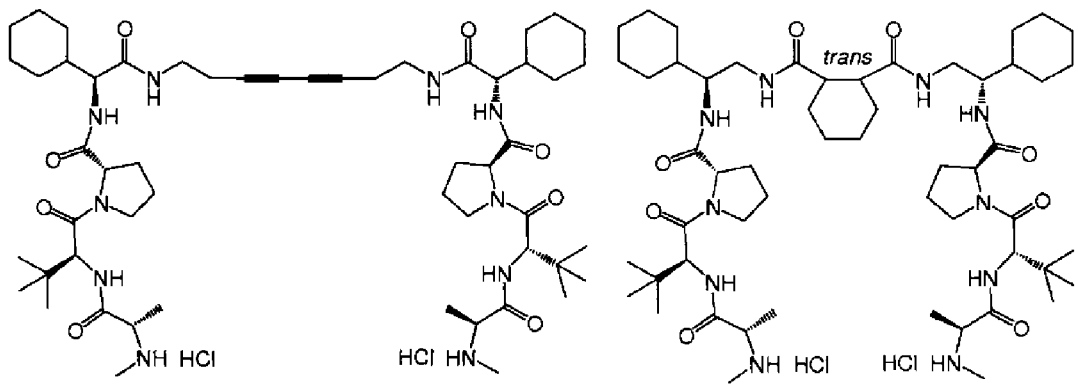

P4-1;                    P4-2;

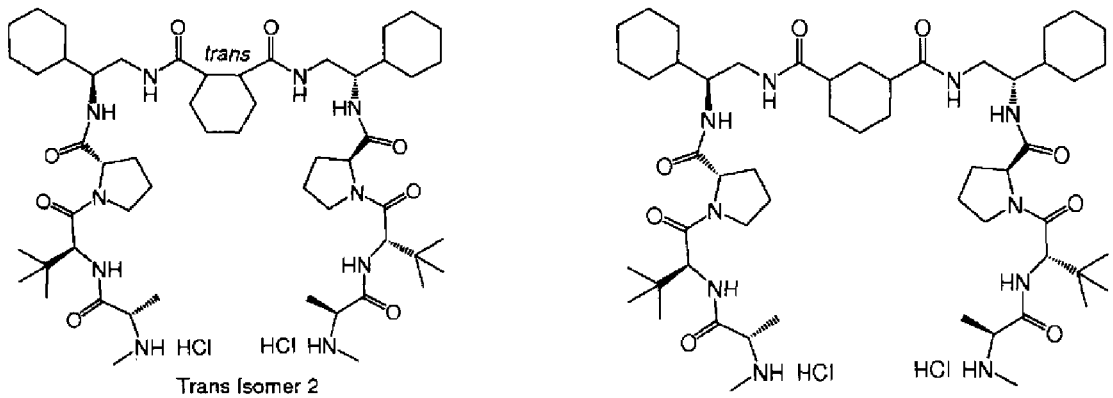

P4-3;                    P4-4;

Signed and Sealed this
Eleventh Day of February, 2014

Michelle K. Lee
*Deputy Director of the United States Patent and Trademark Office*

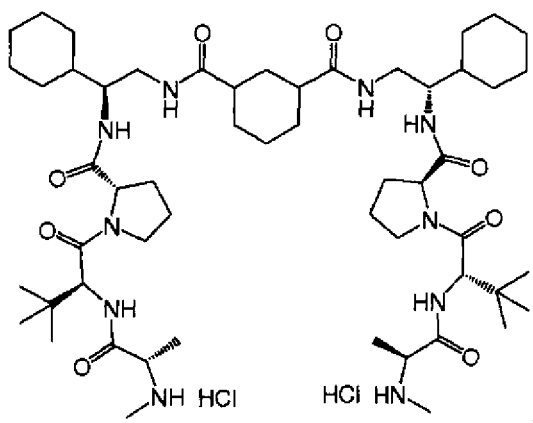
P4-5;
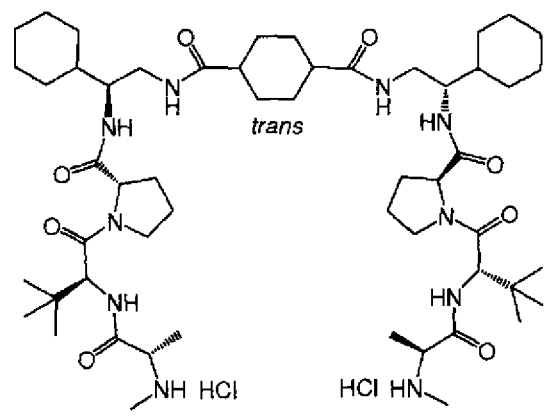
P4-6;
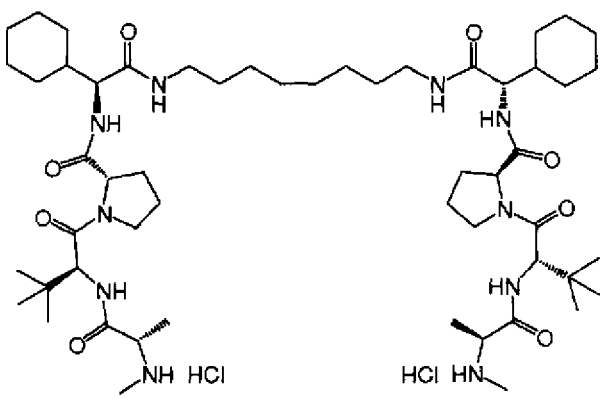
P4-7;
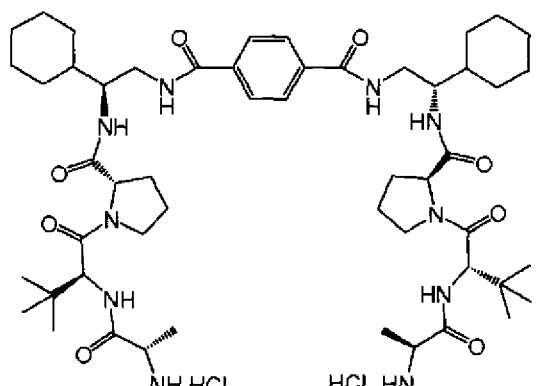
P4-8;
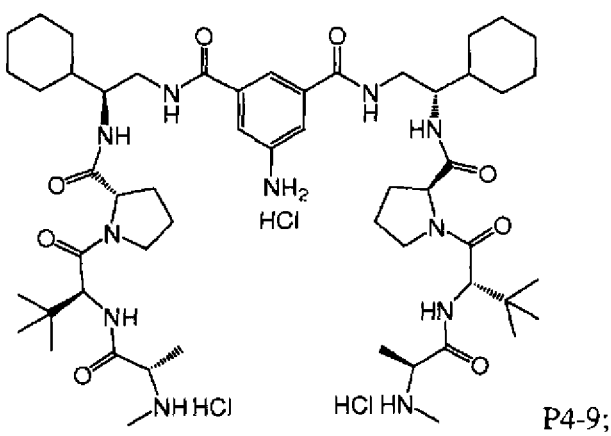
P4-9;
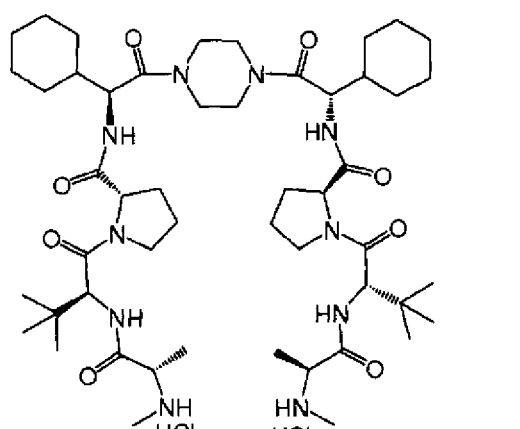
P4-10;

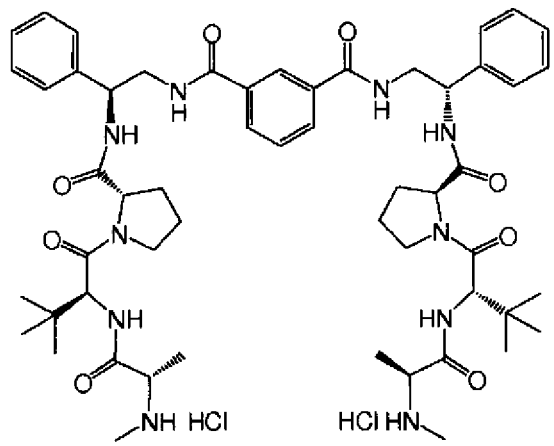
P4-11;
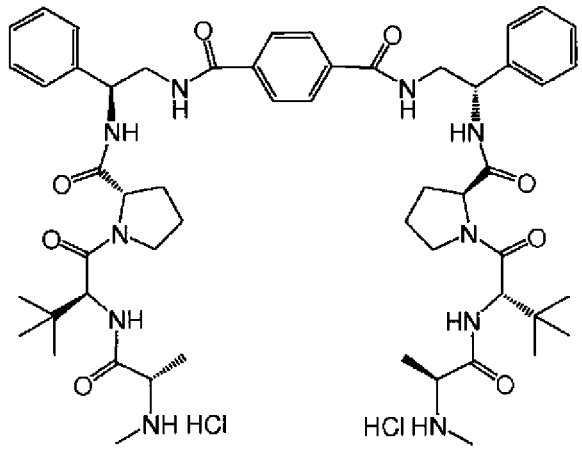
P4-12;
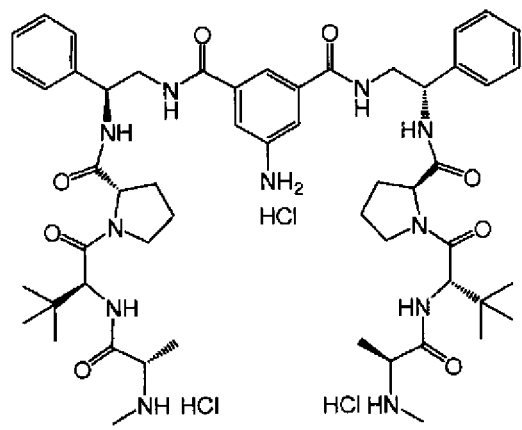
P4-13;
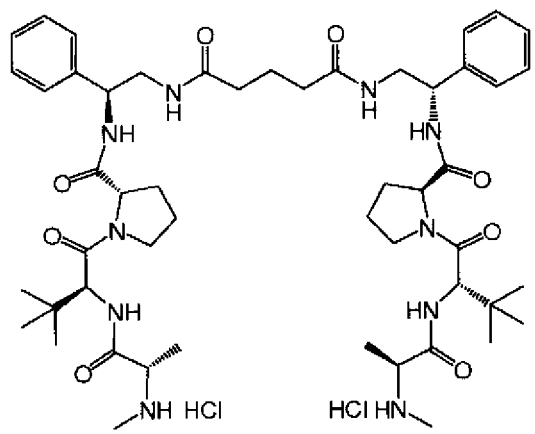
P4-14;
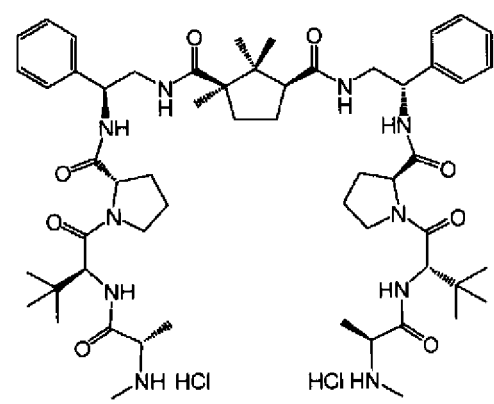
P4-15;
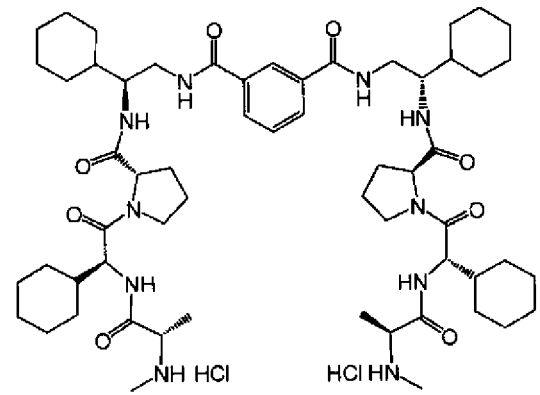
P4-16;

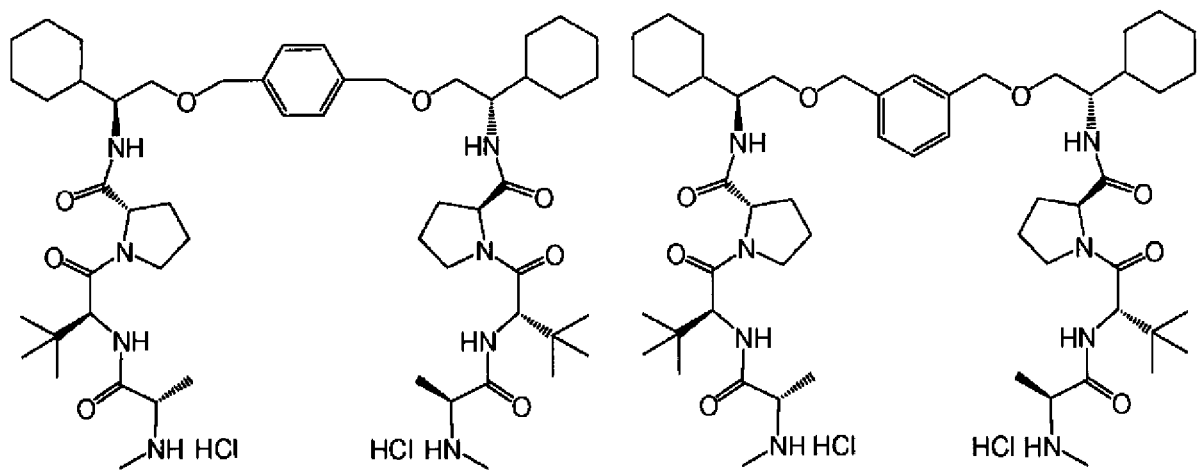
P4-17;
P4-18;
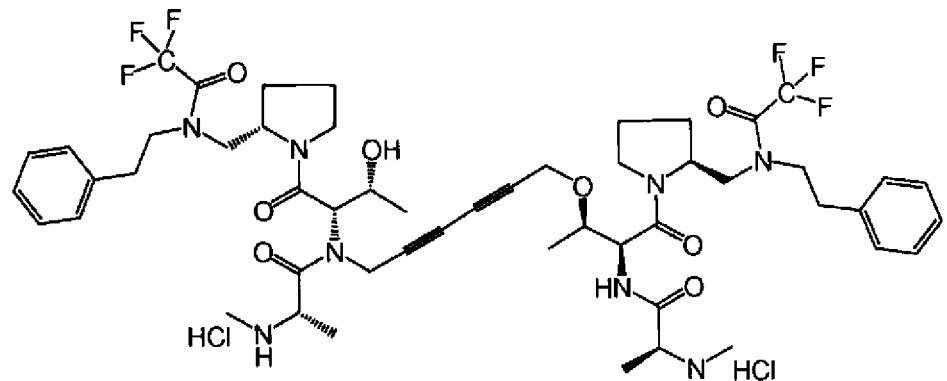
P4-19;
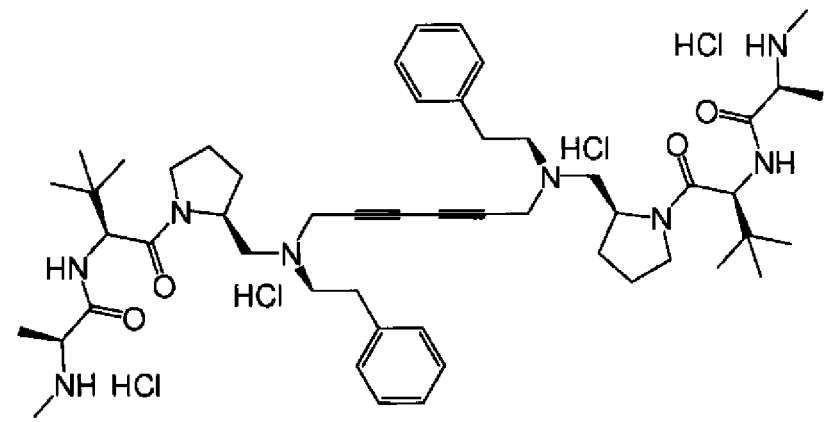
P4-20;

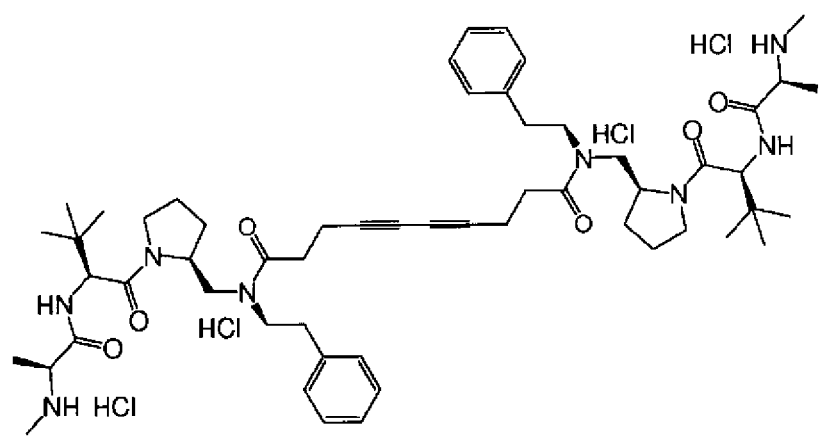
P4-21;
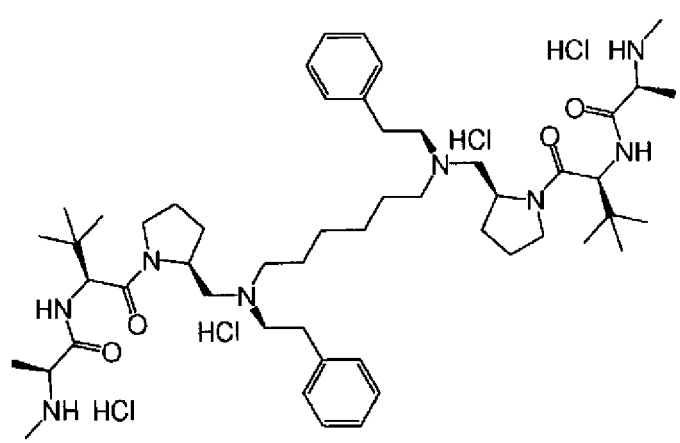
P4-22;
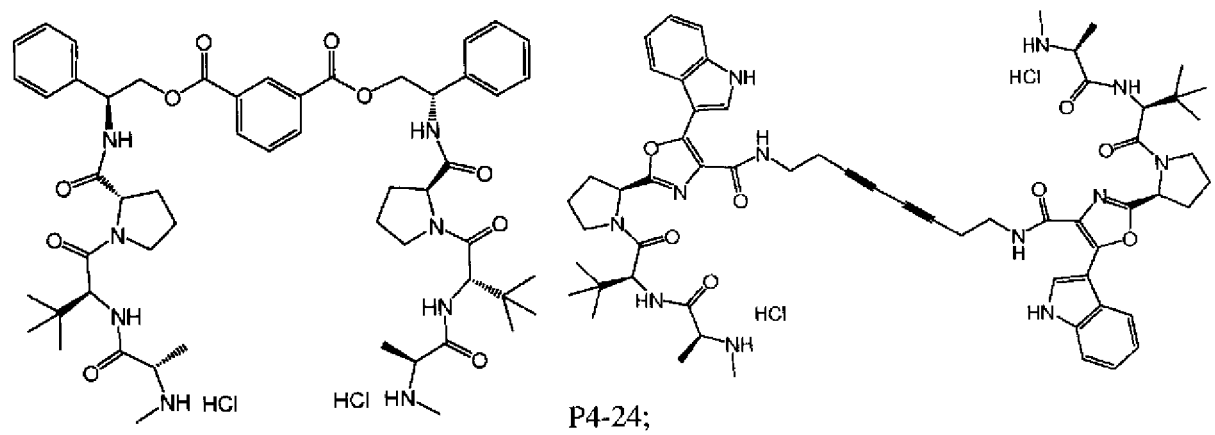
P4-23;
P4-24;

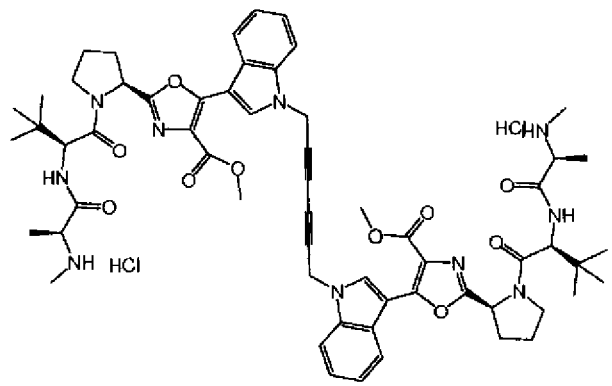
P4-25;
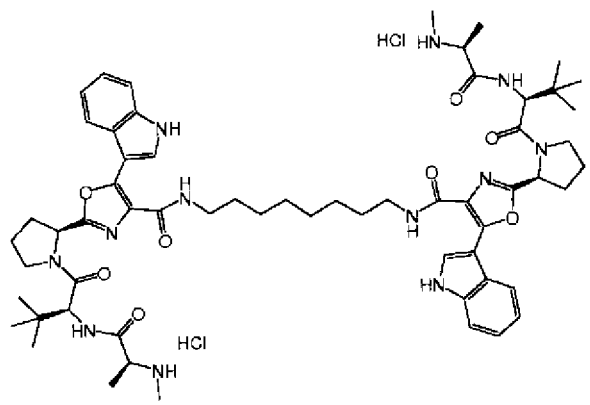
P4-26;
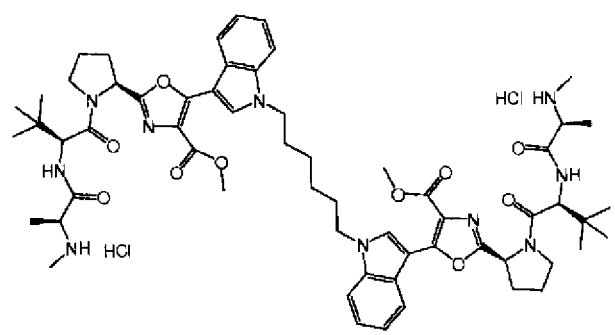
P4-27;
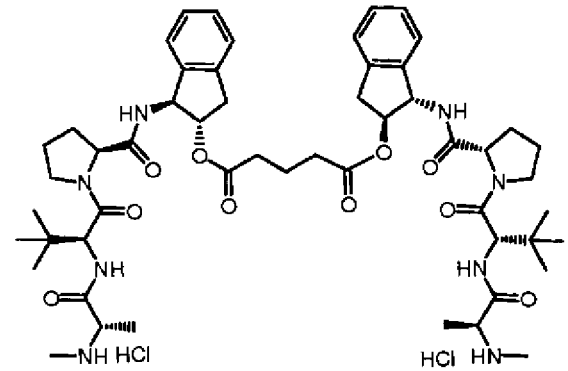
118;
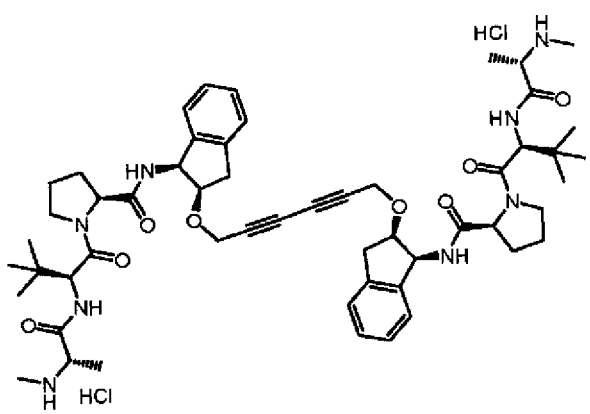
119;
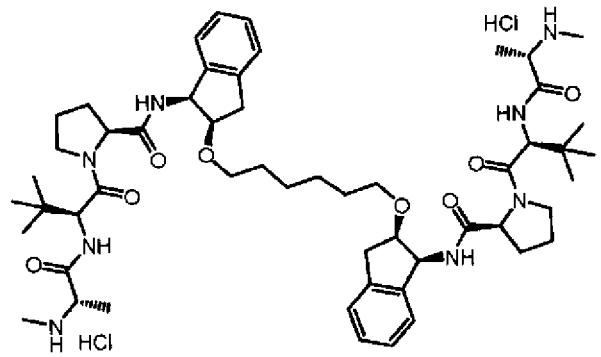
120;

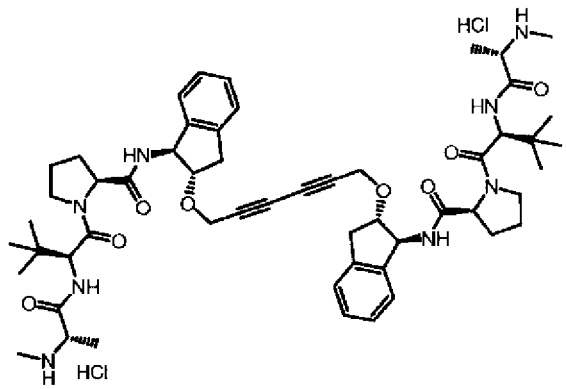
121;
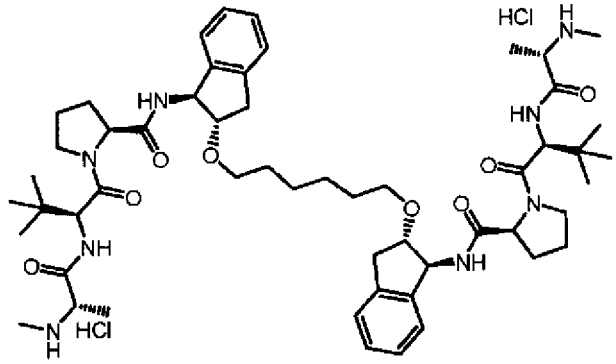
122;
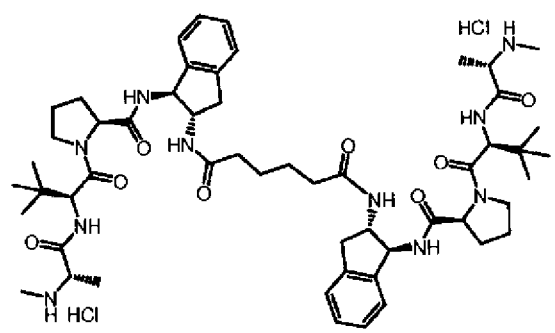
123;
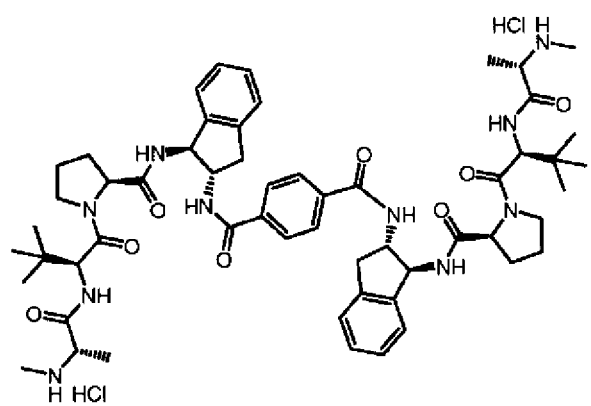
124; and
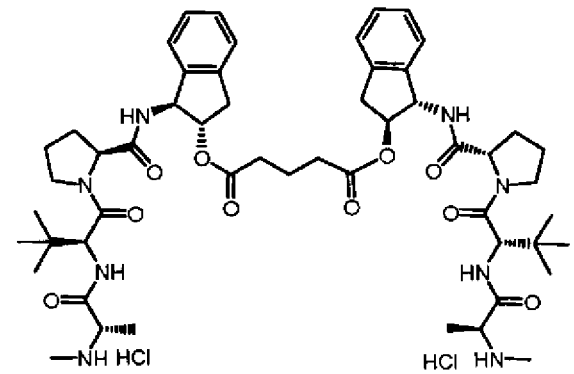
125.